(12) United States Patent
Dekkers et al.

(10) Patent No.: US 9,745,561 B2
(45) Date of Patent: Aug. 29, 2017

(54) GENETIC TEST AND GENETIC BASIS FOR SCID IN PIGS

(71) Applicant: IOWA STATE UNIVERSITY RESEARCH FOUNDATION, INC., Ames, IA (US)

(72) Inventors: Jack C. M. Dekkers, Ames, IA (US); Christopher K. Tuggle, Ames, IA (US); Emily H. Waide, Ames, IA (US); Jason W. Ross, Cambridge, IA (US); N. Matthew Ellinwood, Ames, IA (US); Martine Schroyen, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 40 days.

(21) Appl. No.: 14/592,586

(22) Filed: Jan. 8, 2015

(65) Prior Publication Data
US 2015/0216147 A1   Aug. 6, 2015

Related U.S. Application Data

(60) Provisional application No. 61/925,072, filed on Jan. 8, 2014.

(51) Int. Cl.
| | | |
|---|---|---|
| *A01K 67/027* | (2006.01) | |
| *C12N 9/22* | (2006.01) | |
| *C12Q 1/68* | (2006.01) | |

(52) U.S. Cl.
CPC ............ *C12N 9/22* (2013.01); *A01K 67/0275* (2013.01); *C12Q 1/6883* (2013.01); *A01K 2227/108* (2013.01); *A01K 2267/0387* (2013.01); *C12Q 2600/156* (2013.01); *C12Q 2600/16* (2013.01)

(58) Field of Classification Search
USPC .......................................................... 800/17
See application file for complete search history.

(56) References Cited

U.S. PATENT DOCUMENTS

2014/0359796 A1* 12/2014 Fahrenkrug ........ A01K 67/0276
800/15

OTHER PUBLICATIONS

Powell et al NK cells are intrinsically functional in pigs with Severe Combined Immunodeficiency (SCID) caused by spontaneous mutations in the Artemis gene Veterinary Immunology and Immunopathology 175 (2016) 1-6.*
Waide et al Not All SCID Pigs Are Created Equally: Two Independent Mutations in the Artemis Gene Cause SCID in PigsThe Journal of Immunology 2015; 195:3171-3179.*
Ewen et al Analysis of blood leukocytes in a naturally occurring immunodeficiency of pigs shows the defect is localized to B and T cellsVeterinary Immunology and Immunopathology 162 (2014) 174-179.*
Wyatt et al Journal of Immunology, (May 1, 2013) vol. 190, No. 1, Supp. MeetingAbstracts. Abstract Number: 141.24.*
Basel, Matthew T. et al., "Human Xenografts Are Not Rejected in a Naturally Occurring Immunodeficient Porcine Line: A Human Tumor Model in Pigs", BioResearch Open Access, vol. 1, No. 2, 2012.
Gluckman, Eliane et al., "Cord blood transplant: strategy of alternative donor search", Springer Semin Immun (2004), 26:143-154.
Ito, Mamoru et al., "NOD/SCID/ yc null mouse: an excellent recipient mouse model for engraftment of human cells", Blood, Nov. 1, 2002, vol. 100, No. 9.
Lang, Julie et al., "Generation of hematopoietic humanized mice in the newborn BALB/c-RAG2 null Il2ry null mouse model: A multivariable optimization approach", Clinical Immunology (2011) 140, 102-116.
Moshous, Despina et al., "Artemis, a Novel DNA Double-Strand Break Repair/ V(D)J Recombination Protein, Is Mutated in Human Severe Combined Immune Deficiency", Cell, vol. 105, 177-186, Apr. 20, 2001.
Qzuna, A.G. Cino et al., "Preliminary Findings of a Previously Unrecognized Porcine Primary Immunodeficiency Disorder", Veterinary Pathology, 50(1) 144-146, 2012.
Purcell, Shaun et al., "PLINK: A Tool Set for Whole-Genome Association and Population-Based Linkage Analyses", The American Journal of Human Genetics, vol. 81, Sep. 2007.
Stephens, Matthew et al, "A New Statistical Method for Haplotype Reconstruction from Population Data", Am. J. Hum. Genet., 68:978-989, 2001.
Suzuki, Shunichi et al, "Il2rg Gene-Targeted Severe Combined Immunodeficiency Pigs", Cell Stem Cell 10, 753-758, Jun. 14, 2012.
Wengler, Georg S. et al., "Conditioning of Neonatal Pigs Using Low-Dose Chemotherapy and Murine Fetal Tissue before Murine Hybridoma Transplantation", Transplantation, vol. 79, No. 3, Feb. 15, 2005.

* cited by examiner

*Primary Examiner* — Maria Leavitt
(74) *Attorney, Agent, or Firm* — McKee, Voorhees & Sease, PLC

(57) ABSTRACT

The genetic basis for severe combined immunodeficiency disease (SCID) in pigs is described. In addition, tests for detecting pigs that are carriers for SCID or pigs with SCID are also described. Further, methods for producing pigs or herds of pigs with SCID are also described. Further, methods and compositions for treating, ameilioraing, inhibiting or correcting SCID are provided.

3 Claims, 43 Drawing Sheets

| 15801-sired families | | 1 | 2 | 3 | 4 | 5 | 6 | 7 | 8 | 9 | 10 | 11 | 12 | 13 | 14 | 15 | 16 | 17 | 18 | 19 | 20 | 21 |
|---|---|---|---|---|---|---|---|---|---|---|---|---|---|---|---|---|---|---|---|---|---|---|
| Two Affected | 12 | A | G | A | C | C | C | A | A | G | A | G | G | A | G | A | G | A | G | A | A | G |
| Haplotypes | 16 | G | G | G | C | C | C | A | A | G | A | A | G | A | A | G | A | G | A | A | G | G |
| Normal | 3 | A | A | A | A | A | A | A | G | A | G | G | G | A | G | A | C | G | G | A | A |
| Normal | 9 | A | G | A | C | A | C | A | C | A | G | A | A | A | A | A | G | G | G | A | G | A |
| 11403-sired families | | | | | | | | | | | | | | | | | | | | | | |
| Affected | 16 | G | G | G | C | C | C | A | A | G | A | A | G | A | A | G | A | G | A | A | G | G |
| Normal | 9 | A | G | A | C | A | C | A | C | A | G | A | A | A | A | A | G | G | G | A | G | A |
| Normal | 19 | G | G | G | C | C | C | G | C | G | A | A | A | A | A | A | G | G | G | A | G | A |

Sequence 1, Transcript of 20101 clone 10, longest cDNA sequence from haplotype 16 (SEQ ID NO:1)

GGATCCGTGTTCGCCAACGCTATGAGTTCCTTCGAGGGCCAGATGAGTTCCTTCGA
GGGCCAGATGGCGGAGTACCCAACTATCTCCATAGACCGTTTCGACCGGGAGAATC
TGAGGGCTCGCGCTTATTTCCTGTCCCACTGCCACAAGGATCACATGAAAGGATTAA
GAGCCTCTACCTTGAGAAGAAGGTTGGAGTGCAGCTTGAAGGTCTCCTTATACTG TT
CACCTGTTACTAGAGAATTGTTATTAACCAACCCGAGGTACAGATTTTGGGAGAAAC
GAATTGTGTCAATTGAAGTTGAAACTCCTACCCAGATATCTTTAATTGATGAAGCAT
CAGGCGAGAAGGAAGAAATTGTTGTGACTCTCTTACCAGCTGGTCATTGCCCAGGAT
CAGTTATGTTCTTATTTCAGGGCAACAATGGAACTGTCTTGTATACAGGAGACTTCC
GATTGGCAAAAGGAGAAGCTGCCAGAATGGAGCTTCTGCACTCGGGGGGCAGTGTG
AAAGACATCCAGAGTGTGTACTTAGACACCACTTTCTGCCATCCAAAGTATTACCAA
ATTCCCAGTCGGG(EXON8)TTCACGTGAATAAACTGGACATGTTTCGAAACATGCCT
GACATCCTTCATCATCTCACAACAGACCGTGGCACTCAGATCCATGCCTGTCGGCAT
CCAAAGGCAGAGGAATATTTTCATTGGAATAAGTTACCCTGTGGAATAACATCC AA
AAATAGAATTCCACTCCACATAATCAGCATTAAGCCCTCCACTATGTGGTTTGGAGA
AAGAACTAGAAAAACCAATGTTATTGTGAGGACTGGAGAGAGTTCGTACAGAGCCT
GCTTTTCTTTTCACTCCTCCTACAGTGAGATTAAAGATTTCTTGAGCTACATTAGCCC
TGTGAATGTATATCCAAATGTCATTCCACTGGGCACAACTCTGGAGAAAGTTAAAGA
AATCTTAAAGCCTTTATGCCGATCTT CGCAAAATATCGAGCCAAAGTATAAACCACT
TGGAAAATTGAAGAGAGCTAGAATAATCCATCTAGACTCAGAGGAGGAGGAGGAG
GACGATGACGATCTCTTTGATGATCCTCTGCCAGTACCTTTAAGGCACAAGGTTCCA
AATCAGCAGACTCTTCACTCTGAGGTACTTCCCATGACTGCTCTACCACAAGACCAG
CCTGAAAAACAGACAGAAAGCACAGAATGCTTCAAAGCAGAGAGTATGCCAACATG
TCTCTGGGCAAACTTCGTAGATTGTGAAGAATCCAATAGTGAAAGTGAAGAATTAG
AAATCACGGCTCCAGCTCAAGGAGACACGAGTCCTGTCCCCCATCACCAGCAGAAG
GCTGAAGGGAAGTACCACAGTGGGAAGTGTTCTTTAAAAGAAATGATGAAATCAC
AGATGACTGTTTGGAAAACCTTCCGTCCTCCACAGAGGCAGGGGGCTCTCAGTCCCC
AAAGCTTTTCAGTGACTCTGATGGGGAATCAACTCACATTTCTTCCCAGACTTCTTCT
CAGTCAACACACATATCAGAACAAGGAAGTCAAGGCTGGGACAGCCAATCAGACAC
TGTTTTGTTATCTTCCCAAGAGAGAAAAAGTGGGGATATTACCTCCTTGAACAAAGG

*FIG. 16A*

TGGCTCTAGACCAGAAATCAAAGAGAATATTCCCATCCTTCAGATGGAACAAAATG
TATTTTGCCCGAAGGATACTTACTCTGATTTGAAAGGCAGAGATCAAGATATAAACA
CACTTCCCAGTGCTAGAGAAACAACTACTCTGAGCAGTGGGAAACACATGCCTCAG
GAGAAAAGGCCGCTAAACTGTAACAGTAACACAGATTCACAAGGCTCCTCTGACTT
TGAAATTCCCTCCACTCCAGAAGCTGAGCTACCTCAACAAGAGCATCTGCAATATTT
ATACAAGAAGTTGGCAGGAGGAGAGGGTATAGTAATTGAAAAAAGGAAAAGCGCA
CGTCATTCTAGAGCAACCATTAAAAAACCTACACA AACAGGTAATAGTCAGACTCCT
AATAGA*TGA*GTTCAAATGGAGTACTTAAAAATGTTCAT ATAACCTAAAAGGCAGCT
CTGCGGCCGC

Translation 1 (SEQ ID NO:2)
MSSFEGQMSSFEGQMAEYPTISIDRFDRENLRARAYFLSHCHKDHMKGLRASTLRRRLE
CSLKVSLYCSPVTRELLLTNPRYRFWEKRIVSIEVETPTQISLIDEASGEKEEIVVTLLPAG
HCPGSVMFLFQGNNGTVLYTGDFRLAKGEAARMELLHSGGSVKDIQSVYLDTTFCHPK
YYQIPSRVHVNKLDMFRNMPDILHHLTTDRGTQIHACRHPKAEEYFHWNKLPCGITSKN
RIPLHIISIKPSTMWFGERTRKTNVIVRTGESSYRACFSFHSSYSEIKDFLSYISPVNVYPNV
IPLGTTLEKVKEILKPLCRSSQNIEPKYKPLGKLKRARIIHLDSEEEEEDDDDLFDDPLPVP
LRHKVPNQQTLHSEVLPMTALPQDQPEKQTESTECFKAESMPTCLWANFVDCEESNSES
EELEITAPAQGDTSPVPHHQQKAEGEVPQWEVFFKRNDEITDDCLENLPSSTEAGGSQSP
KLFSDSDGESTHISSQTSSQSTHISEQGSQGWDSQSDTVLLSSQERKSGDITSLNKGGSRP
EIKENIPILQMEQNVFCPKDTYSDLKGRDQDINTLPSARETTTLSSGKHMPQEKRPLNCN
SNTDSQGSSDFEIPSTPEAELPQQEHLQYLYKKLAGGEGIVIEKRKSARHSRATIKKPTQT
GNSQTPNR- Sequence 2, Transcript of 20301 clone 1, longest cDNA sequence from haplotype 12 (SEQ ID
NO:3)
GGATCCGTGTTCGCCAACGCTATGAGTTCCTTCGAGGGCCAGATGGCGGAGTACC
CAACTATCTCCATAGACCGTTTCGACCGGGAGAATCTGAGGGCTCGCGCTTATTTCC
TGTCCCACTGCCACAAGGATCACATGAAAGGATTAAGAGCCTCTACCTTGAAAAGA
AGGTTGGAGTGCAGCTTGAAGGTCTCCTTATACTGTTCACCTGTTACTAGAGAATTG
TTATTAACCAACCCGAGGTACAGATTTTG GGAGAAACGAATTGTGTCAATTGAAGTT

*FIG. 16B*

GAAACTCCTACCCAGATATCTTTAATTGATGAAGCATCAGGCGAGAAGGAAGAAAT
TGTTGTGACTCTCTTACCAGCTGGTCATTGCCCAGGATCAGTTATGTTCTTATTTCAG
GGCAACAATGGAACTGTCTTGTATACAGGAGACTTCCGATTGGCAAGAGGAGAAGC
TGCCAGAATGGAGCTTCTGCACTCGGGGGGCAGTGTGAAAGACATCCAGAGTGTGT
ACTTAGACACCACTTTCTGCCATCCAAAGTATTACCAAATTCCCAGTCGGGAGGAGT
GTCTGAGAGGGATCTTGGAGCTGGTCCGCAGCTGGATCACACGGAGCCCCTACCAC
GTGGTGTGGCTGAACTGCAAAGCGGCCTATGGGTACGAGTACCTGTTCACCAACCTC
AGCGAGGAGTTCGGAGTCCAGGTTCACGTGAATAAACTGGACATGTTTCGAAACAT
GCCTGACATCCTTCATCATCTCACAACAGACCGTGGCACTCAGATCCATGCCTGTCG
GCATCCAAAG(EXON10)AACTGGAGAGAGTTCGTACAGAGCCTGCTTTTCTTTTCACT
CCTCCTACAG*TGA*GATTAAAGATTTCTTGAGCTACATTAGTCCTGTGAATGTATATCC
AAATGTCATTCCACTGGGCACAACTCCGGAGAAAGTTAAAGAAATCTTAAAGCCTTT
ATGCCGATCTTCGCAAAATATCGAGCCAAAGTATAAACCACTTGGAAAATTGAAGA
GAGCTAGAATAATCCATCTAGACTCAGAGGAGGAGGAGGAGGACAATGACGATCTC
TTTGATGATCCTCTGCCAGTACCTTTAAGGCACAAGGTTCCAAATCAGCAGACTCTT
CACTCTGAGGTACTTCCCATGACTGCTCTACCACAAGACCAGCCTGAAAAACAGAC
AGAAAGCACAGAATGCTTCAAAGCAGAGAGTATGCCAACATGTCTCTGGGCAAACT
TCGTAGATTGTGAAGAATCCNATAGTGAAAGTGAAGAATTAGAAATCACGGCTCCA
GCTCAAGGAGACACGAGTCCTGTCCCCATCACCAGCAGAAGGCTGAAGGGGAAGT
ACCACAGTGGGAAGTGTTCTTTAAAAGAAATGATGAAATCACAGATGACTGTTTGG
AAAACCTTCCGTCCTCCACAGAGGCAGGGGGCTCTCAGTCCCCAAAGCTTTTCAGTG
ACTCTGATGGGGAATCAACTCACATTTCTTCCCAGACTTCTTCTCAGTCAACACACAT
ATCAGAACAAGGAAGTCAAGGCTGGGACAGCCAATCAGACACTGTTTTGTTATCTTC
CCAAGAGAGAAAAAGTGGGGATATTACCTCCTTGAACAAAGGTGGCTCTAGACCAG
AAATCAAAGAGAATATTCCCATCCTTCAGATGGAACAAAATGTATTTTGCCCGAAGG
ATACTTACTCTGATTTGAAAGGCAGAGATCAAGATATAAACACACTTCCCAGTGCTA
GAGAAACAACTACTCTGAGCAGTGGGAAACACATGCCTCAGGAGAAAAGGCCGCTA
AACTGTAACAGTAACACAGATTCACAAGGCTCCTCTGACTTTGAAATTCCCTCCACT
CCAGAAGCTGAGCTACCTCAACAAGAGCATCTGCAATATTTATACAAGAAGTTGGC
AGGAGGAGAGGGTATAGTAATTGAAAAAAGGAAAAGCGCACGTCATTCTAGAGCA

*FIG. 16C*

ACCACTAAAAAACCTACACAAACAGGTAATAGTCGGACTCCTAATAGATGAGTTCA
AATGGAGTACTTAAAAATGTTCAT ATAACCTAAAAGGCAGCTCTGCGGCCGC

Translation 2 (SEQ ID NO:4)
MSSFEGQMAEYPTISIDRFDRENLRARAYFLSHCHKDHMKGLRASTLKRRLECSLKVSL
YCSPVTRELLLTNPRYRFWEKRIVSIEVETPTQISLIDEASGEKEEIVVTLLPAGHCPGSVM
FLFQGNNGTVLYTGDFRLARGEAARMELLHSGGSVKDIQSVYLDTTFCHPKYYQIPSRE
ECLRGILELVRSWITRSPYHVVWLNCKAAYGYEYLFTNLSEEFGVQVHVNKLDMFRNM
PDILHHLTTDRGTQIHACRHPKNWREFVQSLLFFSLLLQ- Sequence 3 Transcript of 20106 clone 6, longest cDNA sequence from normal haplotype (SEQ ID NO:5)
GGATCCGTGTTCGCCAACGCTATGAGTTCCTTCGAGGGCCAGATGGCGGAGTACC
CAACTATCTCCATAGACCGTTTCGACCGGGAGAATTTGAGGGCTCGCGCTTATTTCC
TGTCCCACTGCCACAAGGATCACATGAAAGGATTAAGAGCCTCTACCTTGAAAAGA
AGGTTGGAGTGCAGCTTGAAGGTCTCCTTATACTGTTCACCTGTTACTAGAGAATTG
TTATTAACCAACCCGAGGTACAGATTTTGGGAGAAACGAATTGTGTCAATTGAAGTT
GAAACTCCTACCCAGATATCTTTAATTGATGAAGCA TCAGGCGAGAAGGAAGAAAT
TGTTGTGACTCTCTTACCAGCTGGTCATTGCCCAGGATCAGTTATGTTCTTATTTCAG
GGCAACAATGGAACTGTCTTGTATACAGGAGACTTCCGATTGGCAAAAGGAGAAGC
TGCCAGAATGGAGCTTCTGCACTCGGGGGGCAGTGTGAAAGACATCCAGGGTGTGT
ACTTAGACACCACTTTCTGCCATCCAAAGTATTACCAAATTCCCAGTCGGGAGGAGT
GTCTGAGAGGGATCTTGGAGCTGGTCCGCAGCTGGATCACACGGAGCCCCTACCAC
GTGGTGTGGCTGAACTGCAAAGCGGCCTATGGGTACGAGTACCTGTTCACCAACCTC
AGCGAGGAGTTCGGAGTCCAGGTTCACGTGAATAAACTGGACATGTTTCGAAACAT
GCCTGACATCCTTCATCATCTCACAACAGACCGTGGCACTCAGATCCATGCCTGTCG
GCATCCAAAGGCAGAGGAATATTTTCATTGGAATAAATT ACCCTGTGGAATAACATC
CAAAAATAGAATTCCACTCCACATAATCAGTATTAAGCCCTCCACTATGTGGTTTGG
AGAAAGAACTAGAAAAACCAATGTTATTGTGAGAACTGGAGAGAGTTCGTACAGAG
CCTGCTTTTCTTTTCACTCCTCCTACAGTGAGATTAAAGATTTCTTGAGCTACATTAG
TCCTGTGAATGTATATCCAAATGTCATTCCACTGGGCACAACTCTGGAGAAAGTTAA

*FIG. 16D*

AGAAATCTTA AAGCCTTTATGCCGATCTTCGCAAAATATCGAGCCAAAGTATAAACC
ACTTGGAAAATTGAAGAGAGCTAGAATAATCCATCTAGACTCAGAGGAGGAGGAGG
AGGACAATGACGATCTCTTTGATGATCCTCTGCCAGTACCTTTAAGGCACAAGGTTC
CAAATCAGCAGACTCTTCACTCTGAGGTACTTCCCATGACTGCTCTACCACAAGACC
AGCCTGAAAAACAGACAGAAAGCACAGAATGCTTCAAAGCAGAGAGTATGCCAAC
ATGTCTCTGGGCAAACTTCGTAGATTGTGAAGAATCCAATAGTGAAAGTGAAGAATT
AGAAATCACAGCTCCAGCTCAAGGAGACACGAGTCCTGTCCCCATCACCAGCAGA
AGGCTGAAGGGGAAGTACCACAGTGGGAAGTGTTCTTTAAAAGAAATGATGAAATC
ACAGATGACTGTTTGGAAAACCTTCCGTCCTCCACAGAGGCAGGGGGCTCTCAGTCC
CCAAAGCTTTTCAGTGACTCTGATGGGGAATCAACTCACATTTCTTCCCAGACTTCTT
CTCAGTCAACACACATATCAGAACAAGGAAGTCAAGGCTGGACAGCCAATCAGAC
ACTGTTTTGTTATCTTCCCAAGAGAGAAAAAGTGGGGATATTACCTCCTTGAACAAA
GGTGGCTCTAGACCAGAAATCAAAGAGAATATTCCCATCCTTCAGATGGAACAAAA
TGTATTTTGCCCGAAGGATACTTACTCTGATTTGAAAGGCAGA GATCAAGATATAAA
CACACTTCCCAGTGCTAGAGAAACAACTACTCTGAGCAGTGGGAAACACATGCCTC
AGGAGAAAAGGCCGCTAAACTGTAACAGTAACACAGATTCACAAGGCTCCTCTGAC
TTTGAAATTCCCTCCACTCCAGAAGCTGAGCTACCTCAACAAGAGCATCTGCAATAT
TTATACAAGAAGTTGGCAGGAGGAGAGGGTATAGTAATTGAAAAAAGGAAAAGCG
CACGTCATTCTAGAGCAA CCACTAAAAAACCTACACAAACAGGTAATAGTCAGACT
CCTAATAGA TGAGTTCAAATGGAGTACTTAAAAATGTTCAT ATAACCTAAAAGGCA
GCTCTGCGGCCGC

Translation 3 (SEQ ID NO:6)
MSSFEGQMAEYPTISIDRFDRENLRARAYFLSHCHKDHMKGLRASTLKRRLECSLKVSL
YCSPVTRELLLTNPRYRFWEKRIVSIEVETPTQISLIDEASGEKEEIVVTLLPAGHCPGSVM
FLFQGNNGTVLYTGDFRLAKGEAARMELLHSGGSVKDIQGVYLDTTFCHPKYYQIPSRE
ECLRGILELVRSWITRSPYHVVWLNCKAAYGYEYLFTNLSEEFGVQVHVNKLDMFRNM
PDILHHLTTDRGTQIHACRHPKAEEYFHWNKLPCGITSKNRIPLHIISIKPSTMWFGERTR
KTNVIVRTGESSYRACFSFHSSYSEIKDFLSYISPVNVYPNVIPLGTTLEKVKEILKPLCRS
SQNIEPKYKPLGKLKRARIIHLDSEEEEEDNDDLFDDPLPVPLRHKVPNQQTLHSEVLPM
TALPQDQPEKQTESTECFKAESMPTCLWANFVDCEESNSESEELEITAPAQGDTSPVPHH

*FIG. 16E*

QQKAEGEVPQWEVFFKRNDEITDDCLENLPSSTEAGGSQSPKLFSDSDGESTHISSQTSS
QSTHISEQGSQGWDSQSDTVLLSSQERKSGDITSLNKGGSRPEIKENIPILQMEQNVFCPK
DTYSDLKGRDQDINTLPSARETTTLSSGKHMPQEKRPLNCNSNTDSQGSSDFEIPSTPEAE
LPQQEHLQYLYKKLAGGEGIVIEKRKSARHSRATTKKPTQTGNSQTPNR -

Sequence 4, Genomic sequence of exons 7 and 8 (dotted underlined) of 4810, a homozygous haplotype 16 affected animal (SEQ ID NO:7)

TCCCTCACCCATCTGTCTTATATATTATCCTATGGAAATCA CTTTCTAACCATGTCGA
TACAGTAAAAAATTCCAGGGAGCTCTCTTGTGGCCCAGTGGATTAAGGATCTGGCTG
TTGTCACTGCAGCGGCGTGGGAGTGGCCAAAAAGAAAACCCAAGTGGACTGAAAC
CTCCTGTAAAATAACTGAGAGTTTCGACTTCACGCGTGTTGTATTTCACGTGATTAAC
AGCTCTTGTGTTCTGTTTATCTTCAGTGTGAAAGACATCCAGAGTGTGTACTTAGACA
CCACTTTCTGCCATCCAAAGTATTACCAAATTCCCAGTCGG GTACGTCTCTCTGGAC
GGGTGGCTGTATTTCTCAGGGGGCGGGCCGCAGGCTAACAGGTCGGGTGGTAACGG
GCCCCCTGGCCTTAATGTCTGGGGACGCTGGGAACGGACAAGGCCTCAACTGCCTCT
TCAAACCCCTGCCCAGGAGGAGTGTCTGAGAGGGATCTTGGAGCTGGTCCGCAGCT
GGATCACGCGGAGCCCCTACCACGTGGTGTGGCTGAACTGCAAAGCGGCCTATGGG
TACGAGTACCTGTTCACCAACCTCAGCGAGGAGTTCGGAGTCCAG[A]TACCTGAGG
GC

Sequence 5, genomic sequence of exons 7 and 8 (dotted underline) of 1304, a homozygous normal animal (SEQ ID NO:8)

TCCCTCACCCATCTGTCTTATATATTATCCTATGGAAATCACTTCCTAACCATGTCGATAC
AGTAAAAAATTCCAGGGAGCTCTCTTGTGGCCCAGTGGATTAAGGATCTGGCTGTTGTC
ACTGCAGCGGCATGGGAGTGGCCAAAAAGAAAACCCAAGTGGACTGAAACCTCCTGT
AAAATAACTGAGAGTTTCGACTTCACGCGTGTTGTATTTCACGTGATTAACAGCTCTTGT
GTTCTGTTTATCTTCAGTGTGAAAGACATCCAGAGTGTGTACTTAGACACCACTTTCTGC
CATCCAAAGTATTACCAAATTCCCAGTCGGGTACGTCTCTCTGGACGGGTGGCTGTATTT
CTCAGGGGGCGGGCCGCAGGCTAACAGGTCGGGTGGTAACGGGCCCCCTGGCCTTAATG
TCTGGGGACGCTGGGAACGGACAAGGCCTCAACTGCCTCTTCAAACCCCTGCCCAGGAG
GAGTGTCTGAGAGGGATCTTGGAGCTGGTCCGCAGCTGGATCACACGGAGCCCCTACCA

*FIG. 16F*

CGTGGTGTGGCTGAACTGCAAAGCGGCCTATGGGTACGAGTACCTGTTCACCAACCTCA
GCGAGGAGTTCGGAGTCCAG[G]TACCTGAGGGCTC

Sequence 6, Genomic sequence of exons 10 and 11 (underlined) of 20301, a homozygous
haplotype 12 animal (SEQ ID NO:9)
CATGCTAAAAAGTCATCTGCATTTTTTTGAGACCNTGGTACAAATATATTTGTTGAA
AATGTTAAACCATTTTTCTTATTTTAAAATCTTTTTTAGG CAGAGGAATATTTTCATTT
A[GAATAAATTACCCTGTGGAATAACATCCAAAAATAGAATTCCACTCCACATAATC
AGTATTAAGCCCTCCACTATGTGGTTTGGAGAAAGAACTAGAAAAACCAATGTTATT
GTGAGGTAAGCAAGCAGCGTCTTTTGAGAGGAACCTTGCTTTGAGGTAAATCGATA
GTTTAAAGGCAGTCTAGCCTAACCTCAAGAGGGGGGCATATCATGATTGTGGAAAA
TAACTTTTGAAAGTTAAACTCTGTTTAAATTAAAGAGAAGCGGCTTCCAAAAGCTAT
CAATTGCTTACTACCATGAGCCAGTATTTCCTGGGGTCTACTGAGTTTGACTGAGAA
GATGGTTAGAGGCAGGCTGTCTTGCTTGGCCGGAAGTTGGGAATTGACCTTGAAGG
GGTTGGAAGCCCTTAGTGGAGCAGAGGAGGCCCATACTGATCCTCATGTTTTAGCTC
ATGTCCTGAAACATTGGCCGTTTGGAATGTTCACAGATATTTACATTTATGGAAAGA
GTTCCCTCCTGGCCCAGGAAAAAAATCCTTGATGGCAGGGTGATTTCATCCTGCAGT
AGCCTAAAATGAGAAGACTCGGAGTTTGGAACTTAGTTTTGATGAGTGACCCTTAAT
TTTGGGTTTTCCTTTCCCTTTAGAACTGGAGAGAGTTCGTACAGAGCCTGCTTTTCTT
TTCACTCCTCCTACAGTGAGGTAAGAGG Sequence 7, Genomic sequence of exons 10 and 11 (underlined) of 1304, a homozygous normal
animal (SEQ ID NO:10)
CATGCTAAAAAGTCATCTGCATTTTTTTGAGACCCTGGTACAAATATATTTGTTGAAAAT
GTTAAACCATTTTTCTTATTTTAAAATCTTTTTTAGGCAGAGGAATATTTTCATT[G]GAA
TAAATTACCCTGTGGAATAACATCCAAAAATAGAATTCCACTCCACATAATCAGTATTA
AGCCCTCCACTATGTGGTTTGGAGAAAGAACTAGAAAAACCAATGTTATTGTGAGGTAA
GCAAGCAGCGTCTTTTGAGAGGAACCTTGCTTTGAGGTAAATCGATAGTTTAAAGGCAG
TCTAGCCTAACCTCAAGAGGGGGGCATATCATGATTGTGGAAAATAACTTTTGAAAGTT
AAACTCTGTTTAAATTAAAGAGAAGCGGCTTCCAAAAGCTATCAATTGCTTACTACCAT
GAGCCAGTATTTCCTGGGGTCTACTGAGTTTGACTGAGAAGATGGTTAGAGGCAGGCTG
TCTTGCTTGGCCGGAAGTTGGGAATTGACCTTGAAGGGGTTGGAAGCCCTTAGTGGAGC
AGAGGAGGCCCATACTGATCCTCATGTTTTAGCTCATGTCCTGAAACATTGGCCGTTTGG
AATGTTCACAGATATTTACATTTATGGAAAGAGTTCCCTCCTGGCCCAGGAAAAAAATC
CTTGATGGCAGGGTGATTTCATCCTGCAGTAGCCTAAAATGAGAAGACTCGGAGTTTGG
AACTTAGTTTTGATGAGTGACCCTTAATTTTGGGTTTTCCTTTCCCTTTAGAACTGGAGA

FIG. 16G

GAGTTCGTACAGAGCCTGCTTTTCTTTTCACTCCTCCTACAGTGAGGTAAGAGGATCCCA
TACTCAGAACCTCGGCTGC

Porcine DCLRE1C (Artemis) gene sequence (SEQ ID NO:45): Exon regions are underlined; the
haplotype 12 and 16 causative mutations are boxed in light grey and dark grey, respectively.

>ENSSSCG00000011049|ENSSSCT00000012093
<u>ATAACCGCGGAGGGCTGGCGCCCAGTCGGC TGTGTTCGCCAACGCTATGAGTTCCTT
CGAGGGCCAGATGGCGGAGTACCCAACTATCTCCATAGACCGTTTCGACCGGGAGA
ATCTGAGGGCTCGCGCTTATTTCCTGTCCCACTGCCACAAGG</u>GTGAGTGAGCGCGGC
GCGCCGACCCCTCCCGGGGACCAGGGCTGCGGCGGGTCTGGCCCCGCGGGGAGGT
AGCCCAGGGGCTGGAGAGGAGGAAGTTGGGGTGGGGGTCCTGCAGGAGGAGTGCA
GGCTTTGGGAGGTCTGGGGAGAGACTAGCGACTGCATCCTGTCGCAGGCGTGCTCTT
CAGCCTGTTTGAGGCTTTATCGCCTCATAGGTCCCGCGGGGCGGGACAGAGCAGCG
ACTGCCAGTTACTCACTGACCCAGGCCAGTTTGATCAGGCACAGCTATTCGGTTTTT
TGGAAGCTCTCCCAGGGCCCAATAGTCAAGGTTGTCGAGGATTACTTATTCTTCCC
CCAAATCCTCGCGATTTTGTTACAAAGACAGGTTTAAATGAAATTCTGCCATACCTC
CAACCATTTATTAGCAAGCACGCACGCATTCAAATTAAACGTCCTGCCTGTGAGCTT
GACAACGTGCAAGCTCCCCCTCTTTTAGATGTTCTGTTCACATTCAGTATGAAAGGT
TCCTTTTGTCCTAGAGGTGGGATGAGGTTTACCTTACAGATGCCCAGGTCAGGCAAC
CAGAATGTTATTTCACAGCTGCACATGGTTAGGAATTAAGCCTGGAATGTCGCCCCC
TAACGATATGGTCCCCAGGCCAGTTACTCCAGGCAAGTCTGGAGCATCTCTACATTT
TAGCCAGTCTCCAGAGCTAGAGTACCACCAATTTCACTACCATTTTCCATTCTTTTTT
TTTTTTTTTTCTTTTGCCATTTCTTGGGCCGCTCCGGCGGCATATGGAGGTTCCCAG
GCTAGGGGTCCAATCGGAGCTGTAGCTGCCGGCCTACACCATAGCCACAGCAACTC
AGGATCCAAGCCGCGTCTGCAACCTACACCACAGCTCACGGCAACGCCAGATCGTT
AACCCACTGAGCAAGGCCAGGGATCGAACCCGCAACCTCATGGTTCCTAGTCGGAT
TCATTAACCACTGAGCCATGACGGGAAATCCCCATTGTCCATTCTTAACATCTGGTA
TGCTGATGGATAGGTCAGTAACTTTTACCCATGAAAACAGGTTTAATATTCAGTATG
CTAATTAGCACATCCTTGGGCCTTGACCAGAGATGAAGGTTAATTGAAGCATTCTAG
AAGCTACCTCTTGGAGTGCTGATTTCCAGCGTAGCTTAAGTAGGAGACCCCCGACCG
CTCTTTTGAGGAGTGACTCAGATATATTTGCACAAACATACCACACTGTGTGATTTT
AAAGTAAATCAGTGATATGAAAACAGACCCTTGGGCAGGCAGTGGGTGTGAAGACT
AGCTGCTGTGTGTGTGAAATCTTTGAAGTTACTGCTTTGGGGAAATGCGTCTGCTT
TCTGGCTCTAAGCTCTTTTAATTTATCACTCTTTAATGAGGAAATGCTGGACCTCCTC
TCTAGCTGTGCTAAAAACACGTGAGTCCCAGTGAAGGCCTTTCTGTTGCTTCGGGAG
AATAATATTTTGGTTTTGTCTTGTTTTTCATTGAGAAGTCATTCCTGGAAGATGGTG
TTTGTACCTCAAAGGCCCTCTGGCGTCTCTGAACTCATCGAGGATGGTGGACGGGAT
TAAAGAATGGCTTCTTGGGAGTTCCCATTGTGGCGCAGTGGAAATGAACCCGACTA G
GAACCATGAGGTGGCAGGTTCGATCCCTGGCTTCACTCAGTGGGTTAAGGATCTGGT
GTTGTCGTGAGCTGTGGTGTAGGTCACAGACATTGTTGTGCCTGTGGCATAGGCCAG
GAGCTACAGCTCTGATTAGACCCCATAGCTTGGGAACCTCTGTATGCTGCTGGTGCG
GCCCTAAAAAGACAAAAAGACCAAAAAGAAAAAAGAAAAAAGGAAAAAAAACAA
AGAATGGCTTCTTCGGGGCTCAGCCTTCATGCATCAGAGTAGTGGCTTTGGAGAAAG
AGTTTGCCTAAAGGAGTTCGTATTTATATTTTTATTGAATTTATTCTTTTATTATTTA
GTAATTGTAGTTGTGAAATTGTCATTAGTTTGTATATTAAGGAATACTCTCTCCTGCT
GAGCAGTTTATAACTTTTCCTGTCCTCTGTTCCCATGTGGGCCTGTCTTCCCAGTGAG

*FIG. 16H*

```
GATGTACACTCAACAAGGTCAGGAACTCAGCTTCTGTTCTCCAGGGTTGCCACATTG
TCTCTTCGTGGTTTTTAACTTTTTGGGGAAGCTGACGTCCTTGGATGTGCTGTGGGCT
GGCTTGTGTCCTCTCCCTACCCCCATTCATCTTTTGAATCCCTAATCTCCGATGTGGC
TGTATTTGGAGAAAGGGCTTTTAGGAGGTGATGGAGGTTAAATGAGGTCATAAGGG
TGGAGTCCTAATTTTATAGGAGTGGTGGCCTTCTCTACACACACACACACACACA
CACACACACACACTGAGGAATGCCGTGTAGGCACGCGGCATGAAAGTGGCTGCTGG
TAAGGAGAGGCCTCCCCAGAAACCAGCTTTGGTACCTTGATCTTGGACTTGAGCTTC
CAGAACCGTTAGAAATACATTTCTGGGTGTTTGCACTGTGGCACAGTGGGTTAAAAA
CCTGACTGCAGTGGCTCAGATCTCCTGTAGCCGTGTGGGTTCCGTCCCTGGCCCAGT
GCAGTGGGTTAAGGATCCAGCCTTGCCACAGCTGTGGTGTAGGTTGCAGCTGCAGCT
TGGAGTCAATCCCTGCCCTGGGAACTTCCATATGCTGCAGGGACAGCGGTAGGAAA
AAACAAATAAACAAATAAATAAATAAATAAGGAGTTCCCATTGTGGTACAACAGGG
ATGAATCCAACTAGGAACCATGAGGTTGCAGGTTCGATCCCTGGCCTCGCTCAGTGG
GTTAAGGATCCGACATTGCCATGAGCTGTGGTGTGGGTCGAAGATGAGGCTCAGAT
CTGGTGTTGCTATGGCTGTGGTGTAGGCTGGCAGCTGTATTTCAGATTCTACTCCTAG
CCTGGGAATCTCCATGTACTGCACAGGGGCAGCCCTGAAAACCAAAAAAAAAAAAA
AAAAAAAAAAAAAAAAAAAAAAAAAAAATTTAATTACTTAATTTCTCATTAAAGCCA
TCCAGGCTGATATTTTGTTATTGAAGCCTGAGCAGAATAATACAGTATATCTGATAA
GATCTATAGTCTCCTGTGAAAAAAATGCACATAAACATGTTAACATCACATTTTGA  T
AAAAGTTGAGGTAGGGAGTTCCCGTTGTGGCTCAGAGGGTTAAGAACCTGACTAGT
ATCCATGAAGATGTGGGTTTCATCGCTGGTCTTGCTCAATGGGTTAAGGATCCAGCA
TTGCTGTGAGCTGTGAGCTGTGGTATAGGTTGCAAATGTGGCTCGAATCTGACATGA
CTGTGTTATAGGCCTGCAGCTGCAGCTCTGATTTGACCACTACCCCACGAATGTCCA
TATGCTGCAGGTGTGGTCCTAAAAAAAA AAAAAAGGTGAGGTGGGCCATGGACCTG
CTTGATGCCTGTTCATGGTCCATCTGGGATCCAGTGCTGTGTTCAGGGCAGGCTTTA
AAGCATCTGTAAGGCCCAGAGGACAAGATGGGACCCATGGCCTGAGATTGCAGCCC
AGGGAGGGGTAGGACCCCTTCAGGAGGCAGCTTAATTTGATGTATTTTGGTCAAAG
GAAAAGCCAAAGGCCCTGGAAAGGAGGCTTGGGGTGCATCCTGGTGGCAAATAGGG
AACTCACCCAGGTTCCCTCCACTGGTGGGATGGGGTGTCTTGATGGAACAGGATGCT
GCCCAGAGGCTTAGTTTGGGAGCAAGGAGCAGAGTCCAGGATCAGCCTCCTTATTG
CTCTGACTCAAACTCTCTGGAAGACTTGATTAAGGAGAGTCCTGCCTGGGACATAC
TCATTCTTTGGCCCTAAAGCCTGCCTCAGGAGTGCCCTGAGGAGAGGCACCTTCTGA
GGGCACATGGTCTGTCCGTGTGTGGTCTGGTGACTGCCTTGTTTTGAGAAATGAGG
ACCGCCATGTATACATCGAGGGCATGCGTGTTGGTTGTAATTAGGATAATTCAATTT
CTTTTTTTCTTTTTTATGAGAGTGGTAATGTTTATTTCAGGTTCTCTCTCTCTTTTTGTC
TTTTTTAAAAAAAATTTTTTTTTCTTTTTTTGCCACACCCGCAGCATGTGGAAGTTCC
AGGGCCAGGGATTGAACCTGCGCCACACAGCAGTGATCAGAACCACAGTGGGGAA
AATGCAGAAGCCGAGTTCCCATTGTGACACATCGGAAATGAATCTGACTAGTAACC
ATGAGGTTCCGGGTTCGATCCCTGGCCTTGCTCCGTGGGTTAAGGATCCGGCATTGC
CATGGGCTGTGGTGTAGGTCACAGACGCGGCTCGGATCTTTCGTTGCCGTGGCTGTG
GTGTAGGCTGGCAGTTGCAGCTCTGATTAGATCCCTAGCCTGAGAACCTCCATATAC
TGTGGGTGTGGCTCTAAAAAGCAAAAAACCAAAAACAAAAACAAAAGAAGATGC
AGGAGCCTTAACCCACTAGGCTATCAGAGAACTCCCTCGATTTTTTCTGATGGGTG
ATTGTTTAACATCATCTCCCTCACAGCCCAGCTTGACTGCCTTTGCCTTCTGCCTTCA
TCAAGGGCGGTCATGGCAGTGTTTACATATATTCATCAAAAATGCACATGAAAGTC
ATTTTTGGTACATGATTTGACTTTTTTTTTTGGTCTTTTTAGGGCTGTACCCATGGC
```

FIG. 16I

ATGCGAAGGTTCCCAGGCTAGGGGCTAATTGGAGCTGCAGCTGCCAGCCTACACCA
CAGCTCACGGCAACGCCGGATCCTTAACCCACTGAGTAAGGCCAGGGATCGAACCC
ACAACCCCTGGTTCCTAGTCGGATTCATTTTCACCACGATGGGAACTCCCATTTTTGG
TGTATGATTTGAAAAGACTTTCAAAATAACCTGCTTGTTTATGGGTTTGTTTTTGTTT
TTTTAAGTAAAATGAACTTTCCAACAGCATTCATGTATTAACCGCAAAAGAGCTGGA
AAAGCATTATGTAGAAGAATAATTTCGTTTTAATTAGCTTTAAGCTTATTAAACTTAT
GATCAGTGTTTAGAAATCTTATAATGAAGATGGTTATTCATGGTTAGACAGCAATGC
ATTTTTTTTTTTTTTTTGTCTTTTTGCCTTTTTCTAGGGCTGCTCCCGTGGCATGTG
GAGGCTCCCAGGCTAGGGGTCGAATCAGAGCTGTAGCTGTCGGCCTACACCATAGC
CACAGCAATGCCAGATCCGAGCCATGTCTGCGACCTACACCACAGCTCATGGCAAC
GCCAGAACCTTAACCCACGGAGCAAGGCCAGGGATTGAACCCGCAACCTCATGGTT
CCTAGTCGGATTCATTAACCACTGAGCCACGATGGGAACTCCAACAATGCATTTTTT
TTTTAATTTAGTTTTTAAATTTTTTGGTTGCACCCAAGGCCTTGGAAGTTCCCAGGCC
AGAGACTGAATCCGAGCTGCAGGTACGGCAACACCGGATCCTTTAACCCACTGTGT
CAGGTCAGGGATGGAACCTGTGCCAATGCAGGGGTCCAAGACACTGCAGTTGGATT
CTGAACCCACTGTGCCACAGCGAGAGTCCAAGCAATTCATTTTTTAAAAAATTCTTT
TTTTTCCTTTTTCTTTTGGACCCCCTTCACCTGATTCTCCCACCTCCTACCCCCCGACC
TTTGTTAATCAGCAATATGTTCTCAGTATCCGTGAGGTTGAATTTTTGCTTTT TCACA
TTTCATAGAAAGTGAGATCATGCAGTATTTGTCTGTGTCTGACTATTTCACTTAGCT
ATGCCTTTGGGCTCCGTTCATGTCACAAATGGCAAGAGTTCATTCTTTTTTACAGCTG
ACTAATATTCCATTGTGCATATGTATACCACAATGTCTTTATCCATTTATCTCTTGAT
AGACACTGAGGTTGTTTCCATGTCTTGGCTCTTATAAATAATGCTGCAGCAAACACG
AGGGCACAGATACCTTTTCC AGTGAGTGTTTTTGTTTTCTTCAGGTAAATAGCCAGA
AGTGAAATTGTTGGATCTTGTAGTTCTGTTTTTAATGTTTTGAGGAACCTCAGCCTCC
TGTACTGTCTTCCATAGTGGCTGCACCAATTTACATTCCCACCAACAGTGCACAAGC
GTTCCCATTTCTCCACATTCTTTTCAACATTTGTTCTTTGCTTTCTTGTTGATCATAGC
CGTAATGGGCATGATATCTCAATGTGGTTTTGACTTGCATGTCCC TGATGATTAGTG
ATGTGGAGCATTTTTTCGTGTACCTTTTGGCCATACAATATGTCTTGGGGAAAAAAG
TCTATTCAGATCTGCCCATTAAAAAAAAAAAATCTCTTTTTTTTTTTTTTTTTTTTTTTT
GCTGTTAAATTTGTATGAGTTCTTCCCCACCCCTTTCATTTATGCCCAGACTTGCAG
CATGTGGAAGGTCTCATGCTTGGGTCAAATTGGGACTGCAGCTATGGCCTATGCAAC
ACCAACACCAGATCAGAGCCACAACTGAGACCTATGCCAAAGCTTGCGGCAACTCT
GGATCGGTAACCCACTGATGCAGGCCAGGGATTGAATGTACATCTTCTCAAACATTA
TGTTAGGTTCTTTATATATTTTAGATATTAGCCATGCATCAGATACATGATTTGCAAA
TATTTCTCCTCTTAGTAGGTTTTTTCATTTGTTAATGTTCCTTTGCTATGAAGAGC
TTTTTAGTTTGATGTAGTCCCACTGTTTATTTTTGCTTT TGCTTTTGGTGCCATATTCA
AAATAGCATCACCAAGACCTGCATCAGAGAGATTACTGCCTATGTTTCTTATAGAA
ATTTTATGGTTTCAGGTCTTACATTTAAGGCTTTAATCTGTTTTGAGTTATTTTTGTA
TGCAGTGTGGTGTGGTAAGACAGTGCTCAGGTTTCATTGTTTTGCATGTGGTTGTCCA
GTTTTCCCAACACAATTTATTGAAGAGACTTTCTTCATTGTATAGTCTTGACTTCTTT
ACCATAAATTGATTGATGCTATATGTGTGGGTTTATTTCTGGGCCTTGTATTTTTTTCT
ATTGATCTATCTATGTTTTTATGCCAGTGCCTTAATGTTTTTTTGCTTTTTCTTTAGG
GCCACACCATGACACATGGAAGGAAGTTCCCAGGCTAAGGGTTGAATTGGAGCTTC
AGCTGCCGGCCTACACCACAGCCACAACACAGGATCTGAGCTGCATCTGCGACTTG
CACCACAGCTCACAGTAATGCCAGATCCCC AACCCACTGAGTGAGGCCACAGATTG
AACCCGAGTCCTCATGGATGCTAGTCAGATTCATTATTGCTGCACCACAATGGGAAC

*FIG. 16J*

```
TCCCATAATGTTTTAATTACTTTAGCTTTGTAATACATTTTGTAATCAGGGAGCATGA
TGTTTCCAATTCTTTTCTTTTTCAAGGTTGCTTAAAAAGAAATCTTTTGTGGTTCTATA
CTAATTTTAGGATTATTTGTTCTATTTTTATGAAAAATGTCATTGGAATTTTGATA TG
GTTTGCATTGAACCTGTTGATTGCTTTGGGTAATATGGACATTTAATAATATTGATTC
TTTCAACTCATGAGCTTGGATTAGCTTTCCATAACTTTCCATTTATTCGTGTGATGGT
AGTTTTTCTGTTAACGTCTTGTATTTTTCAATATGCAAGTCTTTCACGTCTTTGGTTAA
ACTTATTTATAGATATTCTTTTTGATGCAGTTGTGAATGGGATTGTTTCTAAATTTCT
CTTTCTGATGGTTTGTTTTAAGAATGTAGAAATGGGAGTTCCCATCGTGGCACAGTG
GTTAACGAATCCGACTAGGAACCATGAGGTTGTGGGTTCAATCCCTGGCCTTGCTCA
GTGGGTTAAGGATCTGGCGTTGTCGTGAGCTGTGGTGTAGGTTGCAGATGCGGCTCG
GATCCCATGTTGCTGTGGCTCTGGCGTAGGCCAGTGGCTACAGCTCCGATTGGACCC
CTAGCCTGGGAATCTCCATATGCCGTGGAAGCAGCCCTAGAAGAGGCAA AAAGACA
AAAAAAAAAAAAAAAAAAAAAAAAAAGAATGTAGAAATGCAATGGACTTTTTGTG
TTTATGTATCCTGCAACTTTACTGAATTCTTGTATTAGTTCTAACAGGTTTTGATGGA
GTCTTTAGAGTTTTCTCTGTATGGTGTCATGTTGTGTTTGTAAATAGTGTCAGTTTTAT
TTCCTCCTTTCTACTTTGGATGCCTATTATTTCTTTTTCTTGCCTAATTGCTCTGGCTA
GGACTTATAGTACTATGT TGAATAAAAGGGCAAGAGTGGGCAGTCTTGTCTTGTTCC
TGATATTAGAGGAAGTCTTCATCTTTTGATCATTGATTATGATGTTTGCTGAGGGCTC
ACATATGCCCTTTATTATGTTGAGGTATGTTCCCTCTATACCTGATTTGTTGAGAGTT
TTGTTTTTTTTTTTTTTAATCATAAATGGATGTTGAGTTTTGTTCAATGCTTTTTATG
CATTTCTTGAGATGATTATATCATTTTTTATTCTTCATTTTG TTTATGTGATATATCAC
ATTGGCTGATTTGTGGATTTTGAACCATCTTTATGTCTCCAGAATAATAAATCCCACT
TGATCATGATGTATGATCTTTTTAATGTATTGTTGAATTCTGTTTGCTGGTATTTAGTT
GAAGAGTTTTGCATCTATGTTCATCAGGGATATTGACCTGTAGTTTTATTTATTCTTT
TTTATGGTGTCCTTGTCTGGCTTTGGTACCAGGGTATTGCTAGCCTCATAAAATGAGT
TTTTTGAATGTTTGTAGAATTCACTAGCAAAGCCATCTGGTCCAAGACTGTTTGTTGG
GGTTTTTTAATTACTGATAGTAGAAAGGATATTCAATATCCTTACTAGTTATCAGTCT
GTTCAGGTATTCTGTTTCATCATGGTTCAATCATGGTAGGTTGTATGTTTCTAAGAAC
TTACCCATTTCTTCTAGGTTGTCCAGTTTGTCGATTTATAAATGTTCACAGAAGTTTC
TTACCTTTCTTTTCTGTTGTAATGGTTGTA ATAAATCTTCTTCAATTTCTGATTTTATT
TATTTGAGTCCTATCTCTCTCTCTATTTTTGTTTTTTGGTGAGTCTAGCAAAGGCTTG
TCAATTTTGCTTACCTTTTCAAAGAATAAGTTCTTAGTTTCATTGATTTTCTCTGTTAT
CTTTTTAGGTTCTAGTTCACTTATTTCTTCCCTAATCTTAGTTATTTCTTCCTTCTACT
AATTTTGGGCTTTGTATGTTCTTCTTTTTCTAGTTTCTTTCTTTCTTTTCTTTTTTA
GAGCTGCACCTGCGAAAGTTGCTGGGCTAGGGGTTGAATTGGAGCTGCAGCTGTTG
GCCTGCGACACAGCCACAGCAACACCAGATTTGAGCTGCATCTGTGACCTACACCA
CTGGATCCCGCTGAGCAAGGCCAGGGGTCGAACCCACCTCCTCACGGACACTATTGT
CGGGTTCTTAACCTGCTGTGCCACAACAGGAATTCCTTTATCTCAGTTACTGAAGTGT
AAAGTTAGGTTGATTAT TTGAGATTTTCTTATTCTTGAGGTAAGCACTGAACCCTT
GAATTTCCCCTTTAGAACTGATCTTGCTGCATCCTGAAAATTTGGTATGTTTTTCTTT
TGTCTCAAGGTATTCTTAAATTTCTTTTGATTTTTTCTTTGACCCATTGGTTGTTTAA
TAGCCTGTAACTTAATTTTCACATTTGTGAATTTTCTAGTTTTCTTCCTGTAATTAATT
TTTAGCTTCATACCATTGCAATTGGAAAAGATGCTTTA TATGATTTCAGTCTTCTTAA
ATGCGTTAAACCTTGCTTTGTGGCTTAATATGTGGTCTATCTTGGAAATTGTTCTATG
TGCACTTGAGAAGAATATGTATTCTGTTGCCATTGCATGGAATGTTCTGCATATATTT
GTGAAGTTCATCTGGTCTAATATGTCATTTAAGTCCAATATTTCCATACTGATATTCT
```

*FIG. 16K*

```
ATCTGAAATGTTCTATCCATGATGTAAGTAGAATATTAAAGTCCCCTGCTTTTGCTAT
CTGTTTCTCCTTTTAAGTCTGTTAATATTTGCTTTATATATTTAGATGTTTCTGTGTTG
GGTGTATAAATATTTACAAATGTTGTATCTTCTTATTGGATAGATCCCTTCATCATTG
TATAATATGGTAAGGTCTCTCTCTCTCTCTCTTTTTTTTTTTTTCTTTTTAGGGCTGTA
CCTGCAGCATGTGGAGGTTCCTAGGCTAGGGGTCAGTGTGGAATTGTAGCTGCCAGC
CTATACCACAGCCACAGCAATGCGGA ATCCAAGCTGCATTTGTGACCTATACCATAG
TTCACAGGAGTGCTGGATCCTTAACCCTCTGAACGAGGCCAGGGATCGAACCTGTGT
CCTCATGGATGCTATTCAGATTTGTTCCGCTGAGCCATGATGGGAACCCCATGGTA
ATGTCTCTTATTACTGTCTTTGTTGTTGTTTTACTTTTTATGGGCTGCACACGTGGC
ATATGAAAGTTCCTAGGCTAGCAATTGAAAGTGAGCTGAGGCTGAGGCCTAT GCCA
CAGCCATGGCAACACTGGATCCAAGCTGCATCTGTGACCTACTCTGCAGCTTGTGGC
AATGCCGGATCCTTAACCTACTGAGTGAGGCCAGGGATCAAACCTGCATCCTCACA
GAGACTGTTGGGTCCTTAACCTGCTGAGCCACAGTGGGAACTCCCAGTCTTTGTTTT
AAAGTCTATTTTGTCTAAGTATAGCTACTCTAGCTTTTTTTTTGGTTTCCATTTAGAA
TTAGGGTAATTAGAAGTTCCCAT TGTGGCTCAGCAGATTACAAACACAACTAGGATC
CTTGAGGATGTGGGTTTGATCCTTGCCCTCCCTCAGTGGACCTGGCATTTTCGTGAGC
TATGGTGTAGGTCACAGATGTGACTTGGATCCTGTGTTGCTGTGGCTGTGGCTGTCT
GGTTTGCTTTAAATGTCACCTTTCTCTTTAAGTTGCCTTTCTGTGTTTGTTAATTTGGA
AAGCTGTGGAGCAAGCCTCTGTGGGTGGTAATAACCCACCTTTCAACCCAGCAGTTA
TAGTAGGTTGAGAAGTAATGAAACTTTTTTTTTCCCCTGGCCTAAGCTTGAATGGTTT
CCTCAAGGATTCCATGGAAGCAAACTTGAATATCTAGGTGGACTAACTTAAGTGATT
GGAATTGAATGGGTCACTGAGAGCCTGGACCAAAGGGTAGTTGGATTGCAATGAAA
GAAGAGAGTAAGGGAAAATGATGGAAGCATTTCCCAAGGAGACCCGGTCACCTACT
CTTCTTTGGCTACTCTGAGTCATTTAGACTCTTCCCCCAGGGGTAGGACATCATTCTC
CTTTTAAATGGCTTCTGATGGCTTGGAGATGGTCCATTTTTAGTGGTTCTTATCCTG
TTTTCAGTGGATGCCTCACTTGCAGAAGCAAAAGCCAGTAGCTCATGAATCAATTCT
CTTCTAAAAGTGAAACTCTCATTTATTTTCTCTTAAAAGGAAGCCTAAAAATGATCAG
ATAACTCAGCTTCCTTGGGGCAAGGAATACTCTGAAAAAATAATAT ATTTCTGATTT
TTTTTTTTTTGGCAGATCACATGAAAGGATTAAGAGCCTCTACCTTGAAAAGAAGGT
TGGAGTGCAGGTAATACATGTTGCTACTTATTTGTGCGTGTGTTTTGTCTTTTTAGG
GCCACACCTACGGCGTATGGAAGTTCCCAGGCTAGGAGTCAAATCAGAATTGTAGC
TGCTGGCCAATGCCACAGCCGTGCCTACCTGGGATCCGAGCCATGTCTGCGACCTAC
ACCACAGCTCACCGCAATGCTGGGTCTTTAACCCACTGAGCGAGGCCAGGGATCAA
ACCCACATCCTCGTGGATACTAGTCGGGTTCGTTACTGCTGAGCCACCAGGAGAACT
CCTATGTGTGCGTTTTAAGTAAAATTTTACTTGAGCTGTAACTTCTACACAGAAATG
TACAGACATCATAAGGGAACAGTCTGACAAACATTTGTAAGTGAACAGATCTGTGT
AACTTCTGCCCAGCTCAAGACGTAGGACAGAACCAAAATCCTGGAACAGACCCCGT
CCCTCCCCCAGTCAGTCTTCCCTGCCCACGGGCAACCTCTTTTCTGACGTCTGTTGTC
ATGTTTAACTTGGGCTGTTTTGAACGCTATTTAAATTGTTTCATACTGAATAGACTC
TCCTACTTTTTTCTTTTACTTAGCAGTATATGTGAATGATTCATCTGTGCTATTGGGC
ACAGCAATGGTCTGTCCATTCTGTCCATTTCTTTCTTTCTTTCTTTTCCTTTTCTTTT
CTTTTCAGGGCCACTTCCATGGCATATGGAAGTTCCCAGGCTAGGGGTCGAATCGGG
GCCGCAGCTGCCAGCCTATGCCACAGCCACAGCACTGTGGGATCTCAGCCATGTCCA
AGACCTACACCACAGCTCACAGCAATGCCGGATCCTCAACCCACTGAGGGAGGCCC
GGGATTGAACCTCCATCCTCATGGATTCTAGTCAGGTTCATAAGCTGGTGAGCCACA
GTGGGAACTCCCACGTTTGTTTCTGAAAGGGTGTGTATGTGTGTAAAGGGTTGTTTC
```

*FIG. 16L*

CTTATAAAGAATTAAATAGCGTTGTTGGTTCTCTTCTTAAAGCTGAGCCTTCGCATTC
TTTTCCTTCAGCCATTGCTTAGATTCAAAATTATCAAGATATATCCAGTTGCCTCTTG
AACCATGTGAGGGTTCGGGGTGCTGACTTTCGTCGTGGTTGAAAATTGATGTGTAAC
ATTACAGTCGGCCCTCCCTATCCCCGGGTCTGCATCCATGGATTCAACCAACCGTGG
ACTGTGTCGTGCCATAGCACTCATTTAGTGAAAACAATTTCTCACATAAGTGGATTG
TTGCTGTCGAATCCTGTGTTGTTCAGGGATCAGCTGGGTGTGGAAGGAGTGTCTTG
GCGTTTTGACTCTTTCACCTTTGACTTAGCAGCAGGCTTCTTTGCTAAGTGATATCAG
CAGTCTGTGTTTATGATAATGGTAACAAATACACACATGCACACACACACACACA
CACACACACACACTAGATGTTGATGATATGGTAA TGAGTAAAACAAAAATCCCT
CTCTTCTTGGAGCTGACAGTCTCTTTAGAGCCTCTTTTGGAAAGACACTACTATTGCT
TCTATTTTACAGATGAGGAAACTCAGGAACCAGAGAGGTTAAATTAGTTGCCCAAG
GTCACACAGCTAGTGGCAGGACCAGGATTCCCACCAGGTCTGTCTGATTTTAGAGCC
TATGTATTAGTTGTCCATTGCTGCGTAACAAATTATCCCCTGAAGTGACTTAAAAAC
AACACTCGTCATGTATTGTTATCTGTTGCTGTGCCTCAGGGATTCTGACAGGGCACA
GTGGGAGCGGCTGGTTTCTGCCTGACTGGGTATCATTTGGGGGCGACCTTACCTAAA
GGCTCGTTCATTCAATGTCTGATGCCTGGACTGGGGACACTTAAGTAGTTGGGACAT
TTTGGGTATCTCTGTCTCTAAACAAATCTTTGCAGCATGGTGGTTTCAGGATAGCTAG
CGTCCAAAGTCCTGCAGTGCTATGTCCGTCCCAGTCTGTTGACCAAGGCAGTTACAA
GGGTCTGTCCAGGTTCAAGGGAGGTGAATGGAGACGCCTCCCGTCAAGGGAAAATG
TCCATTCCCATGTGGTTGGAGTGCACGTCAGCGTGGCCAGCTTTGGAAAGTATAATC
TGCCGTAGATTGTACCCCTAACCTTTCAGCTCTAGGGTGAATTTTTCAAGCTTGTCA
TGAAATTGATTTCTGCCCAAAAGACACAGACAGAAGCGACTTGCACGAAGTAAATC
TCAAGCAGACTTTGGCTCCCCCTTCCTGTTTAGCAGAGGTAGTTTATCATTTGGTGGT
GTCTTTCCAGGCATAGCTGATCCTGTAACAACCATGTCTTTAAGATGAAAATAAACA
ATGAGGTCCTGCTGTACAGCACGGGGAACTATATTCAGTCTCCTGGGATAGACCACG
ATGGAAAAGAATATTTTAAAAGTGTGTGTATGTATGACCGAGTCACTTTGCTG
TCCAGCAGAATTGGCATAACAGTGTAAACCAACT ATGCTTTAATACTAATAATAACA
AAAGATGAGAATGGTGAAGACCAAGCTTTGAGGAGGTCAGAGAACATAATATTCAT
TCTCATCTGCTTCTTCCCCTTCACTTTATTTTATTTTTTAATTTATTTTTTTAGGGCCA
CACCTGAGGCATTTAGAAATTCCCAGGCTAGGGGTCGAATCAGAGCCTCAGCTGCC
GGCCCACAGCACAGCCACAGCAACGCCAGATCTGAGCCGCATCTGTGACCTGCACC
ACAGGTCACGGCAATGCCGAATCCCTAACCCACTGAGCGAGGCCAGGGTTTGAACC
TGCATCCTCATGGATCCTAGTCGGGCGCGTTACTGCTGAGCCACGATGGGAACTCCC
CTTCCCTTTACAGTGATGGGGCGGAGGTGGTCATTGGAGGTTAGGCCTATTGGGAAC
CATTCTAACACTTTTGGTGCCAGCTCCGTTTCTGAATTATTCAGGGTATCTGATACAT
GTTGAAACAGGAGATTTCCTAGTCACCCAGATGACTCATTTGGATGGTACTAAAAT
GACTTTTTTTTTTTAATCTCTCTTTTCAG<u>CTTGAAGGTCTCCTTATACTGTTCACC
TGTTACTAGAGAATTGTTATTAACCAACCCGAGGTACAGATTTTGGGAGAAACGAAT</u>
TGTAAGTTTTATTTTTTCGAATGCCACTAATTCTTTTTTTCAAGTGGGAACTACTTTT
CGAGGGAGATGGAACAAATGTATAAATATATTTATCTGCAGTATTTATGGTGTCGCT
ATTCACTCTTTTGTCATTCCTTAATTGTGGAAGAGCTTGGCTTTTATTGTTGTCACTT
TGTCTTTCTTGTCCTTGAACACGTTGACCTAGATTCTTAGTTTTGTCTCGTCTCAAAG
ACCCTCTTGCCCAGCTGCATTTAATAGTTTAAAGCATAAAATGTTCAGTGACATAA
TCGATAGATCCTTTTATTTAGACCATGGGTTAGGTGAGGAAAAATGAAGAGGACTTA
GGAGTTATAATAAGAAGGAATAAT AAGCTGAATAAAAACAGGATGGATAATTTGA
ATCTGACAGAATAAAGTGGATCTCTGCAGTGGGAGGCGGATAGTAGAGGAGAGAAG

*FIG. 16M*

```
ACCATATGGCAGGTAGAAAATGTGAAGATGGCAGAAAAATTTCTGTTGCAACAGTA
GTTGCTATCCACATGAATGGATTTCATTCAATTTGTGATCCAAAGACGAAGTCGTAG
TTTAGGTTTAAAAAAAAAAAACAACCCAGCCTGGAGTTCCCGTCGTGGCTCAGTGG T
TAACAAATCCGACTAGGAACCGTGAGGTTGCGGGTTCGACCCCTGGCCTTGCTCAGT
GGGTTAAGGATCCGGCGTTGCCGTGAACTGTGGTGTAGGTTGCAGATGCGGCTTGGA
CCTGGCATGGATGTGGCTGTGGTGTAGGCTGGTGGCTACAGCTCCAATTTGACCCCT
AGCCTGGGAACCTCCATATGCCGCGGGAGTGGCCCTAGAAAAAGGCAAAAAGACA
AAAGCAAACAAACAAAAAACCTAGCCTTAGTCTATAAGAGACGTAGATGACATTAA
AGGAAAAACACAGGTCGAAATTGGGGAAAAAAAAAAGAGAAAAGATATACTGAA
CAATTAGAAGCTAAAAATGCCAAAGTGGCAACTTTTATATCATGTAAAGAGCTGAA
GGAAAAAAGAAAATCTAAATTTTCAAGAGGGTAAAAGAAGATCAAGAAGATGTG
AACACACACACGTACTCACAACTGACAAAATAACCTCAAACTGGACTCTGTCGT
AGTTGGTCATCTAGTGCTTGATGGGAGAAAGAGAACCGTCATTCGTAGGTAGAATTC
TGCTTCATTATGTGGCTTAAACTGCCAGTAATTGGGGCAGCTGGCAGAGAAGTCTGA
ACAAGCATCTCAAAGAGTCTTTTTGATGTCTGACTGCCAATAACTTACAGCTCCCAC
CTCCAGCTTCCCTTTCTGCCCCACATCTGGGCAAACTGATTAAAAAAAAAAAAAAAA
AAAAAAAAAAAAAAAAAAAAAAAAAAGCCTGTCCTTTCCTGGGTGCCTACATGGAG
TTCAAACATGAAAGCTCAGGGCCACCTGTAACCACAGTGAAAACCAGGGCCCCTTG
TTCCTATTTTCTCAAGCTACCTGGGCCACTTCCTCCCAGCCTGGGTACCAGCCTCCGC
TCCCCAGAACGTCCCAGGATATGGGTAGTGCAGTGTTTTCATACCCTCTTGGGTCAT
GTTTGGTGGAATTTTCAGTCTCAGCTTCTGATCTGTCCCTTAGGTGGGACCCGACAG
AGGCCATCCCTATGGAGAGGGACCCAACAGCAAGGCTGCTAAGTAACCTTGGCCTT
GGTGTTAGGCCTGCAGTTGCTGTGGGTCATTCCGGCCAGCAGTCAGGAAGGGAAGC
TGAGGAAGAAGGGGAGAAGAGCAGGGATAGGCTGGAATCCACGGGGACAAGTGGG
GACCCATGCCTGCCTCTCACTCCTCCCAACCTTGGTAATGCTAACGCTGCTGTTCCCT
TGGCCACTGAGTCACACATACGAGCCCCAGGGCTCCGA GAAGCTGAGCGGGAATAT
CCCGCAGAAGATGGAGCTGCGCTGTCCTGCCCGTGTCAGTGAACTGAGCCTGCAGA
TCAGCAACACAGGAGTTGTTGTCATTCCTGGTGCCTTGCAGAGCATTGAAAAATGCT
GCTGGCTGACGTCTGCCATCCGAGTCTTACCCAGGTGTTTCTTGGGGCTACTGCTGA
CCCAGACGTATACACAGCAGGAGCTTACAGGATAGTCCAGGCTCCGCTGAGTTGAT
GTAATTCAAGGC CACCTCGCAATCTAAGGGGGAAGGGGGCAGCTTGATAGAAGCAG
GTGGAGAGCTTACCAGACACTCTCAGAAACTGAACACGAGGGACGTGGGAAGTAAG
TAAATAGCCAGAAGGCTTAAATGACGTAATGAATGCATGTGAACTGATTGAAACAC
AGAGCTTTAAACCCAGCGAAGGAAGGAAGATCTTTGGGTGCACGTGGAACATTGAC
CAAAATCAGCAAGTGCTTTGTCACTGACGCCTTTCAAGAAATCCTAGTGATTTGTTC
TTTGACCGTAATGCAGTGATATTGGAAATCAGAAATAAAAGGAGAGTTAAATTCAT
GAATGGGAACCTTTAGTTCCCATTCATGTGGAACTAAAGGTTCACCACAAACAACT
CTCAGGTTAAAGAGGAAGTTGTAAAGAAAAATATACAATACTTAGGACTGAGGAAC
AATAAAAAGAGGACATTCAAAATGTGTGGAGCACAGCTCAATTAATACTTAAAAGG
ATGGAGTTCCCATCGTGG CACAGTGGAAATGAATCCAACTAGGGACCATGAGGTTG
CGTGTTCGATCCCCGGCCTAGCTCTGTGGGTTGGTGATCCGGCATTGCTGTGAGCTG
TGGTGTAGGTTGCAGATGCAGCTCGGATCTGGCATTGCTGTGGCTGTGGCGTAGGCC
GGCAACAACAACTCTGATTAGAACCCTAGCCTGGGAACCTCCATATGCTGCAGGTG
CAGCCCTAAAAAGACAAAACCCCAAAAAAAAAAAAAAAAATTAAAGGG AAATTGA
CAGCATTAAATGCATTTCTTAAAAAGCAAAGACGAATTAAATGGAAGAATTCTTTGA
CTTATTAACAAGGAAAAGAAGCAACAAAGCAAATCTAAGGACATGTAAAAGAAGG
```

*FIG. 16N*

```
AAATAATAAAGAGAAAATGACAGATTAGTGATATAGAGACTAACTATCACAGAAAA
TTAACAAAAGTAAAAACTGGCCTTTAGAGAAATAGAGATAATTTTCTGCCAAGATTG
GTGAAAAAGATGTATATAAAAAT ACAGAATGATAGGTGTTCCCATTGTGGCACAG
CGGAAACGAAGCCAACTAGGAACCATGGGGTTGTGGGTTTGATCCCTGGCCTTGCTC
AGTGGGTTAAGGATCTGGCATTGCCATGAGCTGTGGTATAGGTCACAGATGCAGCTC
GGATCCTGTGTTGCTGTGGTGTAGGCTGCCAGCTGTAGCTCCGATTTGACCCCTAGC
CTGGGAACCTCCATATACTGCAGGTATGGCCCTCAAAAGCAAAACAAACAAAC AAA
CCCAAAACAGAATGATAAAAGGAAAATAACTATTAATAAGAGCAATGCACAATGC
CTTATTTTCAAAATTAATGTGGTAGTGTATTTGATAATTTAGACACAGTGGATAAAT
ACCTGGGAAAGTAGGAAAATACCAAATTAAGGCAAGAAAAGTAGGAAACTTGAAT
AAAGAAATAGCCATCAGGCATTCCCATTATGACTCAGTGGGTTTAAGAACCCATATA
GTCCCTGTGAGGCCTTTGTTAGTGNNGTAAGAATCTGGCATGGCTGTACACTAGCAT
AGGTTGTAGATGCAGCTCGGATCCAGCATTGCTGTGGCTGTGGCTGTGGCCTGCAGC
TGCAGCTCTGATTTGACCCCTATCCTGGGAACTTCTATATGCCACAGGTGGAGCTGC
AAAAATGAAAAAAAAATTTTTTTAATTTAAAAATTTTAAAACAGTTTTGAAAGATC
TCTTCTTCAAAAAAGCCCCAGGTCCAGATGGTTTATGGGCACTTTGGCCACATGT T
CAGAGAACAAGTAATTCTTGTTTAGGAGAGAATAAAAAGATAAGCCAGTCAACCT
CACTGGCAAACCGGATAATGGTAGCACATGGGGAAGAAAGTCCATTTCATTCATGA
GCATGTGTGAACATCCAAATTAGGGTAATAGCTAACTGAACCTAACAGTGTTAAAA
AAAAGTGCATCACAAATAGAGTGTTTATTCTAGAAATGCATGAACATTTTTATACCT
GAACCACAGTCACTGTGAGTTTTATGGTAT CAGTGGACTAAAGAGATGAACAATTAT
GTTCATTCATCAGCTACTTACTGAATGCCTCTTTGTGCTGGTGACTGTTCCAGTAAAT
TGTCCAAGGACCCTTGGACCGTTCTGCAGCAGCTTGAATCTGTAAATTTGGCCAGTG
TGTCAGGACTGATGGCAGACTGTTCTGCTGCAGAAAACCTAAACACATAGAACACC
TGACTACCTGTCGTACAAAGACTAAGGTCAAAAGGAAAATGGGATGGGAGCAGGAG
GGATGGGAGGTGAAGGGAGGGAGATTGAATTCATAGAACTGCTGTGTCAAAGGAT
GTATAAGTATATATAATGTATTGCCACCTCCAGAAAGGTATTTTATTTATTTATTTAT
TTATTTATTTTGTTTGTTTGTTTGTTTGGAGCAGAGAAAGGTTTATTGCAGGGC
CCAGCAATGAAAACGGGTGGCTTATGCTCAAAAACTTTGAACACCCTGACGGTACCT
GGGAAAAGTTTTTATAGGTAGAATTTGGA GTGAGGGCTGCAGAGGGTGTGCCCAGA
AAGGTATTTTTTAGCTTTATTATTTTTCAAGCTGTTAAGCCATTACTGTCGTGAAG
TCAGAAATGGTTCCACGGAGTCTATAACTTCTCTTGGTCCCCTTTCTGTGTTTGAGAT
GGCAAAGGCACATAAAGTCATGGAAAAACTGAAAATGTATACTTCTCTTCTTTTAAT
AGGTGTCAATTGAAGTTGAAACTCCTACCCAGATATCTTTAATTGATGAAGCATCA G
GCGAGGTAACTAAGTACTAAATACTGTGTTTTAAAAAAAATCATTACTTAGCATTAA
ATGATTGTGTACCTTTCTCCTTGCTTGTGAATGCTCATTTAACCATAAATAAAATTTA
TAGTAAATGAGTGGGTTTGTAGGGAAAAAAAAAACCATCTGTGATATATTTTCTATG
TCCGAAGGATTAGTCTATGTCAGAGCTGCTTCTTTTAGTATTACGTGCTAATTATAG
GCGCTCCGTAATCATGATATTACTA AAGAATTCTAATTCTAATTCTAATTCTAATTAT
AATTCTACTAAAGAATGTGATTGTCACATTTATTAAGTTTATTATAATGTTCAAGATG
TAAAATGGTGCTCAGTGTTTTGCAGCGTATTTAGGTATATTTGATTTATTTCCCCC
CCCGAATCATTTTTTATTCAAGAAGACATTATCCAGGTGGATCCATTTTATTTTTTG
TCCTTAAATTTAGAAGCAGGTCCTTTTGTGTGGCAGTTATCTTTTTTAA TAGTAAATA
GGACTAAGGACCTACCTTTTATGTATTTATATATTTATAGCTCAAATCATAGGTAGG
GCTAGAAAGTGTTTTCCTCTTTTATGGCAAATCTAGTTAAAATTTATTCTGTAGTCTG
ATTAGAACCTGCTTAATTGACACGTTTAATCTGGAGGGTGTCCTTGGTGATGTGACT
```

*FIG. 16O*

```
ATAATGGGACAGGGGTCACTTTTTTTTTTTTTTGTCTTTTTGCTATTTCTTGGGCTGC
TCCTGCGGCATATGGA GGTTCCCAAGCTAGGGATCTAATCGGAGCTGTAGCTGCTGG
CTTACGCCAGAGCCACAGCAACCCAGGATCCGAGCCACGTCTGCAACCTACACCAC
AGCTCATGGCAACGCCGGATCCTTAACCCACTGAGCAAGGCCAGGGATCGAACCCG
CACCTTCATGGTTCCTAGTCGGATTCGTTAACCACTGCGCCACAACGGGAACTCCAG
GGGGGTCACTTTTTACATTTCCTCCCTGGAGATTAGGCATTGAAGT CCTTTTTTTTTT
TTTTTTTTTTTTTTCTGTTTTTCTTTTGCTTTTTTTCTTTTCTTTCTTGTCTTTTTCT
TTATCTTTCCTTTCTTTTTTTCAGTTTTTATTTTGACTGCCTCACAGCACAGGGAGT
TTCTGGGCCAGGGATTAGATCTGAGCTGCAGTTTCAACCTTTGCACCATGGCAGGGT
CTCCTGAAGTCCTTCTAGAGCTACTGTCCCGAGGGAGGGGAGGCGGGATGCCCTGA
ACCTTGCTAAGTGCCATCCTGAGCTCGGGTTGTGCACACGTTCGGGAGATGCTCTTG
GTGACTGGCAGCCTGTGACATGTGCTGGTGAAAGGCTTTCTCAGAATTGGGCTCCAG
ACAGCAGGTGGCTCTTAAAGAGCAGGGTCCTGGTGCCCCACTCTCGTCCTTTCCTTTT
CTTGTCCTGCACTGAGGCTTGCATGTGTGTGTCTCCAGCTCCAACCTGGGGAGAGC
CCATTTTATATTTATTTTTATTTTATTTTAATTTTT TTTTATGGCTAAGCGTGCAACAT
ATGGAGATTGCCAGGCTAGTAATCAAATCTGAGCCATGACTGAGACCTATGCCAAA
GTTGCCCCAATGCTGGATCCTTTAACCCAATGTACCAGCCTGGGGGTCAAACCCAGG
CCTCCTTAGCGACCTGAGCCACTGCAGTTAGATTCTTAACCCGTTGCACCACAGCAG
GAACTTTTTATTTTTATTTTATTTTTTAATAAATTTTATTGGAGTATAGTTGACTTAG
TTGTATTTCAGGTATTCAGCAAAGTACATCGGTTATACAAATACATACCTTTTTGGAT
TCTTTTCCCATATAGGTTATAGCAGAGTTTTGAGCATAGTTCCCTCTGCCACACTGTG
GGTCCTTGTTACGCAACTCTTTTATACGTAGTAATGTGTATTTGTCAGTCCCAGCCCC
CTAATTTATCCCTCCCACCCCACATGGTAACCCTAAATTTGGTTTCAAAAGGGAGAG
TCTGGAGTTCCCATCGTGGCTCAGTGGTT AACGAATCCGACTGGGAACCATGAGGAT
GTGGGTTCGATCCCTGGCCTTGCTCAGTGGGTTAAGGATCTGGTGTTGTGGTGAGCT
GTGGTGTAGGTTGCAGACATGGCTCAGATCCCGCATTGCTGTGGCTGTGGTGTAGGC
CGGCAGCTCCAGCTCCGATTAGACCCCTAGCCTGGGAACCTCCATATGCTGCGGGAG
CAGCCTTAGAAATGGAAAAAAAAAAAAAAAAAAAAAAAAGGAGAGTCTGTCTAAAGG
GGCCTTTGGAATAAACGATGTCAGACACACCTTATGACTAGAGAGCTGGAGTGTCC
AGAGCTCTGCCCCACCATGTATCAAACCTTCAGAGGCTATGCGTGGTGCCCATGAGG
ATGTGCCTAGTGGGGCAGTACAGCATGCTGTGTGGTGACTTGGGACCAGGCTACATC
AGAGTTTTAAAAAATGTTTTAAAATAACTTTATTGAGACATCATCCACGTACCATCC
CACTCACCCCATTCAAGTTCACAGTTCAGGA GTTTCCATTGTGGTGCAGCGGAAACA
TACCCAACTAGTATCCATTAGGATGCTAGTTTGATCCCTGGCCTCACTCCGTGGGTC
AGGGATCCGGCATTGCTCTGAGCTGTGGTGTAGTTCCCAGATGCACCTGGGGCCTGG
TGTGCCTGTGGCTGTGGTGTAGGCCAGCAGGTGCAGCTCCGATTTGATCCCTAGCCT
GGGAACTTCCATGTGCCGTGGGTGTGGCCCTAAAAAGTGAAAATAAAAATAAAAGA
AATAGGCAGTTCAGTGGCTTTTTGTATATTCACAGAGTTGTATATCCACCATCACAA
GCAATTTCAGAATATTTTCATCACCCAGAAGACCACTTGGTACCCATTAGCAGTCAC
CCTCTATTTCTCCCTCCCTCTGGCTTCTAGTAACTACTAGTCTAGTTTAAGGCTCTAT
GGTTTGCCCATTCTGGACATTTCATAAAAATGGACTCATATAACACGTGGTCTTTTGT
GAGTGCTTTCAGTTTGCATAACTTATCCA TGCTGTGGTGGTTGTCAGTACTTCATGTC
TTTTTATGGCCGAATAACATCCCACTGTATGGCTAGACCACCTGTTGCGTATTCAGTC
ATCAGTTGATGGACATTCGGGCTGTTTCTACTCTTTGGCTGGCATGAAGGATGCTGC
TCTGAATATTCATATATAGGTTTTTGTGTGTGGACCTGTTTTCGTTTCTCAAGTGCAA
GAGTGAAATTGCACTCTTGCACTTGAGTTTCTCACAGCAAGAGTGAAATTGCTGTGT
```

*FIG. 16P*

CATGTTGCAACTCTGCATGTAACCATTTGTTTTGTGGGTGAGGATTCCACTTGTTTCC
AGAATCTGGAGAGTGGGGAAATGAGGAGAAAAGGCATACGTCCTTGGGACGTACTT
GCATCTGTTCTGTTAAGGAGGGCTTTGTTTAACTGGGTCCTAATGATAAATTTCTATT
ATTTTTTTTCTTTATTTTCTTTTTAG AAGGAAGAAATTGTTGTGACTCTCTTACCAGC
TGGTCATTGCCCAGGATCAG TTATGTAAGGGGGTTCATCTCTTTCGCCCATTTATTCT
GCGTAGAAACGTATTGTATTTGTAGAAATAAACATTGAGGGTCTAGAAAACAATAT
GTGTAGGGAGATTTGATTCTCTTGATGGCAGTTCGTTTAATCTTTGTTTCCAAATTGA
ATTTGGGGGACTGTGGTGCAGATCAAGTTTGAAACGTGGCTTTCTGACAATGCAAGA
CTTCAGTAGCCATTTCTCCACTGGCTTTGCATTTTCCTGTCGTGTGGAT TTTTCTCTCC
ACAAACAGGAATGATTTCATTGTACAGTTGAGGGAGCTCACGTATTTTGGGGCCATC
GCTTGCAAACTCAGTGGCATCTCCATCATGTTATTTTTTCCAACCTCCCGGGAAGAG
GTGGCAGCTGAGTGTCTGGTGTGGTTAAGCAGTACGGAAATTCTGTTCATGCCATGT
CAGGGTGGCTGTGTTTGGCAGGCAGCGTGGGCTGTGGCTTTAATATATATTTGCTTT
ACTGGGATTTTGTATGAG ACCTAAGTCACTGAGATATATTTCGTTTTTCAG GTCTTAT
TTCAGGNGCACACATGGAACTGTCTTGTATACAGGAGACTTC GATGGCAAAAAGGA
GAAGCTGCCAGAATGGAGCTTCTGCACTCGGGGGGCAGTACCGGGCTTTATATAAT
ACTCGAATGTTAAGACTATGTTGTTGTAAAGATTTTACTGCTCTTCCCCCCTACACAT
GTATGAGGCTTTGTTGCTTTATTTTTATTTTTTTTGCTTTTTAG GGCCACACCCGCA
GCATATTGAGGTTCTCAGGCTAGGGGTCGAATCAGAGCTGCAGCTGCCAACGAACA
CCACAGCCACAGCAACGCGGGATCCGAGCCCCACATGTGACCTACACCGCAGCTCA
CAGCAATGCCGGATCCTTAACCCATTGAGCGAGGCCAGGAATCGAACTCGTGTCCTC
ATGGTTCCTAGTCAGATTTGTTTCCAGCTGTACCACAACGGAAACTCCTGCCTTTGTT
TCTATTAGAAGTCTAA CTCAATTATAATATTTGCAACAGCAAAGCAAATTTTTCCTCT
TGAAATGAGGGGATGATGACATTCTGTGTGTGAATTGGGGTAGTAGTTACATGAACT
GATCGAAATTCACTGAACCAGGAGTTCCCTGGTGACTCAGTGGGTTAGGGACCTGGC
ATTGTCGCTGCTGCAGTTTGGGTCGCTGCTGTGGTGGGGGTTCAGTCCTTAGCCCAA
GAATTTCCATATGCCCTGGGTGCAGCCAAAAAAGGTAAAAAAA AAAAAAAAAATCC
CTCACCCATCTGTCTTATATATTATCCTATGGAAATCACTTCCTAACCATGTCGATAC
AGTAAAAAATTCCAGGGAGCTCTCTTGTGGCCCAGTGGATTAAGGATCTGGCTGTTG
TCACTGCAGCGGCATGGGAGTGGCCAAAAAAGAAAACCCAAGTGGACTGAAACCTC
CTGTAAAATAACTGAGAGTTTCGACTTCACGCGTGTTGTATTTCACGTGATTAACAG
CTCTTGTGTTCTGTTTATCTTCAG TGTGAAAGACATCCAGAGTGTGTACTTAGACACC
ACTTTCTGCCATCCAAAGTATTACCAAATTCCCAGTCGG GTACGTCTCTCTGGACGG
GTGGCTGTATTTCTCAGGGGGCGGGCCGCAGGCTAACAGGTCGGGTGGTAACGGGC
CCCCTGGCCTTAATGTCTGGGGACGCTGGGAACGGACAAGGCCTCAACTGCCTCTTC
AAACCCCTGCCCAGGAGGAGTGTCTGAGAGGGATCTTGGAGCTGGTCCGCAGCTGG
ATCACACGGAGCCCCTACCACGTGGTGTGGCTGAACTGCAAAGCGGCCTATGGGTA
CGAGTACCTGTTCACCAACCTCAGCGAGGAGTTCGGAGTCCAG TACCTGAGGGCT
CTTTCTCCCACCCCCACCCCCAAAGTCCCCTCTCACTGGAAACCCTATCAGATGGCC
CAGCCTTCCTCACCTTGGTTTACTCACTTCCGCTTGGGAGGACTTGACAGGTGGAAA
GAGCCCTTCGGTGAAAAGTCCCACAAAGGAAGTGTGTTTTGTTCAAAATACTGGGTC
ATGAAATAAACGTAGTGTTTGTCACGAGCATTGAAAATAAATGTGAACTAGGAAGT
ATCCGAGAGTATGGCTTGCAGTCAGAGTGGTTATTGTGTGAATATTTACATGGGGAG
TCAGATATATCAACAGATCTTTCTCGACTTAACCAAAGGGCTGTGTCCCAATAAAGC
CATAAATCTGTCTGGCTCGAGTTCCCTGTAGAGGCTCAGTGGTTAA CGAACCACACT
AGCATCCATGAGGGCGCAGGTTCGATCCCTGGCCTCGCTCAGTGGGTTAAGGCTCCG

*FIG. 16Q*

```
CAGCATTGCCATGAACTGTGATGTAGGTGGCAGACGCGGCTCGTATCTGGTGTTGCT
GTGGCTGTGGTGTAGGCGAGGGGATGCAGCTCTGATTGGACCCCTAGCCTGGGAAC
CAACATATGCCACAGGTGTGGCCCTAAAAAGACATTAAAAACAAACAAAAAATCTG
TCAGGCTCCTCCCCTGGCAGAGGAAGAGCCTCCTCCACTCTCCCTCTCCCTCGGGTT
CTCACTTGCACACAACAAGGATCTGGAGATGCAGGCTGGCAGGTCCTGTAGCCGAG
CCGGGATAGAGCCTGCGGGCTTGTCGTACAAGGATGGAGTCCGGTGGTCTGGCAGG
AGGTTGTTCCTGCCGGGAGGTGCTGCAGCAGCGCCAGGGTAGAGTCAGGGGTCTGG
CGGCACAGGGATGGAGACAGGCCCTCTCTCCAGGCAAGAGCGATCGGCTC AGGACG
GGAGCGGTTCTGAGTGGAAGGGAATTTCCCTTCAAAGGGACACCACCTTCTGACCTG
GGCTCTTTTAACGACCCTTTCAGATCCATGGCCTCAGAGATCACAGTCTTGATCACA
GTTGAAATCAGGTCACCATGAACCAGTTTATGGACGCCTTCAGAGGGTGGGCCACC
CTGGGCTGGGAATGGTCCTGGCTGCCACTGGGTGTGGGTGTTTCCTTAGGTCCCTA
CATCATGGACCTGTTTGGGGAC CCACATTCTCTTGCCCCAGGCCCACTAATTTCCTGT
CCCAGCCCCCGCCCCCGCCCCCGTGCTGTGTGTAAGGGCTGAGTGTTGTTTTGCTCTC
TGCATGGGGTGGGTTTGGATCCTCTGGTCGGTCCCACCTTAGTCACGTGGGGAAAG
GTTATGGGAGGCGCTCCAAGCGCACGCCCTGGTGCCTGCGTGTGTTCATTGTT
TACGCAGGCCTCCTGTTTTGGCAACAGCAAATGGCCTGTTTGAATC ACCCAGGTC
CCCGTCCTGTCCTCTCCTAACAGAGCCATTGCAAATAGCACGTATAAGTTAAACAT
GCATTTAAATAAGTTCCTTTGTATCATTTTTAAAAATTAAATCCCACACGCAAAGGG
ACTTATTTAAAAAACATTCTGAGATTGTTGTTGCTGTGTTTTTGGTGTTAAAATGTC
TTTTCAATTAAACCACAGCGATAATAGACTGTGTGTGTGCGCATGTATACACACGCA
CACGTACACACATCTTTA TATATGCTCTGCTGGGTGCTGGGTTTTTTGTTTTTATTTC
ATGGCTTCTTGACAAAATATAGAGGTACCAGCCACTTACCCGTCCCAAATTTGCTGT
GTAAATTTTCTCGATGTGCGAAATGGAAAAGACCCGGAAGCTCCCGCTCTGAGACCT
GGGGGAGAAACCCCGGGCTGAGGAGGGGGTGGGGAGGGAGGCAGGATTTCAGTGT
GTGGCTCCCTCAAGTCTCTTAATCCCGCTGTAGGGATACAATGCTT GTAGACAACAG
TGAGGTTTTTTGGACAAAGAGACCTGAGAGGTGATTTATGACAGCCTTTTCAAGCA
TCTTCATTTTCACGAGGATGAGCGTTTGTGTCTCTCTGGTGCATCTCCGAGTTTACCT
CTTTTTCTCTCCTTCCTAGGCCGGAAAAGTCAATTCATTGTTCCTGTTAGTCGTTAGT
AAACAGGTAGTGAGAGGACTAGGCTACTGGATAAGTAAGCAGTCATGCCTGGCTGC
TGTGTGACAACAGTCCTGGTAGTAATTACCCCAGCAGTTAACATCCTCCTGGAGTTC
CCGTTGTGGCTCAGTGGTTAACGATTCCGACTAGGAACCTTGAGGTTGCGGGTTTGA
TCCCTGGCCTCGTTCAGTGGGTTGAGGATCCAGCGTTGCCGTGAGCTGTGGTGTAGG
TCGAAGACGTGGCTCGGATCCCGCGTTGCTGTGGCTCTGGCGTAGGCCGGCGGCTAC
AGCTCCGATTCGACCCCTAGCCTGGGAACCTCCATATGCTGAGG GTGCCACCGTAGA
AAAGACAAAAGATAAAACAAAACAAAAAACTTCCTAATCTGTTTGTTGCTCAGA
CTTCAAAATGACAATACTGTTTCTTTTTTTTTCTTTTTCTTTTTCTTTTTTTGGTGCC
ATTTCATTATCTCTGTGTTCATTTAGGTACTTGTTGTTTATTCTGAAATACCCAGAAA
AGATTTAAGCAAAACTGACATGTTGGTTTTAAGTTTTAAGCAGTATTAGCTTTAGGA
GTTCCCTGGTGGCCCAGTAGGTTAAGGAACCAGCATTGTCACTGGAATGGCTTTGGT
TGCTGCTGTGGCACAGGTTCGATCCCTGGCTGGGAACTTCTGCATGCCACAGGTGT
GGCCAAAAAAACTCCAAACAAACAAAAACAAAATTAAAAATGAAATCATTAGCT
TTAAGATTCTAATGGTGGCTGAGATCTTTTTTTTTGGTCTTTTTTCGTCTTTTTAGGGC
TACCACACCTGCGGCATGCGGAGGTTCCCAGGCTAGGGG TTTAATCAGAGCTGTAGC
CGCAGGCCTACACCGCAGCCACAGCAATGCCAGATCCGAGCCGCATCTGCGACTGA
CACCACAGCTCACAGTAATACTGGATCCTTAACCCGCTGAGCGAGGCCAGGGATCA
```

*FIG. 16R*

```
AACCCGCAACCTCATGGTTACTAGTCTGATTCGTTTCCGCTGCACCAAGACAGGAAC
TCCTGAGATTTTTTTGTTGTGTTTTTCTGCATCTGCCCCCTCCCCCTCTGGCCAATCCA
CTGTGGCATA GGAGGATCCAGATCTCGGCTTCCTTGTTACGCTGGCTGCCCACCACC
AGCTGCCCTTAAGTAGCATGTTGTATGTGTCTTCGAGAGCAACCTTCTTGATTATTTT
TGTCTGCTGTATTTACTGCAATACTCCCAATATTTAGAATAAAGCTTTTTTATTGAT
GATTTTTATTTTTATTTTCTAGCACAGCTGGTTACAGTGTTCTGTCCATTTTCTACT
GCACAGCAAGGTGACCCAGTCGTACATACATATA TACCTTCTTTTTCTCACATCATC
ACGCTCCATGATAAGTGACTAGATAGAGTTCCCAGTGCTACACAGCAGGATAGAAT
AAAGCTTGATGTAGAGCAGGTGCACAGTAAATTTTGGTCGAGTGCCTCTTGCTAAAC
TGAGGGACGGATTTACCTGATCCAGTGAAAGCCACCTACAGGAGGCGCTAAATGCC
GGGACCATGATCTCAGCGTCCTGGTGCAGTACTAATGTGCGTGGAAAGAGAGGAAA
ACTAGGTCTCACGGCAGAAGAGAGTTCATTCTAACTGGATGATTTGCCCCGGCCT
AGTTACCCTTGAAACACTTTGTTTACAGGAAATACAATTCCAGTCATGTGCTTATTTG
TGTTGTTTTCCTCAGGTTCACGTGAATAAACTGGACATGTTTCGAAACATGCCTGAC
ATCCTTCATCATCTCACAACAGACCGTGGCACTCAGATCCATGCCTGTCGGCATCCA
AAGGTACACAGTAAACTGCTCTGTTTGCGAGATCCATGCAAGAATTTCAGGTCCAGG
AGGAACCGGCGAAATTCCATTTTCTAGGCCCTTCAGGTCGCAAATGTGAAAACTGAG
GCTTAAGGTGTTAACCCAAGGTCATTACTGTATTGCAGTACCCTGAACTTCATAATG
AGTTAACAGACACAGACACGCCATAGTTTTGTTTTGTTTTGTTTTGCTTTTTAGGGCT
GCACTAGTGGCATGTGGAAGTTCCCAGGCTCTTGAATCGGAGCTGCAGCTGCTGGGC
CCACACCACAGCCACAGCAACGCCAGATCTGAGCCTCATCTGAGACCTACACCGTA
GGTCACAGCAACGCCGGATCCTTTACCCACTGAGCGAGGCCAGGGATCAAACCCAC
ATCCTCAAGTGGCGGATACTAGTTGGTTTAGTTCCCGCTGAGCCACAATGGGAACTC
TGGTTTTCAACCTTTTAAAAATACTTGTCACTTTTCTCCAACTTTATTTTGAAAAATT
TTAAAGCAGTATAGTAGTTAGACTAGTACCAA GACCTCTGTGTACTCTATTTTTTCTA
ACTGGCGTATAGTTGCTATGTACTGTTACGTAATTTACAGGTGTACAGTGTAGTGAT
TCACAATTTTTAAAGGTTGTAATCCATTTATAGTTACTATAAAATATTAGCTATATTC
CCCCTATTGTATGATATACTCTTGTAGCTTCTTTATTTTTAGGTAGTAGTTTGTACCC
CTCAACCCCCCACCCTGTCTTGCCCCTCCCCACTTCCCTCTCCCACTGGTAACCACT
GATTTGTTCTCTATAGCTGTGAGTCTGCTTCTTTTTTTTGTTATATTCACTAATTTGC
TATATTTTTAGATTCCACATGTAAGTGATATCACACAGTATTTGTCTTTCTCTGACT
TATTTCATTGAGTGTAATGTTCTCCAAGTCCATCCGTGTTGCTGCAAATGGCATTATT
TCATTCTTTTATGGCTGACATTCCATTGTGTGTGTGTGTTCCACATCTTCTTTGTC
CATTTATCTACTGATTGACA CTTAGGTTGCTTCCATGTCTTGGCTCTTGTAAACAGTG
CTGCTGTGGACATGGGGATGCAGTATCTCTTTTAATTAGTGTTTTGGTTTTTGTGGG
TATATACCCAGGAGTGGAATTGCTGGCTCCTATGAACACCGTGTCCTCTTCTTCTGG
ATTCCGCAGCTGCCCAGGTGTTAACAGTTTGCTTTCTGGCACCCTCTGTGTCTGTCTG
TCTGTCTCTCTGTGTAAGCAGCACCCCACCGTGCAGCCCACTTGAGAGTCAGATGCA
AACGTCATGACACGTCACCCTAAACAAAGTCGTATAACCACAGTACACTTCCCACAC
TCAGGGAATTTAACATGAATGTGATACGACTGGGTATGATATGGTCCATATTCAGAT
TTCCTCAGTTGTCTCAATCCCTTATGGCTTGGTGGAGTGGGAGCAGGGCCATCCAG
AATTTAATTTAAAAACATGTGTTGCATTCACTCAGGCTGCTTTAGTCTTTTGATGTAG
ATCAAGTCTCCAGCT AAAGTCCAGGCCAGTTGTTTTCTAGAATATTCCTCAATTCGA
ACTTACCTATTTCTTCATGTCTATATATGTATATATATATTTTTTTTTTCATGCTAAAA
AGTCATCTGCATTTTTTGAGACCCTGGTACAAATATATTTGTTGAAAATGTTAAACC
ATTTTTCTTATTTTAAAATCTTTTTTAG GCAGAGGAATATTTCATTGGAATAAATTA
```

*FIG. 16S*

CCCTGTGGAATAACATCCAAAAATAGAATTCCACTCCAC ATAATCAGTATTAAGCCC
TCCACTATGTGGTTTGGAGAAAGAACTAGAAAAACCAATGTTATTGTGAG GTAAGC
AAGCAGCGTCTTTTGAGAGGAACCTTGCTTTGAGGTAAATCGATAGTTTAAAGGCAG
TCTAGCCTAACCTCAAGAGGGGGGCATATCATGATTGTGGAAAATAACTTTTGAAAG
TTAAACTCTGTTTAAATTAAAGAGAAGCGGCTTCCAAAAGCTATCAATTGCTTACTA
CCATGAGCCAGTATTTCCTGGGGTCTACTGAGTTTGACTGAGAAGATGGTTAGAGGC
AGGCTGTCTTGCTTGGCCGGAAGTTGGGAATTGACCTTGAAGGGGTTGGAAGCCCTT
AGTGGAGCAGAGGAGGCCCATACTGATCCTCATGTTTTAGCTCATGTCCTGAAACAT
TGGCCGTTTGGAATGTTCACAGATATTTACATTTATGGAAAGAGTTCCCTCCTGGCC
CAGGAAAAAAATCCTTGATGGCAGGGTGATTTCATCCTG CAGTAGCCTAAAATGAG
AAGACTCGGAGTTTGGAACTTAGTTTTGATGAGTGACCCTTAATTTTGGGTTTTCCTT
TCCCTTTAGAACTGGAGAGAGTTCGTACAGAGCCTGCTTTTCTTTTCACTCCTCCTAC
AGTGAGGTAAGAGGATCCCATACTCAGAACCTCGGCTGCTGAGGCATCTCTCTTCCT
CCTGCTTAAGACTGGTGGGACTCTTGCTCAGGAAACACAGGCGAAGACATCTCGG
TGGATGAGCTACGTTGCTTAAGTAGAAAGGAAATGATCACCCCTTGTATCTAGCCTA
AACTTTGAAGAAAATGTATGAATAAGGTTTTATTCCCAACCTGCTTTCTAAATGTATT
TTAAACCCCTCACTTCAGTTCTGTTCACCCGTCGTAAAAAAATTGTCAGTATTACTAT
ACAGCAGATGGAAATGTGGTCAGTAGCTTGTGATTACCCATACTGGAAAAGAATCT
GAAGCTCTATGCCCGAAACTCACACAGTATTGTAAAT CAACTATAGTTTAATTAAAA
ACCCCAAACAAAACCCCAAAAACTTCTTCAAGAAAGTAATAGTTAAGAATATAAAT
GAAAAGACTCCCAGAGTTGGTGCAATGGATTAAGGATCCAGCATTGTCTCTGCAGTG
GCTTGGGACGCTGCTGAGGTGCCAGTTCGATCCCCGGCCCAGGAATTTCCACATGCC
ACAGGTCCAGCCAAAAATTAAAAAAGCATTTAAGACTTAGAGACTTGAAATAATTT
GACACAAGCCCACCAAGATCTAAAAATGACAAAGCTGAAGCTCGTCTGGGTTATAG
AGATGTTTGAGGAAGAGTGACAGAGTTCCTTTGTTAACATGCTGAGCTTTGCAGA
AAATCAAGGTATTCGTGAAATTTTTGCATGTAGTTGTCCTTGTTTGGATTAGAATAA
ACCATGAAGATGAATCGAGCAGTCTCAAAGATGTACTTCCCCTTGGTATTGCTAACA
ATTATATGTGGGAAGAAAGAAATGCAATTCTAAGTTCTT TCCCTGTGCATATTAAAT
ACTTGGCTAAATTCTAACTTCCTTAAAGGGAATTTGTTAAATATAGGGTGAGTGACT
TTAGATAAGGAAACTAGGAGTTCCCGTCGTGGTTCAGTGGTTAACGAATCCGACTAG
GAACCATGAGGTTGTGGGTTCAGTCCCTGCCCTTGCTCAGTGGGTTATCGATCCGGC
GTTGCCATGAGCTGTGGTGTAGGTTGCAGTCACGGCTCGGATCTGGCATAGCTGTGG
CTCTGGCTCTCAGCTTTGGCTCCCTAGACTGGGAACCTCCATATGCCTTGGATGTGG
ACCTAGAAAAGACAAAATAAAAATAAAAAATTAAAAAAATAAAAATAGATAAGG
AAACTACTGTCCTATAAAGAAATAGAGAATCTTTGAATCCCATTAACAAGTGAGACT
CATTCCTTACTGGGGAACAGAATCACCTGAAGAACATTTAAATATATTGATTCCAGG
TCCCGCTGTAGCTCAGTGTTAGAGGCTCTTTGGGGCTGGGGCATGTGTGTTGGGTAT
TTCTTTTTGAGAGCCCCGCTGGGTGCTCCCGTGCACCTGGCATTAGGAACCACAGCC
TTGAGCGACCTCTGCTCTCTTTCCCCTGGTATCCCTTTATCTGTTGCTCTTACACCCAG
TTTTTTCACCATAGAGATAACTGATGCATTTTATTTTCCTTCTTCCAG ATTAAAGATT
TCTTGAGCTACATTAGTCCTGTGAATGTATATCCAAATGTCATTCCACTGGGCACAA
CTCTGGAGAAAGTTAAAGAAATGTGAGTCATTAGTACTTGCGGAACTTCTGTGGTCC
AATGGGATGGATCCAGAGGATAATTTCAGGCCTGAAAATGGGGACAAGGCTGTAAA
ATGGACGTGGCTGTCAGTAGGGTTCTGGTTGGGAGCATCTGGGCTTTTTCAAGTGAG
TGCGTTTTATATAATCTTAAAAGCTTCTGGGCATCTAGCATAATGGACTGGTTGGCA
ATGAAGACCTTGAAAAGGGCGGGACACCTTCAAATC TTATTTCTGTGCCCTTTTGTA

*FIG. 16T*

```
TTTTATTTTCACTATATCTTAGCTTTCAACCTCTAGAATGAAGAGATCAAATTTGTGA
GATTCTTGCAAGAGATAACCCCATTAAATAGCGAACAGGAGGCAGTTTGCTGTACTG
AATTCCCTGAATGCCAGAAGGTGTTACCCTATTATTTAACAGTTCATCAGAATAGGG
ACATGCTTTTCTGCAGTGCAAGAGCAAAGATAAAAGTTTTGCTTTCCGTCAGTCCTA
CAATTAGATGGGTTGTTTTAAATGCTTATATTTACTACTTTATTATATTGAAGTAATT
TTAAATTATTAAACATTGCTGAAAAGTTTGTTTTTTTTTTTTTTTTTTCTTTTTGGC
CTCTCTGTGGCAGATGAAGCTCCTGGGTCAGGGATCAGATCTAGCTGTTGTTGTGAC
TTAAGCCACAGTTGCGGCAATGCTGGATCCTTAACCCTCTGTGCCAGGGTGGGGATT
GAACCCACGTCCCAGTGCTCCCAAGACGCCACTGATCCCATTGCGCCACAGAGGGA
ACTCCAAACATTGCTGAAAAGTTTTAAAAGCAGTGGTATGATTTCCTCCATAGTCA
AATTTTTATAATCTCTATAAATGATGCTTCTATTCCCAGCTTTCCCAACAGGAAAAAT
AATATCTGTATTCATTTCAG CTTAAAGCCTTTATGCCGATCTTCGCAAAATATCGAGC
CAAAGTATAAACCACTTGGAAAATTGAAGAGAGCTAGAATAATCCATCTAGACTCA
GGTAAGATGAATGACCCTGGGGTCAGAGGTGTGGGTTTCTCTGCAGGAGCACTTTGC
AGAGTTCTCTGGCCTGGTGAAAGCTGCCCTGGGCAGAGTTGGACCCAGGATCCACTG
TCGCTCAGACTTGTCATGTGGTCTTGTAACGTGCTCTGCCCCCTACCTTCAACCTAT
AAATGTAGGAGTCAGATTCCCTTCACAGGTTTAGAAAAAGTGATAAAGAGAACTTA
GTCTGTATTGAATGTTGTCTTCAGCTTTC TGGGAATGTGCCCTGCAGCTTGTATTGGC
CATAAGGAGAGGCTCTGCTGTTACCCTTGAACATTTCCTTCAAGATACTAGTCAGTG
CAGATAATGAGAACTTTGTCTCCCATCATTTCCCATCACATTGATGTGTAGTGTTTAT
ACGAATGGATTCTCTATACCTTCCTGCCTTCTTTCATTTTCTGATTGATTTTTAAAAT
GAAGTATATTTGATTTACAATGTTGTGTTAATTTCTGCTGTACAGCAGAGTGG TGTA
GATATATATATTCTTTTAAAAGTATTCTTTTCTGTTATGGCTTGTCCTAGGATATT
GAATATAGTTCCCTGTGCTGTGGAGTAAGATCTTGTAGTTGATCCATCCTCTCTCTAT
ATATATAATAGCTAACATCTGATAACCCCAGCCTCCCACTCCATCCCTCTCTCAATG
CCCTCCCCACTGGTAACCATAAATCTTCTCTATATCCGTGAATCTGTTCACCTATTTG
GCTTGTTTGCATTTTGGTT ATTACATATAAAGCTGCTTTCATCTGCTTACTTTGGGTT
TATTTTCCTCTTCATTTAAAATTTCTTAATGTGGGAGATGAGGTCATTGATTTGAGCC
CTTTCGCCCTTAATACAAGCATCTAGTGCTATAAATTTCCCTCTTTGACTTGTGTTGT
CATTTCCTCCAGTTCAAAATAGTTTCTAATTTTTCTTTTCCTCCCTCCCTCTCTCCCT
TCTTTCTTTTCTTCATTTTTGGCTGCCCTGAGGCATATGGAA TTCCCAGGCCAGGGGT
CAGATCCAAGCTGCAGTTGTGACTTATGCTGCAGGTGCAGCAATGCCAGTGTGCTGG
GCCAGGGATCGAACCTGCGTCCCAGAGCTCCAGAGATGCCACTATTCCCTTTGCGCC
ACAGCAGGAACTCCTCTAATTTTTCTTCCTTGAGGCGCGGGTTTATTTACAGGTACAT
TATTTCGTTTCTGAATTCTGGAGGAATTTACAAAGATAATTGTGTCATATAATTTAT
TGTGGTCAGAAAAAATACAGTGCATGGATTTACTGAGATTCATGGTCCAGAATAAT
GGTCCATCTTGGTAAATGTTTCATGTGTACATGAAGAAAATATGTATACTGCTGTTG
GGTGGAGTGTTATATAAATGTCTAGTTAATAATGTTCAAGTCTTCTGCATCTTTGCTG
ATTAACTTGTTCTACTTGCTCTATCAATTATTGAACGTTTTGAAATGGTGAATTTGT
CAAAATTTGTTCTTCCACTTTTTGTGTCATCGATTT GAATAATCTTTAAAACTCCTAT
GTCCTCTAGAGGAACTGACCCTTTCACCTTTGGGAAATAACTCCCTTTATCCTTCTTT
TTATTAGCTTTGAAATCTACCTCACTGGATAATAATACATCCATTCCATTTCTTCTG
ATGTGTGTTGGCATAGTATATCTTTTCCATCTCTTTATTTCTCACCTAATTGTCTTTA
TATTTAAAGTGGGTTTCCTGTAGGCAGTGTATTGATGGATCTTGTTTCTTTTTACATC
CATCTGATAAATTCTGCTTTTCAGTTGGAGTGTTTTCAGGCTACTTAGGTTAATGTGA
TTACTGACCTTGTTAGGTTTACCATCTTGCTATTTGTTCCATCTGTTCTTTCTTCTTTCT
```

*FIG. 16U*

```
CTTCTACCTTCTTTTGGATTGAGAACGGATAGAGATTCCATTTAATGTCTTATTTGTT
TTATTAGCTGTAACTCTTTTATTCTTTTAGTGGTTTACAGTTTTCATCTGTAACCTATC
AGAGTGAAAATTTCAAGATATA TATTCTACTTGAAGTATGGTATAGGAAGGTGACA
ACAGTATATTCCATTTCTCCCCTCCCAGTCTTTGTGCTATTATTGTCATACACTTTATT
TCTCTGTTATAAACTCCACAATACATTACTGTTTTTTTTTTTTTTTAACAAAGCTTTA
AAAATTGATCGCTTATAGGATAATTTGGGAGTTCCTTTTGTGGCTCAGCAGTAACGA
ATCCATGAGGATTCAGGTTCGATTCCTCGCCTTGCCAGTGCGTTAGG AGTTGGCATT
GCTGTGAGCTGCAGTGTATGTCGCAGTTGTGGCTCGGATCCTACACTGCTGTGACTG
TGGTGTAGTCTGGCACCTGCAGCTCCAATTCGACCCCTAGCTTGGGAACTTCCATAT
GCCCTGTGGGCCTGAAAAGCAAACAAACAAACAAAAAACCAACTATAATTTATATG
CCATAAATTTCATCCTTTTAAGGTGAACAATTCCATGATTGTTACTGTAACGAAGTA
GGTTACGTGCTAAGGCCTC TTCTCTTGGCTTGTGGATGGGTGCCATGCTGATGTGTGC
TCACATGGCCTTTCCTGGGTGCTTGTGCCTGGTTGGGAGGGGTGAGTAAAGGAGGGG
CTGGGGGATATTTGCTCTCTAATGTCAGTTCCTTCTTTGGAGGCCCCATTTCCACTTT
GGGGATTAGGACTTCGACAGGAATTTGTGTGGGAAGGAACACACACTCAGTCTAAA
ACATACAATAAAATTTACGCTGTAACATGGTAAGAAACTGACAACT GTTCTTCAGAC
AGAACACATTTTCATTCTCACCAGCAATATATACGGATTCCAATCTCTCCACATCCTA
GCTCACACTTTTTAGTGTCTTTGATTTGTAGTTATTTAATGATGTCAAATAATATATC
TCATTGTAGTTTCACTTCCTTTCTCTATTGATGTTGATCTTTTTCCATGTTCTTATTGG
GCATTTATTTATCTTTTCTGGTGAAATGTCTATTCAGACCTTTTTGCCTGTTTTTAAAT
TGGCAAACTCATTCCTGAGTTGTTAAGAGTTCTCTCTATAGGCTGGGTATGTCTAGTA
TTATTTGCAAATATCTTTTTCCAGTCTATAGCTTGTCTTTTCACTCTCTTCATGGTGTC
TTTTGAAGTGTAAAATTTTAAATTCATCTAATTTCTTTTATAGCTTGTGCTTTTGGTGT
CATATCGAAGAAGCTATTGCTTAATCCAAGATCATAAAGATTTATTTTCATACTTTAT
CATTTCTGGGTCAGTTTTGACTTTTCCCCTTAT TTATAGGCCATTTTCCCACCTTTCTA
CACATTTGGTAATTTTTATTGGATGCCACGCTTCTTGAACTTTATGTTGTTAGGCAT
AGCATACCTTTGGATTTCTGAAAACATTCCTAAACTTTATTCTGGCACGTGGTTAAGT
GACTTGGAAAGAGTTTGGTTGTGTCTGGCTTCTGTGCAAGCCTCTTAGGCAAAAGCA
GGGCAGCATTTAGTTTAGAATCCACTTTCCCCACTGCTGAGGCTAGGCGCTTCTTCA
CACTCGTAGGAATAGCCCGAGTTATGAGGCGTTACTGGCTCTTGGGGCAGGTACTG
TTTCCGTCACCGTGTGCATCCTCAGCACGCTTTCCTTTTATTCCTCGGAGTGATTCTCT
CCCTGGCCTCACAGCCAGGCGCTGACTATTCGAGGGGCCCCTTGTGCAGCTCATCAG
AGCTCCTCAGTACTGCTCTCTCCTCTCTGGCCTCAGCTCTGTAAACTCCAGCCAACCT
GGCTTCCTTGGACTCCCAGTTATAT CTCAACTCAGGGATGCCAGTGGGCTCTCCTTGC
CAGGAAACTGTCACAAACCCATACGCTGAGGCAATCTTAGGTATCACTTGTCTTTGT
CTGATGTTTAATTCCTTGAGAGACTTTGTTTCTCATATTTTATCTGGTTTTTAGTTGAC
ATGGGAGGTTAAATTTAGTCCCTGTTAACTCTTTCTTGGCTGGAAGCATAAGTTCTTT
TTTTTTTTTTTAATACTTAAAATTTTGTACCTTTTATCTATCCAAATG ATCCTCGTTT
TTAATGACGGTTTTATTTTTTGGTTGGGCCACTAGTTTAAGAGTTCTTGAGGTTATG
TTCATTTCCACTTCTTCCTGCTTTTTCTTTATTAGCTTCAATTTTGATCCTTCTAGATTC
CTTTGGTTCCTTATTCCTTATCATAGCAACTTTCATACCTTTTATTTGTACAGGTGTAG
ATCTTTCAACGACTCTTCAGTGTCCTTCTGTATTTTGTAAGTCACAGATATTATCAGG
TTTACTTTAGT TGCATGTATGGTACTGACTTTAAAATTCCTACCCTGTCCCATGCATG
TACTTTAAGGTCTCCATGATGATCTCTGCCACTACGTTGACCAGTCTTTCACCTGTTC
TAGTTCTTCTTTTTAATGACCACATCGGTGGCATATGGAAGTTTCCCGGCCAGAGA
CTGAATCTGAGCTACAAGCTATGCTGTTGCTTGAGGCAGTGTTGCATCTTTTAACCC
```

FIG. 16V

ACTGTGCCGTGCTGGGGATCGAACCTGAGTCTCCACAGTGACCTGACCACTGCATTT
GGAACCTTTTCTAGTTCTTAACATGCTCTGTTGATGCAAATTAGTGGTTACTATTACA
CATGCAGTGTTAAATCAGTTGCTCTGTGTTATTCTTTTCTCAGAATCTGAAGGGTACA
TGTAGAAGTCGCTTGTCTCTTAGCATCTTTAAAAATATTTTAATTAGGAGTTCCCGTC
GTGGCGCAGTAGTTAACGAATCCGACTAGGAACCATGAGGTTGCAGGTTTGATCCCT
GGCCTTGCTCAGTGGGTTAAGGATCCAGGTTGCCGTGAGCTGTGGTGTAGGTTGCAG
ACGCGGCTCAGATCCTGTGTTGCTGGGGCTCTGGCGTAGGCCGGTGGCTACAGCTCC
AATTAGACCCCTAGCCTGGGAACCTCCATATGCCATGGGAGCGGCCCTAGAAAAGG
CAAAAAGACCAAAAATATATATATATATTTTAATAAAACTGTGCTCTTTATATAA
GTTTAATCTTTATCTAATTTATATAATTTAATAG TTAACCATTATTATAATTATCTCA
AGACCAATTTTATAAAATTACTGTTCCTTTACTGTAGATAATTTAGAAAATAGTTATG
TAGAACCTTACAACTATATCTTTATTAGCATTTTCATGTATTTCCTTTCCATCCTGAAT
CATTTATATAAATACCTACACAAATCACGGGGGTGATATTGAAAATATTCAACCTTG
GTCTCATTGGTACCTACAATGAGACCAGCAGTAGCCGTAGTGCAAGACCATAGTGC
AAGACCAATTTCTTCATTTGTGCAGCTCTTAGTTCCTGGACTGTGAAGAGGTGGCA
AGGGTCCTTAGGTGTAGGGTCCAGGGCAGTGGGGACAGGAAGGACATCTGGAGCT
GAAGGGAAGAGCCGTTACTAATTAGCCTGGAAGTGTTTACATAACAACTGTAAGAC
TGAATAGGTGTATACAGACTGAAAGGCAGCTTGGATCACTTTGTGTGTATGTGTGTG
TATATATACACATATACATATACTTAACCTCT TTACTGGAAAATTTTTATTCTTCAAA
AGCACCCGTTCAAGGGCTGCATATTTTAAATTGCATTATAACTATATAATTTTTGTCA
TGTACTTTGTCATATAGATTATGAACTTCAGTTTTATAAACATTGTGGTAAACATTGT
ACAGAAGTCTGTGTCATAGCTCTCATTACTGGGTTCGATTATAGAAATTATGGTGCT
TGATATATACATATTGCCAAACTGTTTCCCAAAATGGTTATACCAGTTTATATAGAC
ATCAGCAGTATATGATGGTTGAAAGTATCTATGAAGTATGACATTTGTCCTTTTTAAT
TGAGTTTGGGTATGTTATCAGTTTGTGTAAATGTTAAGGATTTCAACACTTCTGTAAG
TACTGTGATTTTTCTGTGTCTATTTTCATAGAGAAATTTAGTTTTTATATTCTAAAAA
GAATACATGTCAGAATAAACTTCTAATAGTATAAAAACTTTGTTTTTCAGATACATA
GAGGTGAGGTAATGTGAAAATGTTT TATTTTTACAGTTGAAACATACTGTAATGTTG
GTATAGTCACTGATGCGAAACAGGAAGCTGTCCACCTTAGCGATGATACAAAAACA
TTCCATTAAAAGATAATTTTGGCACATCAGTGGAGGAGCTATAACAAATGTATTAAT
CCATGGCTTAAAATGAAGCCATAACTTGGAAACTAGGATGATTCCAAATATAGTGG
CTAGACATCTTAGTCACCTTAAGTCCTTTAGAAAAGACGTAAGATGAAATAATTG CT
TGTTGAAACAATTATAAATTGTAAGAGAACACTAAGAACTGGCTCTCATCCTTAGCT
CCCCCTGTCTGGTTGCAGACCTTCTCTGGGCCTGTCTCCTTGGTAAAATGGGAGCTA
GATGGTGGTTTCTACGGACTCCTTTCTTAAGAGTCCTGAAAAATGAAGTTTTTAGCT
GTGTCTTTGATTGCTGGGAAAAGTTAACTTATAATTTACTTGCTTTTAGCACTAGAAC
AGTAAGTTGCCCTACACAGTAATC CTGTAAGCATTTAACTTCCTTCTCTGGGGGTAA
GTGGTATTAGAGGGCAGGAAAATGTTTGTTTTCCCCCAATGCCACGACATGTCATTT
TAGCTTATGTAAATTTCATGTATTGAATGATAAGAATTTCATTCTTGAAGATTTCCTC
ATTTANAGGACACAGGTGGATATAAACATGCTCATGCAGCATGCTTAACACAGTAA
TATGACACTAAAATGTGGCTTGTCTAACATTTTGGTTCAAGTTGATATAATC TTTCTG
TGTTTCCCCCAGTCTCATGGCCTTGTGCACTTAGCATAGCCTGCGTAACAATTACCAG
AGACTGGGCAACAACTTCTCTCAGTTCTGGATACCACTGGGATGTCCAGAATCAAAG
TGCTGGCAGATGTGGTTCCCAGTAGGGGCCATTTCAGCCACCTTCTCACCTTCAGTG
CACTCGCATGGCCTTTCCTTTGTGCATGGGCATGGAAAAGTGAGAAATCTGCTTCCT
TTTCTCATAAGAACACTAACC CCGTCGCATAGGTGCCCCCCCATGAGTTAATTATCTT

*FIG. 16W*

CTAAAGGTCTTACCTCCAAATACCATCACGTTGCACTTAGGGCTTCAAATTATGAAT
TTTGGCAAGACGTGGACATTCAGCCTATAACATGCACTAAGTGGGTATCAAAAAAT
GTTCATGAGGGCAAACTTTAAAAAACAATTCTTTTTATTGTATCAGCCAACTTGCTG
AGCATCTACTATCTGCAAAGCATACACAGTCTGCAAACCTTGCTTCTAG TCTAGGTG
GTTTGAAAACCTGGCTGACGAACAGAATCAGCTGTAGAACTTATAAAATAAGGCAA
AATCAAATTATTGGATCCTACTTTGAGAGACTGAGTAGGTCTGAAACAAAGCATAG
AAAGCTGTTTAGTTTAAAAAAAAAAAACAAAACTTATCAGATGAGGACCCATGAT
TAAGAATTTGTAGCCTTATGGGGAACACAGATCTCTAGTCTCAATTCACAACCTAGT
GTTGTGACAAGTTGAAGGCTGGTAGTTAAATTGTTGAGAATATCTCAGAGGGGCCTT
TTAGTTTCTCTTGGAAGAAGAGTGAACTCCCAATTCCACAAATTAAAAAATGCAGCT
AAATGCTACAAATTGGATTTTTACTAAAAGCACCAATAGGTTCCGTTTGCATTCTGTT
ACCTACACACCTGTTCTGTTTGTCCCACAG<u>AGGAGGAGGAGGAGGACGATGACGAT
CTCTTTGATGATCCTCTGCCAGTACCTTTAAGGCACAAGGTTCCAAATCAG CAGACT
CTTCACTCTGAGGTACTTCCCATGACTGCTCTACCACAAGACCAGCCTGAAAAACAG
ACAGAAAGCACAGAATGCTTCAAAGCAGAGAGTATGCCAACATGTCTCTGGGCAAA
CTTCGTAGATTGTGAAGAATCCAATAGTGAAAGTGAAGAATTAGAAATCACGGCTC
CAGCTCAAGGAGACACGAGTCCTGTCCCCCATCACCAGCAGAAGGCTGAAGGGGAA
GTACCACAGTGGGAAGTGTTCTTTA AAAGAAATGATGAAATCACAGATGACTGTTTG
GAAAACCTTCCGTCCTCCACAGAGGCAGGGGGCTCTCAGTCCCCAAAGCTTTTCAGT
GACTCTGATGGGGAATCAACTCACATTTCTTCCCAGACTTCTTCTCAGTCAACACAC
ATATCAGAACAAGGAAGTCAAGGCTGGGACAGCCAATCAGACACTGTTTTGTTATCT
TCCCAAGAGAGAAAAAGTGGGGATATTACCTCCTTGAACAAAGGTGGCTCTAG ACC
AGAAATCAAAGAGAATATTCCCATCCTTCAGATGGAACAAAATGTATTTTGCCCGAA
GGATACTTACTCTGATTTGAAAGGCAGAGATCAAGATATAAACACACTTCCCAGTGC
TAGAGAAACAACTACTCTGAGCAGTGGGAAACACATGCCTCAGGAGAAAAGGCCGC
TAAACTGTAACAGTAACACAGATTCACAAGGCTCCTCTGACTTTGAAATTCCCTCCA
CTCCAGAAGCTGAGCTACCTCAACAAGAGCATCTGCAATATTTATACAAGAAGTTGG
CAGGAGGAGAGGGTATAGTAATTGAAAAAAGGAAAAGCGCAC GTCATTCTAGAGC
AACCACTAAAAAACCTACACAAACAGGTAATAGTCAGACTCCTAATAGA *TG4*GTTC
AAATGGAGTACTTAAAAATGTTCATATAACCTAAAAGGCAGCTCTAAAAGGGGAAA
CAATAGGACCAAAAAATACAAAGAAAACAAGAATGGGAGAACTCAGTACAAACAT
ATCAGTAATTACATCAAATGAAAATAGGGAAAAACCATAAGCCAACTATATATTG
TCTATAGGAAACTGGCTTCAAGACTTGGGCAGGTTTACTGGTGAAAGGATGGAAAC
CTTCACCACATAATAAACATGAAAGATGGAGGGGCTATATTACTAGTGATAAAAGG
TCCAGTTCACTGAGACATAAACCCAAATGAGTATGTACTGGACAACAGCCACACAT
ACAGAGCAAAAACAACTGAAAGGAGAAAGATAAACTAAAGCACAATTACAGCTGC
AACAGAATTAGTCTACAGGAAATCAGCAAGGAGACGGAAGAACTGAACAGCACTAT
CAACCAACCAGATCTTCACAGAAGACACCATCTAGCACAGAATACACACTTTTCAA
GTTCACAGAATACAACATTCACCAAGATAGACCATATCCTGGTTCATAAAAACTTGG
ATCTA</u>

*FIG. 16X*

GENETIC TEST AND GENETIC BASIS FOR SCID IN PIGS

CROSS-REFERENCE TO RELATED APPLICATIONS

This application claims priority under 35 U.S.C. §119 to provisional application Ser. No. 61/925,072 filed Jan. 8, 2014, herein incorporated by reference in its entirety.

STATEMENT REGARDING FEDERALLY SPONSORED RESEARCH

This invention was made with government support under Grant No. R24 OD19813 from the National Institutes of Health. The government has certain rights in the invention.

The instant application contains a Sequence Listing which has been submitted electronically via EFS-Web in ASCII format and is hereby incorporated by reference in its entirety. Said ASCII copy, Created on Mar. 27, 2015, is named Dekkers_14592586_Sequence Listing_ST25.txt and is 89,000 bytes in size.

FIELD OF THE INVENTION

The present invention relates to porcine subjects with severe combined immunodeficiency disease (SCID). The invention also relates to modification of the DNA cross-link repair 1C (DCLRE1C) gene, also referred to as the Artemis gene. The invention also relates to methods for generating pigs with SCID. The invention also relates to methods for increasing or decreasing SCID in a pig population. This invention also relates to the use of SCID pigs for investigation of diseases and conditions. This invention also relates to treating or correcting SCID in pigs by providing functional Artemis protein or a gene encoding functional Artemis protein.

BACKGROUND OF THE INVENTION

Pigs, and in particular members of the species *Sus scrofa*, are invaluable as a model organism. Because both the size and anatomy of domesticated pigs closely resembles that of humans, they are used in the research of a variety of important human diseases. However, the existing transgenic models of severe combined immunodeficiency disease (SCID) cannot mimic any of the known human immunodeficiency diseases where conditioning for bone marrow transplants includes irradiation. Further, none of the transgenic models represent a natural porcine model of SCID, and none of the transgenic models target the Artemis gene or any gene which causes radiosensitive immunodeficiency. Thus these transgenic models cannot mimic any of the known human immunodeficiency diseases where conditioning for bone marrow transplants includes irradiation.

SCID is a group of primary immunodeficiency disorders characterized by increased susceptibility to severe infections. SCID is caused by heritable defects of the cellular and humoral immune system, which result in a number of different phenotypes. Individuals with SCID have low numbers of circulating lymphocytes, T cell lymphopenia, and variable defects in B and NK cell populations. As a result, individuals with SCID have increased susceptibility to infections and increased mortality, commonly characterized by a severe deficiency in naïve T-cells. Infants born with SCID typically appear normal at birth, but are at high risk of serious infections after waning of maternal antibodies. If untreated, SCID has 100% mortality. Treatment is generally hematopoietic stem cell transplantation (HSCT), although gene therapy has been successfully used in some forms of SCID.

Characterization of the molecular mechanisms of SCID is integral to the development of diagnostic assays and treatments for the disease. A number of animal models for SCID exist, including several mouse models. However, murine and other small animal models often translate poorly to human disease due to important differences between mice and humans, including differences in immune response molecules and networks. Domestic pigs are much closer to humans, both physiologically and immunologically, and therefore a SCID pig represents a much better model for both the immune-compromised patient and for cancer and stem cell research, but such models have been lacking. While several reports have used molecular technologies to mutate one or more of several genes to cause a SCID phenotype in pigs, these reports are mainly limited to describing the phenotype of the mutated pigs. Further, these mutations are limited to genes that do not cause immunodeficiency syndromes that include a sensitivity to irradiation, as demonstrated for at least six types of human SCID genetic disease Previous work has also demonstrated that human cells transferred into SCID pigs are not destroyed due to lack of an immune system, but a practical model for use in exploiting SCID pigs for vaccine and other biomedical research has not been reported.

The Artemis gene—also referred to as the DNA cross-link repair 1C (DCLRE1C) gene—encodes a nuclear protein that is involved in V(D)J recombination and DNA repair. In pigs, based on build 10.2 of the swine genome, the Artemis gene is located on the forward strand of chromosome 10 and begins at approximately base number 51553277 and ends at approximately base number 51596761. Artemis includes 15 exons spanning 44 kb. The mRNA of porcine Artemis is 2388 nucleotides, encoding a protein that is 762 amino acids long. The protein has endonuclease activity on 5' and 3' overhangs and hairpins when complexed with and phosphorylated by DNA-dependent protein kinase catalytic subunit (PRKDC). Artemis is a member of the SNM1 family, which is defined by homology to yeast SNM1. Artemis is also referred to as SNM1C. Artemis is responsible for the resolution of hairpin coding ends in V(D)J recombination. In DNA double-strand break repair, Artemis is implicated in the end-processing step of the non-homologous end-joining (NHEJ) pathway. Artemis is the nuclease required for the resolution of hairpin coding ends during V(D)J recombination, the process by which B cell antibody genes and T cell receptor genes are assembled from individual V (variable), D (diversity), and J (joining) segments. For example, in joining a V segment to a D segment, the RAG (recombination activating gene) nuclease cuts both DNA strands adjacent to a V segment and adjacent to a D segment. The intervening DNA between the V and D segments is ligated to form a circular DNA molecule that is lost from the chromosome. At each of the two remaining ends, called the coding ends, the two strands of DNA are joined to form a hairpin structure. Artemis nuclease, in a complex with PRKDC, binds to these DNA ends and makes a single cut near the tip of the hairpin. The exposed 3' termini are subject to deletion and addition of nucleotides by a variety of exonucleases and DNA polymerases, before the V and D segments are ligated to restore the integrity of the chromosome. The exact site of cleavage of the hairpin by Artemis is variable, and this variability, combined with random nucleotide deletion and addition, confers extreme diversity upon the resulting antibody and T-cell receptor genes, thus allowing the immune system to mount an immune response to virtually any foreign antigen.

In Artemis-deficient individuals, V(D)J recombination is blocked because the hairpin ends cannot be opened, and so no mature B or T cells are produced, resulting in SCID. Artemis was first identified as the gene defective in a subset of SCID patients that were unusually sensitive to radiation. Cells deficient in Artemis are more sensitive than normal cells to X-rays and to chemical agents that induce double-strand breaks (DSBs), and they show a higher incidence of chromosome breaks following irradiation. Artemis-deficient patients are also among those patients with poorer than average outcomes after bone marrow transplantation, thus a good large animal model that would recapitulate these defects would be useful for testing better methods of bone marrow transplant treatments.

The inventors have identified pigs with SCID, and a novel genetic basis of SCID in pigs. The inventors have further identified the genomic region that harbors the causative mutation, and have developed genetic marker tests that can be used to identify SCID pigs and SCID carriers. Specifically, the inventors provide a pig that possesses a mutated Artemis gene, resulting in the decreased production and/or function of the Artemis protein gene product.

It is an object of the present invention to provide the molecular basis for non-induced SCID in pigs.

It is a further object of the present invention to provide porcine subjects and groups of porcine subjects with SCID.

It is a further object of the present invention to provide porcine subjects and groups of porcine subjects to serve as a model of human SCID for biomedical research.

It is a further object of the present invention to provide porcine subjects and groups of porcine subjects to serve as a xenograft recipient in cancer research.

It is a further object of the present invention to provide porcine subjects and groups of porcine subjects to serve as a xenograft recipient in stem cell research.

It is a further object of the present invention to provide porcine subjects and groups of porcine subjects to serve as a xenograft recipient in vaccine research.

It is a further object of the present invention to provide a genetic test for determining whether a porcine subject has SCID.

It is a further object of the present invention to provide a genetic test that can be used to identify affected pigs or carriers for the defect in pig populations, including commercial populations.

It is a further object of the present invention to provide a genetic test can be used to identify SCID affected piglets at an early age.

It is a further object of the present invention to provide a genetic test that can be used in biomedical research.

It is a further object of the present invention to provide further characterization of the SCID phenotype for animal disease and biomedical research, including research into the immune system, cancer research, the effects of disease, cell and tissue transplantation, and for testing of new vaccines and therapeutic agents for immuno-compromised individuals.

It is yet another object of the invention to provide further information for understanding SCID in pigs.

It is yet another object of the present invention to provide methods of identifying other mutations that are in linkage disequilibrium with or that are causative of SCID in specific lines, populations, or breeds of pigs.

It is a further object of the present invention to provide methods and compositions for curing, treating, alleviating, or inhibiting SCID.

It is a further object of the present invention to provide pharmaceutical compositions for curing, treating, alleviating, or inhibiting SCID.

Other objects will become apparent from the detailed description of the invention which follows.

BRIEF SUMMARY OF THE INVENTION

In its broadest aspect, the present invention provides methods for identifying porcine subjects with SCID. This can be used to select for and create porcine subjects and herds of porcine subjects with SCID as an animal model to study the disease. In a further aspect, the identified and selected porcine subjects and herds of porcine subjects of the invention have SCID resulting from mutation of the genomic sequence of the Artemis gene. In an even further aspect of the invention, the porcine subjects and herds of porcine subjects of the invention have SCID resulting from mutations that modulate the expression or function of the Artemis protein gene product. According to the invention, the inventors have discovered the basis for SCID in porcine, namely mutations that inactivate the Artemis gene. According to the invention, two independent mutations in the Artemis gene result in inactivation of the Artemis gene, when present in homozygous form or as a compound heterozygote. The Inventors have also discovered that pigs harboring these mutations in homozygous or compound heterozygous form show extremely decreased numbers of T and B lymphocytes, as well as circulating antibody, and significantly abnormal thymus and lymph nodes.

In one aspect, the invention includes a genetic test for identifying SCID pigs and SCID carriers. The genetic test can be used to identify carriers for the defect in commercial pig populations, for example to eliminate the identified mutations from breeding populations and thereby eliminate the possibility of creating litters with SCID piglets which after weaning will always die from disease commonly found on commercial farms. The genetic test can also be used to identify SCID affected piglets at an early age. The genetic test can also be used to identify and create an animal model and population of the same for use in biomedical research. Identification and understanding of the genetic basis for the SCID mutation will allow further characterization of the SCID phenotype for animal disease and biomedical research, including research into the immune system, cancer research, the effects of disease, cell and tissue transplantation, and for testing of new vaccines and therapeutic agents for immuno-compromised individuals. SCID pigs provide a much better animal model for such purposes than SCID mice and, thus, development of this model could potentially be extremely valuable.

The invention also provides novel coding sequences that relate to SCID. The mutations of the Artemis gene have been found to decrease expression and/or function of the Artemis protein gene product. The mutant gene and protein allow for the development of in vitro and in vivo models and agents to improve therapies for SCID.

In another aspect, the invention provides methods for generating SCID in animals, including pigs. The methods can be used to target the Artemis gene in a pig or herd of pigs to generate a population of pigs that are affected by SCID or are carriers of SCID. In another aspect, the methods can be used to improve the production of SCID pigs, for example by conducting bone marrow transplants on homozygous mutant SCID pigs, thereby allowing for mating of homozygous mutant SCID pigs to heterozygous carrier pigs, resulting in 50% affected piglets compared to 25% from carrier by carrier matings.

In another aspect of the invention, one may use the Artemis gene to screen for other markers in linkage disequilibrium with the mutation of the invention to create further tests, to identify other potential SCID associated mutations in other species of meat animals, lines, populations, or breeds of the same.

In another aspect of the invention, one may use the polynucleotide and polypeptide sequences provided herein to inhibit, treat, or ameliorate SCID by introducing a heterologous Artemis protein or nucleic acid encoding the same. In one aspect, the invention encompasses pharmaceutical compositions comprising a heterologous Artemis protein or nucleic acid encoding the same.

In another aspect of the invention, one may utilize gene repair mechanisms, including gene editing, to repair defects in the Artemis gene. In one embodiment, these methods may be used to cure, treat, or ameliorate SCID in an individual or animal.

BRIEF DESCRIPTION OF THE DRAWINGS

FIG. 6 shows the 12 and 16 haplotypes that are associated with the SCID phenotype. Sire 15801 carries the 12 haplotype and sire 11403 and the 4 dams that produced the initial four SCID piglets (see FIG. 4) carry the 16 haplotype. The outlined SNPs were used to design allele specific primers, as described in section 4a.

FIG. 16(A-X) shows sequences used in the present invention. In each nucleic acid sequence, primer sequences are shown in bold, correct translation frames are underlined, location of missing sequences are indicated in parentheses, and premature stop codon are shown in italics. Splice donor site mutation indicated by brackets. Point mutations indicated by curly brackets.

Figure 1:
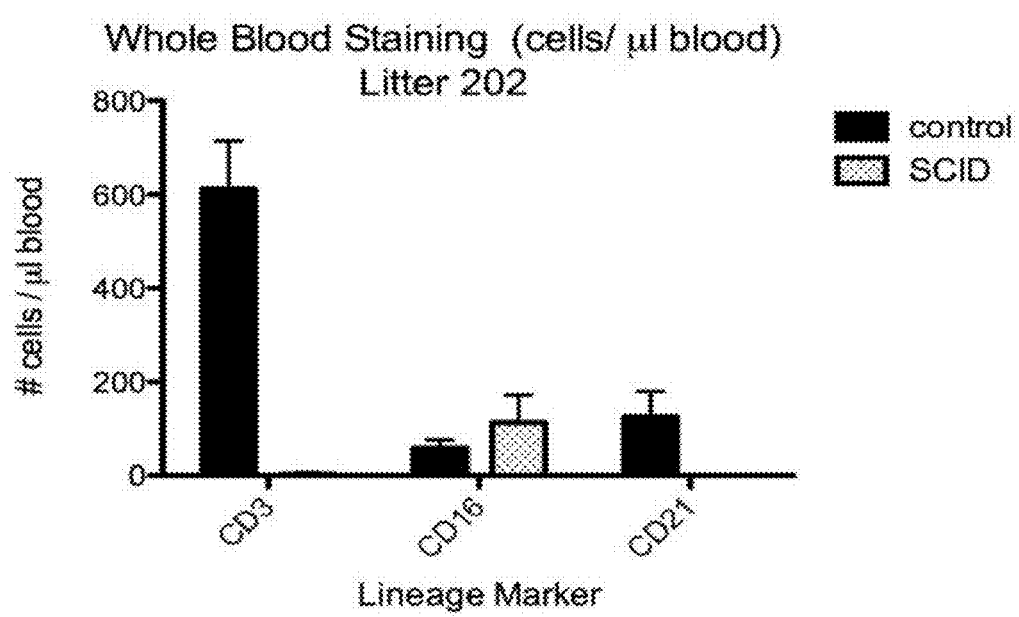
FIG. 1 shows absence of B and T cells in peripheral blood of SCID pigs, measured by flow cytometry. Representative plots were first gated on lymphocyte characteristics, and then the lymphocyte population was characterized by specific antibodies detecting cell-type specific surface proteins. Antibodies specific to CD3 (T cells), CD21 (B cells), and CD16 (NK cells), were used to detect these proteins and enumerate the proportion of lymphocytes consisting of T, B and NK cells.

Various embodiments of the present invention will be described in detail with reference to the drawings, wherein like reference numerals represent like parts throughout the several views. Reference to various embodiments does not limit the scope of the invention. Figures represented herein are not limitations to the various embodiments according to the invention and are presented for exemplary illustration of the invention.

DETAILED DESCRIPTION OF THE INVENTION

The present invention now will be described more fully with reference to the accompanying examples. The invention may be embodied in many different forms and these embodiments should not be construed as limited to the embodiments set forth in this application; rather, these embodiments are provided so that this disclosure will satisfy applicable legal requirements.

Many modifications and other embodiments of the invention will come to mind to one skilled in the art to which this invention pertains, having the benefit of the teachings presented in the descriptions and the drawings herein. As a result, it is to be understood that the invention is not to be limited to the specific embodiments disclosed and that modifications and other embodiments are intended to be included within the scope of the appended claims. Although specific terms are used in the specification, they are used in a generic and descriptive sense only and not for purposes of limitation.

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges recited within the specification are inclusive of the numbers defining the range and include each integer within the defined range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms (5th edition, 1993). The terms defined below are more fully defined by reference to the specification as a whole.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e. g., Diagnostic Molecular Microbiology: Principles and Applications, D. H. Persing et al., Ed., American Society for Microbiology, Washington, D.C. (1993). The product of amplification is termed an amplicon.

As used herein, "antisense orientation" includes reference to a duplex polynucleotide sequence that is operably linked to a promoter in an orientation where the antisense strand is transcribed. The antisense strand is sufficiently complementary to an endogenous transcription product such that translation of the endogenous transcription product is often inhibited.

The term "conservatively modified variants" applies to both amino acid and nucleic acid sequences. With respect to particular nucleic acid sequences, conservatively modified variants refers to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also, by reference to the genetic code, describes every possible silent variation of the nucleic acid.

One of ordinary skill will recognize that each codon in a nucleic acid (except AUG, which is ordinarily the only codon for methionine; and UGG, which is ordinarily the only codon for tryptophan) can be modified to yield a functionally identical molecule. Accordingly, each silent variation of a nucleic acid which encodes a polypeptide of the present invention is implicit in each described polypeptide sequence and is within the scope of the present invention.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7, or 10 alterations can be made.

Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80%, or 90% of the native protein for its native substrate. Conservative substitution tables providing functionally similar amino acids are well known in the art.

The following six groups each contain amino acids that are conservative substitutions for one another:
1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). See also, Creighton (1984) Proteins W. H. Freeman and Company.

By "encoding" or "encoded", with respect to a specified nucleic acid, is meant comprising the information for translation into the specified protein. A nucleic acid encoding a protein may comprise intervening sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. When the nucleic acid is prepared or altered synthetically, advantage can be taken of known codon preferences of the intended host where the nucleic acid is to be expressed.

As used herein "full-length sequence" in reference to a specified polynucleotide or its encoded protein means having the entire amino acid sequence of a native (nonsynthetic), endogenous, biologically active form of the specified protein. Methods to determine whether a sequence is full-length are well known in the art including such exemplary techniques as northern or western blots, primer extension, S1 protection, and ribonuclease protection. Comparison to known full-length homologous (orthologous and/or paralogous) sequences can also be used to identify full-length sequences of the present invention. Additionally, consensus sequences typically present at the 5' and 3' untranslated regions of mRNA aid in the identification of a polynucleotide as full-length. For example, the consensus sequence ANNNN<u>AUG</u>G, where the underlined codon represents the N-terminal methionine, aids in determining whether the polynucleotide has a complete 5' end. Consensus sequences at the 3' end, such as polyadenylation sequences, aid in determining whether the polynucleotide has a complete 3' end.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

By "host cell" is meant a cell which contains a vector and supports the replication and/or expression of the vector. Host cells may be prokaryotic cells such as E. coli, or eukaryotic cells such as yeast, insect, amphibian, or mammalian cells.

The term "hybridization complex" includes reference to a duplex nucleic acid structure formed by two single-stranded nucleic acid sequences selectively hybridized with each other.

The term "introduced" in the context of inserting a nucleic acid into a cell is equivalent to "transfection" or "transformation" or "transduction," and includes reference to the incorporation of a nucleic acid into a eukaryotic or prokaryotic cell where the nucleic acid may be incorporated into the genome of the cell (e. g., chromosome, plasmid, plastid or mitochondrial DNA), converted into an autonomous replicon, or transiently expressed (e.g., transfected mRNA).

The term "isolated" refers to material, such as a nucleic acid or a protein, which is: (1) substantially or essentially free from components that normally accompany or interact with it as found in its naturally occurring environment—the isolated material optionally comprises material not found with the material in its natural environment; or (2) if the material is in its natural environment, the material has been synthetically altered by deliberate human intervention to a composition and/or placed at a location in the cell (e.g., genome or subcellular organelle) not native that material. The alteration to yield the synthetic material can be performed on the material within, or removed from its natural state. For example, a naturally occurring nucleic acid becomes an isolated nucleic acid if it is altered, or if it is transcribed from DNA which has been altered, by means of human intervention performed within the cell from which it originates. See, e.g., Compounds and Methods for Site Directed Mutagenesis in Eukaryotic Cells, Kmiec, U.S. Pat. No. 5,565,350; In Vivo Homologous Sequence Targeting in Eukaryotic Cells; Zarling et al., PCT/US93/03868. Likewise, a naturally occurring nucleic acid (e.g., a promoter) becomes isolated if it is introduced by nonnaturally occurring means to a locus of the genome not native to that nucleic acid. Nucleic acids which are "isolated" as defined herein, are also referred to as "heterologous" nucleic acids.

As used herein, "localized within the chromosomal region defined by and including" with respect to particular markers includes reference to a contiguous length of a chromosome delimited by and including the stated markers. Where applicable, the location of the sequences within the porcine genome assembly (http://useast.ensembl.org/Sus_scrofa/Location/Genome) is provided.

As used herein, "marker" includes reference to a locus on a chromosome that serves to identify a unique position on the chromosome. A "polymorphic marker" includes reference to a marker which appears in multiple forms (alleles) such that different forms of the marker, when they are present in a homologous pair, allow transmission of each of the chromosomes of that pair to be followed. A genotype may be defined by use of one or a plurality of markers.

As used herein, "mutation" includes reference to alterations in the nucleotide sequence of a polynucleotide, such as for example a gene or coding DNA sequence (CDS), compared to the wild-type sequence. The term includes, without limitation, substitutions, insertions, frameshifts, deletions, inversions, translocations, duplications, splice-donor site mutations, point-mutations or the like.

As used herein, "nucleic acid" includes reference to a deoxyribonucleotide or ribonucleotide polymer in either single- or double-stranded form, and unless otherwise limited, encompasses conservatively modified variants and known analogues having the essential nature of natural nucleotides in that they hybridize to single-stranded nucleic acids in a manner similar to naturally occurring nucleotides (e. g., peptide nucleic acids).

By "nucleic acid library" is meant a collection of isolated DNA or RNA molecules which comprise and substantially represent the entire transcribed fraction of a genome of a specified organism. Construction of exemplary nucleic acid libraries, such as genomic and cDNA libraries, is taught in standard molecular biology references such as Berger and Kimmel, Guide to Molecular Cloning Techniques, Methods in Enzymology, Vol. 152, Academic Press, Inc., San Diego, Calif. (Berger); Sambrook et al., Molecular Cloning—A Laboratory Manual, 2nd ed., Vol. 1-3 (1989); and Current Protocols in Molecular Biology, F. M. Ausubel et al., Eds., Current Protocols, a joint venture between Greene Publishing Associates, Inc. and John Wiley & Sons, Inc. (1994).

As used herein "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein, "polynucleotide" includes reference to a deoxyribopolynucleotide, ribopolynucleotide, or conservatively modified variants; the term may also refer to analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art.

The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms also may apply to conservatively modified variants and to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation. It will be appreciated, as is well known and as noted above, that polypeptides are not always entirely linear. For instance, polypeptides may be branched as a result of ubiquitization, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well. Further, this invention contemplates the use of both the methionine-containing and the methionine-less amino terminal variants of the protein of the invention.

As used herein "promoter" includes reference to a region of DNA upstream from the start of transcription and involved in recognition and binding of RNA polymerase and other proteins to initiate transcription. Examples of promoters under developmental control include promoters that preferentially initiate transcription in certain tissues, such as leaves, roots, or seeds. Such promoters are referred to as "tissue preferred". Promoters which initiate transcription only in certain tissue are referred to as "tissue specific". A "cell type" specific promoter primarily drives expression in certain cell types in one or more organs, for example, vascular cells in roots or leaves. An "inducible" or "repressible" promoter is a promoter which is under environmental control. Examples of environmental conditions that may affect transcription by inducible promoters include anaerobic conditions or the presence of light. Tissue specific, tissue preferred, cell type specific, and inducible promoters constitute the class of "non-constitutive" promoters. A "constitutive" promoter is a promoter which is active under most environmental conditions.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under-expressed or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements which permit transcription of a particular nucleic acid in a host cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The term "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass non-natural analogs of natural amino acids that can function in a similar manner as naturally occurring amino acids.

The term "selectively hybridizes" includes reference to hybridization, under stringent hybridization conditions, of a nucleic acid sequence to another nucleic acid sequence or other biologics. When utilizing a hybridization-based detection system, a nucleic acid probe is chosen that is complementary to a reference nucleic acid sequence, and then by selection of appropriate conditions the probe and the reference sequence selectively hybridize, or bind, to each other to form a duplex molecule.

The term "stringent conditions" or "stringent hybridization conditions" includes reference to conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences can be identified which are 100% complementary to the probe (homologous probing).

Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e. g., 10 to 50 nucleotides) and at least about 60° C. for long probes (e.g., greater than 50 nucleotides). Stringent conditions may also be achieved with the addition of destabilizing agents such as formamide. Specificity is typically the function of post-hybridization washes, the critical factors being the ionic strength and temperature of the final wash solution. For DNA/DNA hybrids, the thermal melting point (Tm) can be approximated from the equation of Meinkoth and Wahl, Anal. Biochem., 138: 267-284 (1984): Tm [° C.]=81.5+16.6 (log M)+0.41(% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The Tm is the temperature (under defined ionic strength and pH) at which 50% of a complementary target sequence hybridizes to a perfectly matched probe. Tm is reduced by about 1° C. for each 1% of mismatching; thus, Tm, hybridization and/or wash conditions can be adjusted to hybridize to sequences of the desired identity. For example, if sequences with >90% identity are sought, the Tm can be decreased 10° C. Generally, stringent conditions are selected to be about 5° C. lower than the Tm for the specific sequence and its complement at a defined ionic strength and pH. However, severely stringent conditions can utilize a hybridization and/or wash at 1 to 4° C. lower than the Tm; moderately stringent conditions can utilize a hybridization and/or wash at 6 to 10° C. lower than the Tm; low stringency conditions can utilize a hybridization and/or wash at 11 to 20° C. lower than the Tm. Using the equation, hybridization and wash compositions, and desired Tm, those of ordinary skill will understand that variations in the stringency of hybridization and/or wash solutions are inherently described. An extensive guide to the hybridization of nucleic acids is found in Tijssen, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, New York (1993); and Current Protocols in Molecular Biology, Chapter 2, Ausubel, et al., Eds., Greene Publishing and Wiley-Interscience, New York (1995).

As used herein, "transgenic animal, cell or tissue" includes reference to an animal which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, tissue, or organ, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional breeding methods or by naturally occurring events such as random cross-fertilization, non recombinant viral infection, non-recombinant bacterial transformation, non-recombinant transposition, or spontaneous mutation. "Mutation" as used herein includes without limitation, deletions, inversions, translocations, duplications, splice-donor site mutations, point-mutations or the like.

As used herein, "vector" includes reference to a nucleic acid used in transfection of a host cell and into which can be inserted a polynucleotide. Vectors are often replicons. Expression vectors permit transcription of a nucleic acid inserted therein.

The following terms are used to describe the sequence relationships between a polynucleotide/polypeptide of the present invention with a reference polynucleotide/polypeptide: (a)"reference sequence", (b)"comparison window", (c) "sequence identity", and (d) "percentage of sequence identity".

(a) As used herein, "reference sequence" is a defined sequence used as a basis for sequence comparison with a polynucleotide/polypeptide of the present invention. A reference sequence may be a subset or the entirety of a specified sequence; for example, as a segment of a full-length cDNA or gene sequence, or the complete cDNA or gene sequence.

(b) As used herein, "comparison window" includes reference to a contiguous and specified segment of a polynucleotide/polypeptide sequence, wherein the polynucleotide/polypeptide sequence may be compared to a reference sequence and wherein the portion of the polynucleotide/polypeptide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides/amino acids residues in length, and optionally can be 30, 40, 50, 100, or longer. Those of skill in the art understand that to avoid a high similarity to a reference sequence due to inclusion of gaps in the polynucleotide/polypeptide sequence, a gap penalty is typically introduced and is subtracted from the number of matches.

Methods of alignment of sequences for comparison are well-known in the art. Optimal alignment of sequences for comparison may be conducted by the local homology algorithm of Smith and Waterman, Adv. Appl. Math. 2: 482 (1981); by the homology alignment algorithm of Needleman and Wunsch, J. Mol. Biol. 48: 443 (1970); by the search for similarity method of Pearson and Lipman, Proc. Natl. Acad. Sci. 85: 2444 (1988); and by computerized implementations of these algorithms, including, but not limited to: CLUSTAL in the PC/Gene program by Intelligenetics, Mountain View, Calif.; GAP, BESTFIT, BLAST, FASTA, and TFASTA, and related programs in the GCG Wisconsin Genetics Software Package, Version 10 (available from Accelrys Inc., 9685 Scranton Road, San Diego, Calif., USA). The CLUSTAL program is well described by Higgins and Sharp, Gene 73: 237-244 (1988); Higgins and Sharp, CABIOS 5: 151-153 (1989); Corpet, et al., Nucleic Acids Research 16: 10881-90 (1988); Huang, et al., Computer Applications in the Biosciences 8: 155-65 (1992), and Pearson, et al., Methods in Molecular Biology 24: 307-331 (1994).

The BLAST family of programs that can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Current Protocols in Molecular Biology, Chapter 19, Ausubel, et al., Eds., Greene Publishing and Wiley-Interscience, New York (1995); Altschul et al., J. Mol. Biol., 215: 403-410 (1990); and, Altschul et al., Nucleic Acids Res. 25: 3389-3402 (1997). Software for performing BLAST analyses is publicly available, for example through the National Center for Biotechnology Information (ncbi.nlm.nih.gov/). This algorithm has been thoroughly described in a number of publications. See, e.g., Altschul S F et al., Gapped BLAST and PSI-BLAST: a new generation of protein database search programs, 25 NUCLEIC ACIDS RES. 3389 (1997); National Center for Biotechnology Information, THE NCBI HANDBOOK [INTERNET], Chapter 16: The BLAST Sequence Analysis Tool (McEntyre J, Ostell J, eds., 2002), available at http://www.ncbi.nlm.nih.gov/books/NBK21097/pdf/ch16.pdf. The BLASTP program for amino acid sequences has also been thoroughly described (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul, Proc. Nat'l. Acad. Sci. USA 90: 5873-5877 (1993)). A number of low-complexity filter programs can be employed to reduce such low-complexity alignments. For example, the SEG (Wooten and Federhen, Comput. Chem., 17: 149-163 (1993)) and XNU (Claverie and States, Comput. Chem., 17: 191-201 (1993)) low-complexity filters can be employed alone or in combination.

Unless otherwise stated, nucleotide and protein identity/similarity values provided herein are calculated using GAP (GCG Version 10) under default values. GAP (Global Alignment Program) can also be used to compare a polynucleotide or polypeptide of the present invention with a reference sequence. GAP uses the algorithm of Needleman and Wunsch (J. Mol. Biol. 48: 443-453, 1970) to find the alignment of two complete sequences that maximizes the number of matches and minimizes the number of gaps. GAP represents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff & Henikoff (1989) Proc. Natl. Acad. Sci. USA 89: 10915).

Multiple alignment of the sequences can be performed using the CLUSTAL method of alignment (Higgins and Sharp (1989) CABIOS. 5: 151-153) with the default parameters (GAPPENALTY=10, GAP LENGTH PENALTY=10). Default parameters for pairwise alignments using the CLUSTAL method include KTUPLE 1, GAP PENALTY=3, WINDOW=5 and DIAGONALS SAVED=5.

(c) As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions may be calculated according to the algorithm of Meyers and Miller, Computer Applic. Biol. Sci., 4: 11-17 (1988), for example as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

As used herein, the term "porcine" refers to species which are part of the *Sus* genus of the Suidae family. This includes domestic pigs of any breed. Thus, any of the various pig, swine, or hog species, whether male or female, are included in the term, and adult, fetal and new-born animals are intended to be covered. The term does not denote a particular age. One example of a porcine subject is a member of the Yorkshire breed pig population.

The term "genetic marker" refers to a variable nucleotide sequence (polymorphic) that is present in porcine genomic DNA on a chromosome and that is identifiable with specific oligonucleotides. For example, such a variable nucleotide sequence is distinguishable by nucleic acid amplification and observation of a difference in size or sequence of nucleotides due to the polymorphism. In useful embodiments, such genetic markers may be identified by several techniques known to those skilled in the art, and include typing of microsatellites or short tandem repeats (STR), restriction fragment length polymorphisms (RFLP), detection of deletion or insertion sites, and random amplified polymorphic DNA (RAPD) as well as the typing of single nucleotide polymorphism (SNP) by methods including restriction-fragment-length polymerase chain reaction, allele-specific oligomer hybridization, oligomer-specific ligation assays, mini-sequencing, direct sequencing, fluorescence-detected 5'-exonuclease assays, and hybridization with PNA and LNA probes, single nucleotide primer extension, and others. However, it will be appreciated that other genetic markers and techniques may be applied in accordance with the invention.

SCID in Pigs

According to one aspect of the invention, the causative mutation of pigs with severe combined immunodeficiency disease (SCID) has been identified. This can be used to identify and select for and create an animal model population wherein the pigs possess a gene having one or more mutations that result in reduced numbers or function of immune effectors. "Immune effectors" refers to cells or products of cells that mediate immune functions. Immune effector cells include monocytes, macrophages, dendritic cells, natural killer cells, and lymphocytes. Non-cellular immune effectors include antibodies and immunoglobulins or fragments thereof, cytokines, chemokines, and complement. In a more preferred embodiment, the mutations of the invention result in reduced presence or activity of T-lymphocytes, B-lymphocytes, and/or antibodies and immunoglobulins or fragments thereof.

In a preferred embodiment, the mutations are in the Artemis gene, resulting in reduced expression or function of the Artemis protein gene product. The mutations may be one or more of an insertion, a deletion, an inversion, or a single nucleotide polymorphism in the Artemis gene, including, for example, one ore more single nucleotide polymorphisms including an a G to A substitution at position 25,487 or a G to A substitution at position 31,214, as determined by reference to SEQ ID NO:45.

In one aspect of the invention, the mutations of the present invention result in loss of expression of the gene product encoded by the Artemis gene, or expression of a truncated gene product encoded by the Artemis gene. The loss of expression or truncation may be due to alterations at one or more splice sites in the Artemis gene.

In another aspect of the invention, pigs are provided that have severe combined immunodeficiency disease (SCID). Such SCID-affected pigs may have or more of an insertion, a deletion, an inversion, or a single nucleotide polymorphism in the Artemis gene, including a G to A substitution at position 25,487 or a G to A substituition at position 31,214, as determined by reference to SEQ ID NO:45.

In another aspect of the invention, non-naturally occurring nucleotide sequences encoding Artemis protein are provided. In one embodiment, the nucleotide sequence may be provided to an individual affected by SCID, for example by introducing a vector comprising the nucleotide sequence operatively linked to a heterologous promoter sequence. In one embodiment, the nucleotide sequence is SEQ ID NO:5, or encodes a polynucleotide of SEQ ID NO:6.

In another aspect of the invention, pigs are provided with SCID comprising at least one heterologous gene encoding a disruption of the endogenous Artemis gene of said animal, wherein said disruption inactivates said gene.

In a further aspect, the invention provides porcine semen comprising sperm cells from a porcine subject with SCID, or a genetically modified primary cell or embryo, comprising one or more of an insertion, a deletion, an inversion, or a single nucleotide polymorphism in the Artemis gene of said animal, including one or more of G to A substitution at position 25,487 or a G to A substitution at position 31,214, as determined by reference to SEQ ID NO:45. In a further embodiment, the invention provides a pig or pigs produced from the sperm, cell or embryo.

Genetic Tests

The invention includes the discovery of the causative mutation for SCID in pigs. This can be used to develop genetic tests to screen for the mutation or mutations in genetic disequilibrium to the same to identify the presence of SCID in a biological sample from a pig. This allows one to create test populations of pigs to test for agents which ameliorate the disease, or to identify and treat those subject susceptible to the same, or to cull subjects from a breeding population based upon early detection. The method according to the invention includes the provision of a sample of porcine genetic material. Such porcine genetic (DNA) material may be provided by any conventional method or means. The porcine DNA material may for example be extracted, isolated, and purified from blood (e.g., fresh or frozen), tissue samples (e.g., spleen, buccal smears), hair samples containing follicular cells, or semen.

As previously described, the method of the present invention further comprises a step of detecting in the genetic material the presence or absence of a genetic marker that is linked to or preferably is the causative mutation for SCID. In a more preferred embodiment, the invention provides methods for detecting mutations onto chromosome 10 associated with the SCID phenotype. In an even more preferred embodiment, the invention provides methods for detecting mutations to the Artemis gene, including one or more of a G to A substitution at position 25,487 or a G to A substitution at position 31,214, as determined by reference to SEQ ID NO:45. In another embodiment, the invention provides methods for detecting one or more SNPs in the 5' and 3' regions flanking the Artemis gene, including an A→C substitution at position 51153137 of chromosome 10 (reverse complement of nucleotides at position 20 of SEQ ID NO:12 in the region amplified by the primer pairs of SEQ ID NOS: 11 and 12; and position 19 of SEQ ID NO:14 in the region amplified by the primer pairs of SEQ ID NOS:13 and 14); a G→A substitution at position 51812252 of chromosome 10 (nucleotide at position 25 of SEQ ID NO:17 in the region amplified by the primer pairs of SEQ ID NOS: 16 and 17, and, reverse complement of nucleotide at position 26 of SEQ ID NO:16, respectively, in the region amplified by the primer pairs of SEQ ID NOS: 15 and 16); an A→G substitution at position 51975024 of chromosome 10 (reverse complement of nucleotide at position 19 of SEQ ID NO:20 in the region amplified by the primer pairs of SEQ ID NOS:19 and 20; and nucleotide at position 18 of SEQ ID NO:21, in the region amplified by the primer pairs of SEQ ID NOS:21 and 22); an A→C substitution at position 52066694 of chromosome 10 (reverse complement of nucleotide at position 23 of SEQ ID NO:24 in the region amplified by the primer pairs of SEQ ID NOS:23 and 24; and reverse complement of nucleotide at position 23 of SEQ ID NO: 26 in the region amplified by the primer pairs of SEQ ID NOS:25 and 26); a G→A substitution at position 52086867 of chromosome 10 (reverse complement of nucleotide at position 23 of SEQ ID NO:28 in the region amplified by the primer pairs of SEQ ID NOS:27 and 28; and reverse complement of nucleotide at position 23 of SEQ ID NO:30 in the region amplified by the primer pairs of SEQ ID NOS:29 and 30); A→C substitution at position 52109172 of chromosome 10 (reverse complement of nucleotide at position 18 of SEQ ID NO:32 in the region amplified by the primer pairs of SEQ ID NOS:31 and 32; and reverse complement of nucleotide at position 18 of SEQ ID NO: 34 in the region amplified by the primer pairs of SEQ ID NOS:33 and 34); and/or G→A substitution at position 52174549 of chromosome 10 (reverse complement of nucleotide at position 23 of SEQ ID NO:36 in the region amplified by the primer pairs of SEQ ID NOS:35 and 36; and reverse complement of nucleotide at position 23 of SEQ ID NO:38 in the region amplified by the primer pairs of SEQ ID NOS:37 and 38).

Subjects that have a single allele with mutations to the Artemis gene, and are therefore heterozygous for a SCID mutation, are referred to as "SCID-carrier" subjects. Subjects that have two alleles with mutations to the Artemis gene resulting in decreased expression or activity of the Artemis protein gene product, are referred to as "SCID-affected" subjects or as "SCID pig(s)". A SCID-affected subject may have two alleles with the same mutation or mutations, or two alleles with different mutation or mutations.

In order to detect if the genetic marker is present in the genetic material, standard methods well known to persons skilled in the art may be applied, for example by the use of nucleic acid amplification. In order to determine if the genetic marker is genetically linked to SCID, a lod score can be applied. A lod score, which is also sometimes referred to as $Z_{max}$, indicates the probability (the logarithm of the ratio of the likelihood) that a genetic marker locus and a specific gene locus are linked at a particular distance. Lod scores may be calculated by applying a computer program such as the MLINK program of the LINKAGE package (Lathrop et al., 1985). A lod score of greater than 3.0 is considered to be significant evidence for linkage between the genetic marker and the SCID trait or gene locus.

In one aspect of the invention, determining whether a pig is a SCID-affected or SCID-carrier may be carried out by obtaining a sample of genetic material from one or more pigs, and determining whether one or more mutations are present that cause reduced expression or activity of the Artmeis protein. The method may further include correlating whether an association exists between said allele and SCID in the pig. In a further aspect of the invention, the method may comprise detection of one or more of a G to A substitution at position 25,487 or a G to A substitution at position 31,214, as determined by reference to SEQ ID NO:45, or one or more SNPs in the 5' and 3' regions flanking the Artemis gene, including an A→C substitution at position 51153137 of chromosome 10 (reverse complement of nucleotides at position 20 of SEQ ID NO:12 in the region amplified by the primer pairs of SEQ ID NOS: 11 and 12; and position 19 of SEQ ID NO:14 in the region amplified by the primer pairs of SEQ ID NOS:13 and 14); a G→A substitution at position 51812252 of chromosome 10 (nucleotide at position 25 of SEQ ID NO:17 in the region amplified by the primer pairs of SEQ ID NOS: 16 and 17, and, reverse complement of nucleotide at position 26 of SEQ ID NO:16, respectively, in the region amplified by the primer pairs of SEQ ID NOS: 15 and 16); an A→G substitution at position 51975024 of chromosome 10 (reverse complement of nucleotide at position 19 of SEQ ID NO:20 in the region amplified by the primer pairs of SEQ ID NOS:19 and 20; and nucleotide at position 18 of SEQ ID NO:21, in the region amplified by the primer pairs of SEQ ID NOS:21 and 22); an A→C substitution at position 52066694 of chromosome 10 (reverse complement of nucleotide at position 23 of SEQ ID NO:24 in the region amplified by the primer pairs of SEQ ID NOS:23 and 24; and reverse complement of nucleotide at position 23 of SEQ ID NO: 26 in the region amplified by the primer pairs of SEQ ID NOS:25 and 26); a G→A substitution at position 52086867 of chromosome 10 (reverse complement of nucleotide at position 23 of SEQ ID NO:28 in the region amplified by the primer pairs of SEQ ID NOS:27 and 28; and reverse complement of nucleotide at position 23 of SEQ ID NO:30 in the region amplified by the primer pairs of SEQ ID NOS:29 and 30); A→C substitution at position 52109172 of chromosome 10 (reverse complement of nucleotide at position 18 of SEQ ID NO:32 in the region amplified by the primer pairs of SEQ ID NOS:31 and 32; and reverse complement of nucleotide at position 18 of SEQ ID NO: 34 in the region amplified by the primer pairs of SEQ ID NOS:33 and 34); and/or G→A substitution at position 52174549 of chromosome 10 (reverse complement of nucleotide at position 23 of SEQ ID NO:36 in the region amplified by the primer pairs of SEQ ID NOS:35 and 36; and reverse complement of nucleotide at position 23 of SEQ ID NO:38 in the region amplified by the primer pairs of SEQ ID NOS:37 and 38). In an even more preferred embodiment, such detection is carried out using one or more of the primer pairs disclosed in Table 1, below.

In another aspect of the invention, detection of a mutation or mutations of the invention is carried out using oligonucleotides that hybridizes to either a normal or a mutant Artemis gene that is capable of detecting one or more mutations selected from the group consisting of a G to A substitution at position 25,487 or a G to A substitution at position 31,214, as determined by reference to SEQ ID NO:45., or one or more SNPs in the 5' and 3' regions flanking the Artemis gene, including an A→C substitution at position 51153137 of chromosome 10 (reverse complement of nucleotides at position 20 of SEQ ID NO:12 in the region amplified by the primer pairs of SEQ ID NOS: 11 and 12; and position 19 of SEQ ID NO:14 in the region amplified by the primer pairs of SEQ ID NOS:13 and 14); a G→A substitution at position 51812252 of chromosome 10 (nucleotide at position 25 of SEQ ID NO:17 in the region amplified by the primer pairs of SEQ ID NOS: 16 and 17, and, reverse complement of nucleotide at position 26 of SEQ ID NO:16, respectively, in the region amplified by the primer pairs of SEQ ID NOS: 15 and 16); an A→G substitution at position 51975024 of chromosome 10 (reverse complement of nucleotide at position 19 of SEQ ID NO:20 in the region amplified by the primer pairs of SEQ ID NOS:19 and 20; and nucleotide at position 18 of SEQ ID NO:21, in the region amplified by the primer pairs of SEQ ID NOS:21 and 22); an A→C substitution at position 52066694 of chromosome 10 (reverse complement of nucleotide at position 23 of SEQ ID NO:24 in the region amplified by the primer pairs of SEQ ID NOS:23 and 24; and reverse complement of nucleotide at position 23 of SEQ ID NO: 26 in the region amplified by the primer pairs of SEQ ID NOS:25 and 26); a G→A substitution at position 52086867 of chromosome 10 (reverse complement of nucleotide at position 23 of SEQ ID NO:28 in the region amplified by the primer pairs of SEQ ID NOS:27 and 28; and reverse complement of nucleotide at position 23 of SEQ ID NO:30 in the region amplified by the primer pairs of SEQ ID NOS:29 and 30); A→C substitution at position 52109172 of chromosome 10 (reverse complement of nucleotide at position 18 of SEQ ID NO:32 in the region amplified by the primer pairs of SEQ ID NOS:31 and 32; and reverse complement of nucleotide at position 18 of SEQ ID NO: 34 in the region amplified by the primer pairs of SEQ ID NOS:33 and 34); and/or G→A substitution at position 52174549 of chromosome 10 (reverse complement of nucleotide at position 23 of SEQ ID NO:36 in the region amplified by the primer pairs of SEQ ID NOS:35 and 36; and reverse complement of nucleotide at position 23 of SEQ ID NO:38 in the region amplified by the primer pairs of SEQ ID NOS:37 and 38).

It will be appreciated that, in order to detect the specific allele present in a porcine subject with SCID, more than one genetic marker may be applied in accordance with the invention. Thus, at least one marker can be a combination of two or more genetic markers that are shown to be informative whereby the accuracy of the test can be increased.

Genetic markers of the present invention can be made using different methodologies known to those skilled in the art. Thus, it will be understood that, with the knowledge presented herein and the nucleotide sequences of the porcine Artemis gene, which are known and publically available, that additional markers in this gene may be identified and used according to the invention.

Genotyping is based on the analysis of genomic DNA that can be provided by using standard DNA extraction methods as described herein. When the genomic DNA is isolated and purified, nucleic acid amplification (e.g. polymerase chain reaction) can be used to amplify the region of the DNA corresponding to each genetic marker to be used in the analysis for detecting the presence in a porcine subject of a genetic marker associated with SCID.

In another embodiment, the invention comprises a method for identifying genetic markers for SCID in general. Once a major effect gene has been identified, it is expected that other variations present in the same gene, allele or in sequences in useful linkage disequilibrium therewith, may be used to identify similar effects on these traits without undue experimentation. The identification of other such genetic variation, once a major effect gene has been discovered, represents no more than routine screening and optimization of parameters well known to those of skilled in the art and is intended to be within the scope of this invention. This can include other lines, breeds, or even other meat animals.

The present invention provides a method of genotyping an animal comprising a polynucleotide of the present invention. Genotyping provides a means of distinguishing homologs of a chromosome pair and can be used to differentiate segregants in an animal population. Molecular marker methods can be used for phylogenetic studies, characterizing genetic relationships among animal species, identifying crosses or somatic hybrids, localizing chromosomal segments affecting monogenic traits, map based cloning, and the study of quantitative inheritance. The particular method of genotyping in the present invention may employ any number of molecular marker analytic techniques described hereinafter.

In the present invention, the nucleic acid probes may be employed for molecular marker mapping of nuclear genomes which hybridize, under selective hybridization conditions, to the variant polynucleotide of the present invention. In preferred embodiments, the probes are selected from polynucleotides of the present invention. Typically, these probes are cDNA probes or restriction enzyme treated (e.g., PST I) genomic clones. The length of the probes is typically at least 15 bases in length, more preferably at least 20, 25, 30, 35, 40, or 50 bases in length. Generally, however, the probes are less than about 1 kilobase in length. Preferably, the probes are single copy probes that hybridize to a unique locus in a haploid chromosome complement.

Methods for detecting or differentiating polymorphic or allelic variants of polynucleotides would be known to one of ordinary skill in the art, including restriction fragment length polymorphism (RFLP); single stranded conformation analysis (SSCA); denaturing gradient gel electrophoresis (DGGE); RNase protection assays; allele-specific oligonucleotides (ASOs); the use of proteins which recognize nucleotide mismatches, such as the E. coli mutS protein; and allele-specific PCR. Other approaches based on the detection of mismatches between the two complementary DNA strands include clamped denaturing gel electrophoresis (CDGE); heteroduplex analysis (HA); and chemical mismatch cleavage (CMC). Thus, the present invention further provides a method of genotyping comprising the steps of contacting, under stringent hybridization conditions, a sample suspected of comprising a polynucleotide of the present invention with a nucleic acid probe. The nucleic acid probe selectively hybridizes, under stringent conditions, to a subsequence of a polynucleotide of the present invention comprising a polymorphic marker. Selective hybridization of the nucleic acid probe to the polymorphic marker nucleic acid sequence yields a hybridization complex. Detection of the hybridization complex indicates the presence of that polymorphic marker in the sample. In preferred embodiments, the nucleic acid probe comprises a polynucleotide of the present invention.

The following is a general overview of techniques that can be used to assay for the polymorphisms of the invention.

In the present invention, a sample of genetic material is obtained from an animal. Samples can be obtained from blood, tissue, semen, etc. Generally, peripheral blood cells are used as the source, and the genetic material is DNA. A sufficient amount of cells are obtained to provide a sufficient amount of DNA for analysis. This amount will be known or readily determinable by those skilled in the art. The DNA is isolated from the blood cells by techniques known to those skilled in the art.

Artemis Protein and Artemis-Encoding Polynucleotides

In one aspect of the invention, novel polynucleotide sequences are provided. These sequences relate to the Artemis gene, and include novel mutations that result in, or are related to, a loss of expression or function of Artemis protein causing SCID. These sequences include non-naturally occurring cDNA sequences, as well as novel sequences encompassing non-coding regions of the Artemis gene and surrounding untranslated regions (UTRs). In one embodiment, the sequences include, for example, SEQ ID NOS:1, 3, 5, and 7-10. In another embodiment, the sequences include the regions amplified by the primer pairs provided in Table 1 (SEQ ID NOS:11-38).

In another aspect, the invention encompasses these novel sequences within polynucleotide constructs such as, for example, vectors. In one embodiment, these constructs may be used to generate cells or animals with reduced Artemis expression or activity. In another aspect, these constructs may be used to enhance Artemis expression or activity, or to correct an existing defect in the expression or activity of endogenous Artemis in a cell or organism. In one embodiment, the constructs may be provided as a pharmaceutical composition for the treatment of SCID.

Isolation and Amplification of Nucleic Acid

Samples of genomic DNA are isolated from any convenient source, including saliva, buccal cells, hair roots, blood, cord blood, amniotic fluid, interstitial fluid, peritoneal fluid, chorionic villus, and any other suitable cell or tissue sample with intact interphase nuclei or metaphase cells. The cells can be obtained from solid tissue, as from a fresh or preserved organ, or from a tissue sample or biopsy. The sample can contain compounds that are not naturally intermixed with the biological material, such as preservatives, anticoagulants, buffers, fixatives, nutrients, antibiotics, or the like.

Methods for isolation of genomic DNA from these various sources are described in, for example, Kirby, *DNA Fingerprinting, An Introduction*, W.H. Freeman & Co. New York (1992). Genomic DNA can also be isolated from cultured primary or secondary cell cultures or from transformed cell lines derived from any of the aforementioned tissue samples.

Samples of animal RNA can also be used. RNA can be isolated from tissues expressing the major effect gene of the invention, as described in Sambrook et al., supra. RNA can be total cellular RNA, mRNA, poly A+RNA, or any combination thereof. For best results, the RNA is purified, but can also be unpurified cytoplasmic RNA. RNA can be reverse transcribed to form DNA, which is then used as the amplification template, so that the PCR indirectly amplifies a specific population of RNA transcripts. See, e.g., Sambrook, supra, Kawasaki et al., Chapter 8 in *PCR Technology*, (1992) supra, and Berg et al., *Hum. Genet.* 85:655-658 (1990).

In one aspect, nucleic acid may be obtained and amplified to determine the presence or absence of one or more mutations associated with SCID in a pig. In a preferred embodiment, nucleic acid may be obtained and amplified to detect one or more of a G to A substitution at position 25,487 or a G to A substitution at position 31,214, as determined by reference to SEQ ID NO:45, or one or more SNPs in the 5' and 3' regions flanking the Artemis gene, including an A→C substitution at position 51153137 of chromosome 10 (reverse complement of nucleotides at position 20 of SEQ ID NO:12 in the region amplified by the primer pairs of SEQ ID NOS: 11 and 12; and position 19 of SEQ ID NO:14 in the region amplified by the primer pairs of SEQ ID NOS:13 and 14); a G→A substitution at position 51812252 of chromosome 10 (nucleotide at position 25 of SEQ ID NO:17 in the region amplified by the primer pairs of SEQ ID NOS: 16 and 17, and, reverse complement of nucleotide at position 26 of SEQ ID NO:16, respectively, in the region amplified by the primer pairs of SEQ ID NOS: 15 and 16); an A→G substitution at position 51975024 of chromosome 10 (reverse complement of nucleotide at position 19 of SEQ ID NO:20 in the region amplified by the primer pairs of SEQ ID NOS:19 and 20; and nucleotide at position 18 of SEQ ID NO:21, in the region amplified by the primer pairs of SEQ ID NOS:21 and 22); an A→C substitution at position 52066694 of chromosome 10 (reverse complement of nucleotide at position 23 of SEQ ID NO:24 in the region amplified by the primer pairs of SEQ ID NOS:23 and 24;

and reverse complement of nucleotide at position 23 of SEQ ID NO: 26 in the region amplified by the primer pairs of SEQ ID NOS:25 and 26); a G→A substitution at position 52086867 of chromosome 10 (reverse complement of nucleotide at position 23 of SEQ ID NO:28 in the region amplified by the primer pairs of SEQ ID NOS:27 and 28; and reverse complement of nucleotide at position 23 of SEQ ID NO:30 in the region amplified by the primer pairs of SEQ ID NOS:29 and 30); A→C substitution at position 52109172 of chromosome 10 (reverse complement of nucleotide at position 18 of SEQ ID NO:32 in the region amplified by the primer pairs of SEQ ID NOS:31 and 32; and reverse complement of nucleotide at position 18 of SEQ ID NO: 34 in the region amplified by the primer pairs of SEQ ID NOS:33 and 34); and/or G→A substitution at position 52174549 of chromosome 10 (reverse complement of nucleotide at position 23 of SEQ ID NO:36 in the region amplified by the primer pairs of SEQ ID NOS:35 and 36; and reverse complement of nucleotide at position 23 of SEQ ID NO:38 in the region amplified by the primer pairs of SEQ ID NOS:37 and 38). In an even more preferred embodiment, such detection is carried out using one or more of the primer pairs disclosed in Table 1, below.

PCR Amplification

The most common means for amplification is polymerase chain reaction (PCR), as described in U.S. Pat. Nos. 4,683, 195, 4,683,202, 4,965,188 each of which is hereby incorporated by reference. Without limitation, PCR may be used to amplify genetic material obtained from blood cells, tissues, or other physiological sources. One of skill in the art would understand that if PCR is used to amplify the target regions in blood cells, for example, the blood can be fresh or frozen, heparinized, or untreated, or otherwise processed. Cells in other physiological fluids may also be assayed.

One of skill in the art would understand how to process fresh or preserved tissues. For example, and without limitation, tissues may be roughly minced using a sterile, disposable scalpel and a sterile needle (or two scalpels) in a 5 mm Petri dish. Procedures for removing paraffin from tissue sections are described in a variety of specialized handbooks well known to those skilled in the art.

To amplify a target nucleic acid sequence in a sample by PCR, the sequence must be accessible to the components of the amplification system. One of ordinary skill in the art would understand various methods for isolating target DNA. For example, one method useful for isolating target DNA from relatively large samples is crude extraction. Briefly, mononuclear cells from samples of blood, amniocyte from amniotic fluid, cultured chorionic villus cells, or the like are isolated by layering on sterile Ficoll-Hypaque gradient by standard procedures. Interphase cells are collected and washed three times in sterile phosphate buffered saline before DNA extraction. The cells are resuspended ($10^6$ nucleated cells per 100 µl) in a buffer of 50 mM Tris-HCl (pH 8.3), 50 mM KCl 1.5 mM $MgCl_2$, 0.5% Tween 20, 0.5% NP40 supplemented with 100 µg/ml of proteinase K. After incubating at 56° C. for 2 hr. the cells are heated to 95° C. for 10 min to inactivate the proteinase K and immediately moved to wet ice (snap-cool). If gross aggregates are present, another cycle of digestion in the same buffer should be undertaken. Ten µl of this extract is used for amplification.

One of ordinary skill in the art would understand methods for extracting DNA from tissues. For example, and without limitation, when extracting DNA from tissues, such as chorionic villus cells or confluent cultured cells, the amount of the above mentioned buffer with proteinase K may vary according to the size of the tissue sample. The extract is incubated for 4-10 hrs at 50°-60° C. and then at 95° C. for 10 minutes to inactivate the proteinase. During longer incubations, fresh proteinase K should be added after about 4 hr at the original concentration.

When the sample contains a small number of cells, extraction may be accomplished by methods as described in Higuchi, "Simple and Rapid Preparation of Samples for PCR", in *PCR Technology*, Ehrlich, H. A. (ed.), Stockton Press, New York, which is incorporated herein by reference. PCR can be employed to amplify target regions in very small numbers of cells (1000-5000) derived from individual colonies from bone marrow and peripheral blood cultures. The cells in the sample are suspended in 20 µl of PCR lysis buffer (10 mM Tris-HCl (pH 8.3), 50 mM KCl, 2.5 mM $MgCl_2$, 0.1 mg/ml gelatin, 0.45% NP40, 0.45% Tween 20) and frozen until use. When PCR is to be performed, 0.6 µl of proteinase K (2 mg/ml) is added to the cells in the PCR lysis buffer. The sample is then heated to about 60° C. and incubated for 1 hr. Digestion is stopped through inactivation of the proteinase K by heating the samples to 95° C. for 10 min and then cooling on ice.

A relatively easy procedure for extracting DNA for PCR is a salting out procedure adapted from the method described by Miller et al., *Nucleic Acids Res.* 16:1215 (1988), which is incorporated herein by reference. Mononuclear cells are separated on a Ficoll-Hypaque gradient. The cells are resuspended in 3 ml of lysis buffer (10 mM Tris-HCl, 400 mM NaCl, 2 mM $Na_2$ EDTA, pH 8.2). Fifty µl of a 20 mg/ml solution of proteinase K and 150 µl of a 20% SDS solution are added to the cells and then incubated at 37° C. overnight. Rocking the tubes during incubation will improve the digestion of the sample. If the proteinase K digestion is incomplete after overnight incubation (fragments are still visible), an additional 50 µl of the 20 mg/ml proteinase K solution is mixed in the solution and incubated for another night at 37° C. on a gently rocking or rotating platform. Following adequate digestion, one ml of a 6 M NaCl solution is added to the sample and vigorously mixed. The resulting solution is centrifuged for 15 minutes at 3000 rpm. The pellet contains the precipitated cellular proteins, while the supernatant contains the DNA. The supernatant is removed to a 15 ml tube that contains 4 ml of isopropanol. The contents of the tube are mixed gently until the water and the alcohol phases have mixed and a white DNA precipitate has formed. The DNA precipitate is removed and dipped in a solution of 70% ethanol and gently mixed. The DNA precipitate is removed from the ethanol and air-dried. The precipitate is placed in distilled water and dissolved.

Kits for the extraction of high-molecular weight DNA for PCR include a Genomic Isolation Kit A.S.A.P. (Boehringer Mannheim, Indianapolis, Ind.), Genomic DNA Isolation System (GIBCO BRL, Gaithersburg, Md.), Elu-Quik DNA Purification Kit (Schleicher & Schuell, Keene, N.H.), DNA Extraction Kit (Stratagene, LaJolla, Calif.), TurboGen Isolation Kit (Invitrogen, San Diego, Calif.), DNeasy Blood & Tissue Kit (Qiagen Inc, Valencia, Calif.), and the like. Use of these kits according to the manufacturer's instructions is generally acceptable for purification of DNA prior to practicing the methods of the present invention.

The concentration and purity of the extracted DNA can be determined by spectrophotometric analysis of the absorbance of a diluted aliquot at 260 nm and 280 nm. After extraction of the DNA, PCR amplification may proceed. The first step of each cycle of the PCR involves the separation of the nucleic acid duplex formed by the primer extension. Once the strands are separated, the next step in PCR involves hybridizing the separated strands with primers that flank the target sequence. The primers are then extended to form complementary copies of the target strands. For successful PCR amplification, the primers are designed so that the position at which each primer hybridizes along a duplex sequence is such that an extension product synthesized from one primer, when separated from the template (complement), serves as a template for the extension of the other primer. The cycle of denaturation, hybridization, and extension is repeated as many times as necessary to obtain the desired amount of amplified nucleic acid.

In a particularly useful embodiment of PCR amplification, strand separation is achieved by heating the reaction to a sufficiently high temperature for a sufficient time to cause the denaturation of the duplex but not to cause an irreversible denaturation of the polymerase (see U.S. Pat. No. 4,965,188, incorporated herein by reference). Typical heat denaturation involves temperatures ranging from about 80° C. to 105° C. for times ranging from seconds to minutes. Strand separation, however, can be accomplished by any suitable denaturing method including physical, chemical, or enzymatic means. Strand separation may be induced by a helicase, for example, or an enzyme capable of exhibiting helicase activity. For example, the enzyme RecA has helicase activity in the presence of ATP. The reaction conditions suitable for strand separation by helicases are known in the art (see Kuhn Hoffman-Berling, 1978, *CSH-Quantitative Biology*, 43:63-67; and Radding, 1982, *Ann. Rev. Genetics* 16:405-436, each of which is incorporated herein by reference).

Template-dependent extension of primers in PCR is catalyzed by a polymerizing agent in the presence of adequate amounts of four deoxyribonucleotide triphosphates (typically dATP, dGTP, dCTP, and dTTP) in a reaction medium comprised of the appropriate salts, metal cations, and pH buffering systems. Suitable polymerizing agents are enzymes known to catalyze template-dependent DNA synthesis. In some cases, the target regions may encode at least a portion of a protein expressed by the cell. In this instance, mRNA may be used for amplification of the target region. Alternatively, PCR can be used to generate a cDNA library from RNA for further amplification, the initial template for primer extension is RNA. Polymerizing agents suitable for synthesizing a complementary, copy-DNA (cDNA) sequence from the RNA template are reverse transcriptase (RT), such as avian myeloblastosis virus RT, Moloney murine leukemia virus RT, or *Therms thermophilus* (Tth) DNA polymerase, a thermostable DNA polymerase with reverse transcriptase activity marketed by Perkin Elmer Cetus, Inc. Typically, the genomic RNA template is heat degraded during the first denaturation step after the initial reverse transcription step leaving only DNA template. Suitable polymerases for use with a DNA template include, for example, *E. coli* DNA polymerase I or its Klenow fragment, T4 DNA polymerase, Tth polymerase, and Taq polymerase, a heat-stable DNA polymerase isolated from *Thermus aquaticus* and commercially available from Perkin Elmer Cetus, Inc. The latter enzyme is widely used in the amplification and sequencing of nucleic acids. The reaction conditions for using Taq polymerase are known in the art and are described in Gelfand, 1989, *PCR Technology*, supra.

Allele Specific PCR

Allele-specific PCR differentiates between target regions differing in the presence of absence of a variation or polymorphism. PCR amplification primers are chosen that bind only to certain alleles of the target sequence. This method is described by Gibbs, *Nucleic Acid Res.* 17:12427-2448 (1989).

Allele Specific Oligonucleotide Screening Methods

Further diagnostic screening methods employ the allele-specific oligonucleotide (ASO) screening methods, as described by Saiki et al., *Nature* 324:163-166 (1986). Oligonucleotides with one or more base pair mismatches are generated for any particular allele. ASO screening methods detect mismatches between variant target genomic or PCR amplified DNA and non-mutant oligonucleotides, showing decreased binding of the oligonucleotide relative to a mutant oligonucleotide. Oligonucleotide probes can be designed that under low stringency they will bind to both polymorphic forms of the allele, but at high stringency, bind to the allele to which they correspond. Alternatively, stringency conditions can be devised in which an essentially binary response is obtained—an ASO corresponding to a variant form of the target gene will hybridize to that allele, and not to the wild type allele.

Ligase Mediated Allele Detection Method

Target regions of a test subject's DNA can be compared with target regions in unaffected and affected family members by ligase-mediated allele detection. See Landegren et al., *Science* 241:107-1080 (1988). Ligase may also be used to detect point mutations in the ligation amplification reaction described in Wu et al., *Genomics* 4:560-569 (1989). The ligation amplification reaction (LAR) utilizes amplification of specific DNA sequence using sequential rounds of template dependent ligation as described in Wu, supra, and Barany, *Proc. Nat. Acad. Sci.* 88:189-193 (1990).

Denaturing Gradient Gel Electrophoresis

Amplification products generated using the polymerase chain reaction can be analyzed by the use of denaturing gradient gel electrophoresis. Different alleles can be identified based on the different sequence-dependent melting properties and electrophoretic migration of DNA in solution. DNA molecules melt in segments, termed melting domains, under conditions of increased temperature or denaturation. Each melting domain melts cooperatively at a distinct, base-specific melting temperature (Tm). Melting domains are at least 20 base pairs in length, and may be up to several hundred base pairs in length.

Differentiation between alleles based on sequence specific melting domain differences can be assessed using polyacrylamide gel electrophoresis, as described in Chapter 7 of Erlich, ed., PCR Technology, Principles and Applications for *DNA Amplification*, W.H. Freeman and Co., New York (1992), the contents of which are hereby incorporated by reference.

Generally, a target region to be analyzed by denaturing gradient gel electrophoresis is amplified using PCR primers flanking the target region. The amplified PCR product is applied to a polyacrylamide gel with a linear denaturing gradient as described in Myers et al., *Meth. Enzymol.* 155:501-527 (1986), and Myers et al., in *Genomic Analysis, A Practical Approach*, K. Davies Ed. IRL Press Limited, Oxford, pp. 95-139 (1988), the contents of which are hereby incorporated by reference. The electrophoresis system is maintained at a temperature slightly below the Tm of the melting domains of the target sequences.

In an alternative method of denaturing gradient gel electrophoresis, the target sequences may be initially attached to a stretch of GC nucleotides, termed a GC clamp, as described in Chapter 7 of Erlich, supra. Preferably, at least 80% of the nucleotides in the GC clamp are either guanine or cytosine. Preferably, the GC clamp is at least 30 bases long. This method is particularly suited to target sequences with high Tm's.

Generally, the target region is amplified by the polymerase chain reaction as described above. One of the oligonucleotide PCR primers carries at its 5' end, the GC clamp region, at least 30 bases of the GC rich sequence, which is incorporated into the 5' end of the target region during amplification. The resulting amplified target region is run on an electrophoresis gel under denaturing gradient conditions as described above. DNA fragments differing by a single base change will migrate through the gel to different positions, which may be visualized by ethidium bromide staining.

Temperature Gradient Gel Electrophoresis

Temperature gradient gel electrophoresis (TGGE) is based on the same underlying principles as denaturing gradient gel electrophoresis, except the denaturing gradient is produced by differences in temperature instead of differences in the concentration of a chemical denaturant. Standard TGGE utilizes an electrophoresis apparatus with a temperature gradient running along the electrophoresis path. As samples migrate through a gel with a uniform concentration of a chemical denaturant, they encounter increasing temperatures. An alternative method of TGGE, temporal temperature gradient gel electrophoresis (TTGE or tTGGE) uses a steadily increasing temperature of the entire electrophoresis gel to achieve the same result. As the samples migrate through the gel the temperature of the entire gel increases, leading the samples to encounter increasing temperature as they migrate through the gel. Preparation of samples, including PCR amplification with incorporation of a GC clamp, and visualization of products are the same as for denaturing gradient gel electrophoresis.

Single-Strand Conformation Polymorphism Analysis

Target sequences or alleles at an particular locus can be differentiated using single-strand conformation polymorphism analysis, which identifies base differences by alteration in electrophoretic migration of single stranded PCR products, as described in Orita et al., *Proc. Nat. Acad. Sci.* 85:2766-2770 (1989). Amplified PCR products can be generated as described above, and heated or otherwise denatured, to form single stranded amplification products. Single-stranded nucleic acids may refold or form secondary structures which are partially dependent on the base sequence. Thus, electrophoretic mobility of single-stranded amplification products can detect base-sequence difference between alleles or target sequences.

Chemical or Enzymatic Cleavage of Mismatches

Differences between target sequences can also be detected by differential chemical cleavage of mismatched base pairs, as described in Grompe et al., *Am. J. Hum. Genet.* 48:212-222 (1991). In another method, differences between target sequences can be detected by enzymatic cleavage of mismatched base pairs, as described in Nelson et al., *Nature Genetics* 4:11-18 (1993). Briefly, genetic material from an animal and an affected family member may be used to generate mismatch free heterohybrid DNA duplexes. As used herein, "heterohybrid" means a DNA duplex strand comprising one strand of DNA from one animal, and a second DNA strand from another animal, usually an animal differing in the phenotype for the trait of interest. Positive selection for heterohybrids free of mismatches allows determination of small insertions, deletions or other polymorphisms that may be associated with polymorphisms.

Non-Gel Systems

Other possible techniques include non-gel systems such as TaqMan™ (Perkin Elmer). In this system oligonucleotide PCR primers are designed that flank the mutation in question and allow PCR amplification of the region. A third oligonucleotide probe is then designed to hybridize to the region containing the base subject to change between different alleles of the gene. This probe is labeled with fluorescent dyes at both the 5' and 3' ends. These dyes are chosen such that while in this proximity to each other the fluorescence of one of them is quenched by the other and cannot be detected. Extension by Taq DNA polymerase from the PCR primer positioned 5' on the template relative to the probe leads to the cleavage of the dye attached to the 5' end of the annealed probe through the 5' nuclease activity of the Taq DNA polymerase. This removes the quenching effect allowing detection of the fluorescence from the dye at the 3' end of the probe. The discrimination between different DNA sequences arises through the fact that if the hybridization of the probe to the template molecule is not complete—i.e. there is a mismatch of some form—the cleavage of the dye does not take place. Thus, only if the nucleotide sequence of the oligonucleotide probe is completely complimentary to the template molecule to which it is bound will quenching be removed. A reaction mix can contain two different probe sequences each designed against different alleles that might be present thus allowing the detection of both alleles in one reaction.

Yet another technique includes an Invader Assay which includes isothermic amplification that relies on a catalytic release of fluorescence. See Third Wave Technology Non-PCR Based DNA Diagnostics The identification of a DNA sequence linked to an allele sequence can be made without an amplification step, based on polymorphisms including restriction fragment length polymorphisms in an animal and a family member. Hybridization probes are generally oligonucleotides which bind through complementary base pairing to all or part of a target nucleic acid. Probes typically bind target sequences lacking complete complementarity with the probe sequence depending on the stringency of the hybridization conditions. The probes are preferably labeled directly or indirectly, such that by assaying for the presence or absence of the probe, one can detect the presence or absence of the target sequence. Direct labeling methods include radioisotope labeling, such as with 32P or 35S. Indirect labeling methods include fluorescent tags, biotin complexes which may be bound to avidin or streptavidin, or peptide or protein tags. Visual detection methods include photoluminescents, Texas red, rhodamine and its derivatives, red leuco dye and 3,3',5,5'-tetramethylbenzidine (TMB), fluorescein, and its derivatives, dansyl, umbelliferone and the like or with horse radish peroxidase, alkaline phosphatase and the like.

Hybridization probes include any nucleotide sequence capable of hybridizing to a porcine chromosome where one of the major effect genes resides, and thus defining a genetic marker linked to one of the major effect genes, including a restriction fragment length polymorphism, a hypervariable region, repetitive element, or a variable number tandem repeat. Hybridization probes can be any gene or a suitable analog. Further suitable hybridization probes include exon fragments or portions of cDNAs or genes known to map to the relevant region of the chromosome.

Preferred tandem repeat hybridization probes for use according to the present invention are those that recognize a small number of fragments at a specific locus at high stringency hybridization conditions, or that recognize a larger number of fragments at that locus when the stringency conditions are lowered.

One or more additional restriction enzymes and/or probes and/or primers can be used. Additional enzymes, constructed probes, and primers can be determined by routine experimentation by those of ordinary skill in the art and are intended to be within the scope of the invention.

Although the methods described herein may be in terms of the use of a single restriction enzyme and a single set of primers, the methods are not so limited. One or more additional restriction enzymes and/or probes and/or primers can be used, if desired. Indeed in some situations it may be preferable to use combinations of markers giving specific haplotypes. Additional enzymes, constructed probes and primers can be determined through routine experimentation, combined with the teachings provided and incorporated herein.

According to one embodiment of the invention, polymorphisms in a major effect gene cause SCID. The presence or absence of the markers, in one embodiment may be assayed by PCR RFLP analysis using if needed, restriction endonucleases, and amplification primers which may be designed using analogous human, pig or other of the sequences due to the high homology in the region surrounding the polymorphisms, or may be designed using known sequences (for example, human) as exemplified in GenBank or even designed from sequences obtained from linkage data from closely surrounding genes based upon the teachings and references herein. The sequences surrounding the polymorphism will facilitate the development of alternate PCR tests in which a primer of about 4-30 contiguous bases taken from the sequence immediately adjacent to the polymorphism is used in connection with a polymerase chain reaction to greatly amplify the region before treatment with the desired restriction enzyme. The primers need not be the exact complement; substantially equivalent sequences are acceptable. The design of primers for amplification by PCR is known to those of skill in the art and is discussed in detail in Ausubel (ed.), *Short Protocols in Molecular Biology*, Fourth Edition, John Wiley and Sons 1999. The following is a brief description of primer design.

In one embodiment, such non-PCR based DNA diagnostic_ methods may be used to detect one or more of a G to A substitution at position 25,487 or a G to A substitution at position 31,214, as determined by reference to SEQ ID NO:45, or one or more SNPs in the 5' and 3' regions flanking the Artemis gene, including an A→C substitution at position 51153137 of chromosome 10 (reverse complement of nucleotides at position 20 of SEQ ID NO:12 in the region amplified by the primer pairs of SEQ ID NOS: 11 and 12; and position 19 of SEQ ID NO:14 in the region amplified by the primer pairs of SEQ ID NOS:13 and 14); a G→A substitution at position 51812252 of chromosome 10 (nucleotide at position 25 of SEQ ID NO:17 in the region amplified by the primer pairs of SEQ ID NOS: 16 and 17, and, reverse complement of nucleotide at position 26 of SEQ ID NO:16, respectively, in the region amplified by the primer pairs of SEQ ID NOS: 15 and 16); an A→G substitution at position 51975024 of chromosome 10 (reverse complement of nucleotide at position 19 of SEQ ID NO:20 in the region amplified by the primer pairs of SEQ ID NOS:19 and 20; and nucleotide at position 18 of SEQ ID NO:21, in the region amplified by the primer pairs of SEQ ID NOS:21 and 22); an A→C substitution at position 52066694 of chromosome 10 (reverse complement of nucleotide at position 23 of SEQ ID NO:24 in the region amplified by the primer pairs of SEQ ID NOS:23 and 24; and reverse complement of nucleotide at position 23 of SEQ ID NO: 26 in the region amplified by the primer pairs of SEQ ID NOS:25 and 26); a G→A substitution at position 52086867 of chromosome 10 (reverse complement of nucleotide at position 23 of SEQ ID NO:28 in the region amplified by the primer pairs of SEQ ID NOS:27 and 28; and reverse complement of nucleotide at position 23 of SEQ ID NO:30 in the region amplified by the primer pairs of SEQ ID NOS:29 and 30); A→C substitution at position 52109172 of chromosome 10 (reverse complement of nucleotide at position 18 of SEQ ID NO:32 in the region amplified by the primer pairs of SEQ ID NOS:31 and 32; and reverse complement of nucleotide at position 18 of SEQ ID NO: 34 in the region amplified by the primer pairs of SEQ ID NOS:33 and 34); and/or G→A substitution at position 52174549 of chromosome 10 (reverse complement of nucleotide at position 23 of SEQ ID NO:36 in the region amplified by the primer pairs of SEQ ID NOS:35 and 36; and reverse complement of nucleotide at position 23 of SEQ ID NO:38 in the region amplified by the primer pairs of SEQ ID NOS:37 and 38).

Primer Design Strategy

Increased use of polymerase chain reaction (PCR) methods has stimulated the development of many programs to aid in the design or selection of oligonucleotides used as primers for PCR. Four examples of such programs that are freely available via the Internet are: PRIMER by Mark Daly and Steve Lincoln of the Whitehead Institute (UNIX, VMS, DOS, and Macintosh), Oligonucleotide Selection Program (OSP) by Phil Green and LaDeana Hiller of Washington University in St. Louis (UNIX, VMS, DOS, and Macintosh), PGEN by Yoshi (DOS only), and Amplify by Bill Engels of the University of Wisconsin (Macintosh only). Generally these programs help in the design of PCR primers by searching for bits of known repeated-sequence elements and then optimizing the $T_m$ by analyzing the length and GC content of a putative primer. Commercial software is also available and primer selection procedures are rapidly being included in most general sequence analysis packages.

Sequencing and PCR Primers

Designing oligonucleotides for use as either sequencing or PCR primers requires selection of an appropriate sequence that specifically recognizes the target, and then testing the sequence to eliminate the possibility that the oligonucleotide will have a stable secondary structure. Inverted repeats in the sequence can be identified using a repeat-identification or RNA-folding program such as those described above (see prediction of Nucleic Acid Structure). If a possible stem structure is observed, the sequence of the primer can be shifted a few nucleotides in either direction to minimize the predicted secondary structure. The sequence of the oligonucleotide should also be compared with the sequences of both strands of the appropriate vector and insert DNA. Obviously, a sequencing primer should only have a single match to the target DNA. It is also advisable to exclude primers that have only a single mismatch with an undesired target DNA sequence. For PCR primers used to amplify genomic DNA, the primer sequence should be compared to the sequences in the GenBank database to determine if any significant matches occur. If the oligonucleotide sequence is present in any known DNA sequence or, more importantly, in any known repetitive elements, the primer sequence should be changed.

The methods and materials of the invention may also be used more generally to evaluate animal DNA, genetically type individual animals, and detect genetic differences in animals. In particular, a sample of animal genomic DNA may be evaluated by reference to one or more controls to determine if a polymorphism in one of the sequences is present. Preferably, RFLP analysis is performed with respect to the animal's sequences, and the results are compared with a control. The control is the result of a RFLP analysis of one or both of the sequences of a different animal where the polymorphism of the animal gene is known. Similarly, the genotype of an animal may be determined by obtaining a sample of its genomic DNA, conducting RFLP analysis of the gene in the DNA, and comparing the results with a control. Again, the control is the result of RFLP analysis of one of the sequences of a different animal. The results genetically type the animal by specifying the polymorphism(s) in its gene. Finally, genetic differences among animals can be detected by obtaining samples of the genomic DNA from at least two animals, identifying the presence or absence of a polymorphism in one of the nucleotide sequences, and comparing the results.

These assays are useful for identifying the genetic markers relating to SCID, as discussed above, for identifying other polymorphisms in the same genes or alleles that may be correlated with other characteristics, and for the general scientific analysis of animal genotypes and phenotypes.

Once a polymorphism has been identified and a correlation to a particular trait established, one of skill in the art will understand that there are many ways to genotype animals for this polymorphism. The design of such alternative tests merely represents optimization of parameters known to those of skill in the art and is intended to be within the scope of this invention as fully described herein. In a preferred embodiment, PCR-based assays use the primers set out in Table 1.

In accordance with the present invention there may be employed conventional molecular biology, microbiology, and recombinant DNA techniques within the skill of the art. Such techniques are explained fully in the literature. See, e.g., Maniatis, Fritsch & Sambrook, *Molecular Cloning: A Laboratory Manual* (1982); *DNA Cloning: A Practical Approach*, Volumes I and II (D. N. Glover ed. 1985); *Oligonucleotide Synthesis* (M. J. Gait ed. 1984); *Nucleic Acid Hybridization* (B. D. Hames & S. J. Higgins eds. (1985)); *Transcription and Translation* (B. D. Hames & S. J. Higgins eds. (1984)); *Animal Cell Culture* (R. I. Freshney, ed. (1986)); *Immobilized Cells And Enzymes* (IRL Press, (1986)); B. Perbal, *A Practical Guide To Molecular Cloning*, (1984).

In one embodiment, a multiplex PCR system is used to detect one or more genetic markers relating to SCID, as discussed above, for identifying other polymorphisms in the same genes or alleles that may be correlated with other characteristics, and for the general scientific analysis of animal genotypes and phenotypes. In a particular embodiment, the multiplex PCR system detects the causative mutation in haplotype 16, found at position 615 of Sequence 4 (SEQ ID NO:7), and/or for the causative mutation in haplotype 12, found at position 116 of Sequence 6 (SEQ ID NO:9). The multiplex PCR system can be any suitable system that can be used to distinguish between nucleotides at one or more locations, such as, for example, the ABI PRISM SNaPshot system.

Creation of Transgenic Animals

Transgenic animals are animals which have had genetic material artificially inserted into the genome. Typically, this material is present as either an extra chromosomal element or is stably integrated into the chromosomal DNA of the organism in at least a subset of cells. Preferably, this includes stable integration into the germline cells. In one aspect, the genetic material comprises a heterologous gene. Typically, a chimeric animal (chimera) is produced, where only a subset of the somatic cells possess the desired transgene. These chimeras are then used for further breeding to generate the ultimate transgenic animal.

A transgenic animal can be a knock-out having a partial or complete loss of function of the target gene. A knock-out of Artemis means that Artemis gene expression is undetectable or insignificant. This can be accomplished through a variety of means including: introduction of a disruption of the coding sequence (e.g. substitutions at splice sites, insertion of one or more stop codons and/or insertion of a DNA fragment), deletion of coding sequence, substitution of stop codons for coding sequence, chromosomal deletion of all or part of the native gene may be induced (including deletions of the non-coding regions, particularly the promoter region, 3' regulatory sequences, enhancers, or deletions of gene that activate expression of 5-HT6 genes), and/or introduction of an antisense construct that blocks expression of the native genes (for example, see Li and Cohen (1996) Cell 85:319-329). "Knock-outs" also include conditional knockouts, for example where alteration of the target gene occurs upon exposure of the animal to a substance that promotes target gene alteration, introduction of an enzyme that promotes recombination at the target gene site (e.g. Cre in the Cre-lox system), or other method for directing the target gene alteration postnatally.

For embryonic stem (ES) cells, an ES cell line may be employed, or embryonic cells may be obtained freshly from a host. Such cells are grown on an appropriate fibroblast-feeder layer or grown in the presence of appropriate growth factors, such as leukemia inhibiting factor (LIF). When ES cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting progeny are screened for mutant cells having the construct. By providing for a different phenotype of the blastocyst and the ES cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in in vitro culture.

In one aspect, these methods are used to produce a SCID pig. In a preferred embodiment, the methods may be used to produce a transgenic pig comprising one or more mutations to the Artemis gene. In a more preferred embodiment, the mutation comprises one or more of a G to A substitution at position 25,487 or a G to A substitution at position 31,214, as determined by reference to SEQ ID NO:45. In one embodiment, the transgenic pig comprises a heterologous gene comprising one or more of the mutations. The heterologous gene can be operatively linked to a heterologous promoter sequence and or a terminator sequence.

In another aspect, these methods are used to produce a pig with increased expression of Artermis gene and/or increased activity of Artemis protein. In one aspect, the methods are used to inhibit, treat, or ameliorate a disease or condition. In one embodiment, the invention encompasses a pig comprising a non-naturally occurring nucleotide sequence encoding an Artemis protein operatively linked to a heterologous promoter, wherein the Artemis protein encoded by the nucleotide sequence has nuclease activity.

Increasing the Activity and/or Level of Artemis

Methods are provided to increase the activity and/or level of the Artemis polypeptides to ameliorate the affects caused by loss of function mutations. These methods can be carried out in cell culture. Alternatively, the methods can be carried out in an animal. In one aspect, an increase in the level and/or activity of an artemis polypeptide can be achieved by providing to the animal an artemis polypeptide. The polypeptide can be provided by introducing polypeptide to the animal, introducing to the animal a nucleotide sequence encoding a functional artemis polypeptide, or alternatively by modifying a genomic locus encoding the aberrant artemis polypeptide so that function is restored.

As discussed elsewhere herein, many methods are known in the art of providing a polypeptide to an animal including, but not limited to, direct introduction of the polypeptide to animal, introducing into the animal (transiently or stably) a polynucleotide construct encoding a polypeptide having artemis activity. It is also recognized that the methods of the invention may employ a polynucleotide that is not capable of directing, in the transformed cell, the expression of a protein or an RNA. Thus, the level and/or activity of an artemis polypeptide may be increased by altering the gene encoding the polypeptide or its promoter. See, e.g., Kmiec, U.S. Pat. No. 5,565,350; Zarling, et al., PCT/US93/03868. Therefore mutagenized animals that carry corrective mutations in the Artemis gene, where the mutations increase expression of a functional gene or increase the activity of the encoded polypeptide are provided.

Reducing the Activity and/or Level of Artemis

Methods are also provided to reduce or eliminate the activity of Artemis by transforming a cell with an expression cassette that expresses a polynucleotide that inhibits the expression of Artemis. These methods can be carried out in cell culture. Alternatively, the methods can be carried out in an animal. The polynucleotide may inhibit the expression of the Artemis directly, by preventing transcription or translation of Artemis messenger RNA, or indirectly, by encoding a polypeptide that inhibits the transcription or translation of an Artemis gene encoding an Artemis. Methods for inhibiting or eliminating the expression of a gene in a cell or animal are well known in the art, and any such method may be used in the present invention to inhibit the expression of the Artemis gene. Many methods may be used to reduce or eliminate the activity of Artemis polypeptide. In addition, more than one method may be used to reduce the activity.

Polypeptide-Based Inhibition of Gene Expression

In one embodiment, the polynucleotide encoding a zinc finger protein that binds to a gene encoding Artemis may be provided, resulting in reduced expression of the gene. Methods of selecting sites for targeting by zinc finger proteins have been described, for example, in U.S. Pat. No. 6,453, 242, and methods for using zinc finger proteins to inhibit the expression of genes are described, for example, in U.S. Patent Publication Nos. 2003/0037355; each of which is herein incorporated by reference. In another aspect, a polynucleotide may be provided that encodes a TAL effector protein that targets and disrupts the gene encoding Artemis, resulting in reduced expression of the gene Methods of selecting sites for targeting by TAL effector proteins have been described, and methods for using zinc finger proteins to inhibit the expression of genes are described, for example, in U.S. Pat. No. 8,586,363; which is herein incorporated by reference.

Gene Disruption

In some embodiments of the present invention, the activity of the Artemis protein polypeptide is reduced or eliminated by disrupting the gene encoding the Artemis polypeptide. The gene encoding the Artemis polypeptide may be disrupted by any method known in the art. For example, in one embodiment, the gene is disrupted by transposon tagging. In another embodiment, the gene is disrupted by mutagenizing cells using random or targeted mutagenesis, and selecting for cells or animals that have SCID phenotype or reduced Artemis gene product or activity.

Gene Editing

In some embodiments of the present invention, gene editing techniques may be used to alter the nucleotide sequence in the endogenous Artemis gene of pigs. Gene editing may be accomplished using a variety of compositions and methods known in the art, including zinc-finger nucleases (ZFNs), TALENs, the CRISPR/Cas9 system, or equivalent genome editors. Methods for designing and using zinc finger proteins and TALENs are described, for example, in U.S. Pat. Nos. 6,453,242 and 6,534,261, which are incorporated herein in their entirety. In one aspect, the gene editing techniques may be used to introduce a disruption into the Artemis gene, thereby causing SCID in the pig. The disruption may be an insertion, a deletion, an inversion, or a single nucleotide polymorphism in the Artemis gene of said animal. The disruption may be to a coding region, or a non-coding region, including for example, promoter regions, enhancer regions, and/or splice sites. In one embodiment, the gene editing techniques may be used to introduce a G to A substitution at position 25,487 or a G to A substitution at position 31,214, as determined by reference to SEQ ID NO:45. In another aspect gene editing techniques may be used to correct a defect in the Artemis gene in an individual or animal with SCID.

Gene Silencing Using RNA Interference

MicroRNAs (miRNAs) are small non-coding RNAs which negatively regulate protein-coding genes primarily by decreasing stability of RNA transcripts. Decreased stability is typically accomplished through the binding of the miRNA to the target transcript. These binding sites preferentially reside in the 3' UTRs of the genes, however, they can occur throughout the entire transcript. Generally, miRNA binding sites are well conserved. Some genes which are heavily expressed (e.g. housekeeping genes) have smaller 3' UTR regions which may reduce the likelihood of binding to miRNAs. Genes with a 3' UTR longer than 4 kB are less affected by miRNA. Other factors influence the selection and effectiveness of miRNAs. For example, many miRNAs are known to regulate genes involved in cell development processes. Another example is that miRNAs appear to preferentially target genes with high CpG promoters. Also, as highly expressed genes transcribe a large number of mRNAs, the miRNA regulation of those mRNAs can be different from those of weakly expressed genes, although current analyses disagree on whether miRNAs affect highly expressed genes more or less than medium or lowly expressed genes.

Potential miRNAs can be screened using high throughput experiments using microarrays or proteomics. Examples of these high-throughput systems are described in: Lim L P, et al. Nature 2005, 433:769-773; Grimson A, et al., Mol Cell 2007, 27:91-105; Selbach M, Schwanhausser B, et al, Nature 2008, 455:58-63; Baek D, Villén J, et al, Nature 2008, 455:64-71. All of these references are incorporated by reference as if set forth fully herein. Well designed and effective RNA interference will reduce expression by approximately 50%, 60%, 70%, 80%, 90% and/or 100% depending on site selection and other factors listed above. It is well within the skill in the art to design miRNAs which will bind to a target transcript and screen the same for determining effectiveness of the miRNA.

Creation of Microarrays

Microarrays are used to perform large parallel analysis of various biological and chemical samples. A microarray is an array of spots of samples (probes) which are immobilized at specified positions on a substrate. Each spot contains chemical or biological material which is capable of interacting with certain target molecules (such as a DNA sample). In order to use a microarray, it is flooded with a solution containing target molecules. For DNA/RNA applications, the probes are short oligonucleotides which are complimentary to target DNA/RNA samples. When the samples are labeled using fluorescent or radioactive labels, the microarray can be scanned to determine which spots interact with the target. The polynucleotides in the target hybridize with the spots that contain complimentary probe polynucleotides. The presence of hybridized target molecules is then detected by a microarray reader which reports the position and intensity of the label emissions. The identity of the probes which hybridize to the target can be determined by mapping the reported location to records indicating which probe was placed in the reported location.

Microarrays are typically fabricated using one of two techniques: photolighography and robotic spotting. Detailed instructions for using photolithography can be found in U.S. Pat. Nos. 5,445,934 and 5,744,305 which are both incorporated by reference as if set forth fully herein. The photolithographic technique takes approaches used in the design of integrated circuits and applies them in this biological context. While this technique has very high initial costs, it can be used to mass produce arrays at a low incremental cost. Robot spotting techniques are provided in U.S. Pat. No. 5,807,522 which is incorporated by reference as if set forth fully herein. This technique uses a robot to place the probes on the substrate. Techniques used include the use of a pin, capillaries, and inkjet technology. Depending on the technology used, the probes can be manufactured on the substrate or can be manufactured off site and then placed on the substrate. Robotic technology has a lower startup cost but can take time to create a single array. Additionally, the incremental cost per array is higher.

The design of the microarray probe sets has been discussed in detail and commercial software is readily available to perform this task. One such program is explained in Xu, Bioinformatics 2002 Vol. 18, Pages 1432-1437.

Once the data is captured, a number of software programs are available to perform analysis on the resulting data. An example of such software is the TM4 suite of tools available at www.tm4.org.

Selective Breeding Techniques

Selective breeding is the preferential breeding of animals with desired traits in order to increase the prevalence of the trait within the breeding herd. Before starting with selective breeding, a desired goal should be identified. In this case, the trait is SCID, which is not desired in commercial production and thus one goal is to remove the mutations causing SCID in commercial pigs. In order to decrease the frequency of the mutant Artemis alleles, and more particularly the 12 and 16 haplotypes, it is desirable to use selective breeding to decrease the frequency of the allele within a herd. By decreasing the frequency of the allele, fewer animals in the herd will have SCID.

It is also possible that it is of interest to create a herd with a high frequency of the SCID mutation(s) to provide animals that can serve as biomedical models. Thus in some situations, the goal would be to increase the frequency of the SCID mutation in a herd.

Once the goals have been identified, selection and mating are used to produce animals which carry only genes without mutations causing SCID in commercial populations, or which carry one or two copies of the SCID mutation for biomedical purposes.

In both cases, the technology described herein can be used. For elimination of the SCID mutation(s) in a commercial herd, the PCR assays described below would be used to identify animals with a single copy of a mutant gene. Those animals would be removed from the breeding herd; i.e., would NOT be selected for future breeding. Aggressive use of this technique would eliminate the mutant gene in one or two generations. If SCID carrier animals have otherwise useful genetics and are needed for other breeding goals at a commercial breeding company, such carrier animals could be used, but their offspring would again have to be tested for carrying the mutant SCID genes. For creation of a herd for biomedical purposes that would have a high frequency of the mutant genes, marker-assisted introgression (MAI) would be used. MAI is the movement of a target gene or genes from one breed or species (the donor species) into the gene pool of another breed or species (the recipient species) by the repeated backcrossing of a carrier with pigs representing the genetic population into which the SCID mutation is desired. With each repeated round of backcrossing, the amount of non-target genes from the donor line is decreased. As such, depending on the permissible amount of donor genetic material, backcrossing can be conducted for 2, 3, 4, 5, 6, 7, 8, 9, 10, 11, 12, 13, 14, 15, 16, 17, 18, 19, 20 or more generations. Detailed procedures for performing introgression are well known in the art and are discussed in Frisch M, Melchinger A E, Genetics. 2005 June; 170(2):909-17 which is incorporated by reference in its entirety as if set forth fully herein. The offspring of each backcross would be tested for the SCID mutation using the technology described herein, and carrier animals selected for the next backcross mating. Over time, the SCID mutation would be introgressed into the new genetic line.

According to an aspect of the invention, methods for improving production of SCID piglets are provided. In one aspect, pigs with SCID according to the invention may be provided with a bone marrow transfer, thereby reconstituting the immune system of pigs that are homozygous for SCID mutations, such that they can be raised to breeding age, and then mated with SCID carrier pigs or other SCID homozygous pigs. Procedures for performing bone marrow transfers are well known in the art.

The invention also includes novel nucleotide and protein sequences which are causative of SCID. This molecular information can be used in a variety of methods for studying the effects of, the causes of, and possibly the prevention of SCID.

In another embodiment, the invention comprises a method for identifying a genetic marker for SCID in a particular line, strain, breed, population or animal.

It is also possible to establish linkage between specific alleles of alternative DNA markers and alleles of DNA markers known to be associated with a particular gene (e.g. the Artemis gene discussed herein), which have previously been shown to be associated with a particular trait. Thus, in the present situation, taking the Artemis gene, it would be possible, to eliminate animals likely to exhibit SCID or to select for animals likely to exhibit SCID by identifying animals carrying certain alleles of an Artemis associated marker or the Artemis mutations themselves through the use of the allele-specific technology described herein. As used herein, the term "genetic marker" shall include not only the polymorphism disclosed by any means of assaying for the protein changes associated with the polymorphism, but also linked markers, use of microsatellites, or even other means of assaying for the causative protein changes indicated by the marker and the use of the same to influence SCID in an animal.

Use of SCID Pigs

In one aspect, the pigs and cells of the present invention may be used to study a variety of diseases and conditions. Examples of such diseases or conditions include, but are not limited to, endogenous cancers; human immune function, including human autoimmune and immune-mediated diseases; human infectious agents and disease; human vaccine efficacy; human stem cells and regenerative therapeutics; hematopoietic stem cell transplantation and associated diseases; and/or porcine immune function.

The efficacy of the compositions in treating or preventing a particular disease, disorder, or condition using the cells or pigs of the present invention can be evaluated both in vitro and in vivo. As used herein, the term "treating" refers to: (i) preventing a disease, disorder or condition from occurring in a mammal, animal or human that may be predisposed to the disease, disorder and/or condition but has not yet been diagnosed as having it; (ii) inhibiting the disease, disorder or condition, i.e., arresting its development; and/or (iii) relieving the disease, disorder or condition, i.e., causing regression of the disease, disorder and/or condition. For example, with respect to SCID, the ability to respond to infection and/or cancers, or to augment other treatments such as bone marrow transplant or adoptive transfer of immune effectors can be assessed. Further, SCID pigs of the present invention may be used to assess the efficacy of compositions in treating or preventing a particular disease, disorder, or condition using the SCID pigs or cells of the invention as a model organism. The efficacy of such compositions treatment may be measured quantitatively or qualitatively to determine the presence/absence of the disease, or its progression or regression using, in the example of cancer, reduction in tumor size, a reduction in the rate of metastasis, and/or a slowing of tumor growth, and/or no worsening in disease over a specified period of time or other symptoms associated with the disease or clinical indications associated with the pathology of cancer development. In one aspect, this screening may be accomplished using a xenograft transplant, or xenotransplant, porcine SCID model.

All publications and patent applications in this specification are indicative of the level of ordinary skill in the art to which this invention pertains. All publications and patent applications are herein incorporated by reference to the same extent as if each individual publication or patent application was specifically and individually indicated as incorporated by reference.

Inhibition, Treatment, and Amelioration of SCID

In one aspect, the invention encompasses methods and compositions for inhibition, treatment, and amelioration of SCID. Compositions include compounds, effectors, and constructs that replace or augment defective Artemis expression or function in SCID affected individuals, or correct the genetic defect causing SCID in affected individuals. In one aspect, the compositions comprise the novel DNA or proteins sequences of the invention. In another aspect, compositions may be pharmaceutical compositions that include Artemis protein or polynucleotides encoding Artemis protein, wherein the Artemis protein has nuclease activity.

In another aspect, the invention encompasses methods for inhibiting, treating, or ameliorating SCID. These methods may include providing or administering Artemis protein or polynucleotides encoding Artemis protein, wherein the Artemis protein has nuclease activity. In one embodiment, the Artemis protein has or is homologous to SEQ ID NO:2, 4, or 6. In another embodiment, the methods utilize polynucleotides encoding proteins having or homologous to SEQ ID NO:2, 4, or 6. In one aspect, the polynucleotides have or are homologous to SEQ ID NO:1, 3, 5, or 7-10.

Pharmaceutical Compositions

According to one aspect of the invention, compositions containing Artemis protein or polynucleotides encoding Artemis protein may be administered to treat SCID. Compositions may be formulated in any conventional manner. Proper formulation is dependent upon the route of administration chosen. Suitable routes of administration include, but are not limited to, oral, parenteral (e.g., intravenous, intraarterial, subcutaneous, rectal, subcutaneous, intramuscular, intraorbital, intracapsular, intraspinal, intraperitoneal, or intrasternal), topical (nasal, transdermal, intraocular), intravesical, intrathecal, enteral, pulmonary, intralymphatic, intracavital, vaginal, transurethral, intradermal, aural, intramammary, buccal, orthotopic, intratracheal, intralesional, percutaneous, endoscopical, transmucosal, sublingual and intestinal administration.

Pharmaceutically acceptable carriers for use in the compositions of the present invention are well known to those of ordinary skill in the art and are selected based upon a number of factors: concentration and intended bioavailability of the protein or polynucleotide; the disease, disorder or condition being treated with the composition; the subject, his or her age, size and general condition; and the route of administration. Suitable carriers are readily determined by one of ordinary skill in the art (see, for example, J. G. Nairn, in: Remington's Pharmaceutical Science (A. Gennaro, ed.), Mack Publishing Co., Easton, Pa., (1985), pp. 1492-1517, the contents of which are incorporated herein by reference).

The Artemis protein or polynucleotide containing compositions of the present invention may be preferably formulated for parenteral administration, e.g., formulated for injection via intravenous, intraarterial, subcutaneous, rectal, subcutaneous, intramuscular, intraorbital, intracapsular, intraspinal, intraperitoneal, or intrasternal routes. The compositions of the invention for parenteral administration comprise an effective amount of hydroxytyrosol in a pharmaceutically acceptable carrier. Dosage forms suitable for parenteral administration include solutions, suspensions, dispersions, emulsions or any other dosage form which can be administered parenterally. Techniques and compositions for making parenteral dosage forms are known in the art. For oral administration, the hydroxytyrosol containing compositions are preferably formulated as tablets, dispersible powders, pills, capsules, gelcaps, caplets, gels, liposomes, granules, solutions, suspensions, emulsions, syrups, elixirs, troches, dragees, lozenges, or any other dosage form which can be administered orally. Techniques and compositions for making oral dosage forms useful in the present invention are described in the following references: 7 Modern Pharmaceutics, Chapters 9 and 10 (Banker & Rhodes, Editors, 1979); Lieberman et al., Pharmaceutical Dosage Forms:

Tablets (1981); and Ansel, Introduction to Pharmaceutical Dosage Forms 2nd Edition (1976).

Suitable carriers used in formulating liquid dosage forms for oral or parenteral administration include nonaqueous, pharmaceutically-acceptable polar solvents such as oils, alcohols, amides, esters, ethers, ketones, hydrocarbons and mixtures thereof, as well as water, saline solutions, dextrose solutions (e.g., DW5), electrolyte solutions, or any other aqueous, pharmaceutically acceptable liquid. Suitable nonaqueous, pharmaceutically-acceptable polar solvents include, but are not limited to, alcohols (e.g., .alpha.-glycerol formal, .beta.-glycerol formal, 1,3-butyleneglycol, aliphatic or aromatic alcohols having 2-30 carbon atoms such as methanol, ethanol, propanol, isopropanol, butanol, t-butanol, hexanol, octanol, amylene hydrate, benzyl alcohol, glycerin (glycerol), glycol, hexylene glycol, tetrahydrofurfuryl alcohol, lauryl alcohol, cetyl alcohol, or stearyl alcohol, fatty acid esters of fatty alcohols such as polyalkylene glycols (e.g., polypropylene glycol, polyethylene glycol), sorbitan, sucrose and cholesterol); amides (e.g., dimethylacetamide (DMA), benzyl benzoate DMA, dimethylformamide, N-(.beta.-hydroxyethyl)-lactamide, N,N-dimethylacetamide amides, 2-pyrrolidinone, 1-methyl-2-pyrrolidinone, or polyvinylpyrrolidone); esters (e.g., 1-methyl-2-pyrrolidinone, 2-pyrrolidinone, acetate esters such as monoacetin, diacetin, and triacetin, aliphatic or aromatic esters such as ethyl caprylate or octanoate, alkyl oleate, benzyl benzoate, benzyl acetate, dimethylsulfoxide (DMSO), esters of glycerin such as mono, di, or tri-glyceryl citrates or tartrates, ethyl benzoate, ethyl acetate, ethyl carbonate, ethyl lactate, ethyl oleate, fatty acid esters of sorbitan, fatty acid derived PEG esters, glyceryl monostearate, glyceride esters such as mono, di, or tri-glycerides, fatty acid esters such as isopropyl myristrate, fatty acid derived PEG esters such as PEG-hydroxyoleate and PEG-hydroxystearate, N-methylpyrrolidinone, pluronic 60, polyoxyethylene sorbitol oleic polyesters such as poly(ethoxylated)30-60 sorbitol poly(oleate)2-4, poly(oxyethylene)15-20 monooleate, poly(oxyethylene) 15-20 mono 12-hydroxystearate, and poly(oxyethylene)15-20 mono ricinoleate, polyoxyethylene sorbitan esters such as polyoxyethylene-sorbitan monooleate, polyoxyethylene-sorbitan monopalmitate, polyoxyethylene-sorbitan monolaurate, polyoxyethylene-sorbitan monostearate, and Polysorbate® 20, 40, 60 or 80 from ICI Americas, Wilmington, Del., polyvinylpyrrolidone, alkyleneoxy modified fatty acid esters such as polyoxyl 40 hydrogenated castor oil and polyoxyethylated castor oils (e.g., Cremophor® EL solution or Cremophor® RH 40 solution), saccharide fatty acid esters (i.e., the condensation product of a monosaccharide (e.g., pentoses such as ribose, ribulose, arabinose, xylose, lyxose and xylulose, hexoses such as glucose, fructose, galactose, mannose and sorbose, trioses, tetroses, heptoses, and octoses), disaccharide (e.g., sucrose, maltose, lactose and trehalose) or oligosaccharide or mixture thereof with a C4-C22 fatty acid(s)(e.g., saturated fatty acids such as caprylic acid, capric acid, lauric acid, myristic acid, palmitic acid and stearic acid, and unsaturated fatty acids such as palmitoleic acid, oleic acid, elaidic acid, erucic acid and linoleic acid)), or steroidal esters); alkyl, aryl, or cyclic ethers having 2-30 carbon atoms (e.g., diethyl ether, tetrahydrofuran, dimethyl isosorbide, diethylene glycol monoethyl ether); glycofurol (tetrahydrofurfuryl alcohol polyethylene glycol ether); ketones having 3-30 carbon atoms (e.g., acetone, methyl ethyl ketone, methyl isobutyl ketone); aliphatic, cycloaliphatic or aromatic hydrocarbons having 4-30 carbon atoms (e.g., benzene, cyclohexane, dichloromethane, dioxolanes, hexane, n-decane, n-dodecane, n-hexane, sulfolane, tetramethylenesulfon, tetramethylenesulfoxide, toluene, dimethylsulfoxide (DMSO), or tetramethylenesulfoxide); oils of mineral, vegetable, animal, essential or synthetic origin (e.g., mineral oils such as aliphatic or wax-based hydrocarbons, aromatic hydrocarbons, mixed aliphatic and aromatic based hydrocarbons, and refined paraffin oil, vegetable oils such as linseed, tung, safflower, soybean, castor, cottonseed, groundnut, rapeseed, coconut, palm, olive, corn, corn germ, sesame, persic and peanut oil and glycerides such as mono-, di- or triglycerides, animal oils such as fish, marine, sperm, cod-liver, haliver, squalene, squalane, and shark liver oil, oleic oils, and polyoxyethylated castor oil); alkyl or aryl halides having 1-30 carbon atoms and optionally more than one halogen substituent; methylene chloride; monoethanolamine; petroleum benzin; trolamine; omega-3 polyunsaturated fatty acids (e.g., alpha-linolenic acid, eicosapentaenoic acid, docosapentaenoic acid, or docosahexaenoic acid); polyglycol ester of 12-hydroxystearic acid and polyethylene glycol (Solutol® HS-15, from BASF, Ludwigshafen, Germany); polyoxyethylene glycerol; sodium laurate; sodium oleate; or sorbitan monooleate.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

Example 1: Initial Characterization of SCID Pigs

The SCID defect was identified in a line of pigs that was initially (1997) derived from pigs that were sourced from private pig breeders in the Midwest, primarily Iowa, and that has since then been selected for increased feed efficiency at Iowa State University. The affected pigs were part of a group of 100 purebred Yorkshire pigs produced after selecting over 7 generations for increased feed efficiency. Parents were partially related, resulting in the offspring having 12-14% inbreeding. The defect was identified in four pigs from this line that died early after challenge in an experimental infection challenge with PRRS virus. The routine necropsy that was conducted on the pigs identified the anomaly, which was confirmed to at least be similar to SCID. Four pigs that were challenged with PRRS virus did not develop an antibody response and, upon necropsy, had both atrophied lymph nodes and thymus. Severe lymphoid hypoplasia/depletion was identified in four 5 to 7 week-old pigs that died unexpectedly or were euthanized because of illness during a porcine reproductive and respiratory syndrome virus (PRRSV) challenge study. Two of the pigs had been inoculated at 4 weeks of age with PRRSV. At necropsy, all four were thin, had rough hair coats, and were smaller than their pen mates. One of the PRRSV inoculated pigs displayed antemortem clinical signs of respiratory disease and had severe fibrinosuppurative bronchopneumonia from which Streptococcus suis was isolated. The thymus was not found in any of the four. Microscopically, there was diffuse, severe lymphoid hypoplasia/depletion with a complete lack of follicles in lymph nodes, tonsils, and Peyer's patches, and an absence of perivascular lymphoid sheaths in the spleen. Immunohistochemical staining for porcine circovirus type-2 was negative for all animals. Immunohistochemical staining revealed scattered T lymphocytes and an absence of B lymphocytes in lymph nodes, spleen, tonsil, and Peyer's patches. Each affected pig was from a different litter, but three had the same sire. Lymphoid tissues from the other 96 pigs in the group, including littermates, were normal. The lesions resemble descriptions of primary immunodeficiency in other species, which have autosomal recessive penetration. This suggests a possible genetic basis to the lymphoid hypoplasia/depletion in these pigs, possibly caused by a recessive mutation.

Unusually low lymphocyte percentages in complete blood counts (CBC) were used to identify additional affected pigs. Using CBC data, >15 affected animals have been identified (all closely related), which upon phenotypic evaluation of the thymus and lymph nodes, as well as immunohistochemistry staining for B cell and T cell markers, have been confirmed as SCID. No effect on neutrophil number was observed. SCID piglets thrive while protected by maternal antibodies from milk, and delayed weaning up to 35 days protects piglets, but piglets at the farm succumb to infections soon thereafter; antibiotics and high biosecurity may extend survival.

Example 2: Phenotypic Characterization of the SCID Phenotype

Figure 2:
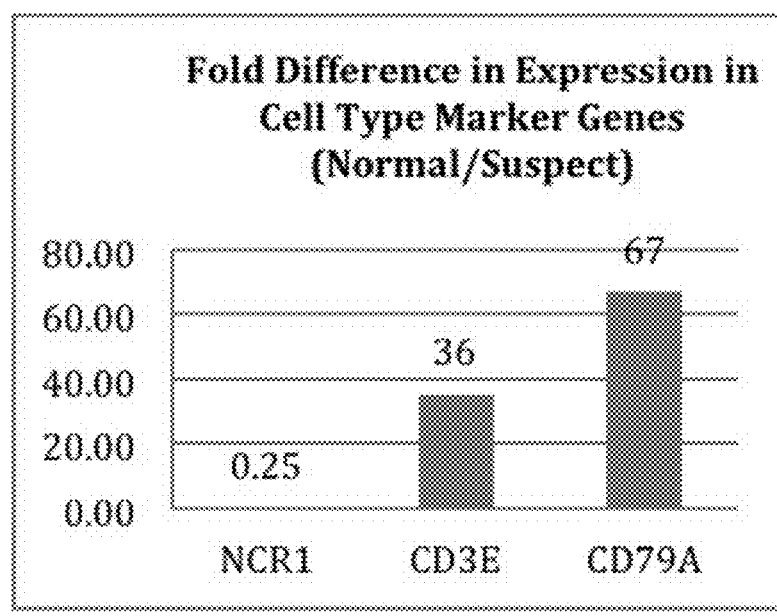
FIG. 2 shows quantitative PCR analysis of NCR1 (NK cells), CD3E (T cells), and CD79A (B cells) expression, demonstrating very low levels of B and T marker gene expression in suspect SCID pig whole blood ($p<0.01$) compared to normal littermates.

Flow cytometry (FIG. 1) identified near absence of T and B cells but presence of natural killer (NK) cells in the SCID pigs. The presence and absence of these respective immune cell types was confirmed by quantitative PCR gene expression (FIG. 2). Furthermore, unpublished work at ISU by Dr. J. Cunnick and S. Knetter, in collaboration with Dr. Tuggle, found no clear difference in NK cell activity between SCID and normal pigs but also showed that NK cells could perform their normal killing function only if the cells are stimulated with either IL2, which is expected to be absent in the SCID pigs or IL12/IL18, which may be present in pigs in an inflammatory state. Thus, although our SCID pigs have NK cells, these cells are apparently not functional in vivo.

Figure 3:
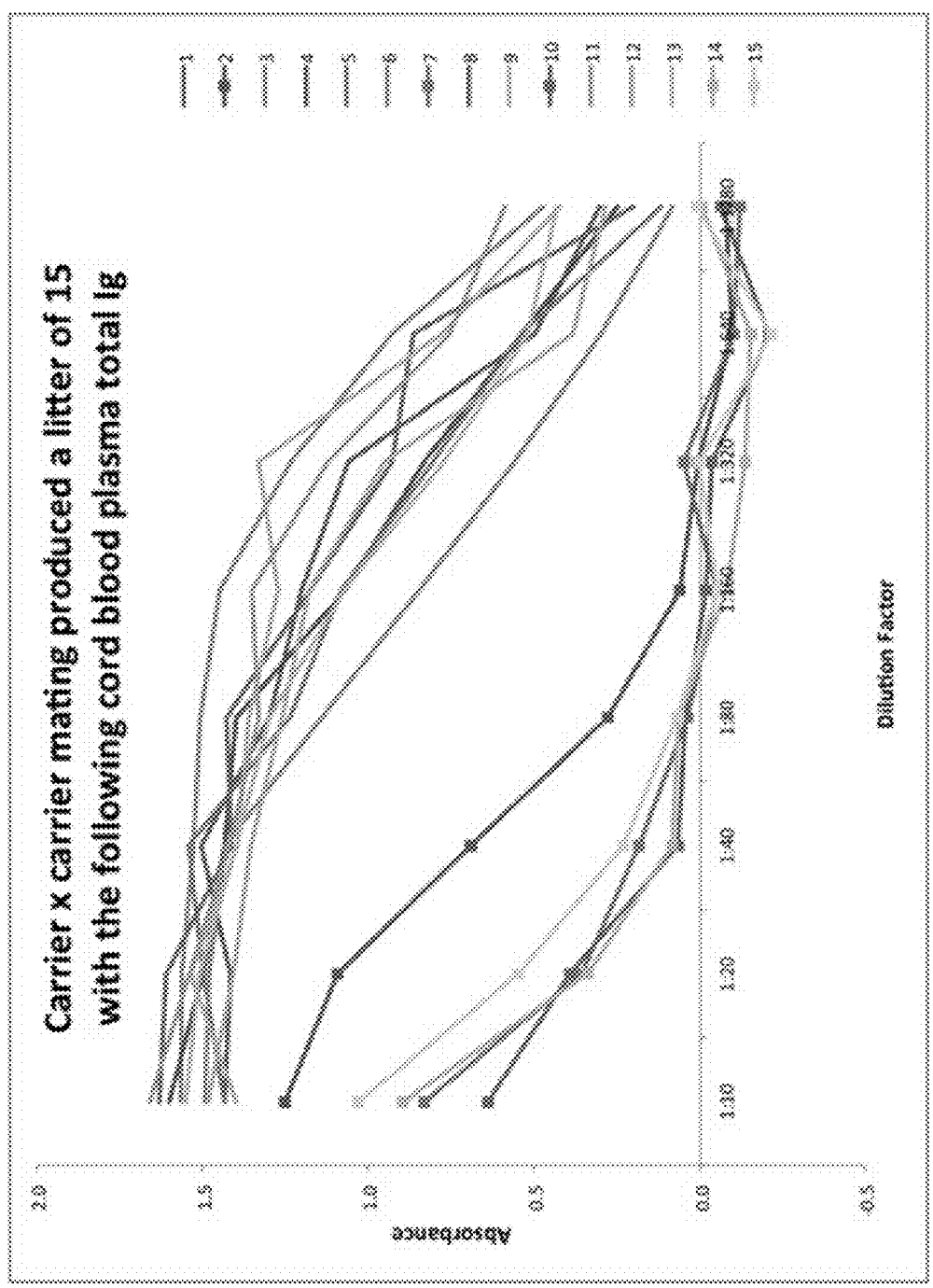
FIG. 3 shows immunoglobulin (Ig) measured in umbilical cord blood from SCID piglets versus normal littermates, demonstrating the lack of antibodies in newborn SCID pigs (#2, 7, 10, 14, 15) compared to non-SCID pigs (all other data).

Finally, assays to quantify the amount of antibody present in umbilical cord blood collected immediately after birth showed much lower levels of total immunoglobulin (Ig) in SCID piglets versus normal littermates (FIG. 3), demonstrating that SCID piglets have a substantially impaired or lack the ability to produce antibodies. Jointly, these findings clearly demonstrate that the affected piglets have SCID.

Example 3: Genetic Basis of SCID

Figure 4:
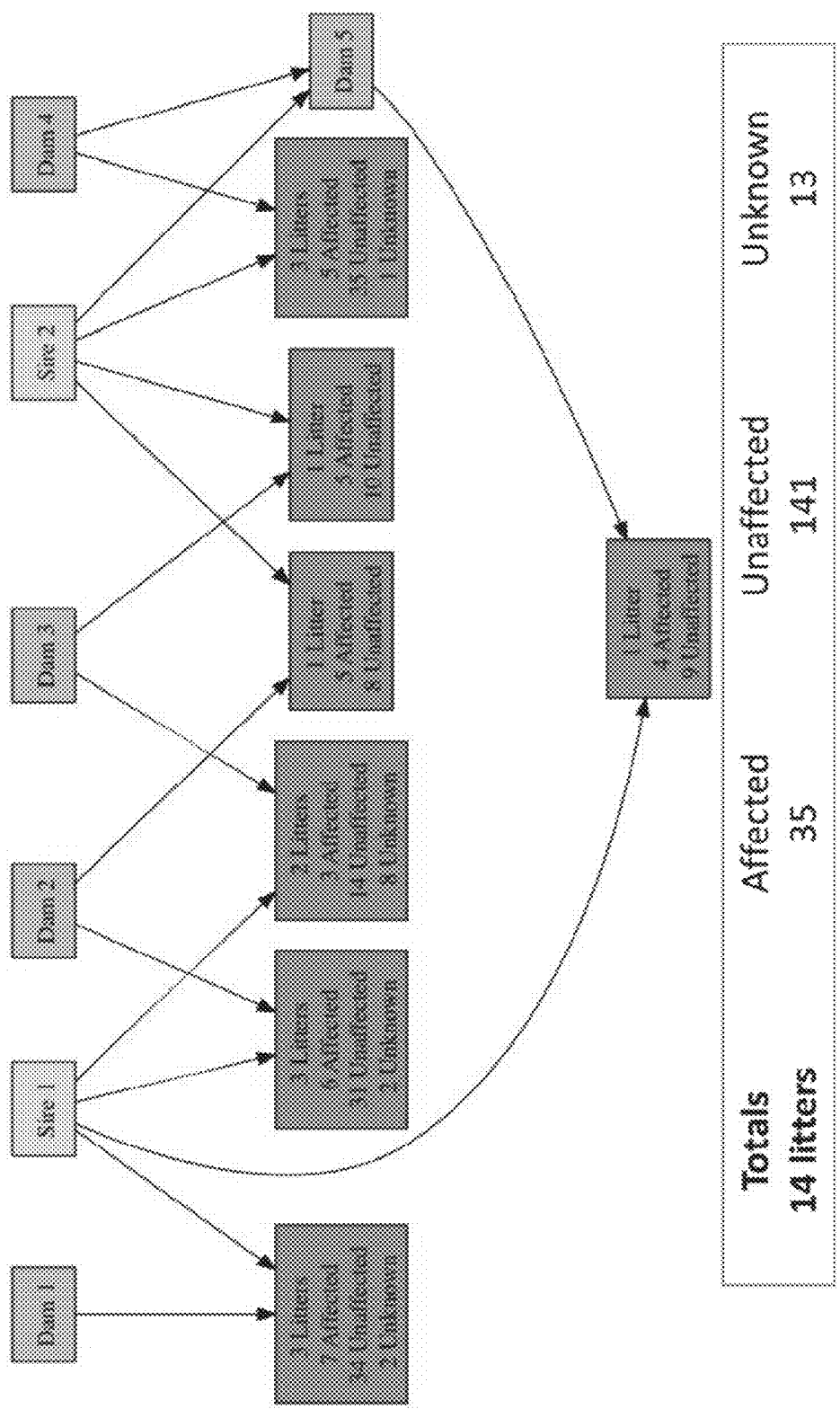
FIG. 4 shows segregation of the SCID phenotype as a recessive autosomal mutation. The 4 dams and 2 sires produced the initial 4 SCID piglets.

The four piglets that led to the initial discovery of SCID were progeny from four dams and two sires. The four matings that resulted in these piglets were repeated and each mating resulted in at least one SCID piglet, as illustrated in FIG. 4, confirming a genetic basis for the SCID phenotype. The SCID phenotype was found in 35 out of 176 piglets that could be evaluated, i.e. 20%. These 35 pigs were of both sexes as well. The 13 piglets for which the SCID phenotype is unknown died before SCID status was determined. Assuming that they died of SCID, the percentage of SCID progeny would be 48/189=25.4%, suggesting a single recessive autosomal mutation, with parents that produce SCID piglets being carriers.

Figure 5:
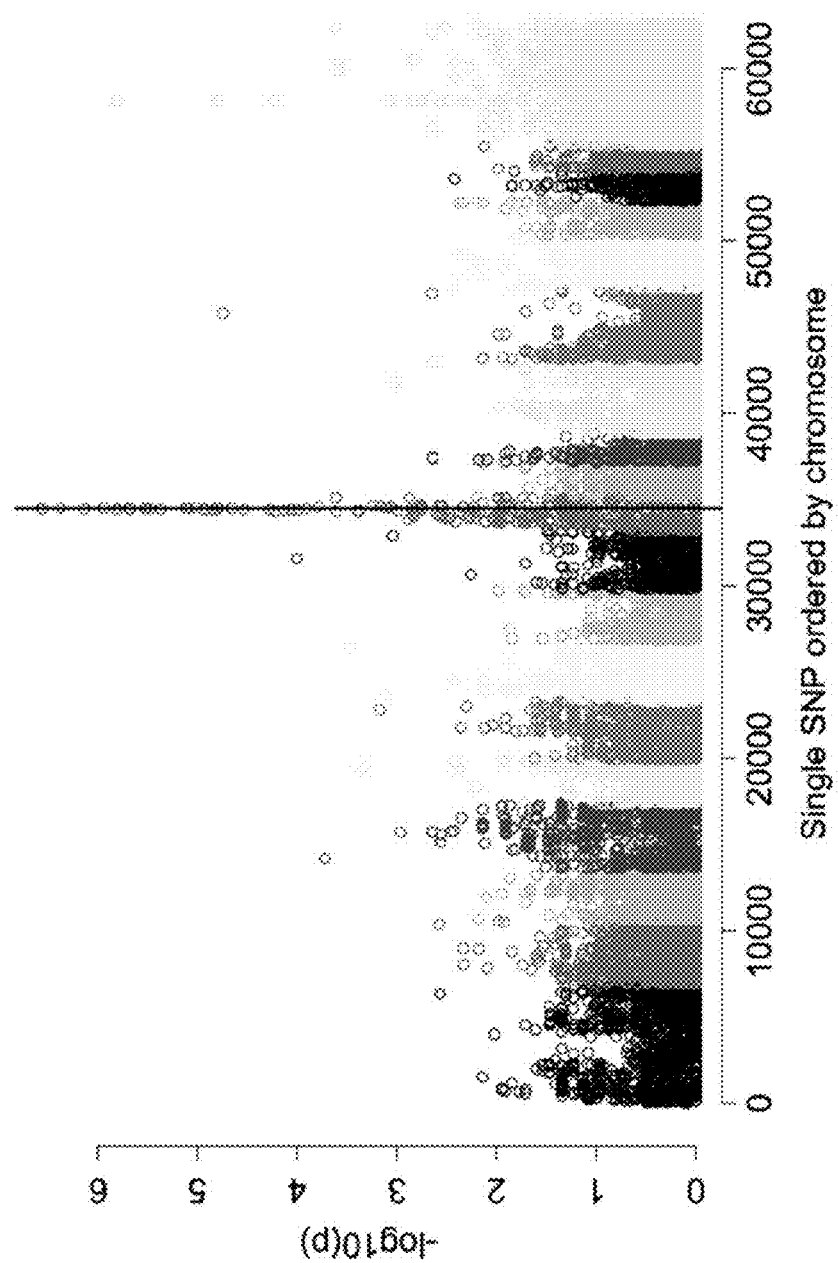
FIG. 5 shows Genome-Wide Association results for the SCID phenotype, showing a region on porcine chromosome 10 to be associated with the SCID phenotype. The solid black line shows the position of the Artemis gene.
Figure 7A:
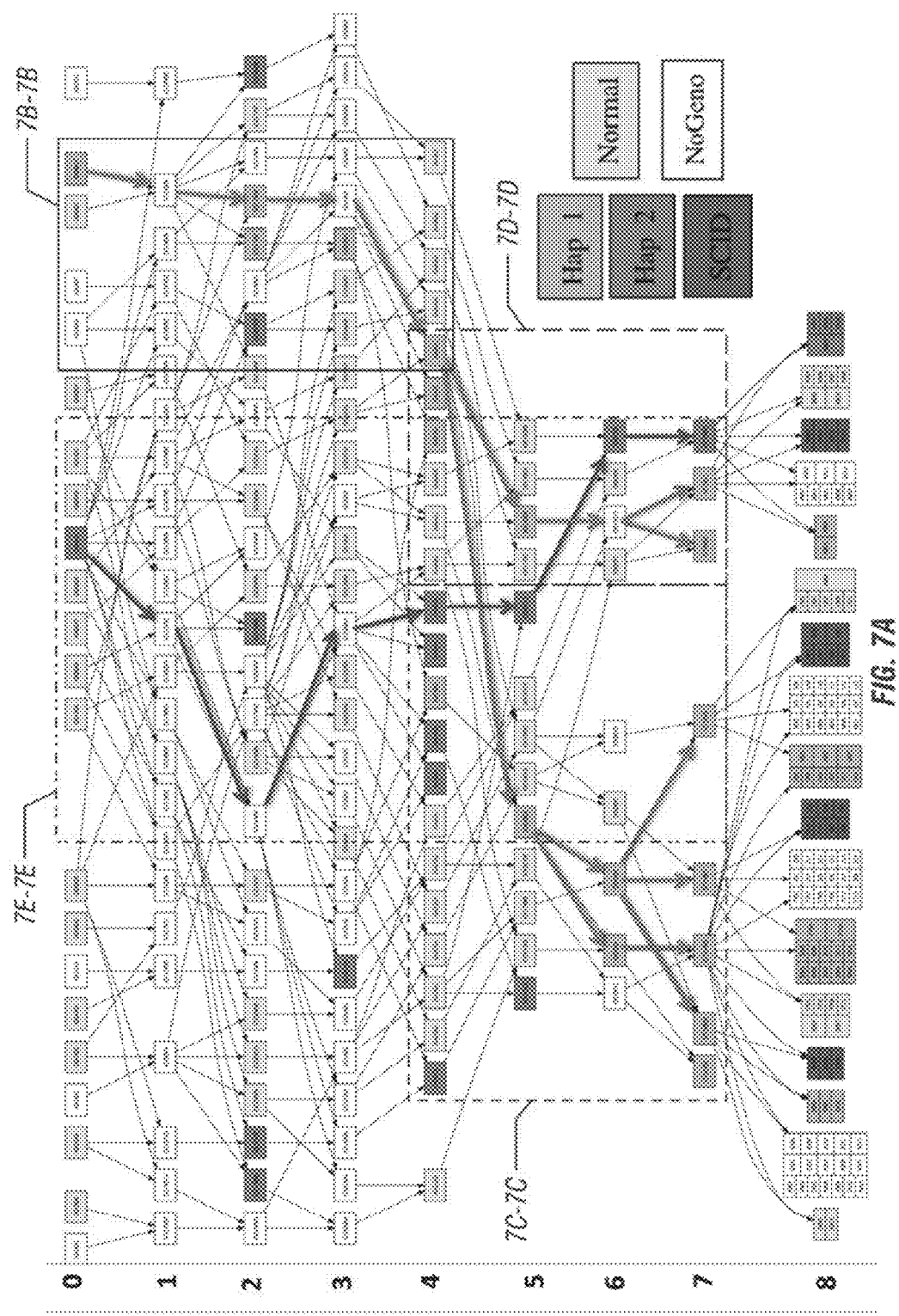
FIG. 7(A-E) shows the SCID pedigree, tracing the 12 and 16 haplotypes that were identified in generation 8 back to the founder generation of the population.
Figure 7B:
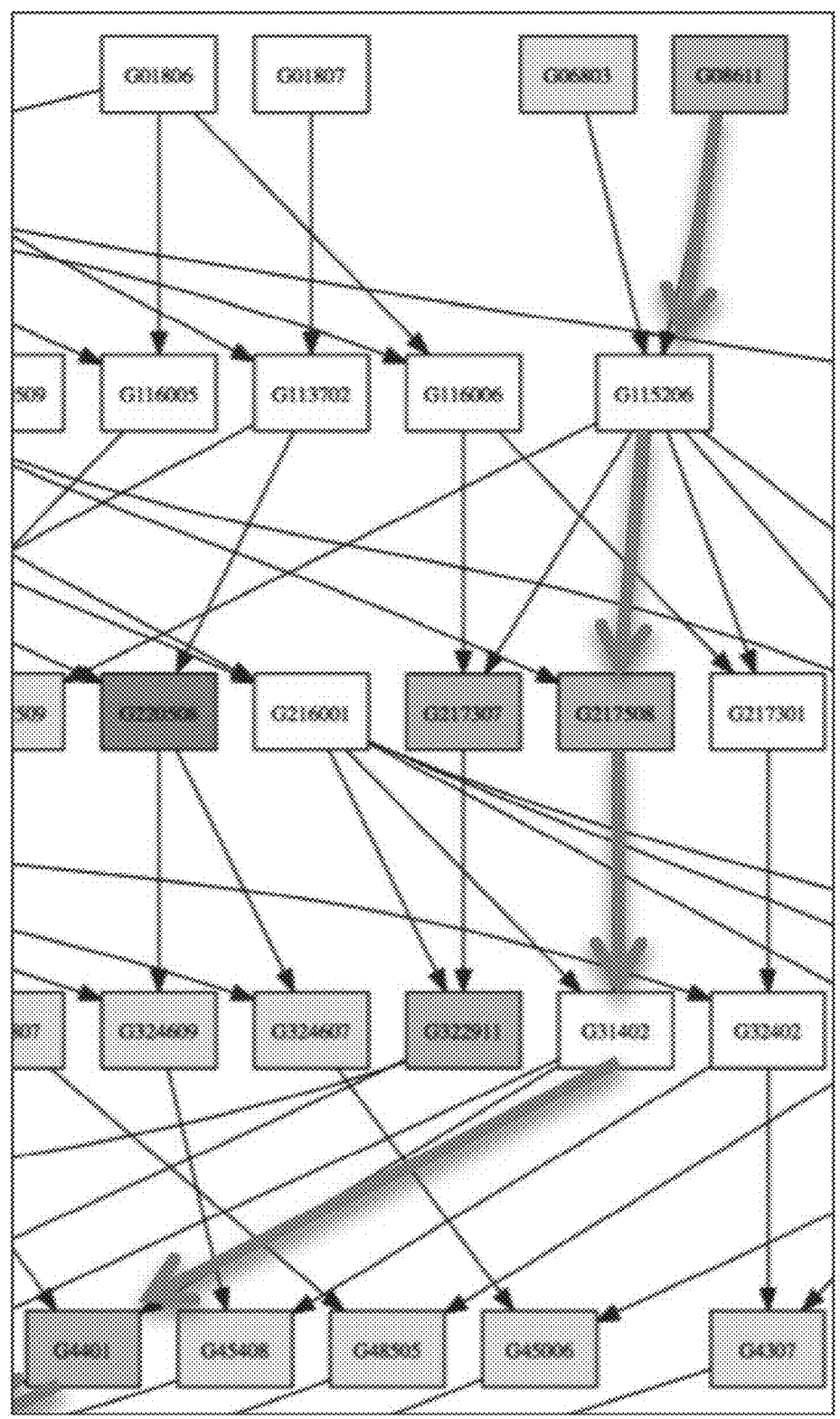
Figure 7C:
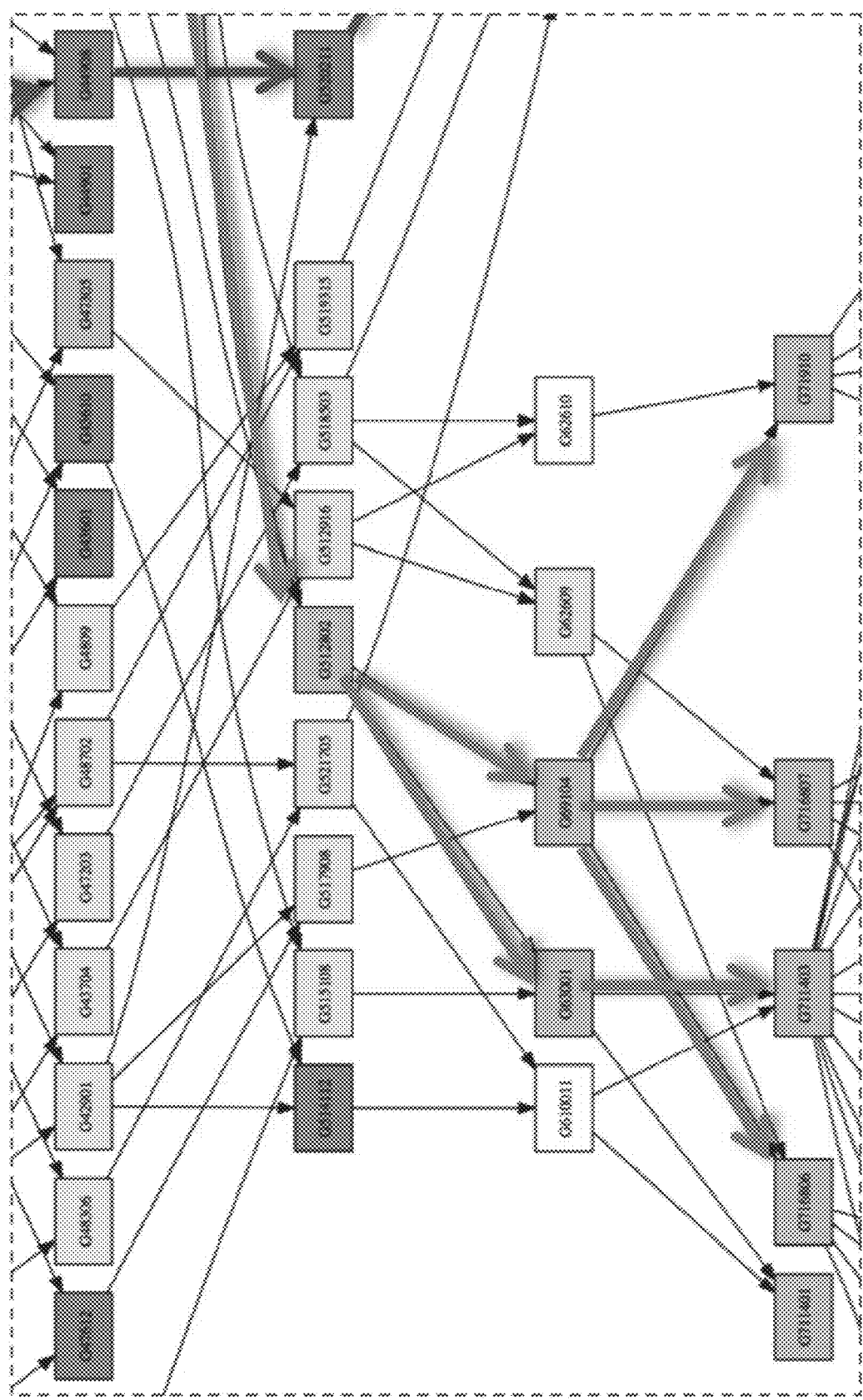
Figure 7D:
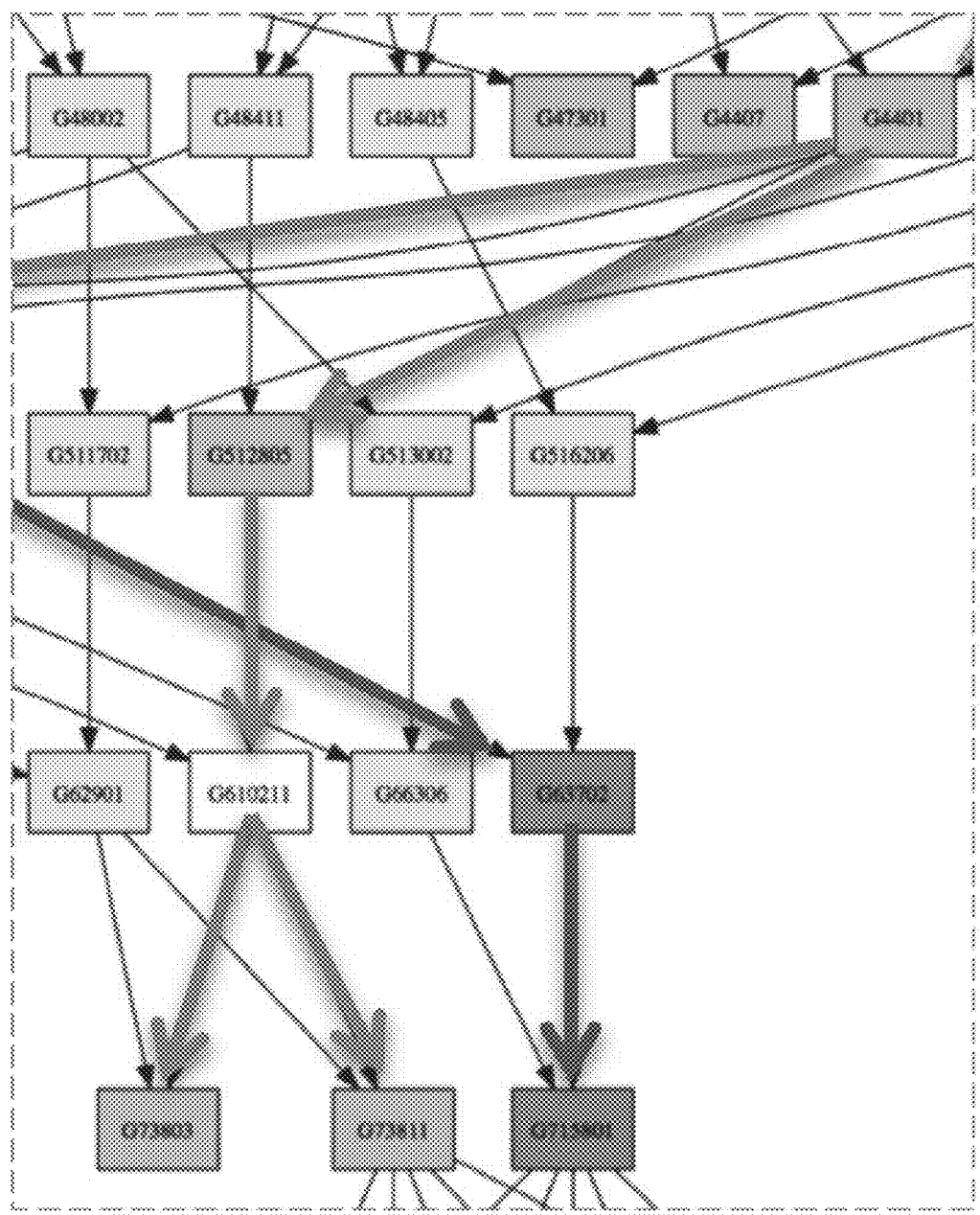
Figure 7E:
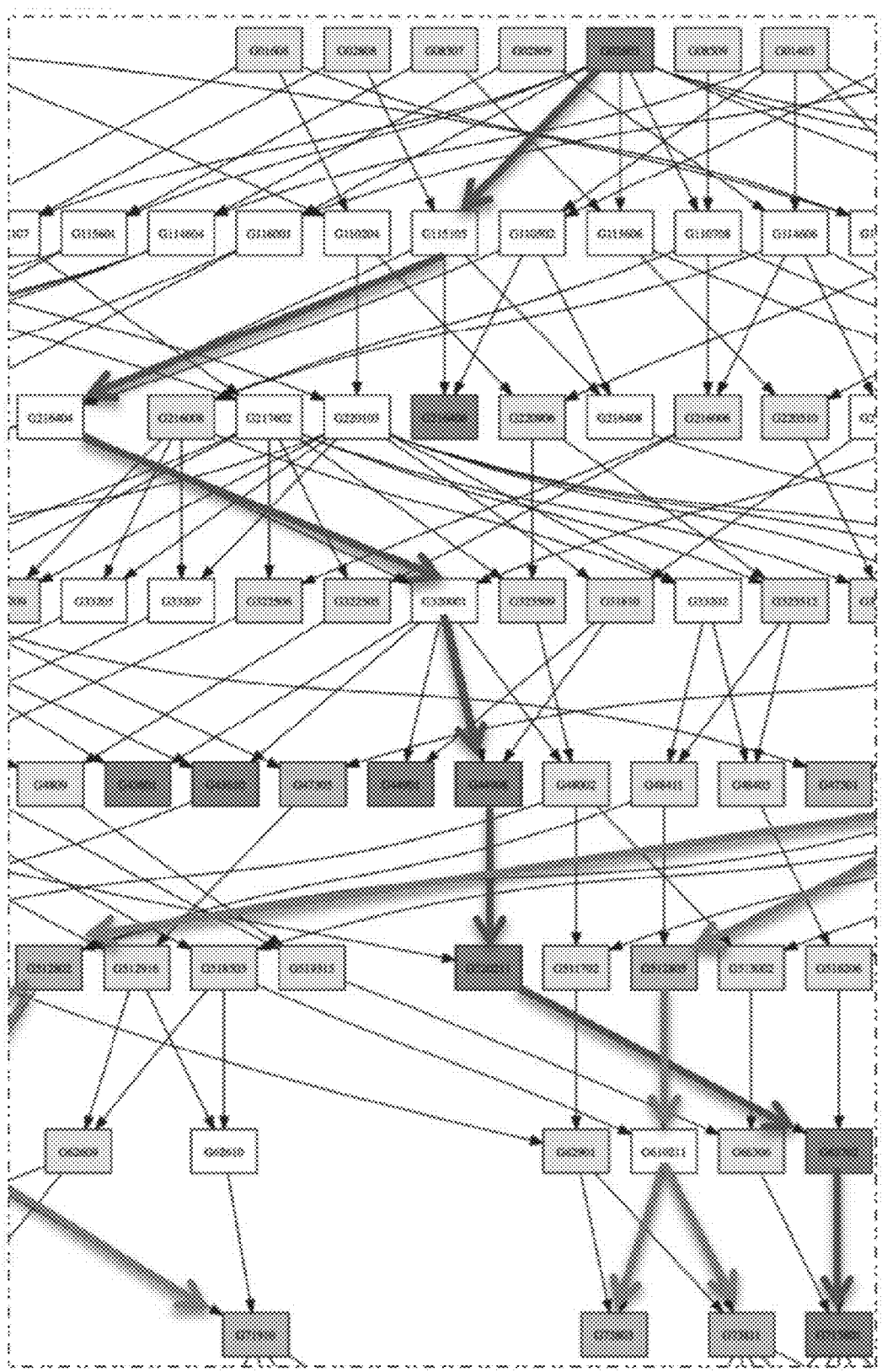

To map the genomic location of the SCID mutation, a total of 172 pigs were genotyped using the Illumina 60k Porcine Beadchip. This included 20 affected piglets, their 6 parents, 50 unaffected littermates, and 96 ancestors from the previous 7 generations. Genome-wide Association Analysis of the resulting data using the dfam option of the PLINK software (Purcell et al, 2007), identified a 5.6 Mb region on chromosome 10 that was associated with the SCID phenotype (FIG. 5), with a p-value of $2.7 \times 10^{-7}$. Using the Ensemble annotation of the genome, this region was found to contain the Artemis gene, which encodes a ubiquitously expressed protein involved in double-strand DNA break repair processes. Mutations in the Artemis gene in humans have been shown to cause SCID (Moshous et al, 2001).

The SNP genotypes in the 1 Mb region in and around the Artemis gene were then phased into haplotypes, using the program Phase. This included a total of 21 SNPs and resulted in the identification of two separate haplotypes that were associated with the SCID phenotype: the 12 haplotype and the 16 haplotype (FIG. 6). Five of the 6 parents of the initial 4 SCID piglets (FIG. 4) were identified to be carriers of haplotype 16, one parent carried haplotype 12, and the resulting SCID progeny were either homozygous for haplotype 16 or heterozygous 12/16. None of the unaffected progeny were homozygous for 16, homozygous for 12, or heterozygous for 12/16. Subsequently, genetic tests were developed to identify carriers of 12 and 16 haplotypes.

The defect was identified in a line of pigs that was initially (1997) derived from pigs that were sourced from private pig breeders in the Midwest, primarily Iowa, and that has since then been selected for increased feed efficiency. It is unlikely that the described discovery was the result of the selection that was conducted in these lines. More likely, it was either a mutation that occurred in this line or that already existed in the original pigs that created the line and that manifested itself because of some level of inbreeding that occurred in the line. In fact, using phased 60k SNP genotypes of ancestors from the population, the 12 and 16 haplotypes could be traced back from the identified SCIDs to the founder generation of the population, as illustrated in FIG. 7.

Example 4: Molecular Genetic Tests and Basis of the Artemis Mutations Haplotype Tests In order to identify affected, carrier, and homozygous normal pigs in the ISU population that do not have genotype data, allele-specific primer sets were designed for seven SNPs in the region surrounding the Artemis gene, using Web-based Allele-Specific PCR (WASP; Wangkumhang et al, 2007). PCR cycling conditions for each test included denaturation at 94° C. for 30 seconds (30 s), annealing at temperatures indicated for each primer pair in table 1 for 30 seconds, and elongation at 72° C. for the time indicated in table 1 (E-Time). Each PCR was begun with an initial hot start of 95° C. for 2 minutes (2 m), 40 cycles of amplification, and ended with a final elongation step at 72° C. for 5 m. Table 1 gives the primer sequences, PCR condition information, location, and genotypes for the seven SNPs for which allele specific primers were designed. The bottom portion of the table indicates genotypes, locations of the SNPs, and the number of the SNP in the 1 Mb haplotype from FIG. 6 in parentheses. Three of these SNPs are part of the 21 SNPs in the 1 Mb used for haplotype analysis, as indicated in Table 1. The remaining allele-specific primer sets were designed for SNPs in the 1 Mb upstream of Artemis. These SNPs were chosen as they segregated with the phenotype and the primer design software was able to produce primers sets that were very specific for each allele.

DNA and cDNA Sequencing to Identify the Causative Mutations

Total RNA was extracted from two sources: whole tissue from ears of 1-day-old piglets, and fibroblasts that were cultured from ear snip tissue. mRNA was reverse transcribed

TABLE 1

Primer and PCR conditions, genotypes, location and number of the SNPs.

| SNP Name | Allele | Product Size | FWD Primer Sequence | REV Primer Sequence | Anneal Temp | E-Time |
|---|---|---|---|---|---|---|
| ASGA-0048074 | A | 177 | TCCTCTGACCAAGCCTCTGT (SEQ ID NO: 11) | TCGTCCATGTACCAGAGCCT (SEQ ID NO: 12) | 56 | 30s |
|  | C | 177 | TCCTCTGACCAAGCCTCTGT (SEQ ID NO: 13) | CGTCCATGTACCAGAGCCG (SEQ ID NO: 14) | 56 | 30s |
| ASGA-0048114 | A | 659 | AACCAGTCCCTGACCAACTG (SEQ ID NO: 15) | TCCATATTTGTTAAGGGCAGTAATCT (SEQ ID NO: 16) | 54 | 30s |
|  | G | 131 | TGCTCAGAGCTTTACATGGATTTAG (SEQ ID NO: 17) | GGCCCATGTTGACATAAAGC (SEQ ID NO: 18) | 54 | 30s |
| ALGA-0059043 | A | 643 | TCCTCTGCAGGGTTTCAAAG (SEQ ID NO: 19) | CAGGGTGTGGGACTTTGTT (SEQ ID NO: 20) | 54 | 30s |
|  | G | 127 | TCAGCTTGGGCAGCTAGG (SEQ ID NO: 21) | CCACAGGCACATTGATCTTG (SEQ ID NO: 22) | 54 | 30s |
| H3GA-0030245 | A | 576 | AGTTGAAATCAAAGTATCCCAA (SEQ ID NO: 23) | AACTGTAACAAGCGTCCCTTTCT (SEQ ID NO: 24) | 55 | 30s |
|  | C | 576 | AGTTGAAATCAAAGTATCCCAA (SEQ ID NO: 25) | AACTGTAACAAGCGTCCCTTTCG (SEQ ID NO: 26) | 55 | 30s |
| ALGA-059061 | A | 593 | GGTATTCTCCTCCTCTACCTCT (SEQ ID NO: 27) | CTGGATTGGCAGAGGCTCTTTAT (SEQ ID NO: 28) | 55 | 30s |
|  | G | 593 | GGTATTCTCCTCCTCTACCTCT (SEQ ID NO: 29) | CTGGATTGGCAGAGGCTCTTTAC (SEQ ID NO: 30) | 55 | 30s |
| ALGA-0059066 | A | 475 | GAATGGGAGGTGAGTAAGTAAA (SEQ ID NO: 31) | CCAGCTGCAAGGGAGACT (SEQ ID NO: 32) | 55 | 30s |
|  | C | 475 | GAATGGGAGGTGAGTAAGTAAA (SEQ ID NO: 33) | CCAGCTGCAAGGGAGACG (SEQ ID NO: 34) | 55 | 30s |
| ALGA-0059080 | A | 425 | AGCATTAAGACTGTGTGTGTGT (SEQ ID NO: 35) | GGTCAAAGTCGTGGGTGTGTTT (SEQ ID NO: 36) | 55 | 30s |
|  | G | 425 | AGCATTAAGACTGTGTGTGTGT (SEQ ID NO: 37) | GGTCAAAGTCGTGGGTGTGTTC (SEQ ID NO: 38) | 55 | 30s |

Figures 8A, 8B:
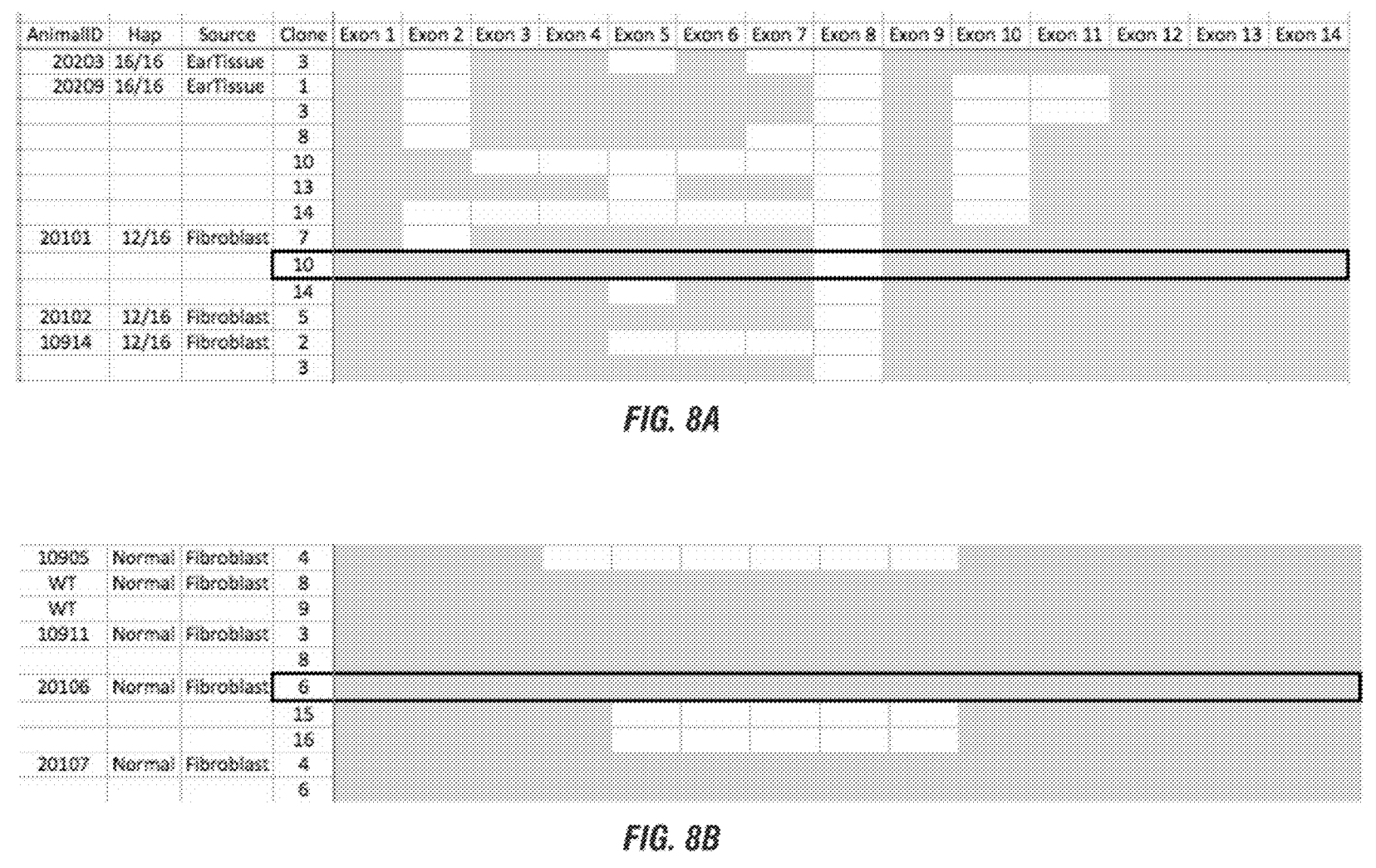
Figure 8C:
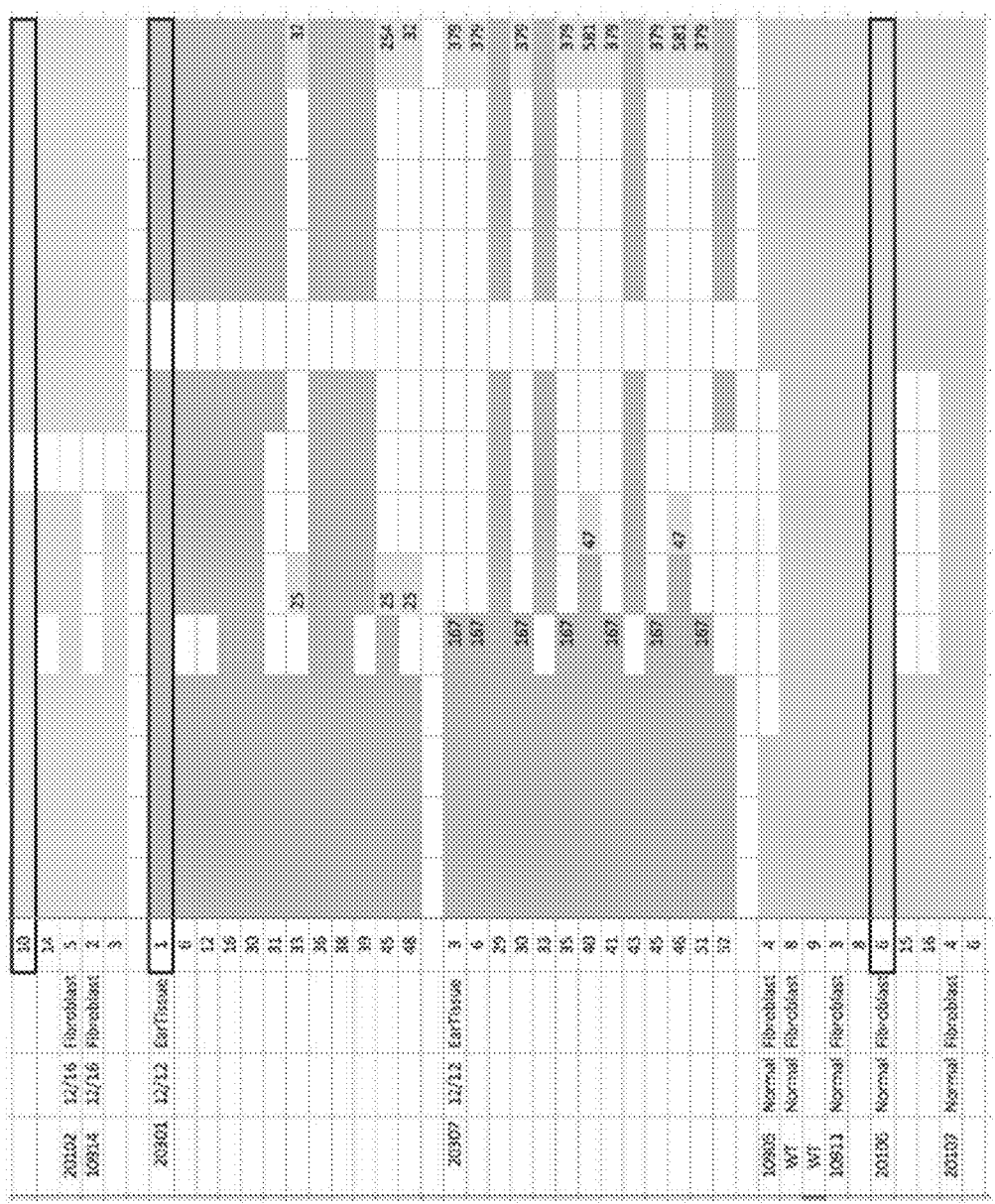
FIG. 8(A-C) shows presence or absence of exons in transcripts sequenced from haplotype 16 (A), haplotype 12 (C), and normal (B) using Full cDNA primers (SEQ ID NO:39 and 40). Exon 8 is absent in all haplotype 16 sequences, while exon 10 is absent in all haplotype 12 sequences. Light pink boxes indicate splicing of partial exons, with numbers showing the number of bases present for that exon. Purple boxes indicate that the transcript included 167 bases of intron 4 after exon 4.

|  | ASGA-0048074 | ASGA-0048114 | ALGA-0059043 | H3GA-0030245 | ALGA-059061 | ALGA-0059066 | ALGA-0059080 |
|---|---|---|---|---|---|---|---|
| Location | 51153137 (5) | 51812252 (16) | 51975024 (21) | 52066694 | 52086867 | 52109172 | 52174549 |
| h12 | C | G | G | C | A | C | A |
| h16 | C | A | G | C | A | C | A |
| Normal | A | G | A | A | G | A | G | to cDNA. Artemis transcripts were then amplified from the cDNA using the following primers: forward 5'-GGATC-CGTGTTCGCCAACGCT-3' (SEQ ID NO:39) and reverse 5'-GCGGCCGCAGAGCTGCCTTTTAGGTTAT-3' (SEQ ID NO:40), using an annealing temperature of 60° C. and an extension time of 2 m 30 s. The full Artemis cDNA was amplified using PCR technique, cloned into a TOPO vector, then plasmids transferred into E. coli bacteria which were then grown on LB plates with Ampicillin. Individual colonies were then picked into LB-Ampicillin media and PCR amplified to ensure that each colony contained a vector with Artemis cDNA. Positive PCR products were cleaned using Exo-Sap and sent to the Iowa State University DNA Facility for sequencing. FIG. 8 shows the different transcripts observed in cells from affected pigs. While many types of transcripts were observed, specific parts of the gene are missing for transcripts from the 12 and the 16 haplotypes.

For haplotype 16, all transcripts were found to lack exon 8, which results in a transcript that is 141 bases shorter than the expected full transcript. The sequence and translation of the longest cDNA clone from haplotype 16 is shown in Sequence and Translation 1 (SEQ ID NOS:1 and 2, respectively). Exon 8 and the surrounding region were amplified from genomic DNA extracted from ear snip tissue to investigate the presence or absence of signal sequences required for normal splicing. Exons 7 and 8 and portions of the surrounding introns were amplified using the following primers: forward 5'-CTCAGTGGGTTAGGGACCTG-3' (SEQ ID NO:41) and reverse 5'-GCCATCTGA-TAGGGTTTCCA-3' (SEQ ID NO:42), with annealing temperature of 54° C. and elongation time of 1 m. Animals homozygous for the 16 haplotype were found to have a point mutation of GA at the 615th base of the PCR product (Sequence 4; SEQ ID NO:7). This base is part of the signal sequence for a splice donor site for exon 8, and is required for proper splicing. The A mutation was seen only in homozygous 16 haplotype animals (Sequence 4; SEQ ID NO:7), but a G at this position was seen in the 12 haplotype and all normal haplotypes (Sequence 5; SEQ ID NO:8) that were sequenced.

Transcripts from the 12 haplotype were found to lack a 137 base pair long exon 10, which would cause a frameshift mutation, resulting in a stop codon shortly after the missing exon. Sequence and translation of the longest cDNA clone from haplotype 12 are shown in Sequence and Translation 2 (SEQ ID NOS:3 and 4). Exons 10 and 11 and portions of the surrounding introns were amplified from genomic DNA of homozygous haplotype 12 animals using the following primers: forward 5'-GCTAAAGTCCAGGCCAGTTG-3' (SEQ ID NO:43) and reverse 5'-CAAGAGTCCCCACCA-GTCTT-3' (SEQ ID NO:44), with annealing temperature of 56° C. and elongation time of 1 m. The signal sequence required for splicing of exon 10 was the same as that seen for normal and reference sequences. However, sequencing of the genomic region around exon 10 identified a nonsense point mutation in the 12 haplotype exon 10 sequence at base 116 of the PCR product (Sequence 6; SEQ ID NO:9), with a mutation from G→A. Under normal transcription, splicing and translation, this mutation from G→A would change a Tryptophan amino acid codon to a stop codon, resulting in a protein that ends with 266 of the total 712 amino acids of the normal Artemis protein. We have not observed such a transcript in 12/12 animal cells thus far. For the 12 haplotype transcript we do observe, the predicted protein translation would be 277 amino acids long (Translation 2; SEQ ID NO:2). The genomic sequences for exons 10 and 11 are shown in sequence 7 (SEQ ID NO:10).

These results for the 12 and 16 haplotype sequencing did not show any transcripts containing all exons expressed in pig cells that were homozygous for 12 or the 16 through rt-PCR amplification using primers at the beginning and end of the normal transcript. Thus a normal Artemis protein cannot be produced from any of the RNAs observed. For the 16 haplotype, a normal amount of RNA should be present in these cells, which will make a protein that missing 47 amino acids. For the 12 haplotype, the protein produced would be severely truncated if a transcript containing exon 10 was produced; however, no evidence that such a transcript is stably produced in 12/12 homozygous animals was found. Translation of the transcript observed would also result in a truncated protein. While >150 different mutated alleles of Artemis have been found through 2010 (Pannicke et al. 2010), none of the reported mutant alleles are exactly the same as the two mutants we have identified or as their predicted RNAs/proteins. Thus, it is difficult to be sure of the actual resulting residual level of activity expressed by these mutations. We anticipate that the protein predicted to be expressed from the 16 mutation may have some residual activity, while the protein predicted to be expressed from the 12 mutation would be completely non-functional.

Genotyping Methods Used for Crossbred Animals

Known carrier pigs were mated to Duroc, Landrace, or crossbred animals in order to introduce a more diverse genetic background into the SCID carrier population. Offspring that resulted from these matings were tested for carrier status (50% of each litter produced expected to be SCID carriers) using the seven sets of allele-specific primers described above. The genetic tests performed were not able to accurately distinguish carriers from homozygous normal piglets. To genotype these crossbred animals, genomic regions containing exons with causative mutations (exon 8 for suspected haplotype 16 carriers and exon 10 for suspected haplotype 12 carriers) were amplified, cleaned using Exo-Sap, then sequenced, as described in section 4b. This method of genotyping is most accurate in animals outside of the ISU Yorkshire population, such as animals of other breeds or commercial animals.

Example 5: Cellular Evidence of Artemis as the Causative Gene

Figure 9:
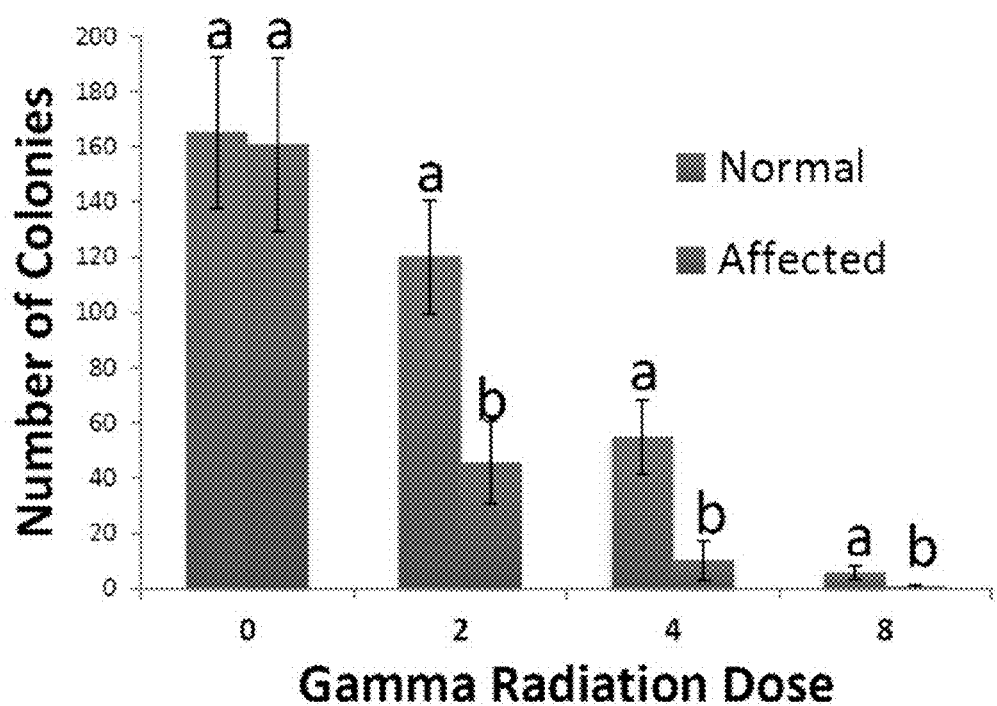
FIG. 9 shows SCID cells are highly sensitive to radiation compared to cells from normal pigs. Fibroblasts from affected and unaffected animals (n=7-10) were subjected to gamma rays at 0, 2, 4, or 8 Grays. Letters denote significant differences between genotypes within gamma radiation level ($p<0.0001$).

A specific property of mutations in the Artemis gene, compared to mutations in RAG1/2 genes, is that a non-functional Artemis gene causes increased sensitivity of cells to irradiation because Artemis is involved in DNA repair. This was evaluated by irradiation of fibroblasts from SCID piglets and their normal litter mates. Results (FIG. 9) clearly established the increased sensitivity of fibroblasts from the SCID piglets to irradiation, eliminating RAG1/2 genes as causes for the SCID mutation in the ISU pigs of the present invention.

Figure 15:
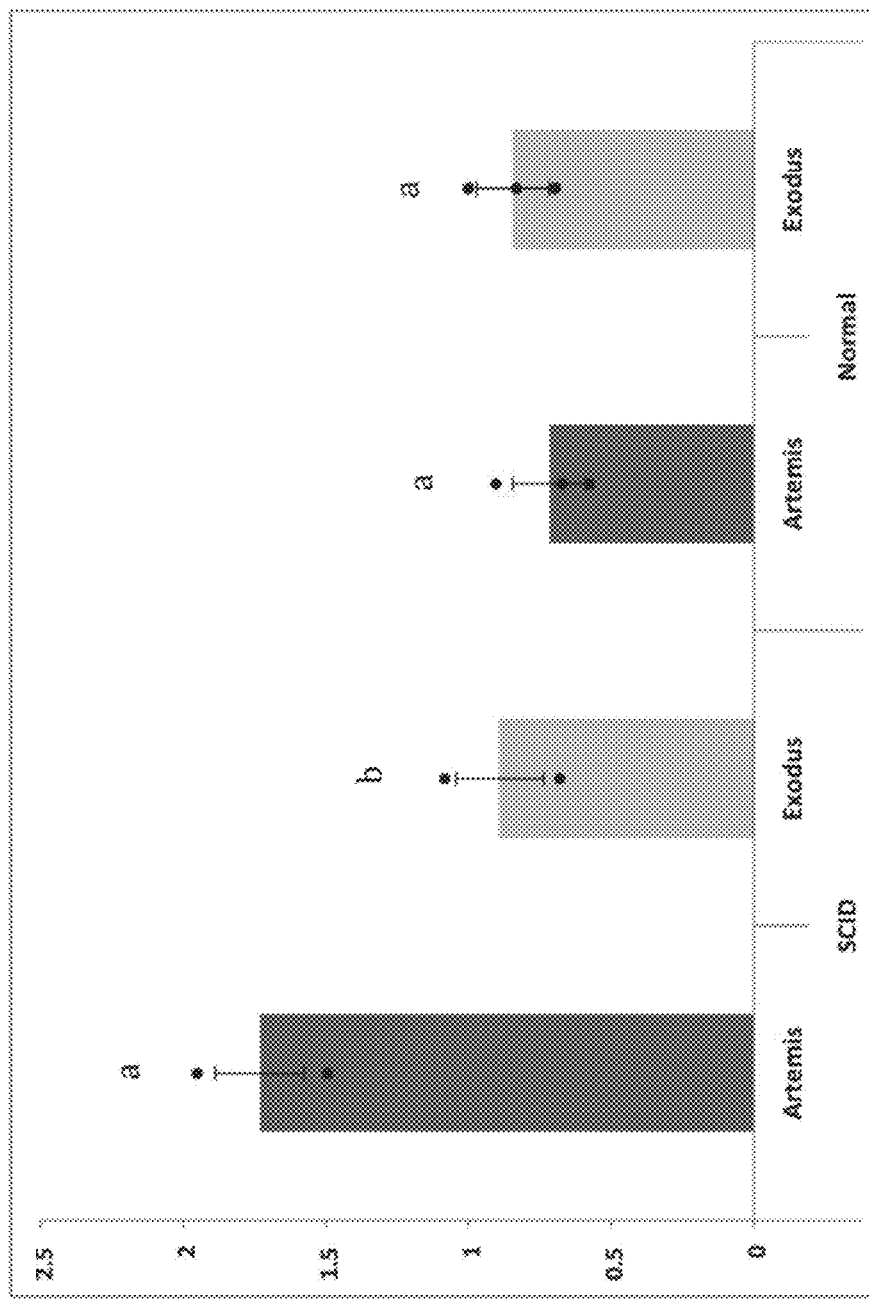
FIG. 15 shows rescue of sensitivity to ionizing radiation. Fibroblasts from SCID (n=2) and normal (n=3) pigs were transfected with 5 μg Artemis, 3.45 μg Exodus plasmid without Artemis gene, or were shocked without plasmid added. Fibroblasts were exposed to 4 Gy irradiation dose 24 hours after transfection. Colonies were counted after 14 days of growth. Error bars represent the standard error of the least squares means. Dots show individual observations. Different letters within affected status represent statistical differences between means with $p<0.01$.

Further, we have demonstrated that the radiosensitivity is due to the lack of Artemis protein activity in the SCID pig-derived fibroblasts. We inserted a plasmid containing the human Artemis cDNA (pArt, which expresses a functional Artemis protein) into fibroblasts from SCID pigs (n=2) or normal animals (n=3). Transfected cells were incubated overnight in cell culture media. One day after transfection, fibroblasts were subjected to 4 Gy irradiation and plated in triplicate. Addition of pArt increased the radioresistance of SCID fibroblasts (p=0.0012), but normal cells were unaffected (p=0.11; FIG. 15). This demonstrates that mutations creating the lack of Artemis function cause the radiosensitivity seen in fibroblasts from SCID pigs, as the addition of Artemis protein can rescue the phenotype.

Example 6: Bone Marrow Transfer Rescues

Figure 10:
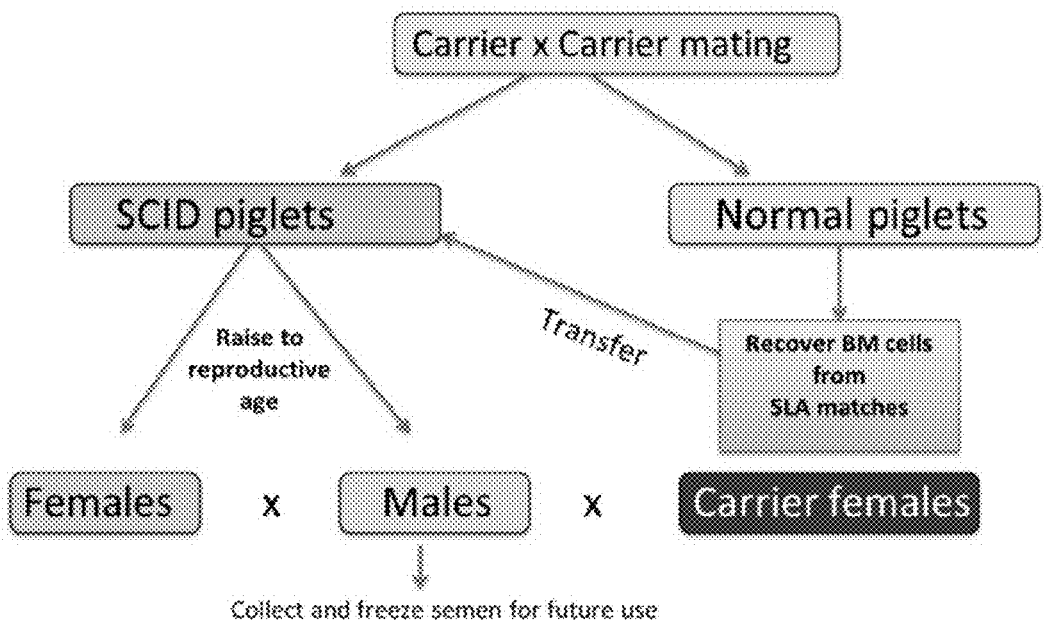
FIG. 10 shows design for the use of Bone Marrow Transfer to produce homozygous SCID pigs for breeding.

In order to both establish the SCID as a model for bone marrow transplantation research, as well as rescue SCID affected piglets by providing them with an immune system such that they could be raised to breeding age (FIG. 10), nine affected piglets from four litters were given bone marrow transfers. Marrow donors were matched based on low-density MHC genotyping. All nine piglets were successfully transplanted, however, five of the nine showed signs of graft versus host disease after transfer and were euthanized.

Figure 11:
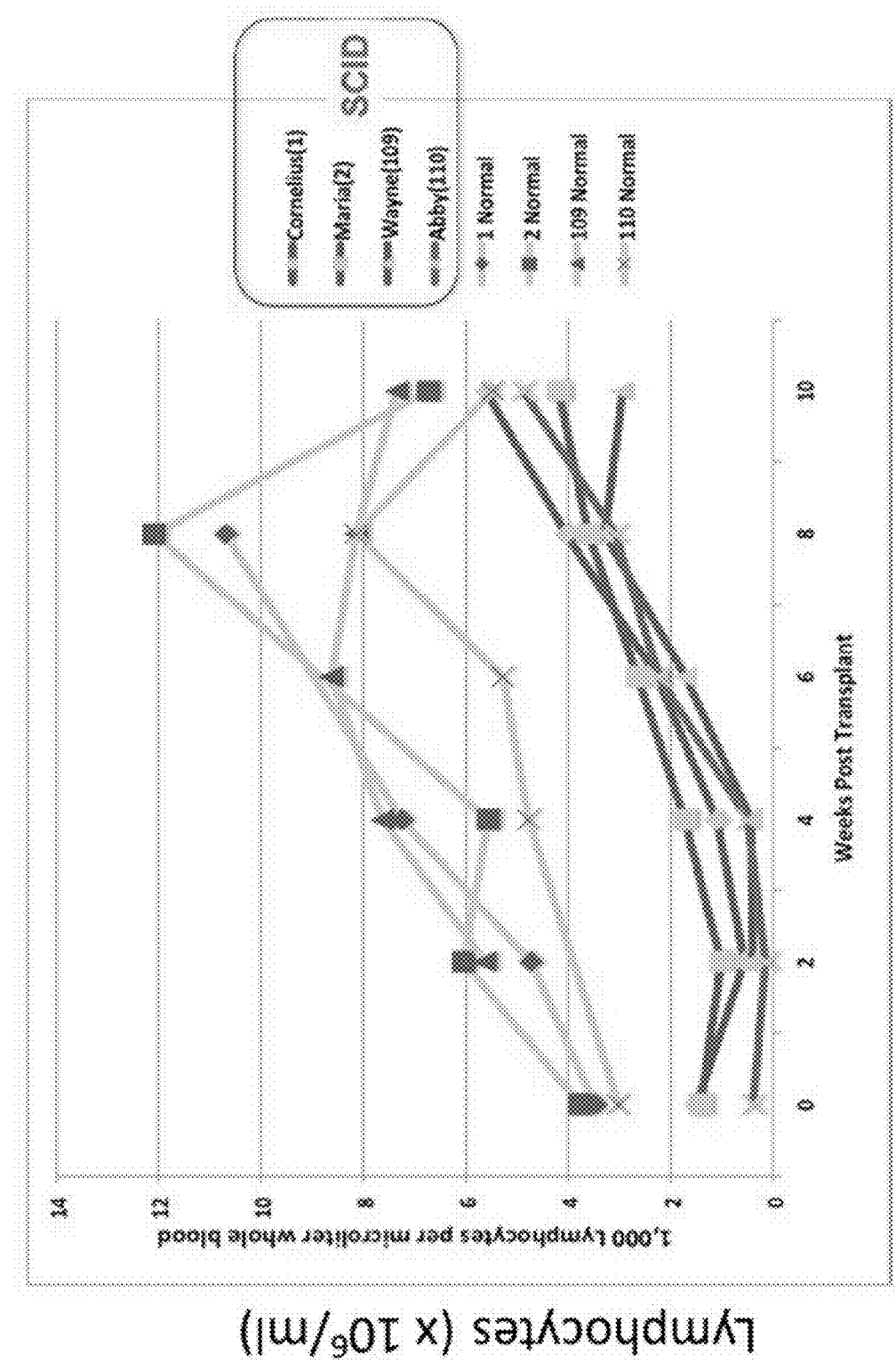
FIG. 11 shows evidence of recovery of blood lymphocyte counts in Bone Marrow Transfer SCID recipients.
Figure 12A:
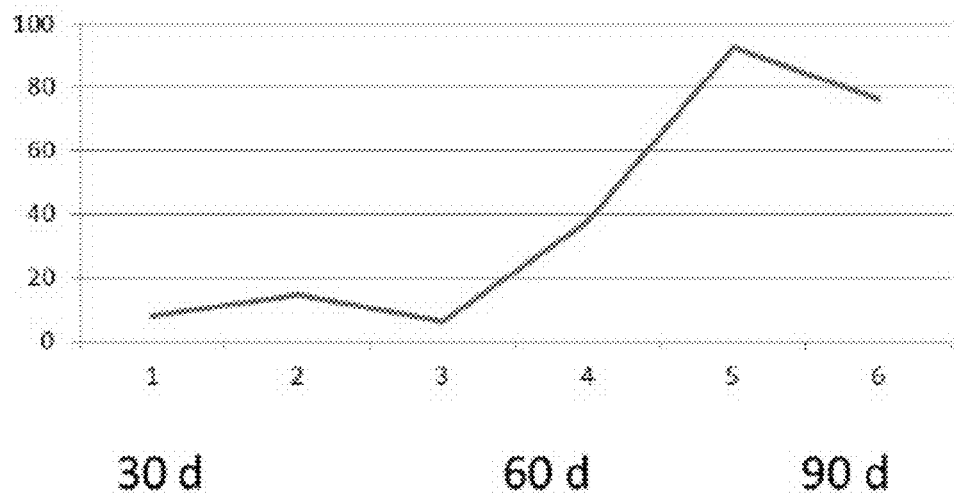
FIG. 12(A-B) shows evidence of donor increasing donor origin of PBMC's in female Bone Marrow Transfer recipients that received bone marrow cells from male donors. Assays based on presence of SRY sequences.
Figure 12B:
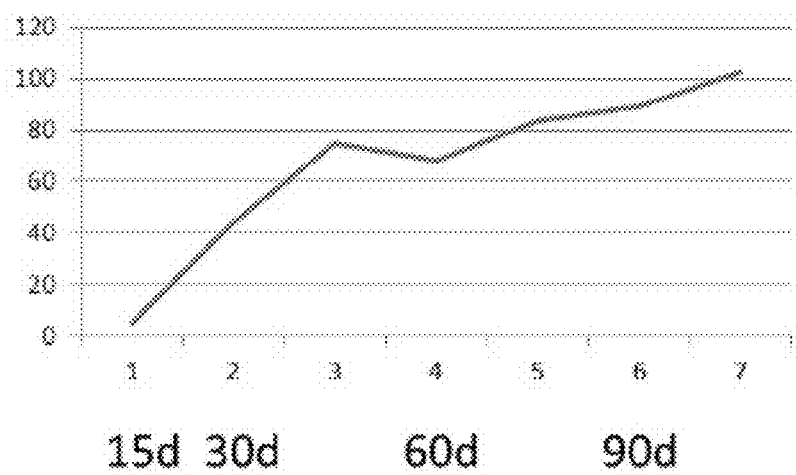
Figure 13:
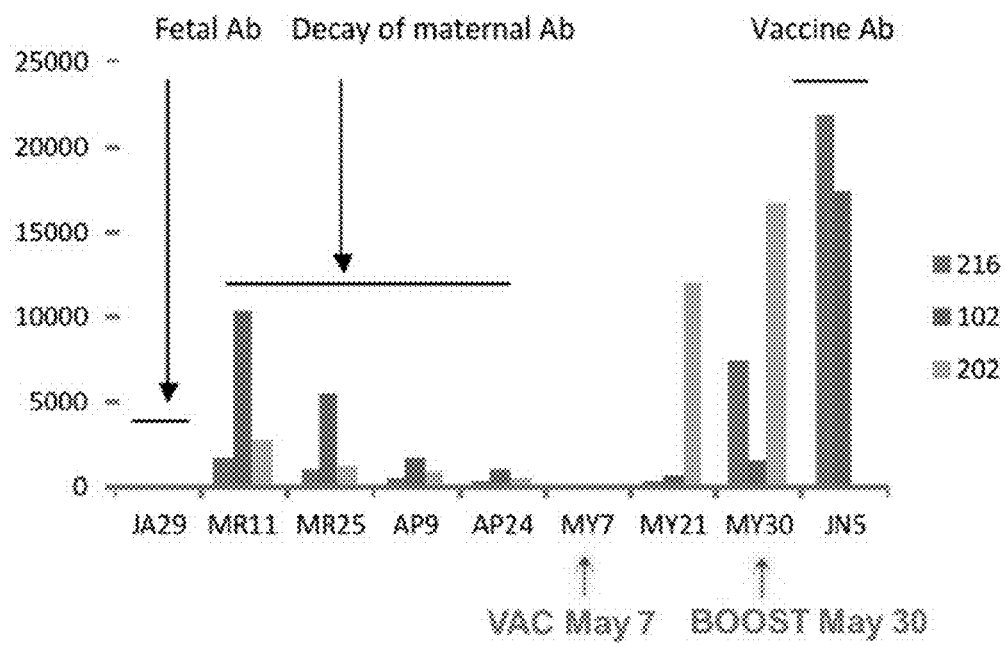
FIG. 13 shows evidence of an active adaptive immune system in Bone Marrow Transfer SCID recipients. Serum antibody to vaccination with Circumvent: Circovirus-Mycoplasma.

Engraftment and establishment of a functional adaptive immune system was documented in the four successful BMT recipients based on lymphocyte counts (FIG. 10), donor origin of those lymphocytes (FIG. 11), presence of normal major lymphocyte populations based on flow cytometry, and response to vaccination (FIG. 12).

Example 7: Spontaneous Cancer Development in Bone Marrow Transfer SCID Recipients Three of the four successful BMT SCID recipients developed spontaneous cancers when they were about 1 year of age. (Table 2). The development of these cancers likely is related to the fact that they have a mutation in Artemis, which is involved in DNA repair, and that the BMT SCID pig's genetics were either 16/16 or 12/16 and thus their immune cells may have had some residual activity, leading to aberrant DNA recombination and oncogene activation, which is seen in some human Artemis patients (Moshous et al., 2003 PMID: 12569164) and in some mouse models (Jacobs et al. 2011 PMID: 21147755).

TABLE 2

List of successful BMT transfers and their fate.

| Animal ID | Genotype | Necropsy Date | Necropsy Age | Type of cancer |
|---|---|---|---|---|
| Cornelius | 16/16 | Feb. 19, 2013 | 12 mo 21 d | T cell lymphoma |
| Maria | 16/16 | Dec. 31, 2012 | 11 mo 2 d | Lymphoma/leukemia |
| Abby | 12/16 | May 22, 2013 | 11 mo 20 d | Nephroblastoma |
| Wayne | 12/16 | N/A - Still alive | | |

Example 8: Direct Genetic Tests for the SCID Mutations

Figure 14:
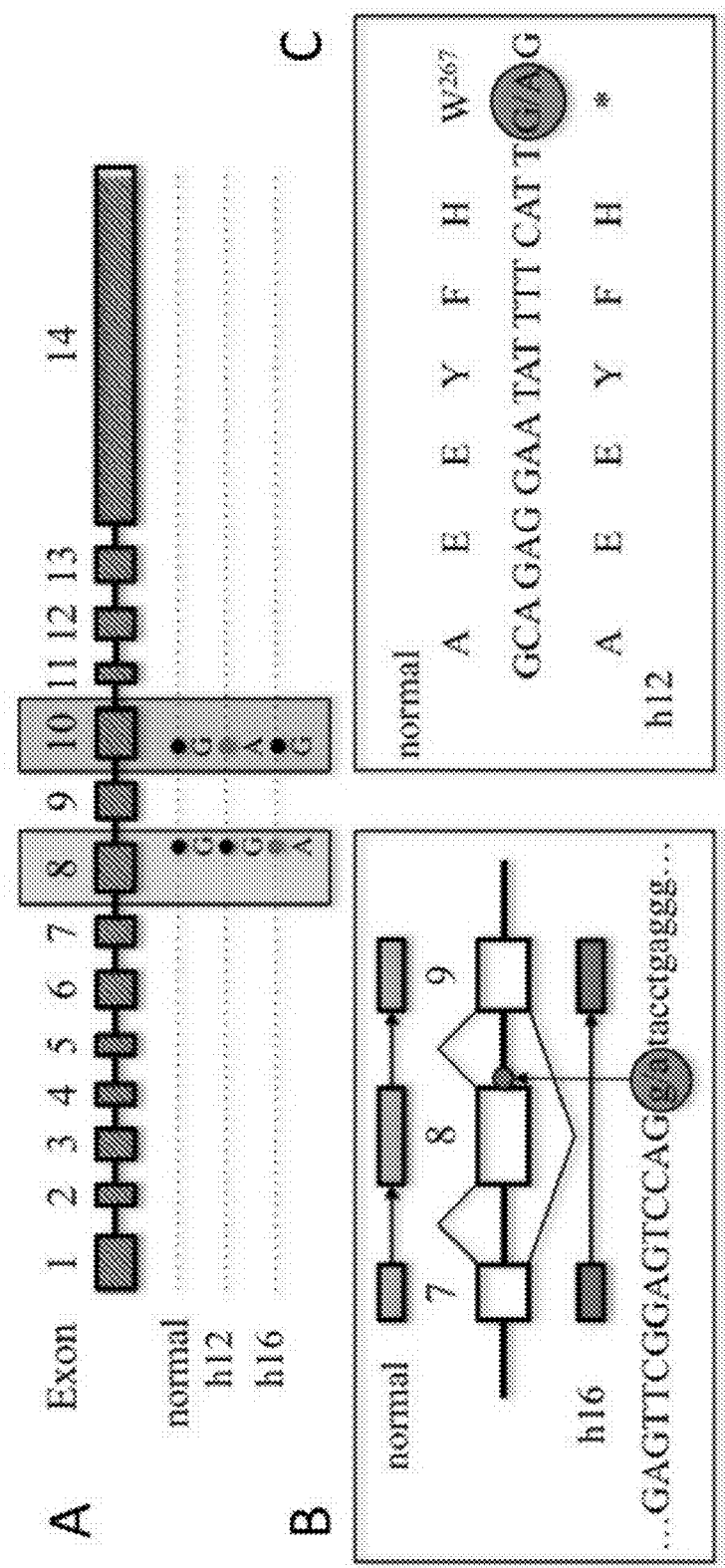
FIG. 14(a-c) shows two independent mutations in Artemis causing SCID. (a) The exons are shown as blocks, the coding region of the Artemis transcript is indicated by cross-hatch within these blocks, and the normal, h12, and h16 genotypes at mutated positions are shown. Mutant alleles that cause SCID are shown by pink dots. (b) Genomic sequence of h16 shows a splice donor site mutation (g→a) responsible for the lack of exon 8 in all h16 transcripts. (c) A point mutation (G→A) in exon 10 changes the Tryptophan at position 267 to a stop codon in h12.

FIG. 14 shows the orientation to the two different mutations, their relationship to each other along the chromosome, and the new genetics tests for SCID in pigs.

Specific tests were developed for the mutant sequence at each of the two variants in the Artemis/DCLRE1C gene. For the causative mutation in haplotype 16, found at position 615 of Sequence 4 (SEQ ID NO:7), the test was established for all animals in which it was assessed. For the causative mutation in haplotype 12, found at position 116 of Sequence 6 (SEQ ID NO:9), the test was able to genotype most animals but not all (see information below).

The ABI PRISM® SNaPshot™ Multiplex Kit (Lifetechnologies, P/N 4323151) technology was used for the tests. SNaPshot can be used to distinguish four nucleotides at a specific position in a sequence by color. First, a PCR is performed to amplify the region surrounding the SNP of interest, i.e. one PCR for the region surrounding haplotype 12 (h12) SNP and one for the region surrounding haplotype 16 (h16) SNP. The primers used are called the outside primers for the h12 SNP and for the h16 SNP in Table 3. The melting temperature for both PCRs is Tm=54° C. Next, the PCR products are cleaned from remaining primers and dNTPs through adding 5 units of Shrimp Alkaline Phosphatase (SAP, USB Corporation, P/N 70092) and 2 units of Exonuclease I (ExoI, New England BioLabs, P/N M0293) to every 15 ul of PCR product. To get to the right concentration, ExoI is diluted in a buffer containing 80 mM Tris-HCl and 2 mM $MgCl_2$. The mixture of PCR product, SAP and ExoI is incubated at 37° C. for 1 hour and deactivated at 75° C. for 15 minutes. The cleaned PCR products (one for each SNP) of one animal can thereafter be pooled and analyzed together with the SNaPshot™ Multiplex Kit. This kit encloses a SNaPshot Multiplex Ready Reaction Mix that contains fluorescently labeled ddNTPs and AmpliTaq® DNA polymerase in a reaction buffer. In a reaction volume of 10 ul, we have 5 ul of the SNaPshot Multiplex Ready Reaction Mix, 3 ul of pooled PCR products and 0.2 uM of each extension primer (for sequence see table 1). The extension reaction goes as followed: 25 cycles of 10 minutes at 96° C., 5 minutes at 50° C. and 30 minutes at 60° C. 1 unit of SAP is added after this reaction to remove unincorporated fluorescent ddNTPs from the reaction. This SAP incubation is done at 37° C. for 1 hour and deactivated at 75° C. for 15 minutes. To read the fluorescent signal, this product needs to run on an ABI Prism 3700 DNA Analyzer (or 310 or 3100 Genetic Analyzer), using the GeneScan 120 LIZ size standard, with dye set E5.

TABLE 3

PCR Primers and Oligonucleotides used in SNaPshot Direct Genetic Tests for the Causative Mutations

| Haplotype | Primer Use | Primer Direction | Primer Sequence 5'-3' | SCID allele | Normal allele |
|---|---|---|---|---|---|
| h16 | PCR | Forward | CTCAGTGGGTTAGGGACCTG (SEQ ID NO: 46) | | |
| | | Reverse | GCCATCTGATAGGGTTTCCA (SEQ ID NO: 47) | | |
| | SNaPshot | Forward | GAGGAGTTCGGAGTCCAG (SEQ ID NO: 48) | A | G |
| | | Reverse | TCTCTGGGAGAAAGAGCCCTCAGGTA (SEQ ID NO: 49) | T | C |

TABLE 3-continued

PCR Primers and Oligonucleotides used in SNaPshot Direct
Genetic Tests for the Causative Mutations

| Haplotype | Primer Use | Primer Direction | Primer Sequence 5'-3' | SCID allele | Normal allele |
|---|---|---|---|---|---|
| h12 | PCR | Forward | GCATTCACTCAGGCTGCTTT (SEQ ID NO: 50) | | |
| | | Reverse | CCCAGGAAATACTGGCTCAT (SEQ ID NO: 51) | | |
| | SNaPshot | Forward | CCCCATCTTTTTTAGGCAGAGGAATATTTTCATT (SEQ ID NO: 52) | A | G |
| | | Reverse | CTCTCTCTCTCTCCGGATGTTATTCCACAGGGTAAT TTATTC (SEQ ID NO: 53) | T | C |

Both tests are performed in matings in which the parents contain both the h16 and h12 alleles, in order to correctly determine the combined genotype at both positions. In matings where only one SCID haplotype is segregating, only one of the two tests needs to be performed. We have not observed an animal that carries both mutations on the same chromosome, the two mutations appear to always be on separate chromosomes.

H16 Test (Position 615 of Sequence 4; SEQ ID NO:7)

The h16 test correctly determines the allele at the h16 position (either G/C or A/T) for all possible genotypes. These include a GG result for normal animals at both the h12 and h16 positions, as well as h12/h12 animals, a GA result for h12/h16 and normal/h16 animals, and a AA result for h16/h16 animals (see FIG. 14A).

H12 Test (Position 116 of Sequence 6; SEQ ID NO:9)

The h12 test detects the h12 mutant sequence at position 116 of SEQ ID NO:9 but will not always detect the normal sequence on the other chromosome in a h12/h16 or a h12/normal animal. Recent results from SNaPshot genotyping of h12 mutation carriers have shown that the primers given above may preferentially amplify the h12 mutated allele when present. In the absence of the h12 mutated allele, SNaPshot results show the expected GG (normal/normal at this position) genotype. In certain cases, SNaPshot genotyping of animals with the known genotype of h12/h16 or h12/normal have shown only the h12 mutant allele (AA).

Combining Technologies to Obtain Exact Genotype at the Artemis Locus

Correct identification of genotypes for animals that have resulted in these SNaPshot genotyping errors have been found through the use of the primers discussed in Table 1 of Example 4 above, in addition to SNaPshot results from h16 allele genotyping. The primers of Table 1 of Example 4 are capable of determining whether an animal is SCID affected, carrier, or normal. This information, combined with the genotype from h16 SNaPshot will show the exact genotype of that animal.

Example 8: Sequences

In each nucleic acid sequence, unless otherwise noted, primer sequences are shown in bold, correct translation frames are underlined, location of missing sequences are indicated in parentheses, and premature stop codon are shown in italics. Splice donor site mutation indicated by brackets. Point mutations indicated by curly brackets.

Sequence 1, Transcript of 20101 clone 10, longest cDNA sequence from haplotype 16

(SEQ ID NO: 1)

GGATCCGTGTTCGCCAACGCTATGAGTTCCTTCGAGGGCCAGATGAGTTCCT

TCGAGGGCCAGATGGCGGAGTACCCAACTATCTCCATAGACCGTTTCGACCGG

GAGAATCTGAGGGCTCGCGCTTATTTCCTGTCCCACTGCCACAAGGATCACAT

GAAAGGATTAAGAGCCTCTACCTTGAGAAGAAGGTTGGAGTGCAGCTTGAAGG

TCTCCTTATACTGTTCACCTGTTACTAGAGAATTGTTATTAACCAACCCGAGGT

ACAGATTTTGGGAGAAACGAATTGTGTCAATTGAAGTTGAAACTCCTACCCAG

ATATCTTTAATTGATGAAGCATCAGGCGAGAAGGAAGAAATTGTTGTGACTCT

CTTACCAGCTGGTCATTGCCCAGGATCAGTTATGTTCTTATTTCAGGGCAACAA

TGGAACTGTCTTGTATACAGGAGACTTCCGATTGGCAAAAGGAGAAGCTGCCA

GAATGGAGCTTCTGCACTCGGGGGGCAGTGTGAAAGACATCCAGAGTGTGTAC

TTAGACACCACTTTCTGCCATCCAAAGTATTACCAAATTCCCAGTCGGG(EXON

8)TTCACGTGAATAAACTGGACATGTTTCGAAACATGCCTGACATCCTTCATCAT

CTCACAACAGACCGTGGCACTCAGATCCATGCCTGTCGGCATCCAAAGGCAGA

-continued

GGAATATTTTCATTGGAATAAGTTACCCTGTGGAATAACATCCAAAAATAGAA
TTCCACTCCACATAATCAGCATTAAGCCCTCCACTATGTGGTTTGGAGAAAGA
ACTAGAAAAACCAATGTTATTGTGAGGACTGGAGAGAGTTCGTACAGAGCCTG
CTTTTCTTTTCACTCCTCCTACAGTGAGATTAAAGATTTCTTGAGCTACATTAGC
CCTGTGAATGTATATCCAAATGTCATTCCACTGGGCACAACTCTGGAGAAAGT
TAAAGAAATCTTAAAGCCTTTATGCCGATCTTCGCAAAATATCGAGCCAAAGT
ATAAACCACTTGGAAAATTGAAGAGAGCTAGAATAATCCATCTAGACTCAGAG
GAGGAGGAGGAGGACGATGACGATCTCTTTGATGATCCTCTGCCAGTACCTTT
AAGGCACAAGGTTCCAAATCAGCAGACTCTTCACTCTGAGGTACTTCCCATGA
CTGCTCTACCACAAGACCAGCCTGAAAAACAGACAGAAAGCACAGAATGCTTC
AAAGCAGAGAGTATGCCAACATGTCTCTGGGCAAACTTCGTAGATTGTGAAGA
ATCCAATAGTGAAAGTGAAGAATTAGAAATCACGGCTCCAGCTCAAGGAGAC
ACGAGTCCTGTCCCCCATCACCAGCAGAAGGCTGAAGGGGAAGTACCACAGTG
GGAAGTGTTCTTTAAAAGAAATGATGAAATCACAGATGACTGTTTGGAAAACC
TTCCGTCCTCCACAGAGGCAGGGGCTCTCAGTCCCCAAAGCTTTTCAGTGACT
CTGATGGGAATCAACTCACATTTCTTCCCAGACTTCTTCTCAGTCAACACACA
TATCAGAACAAGGAAGTCAAGGCTGGACAGCCAATCAGACACTGTTTTGTTA
TCTTCCCAAGAGAGAAAAAGTGGGGATATTACCTCCTTGAACAAAGGTGGCTC
TAGACCAGAAATCAAAGAGAATATTCCCATCCTTCAGATGGAACAAAATGTAT
TTTGCCCGAAGGATACTTACTCTGATTTGAAAGGCAGAGATCAAGATATAAAC
ACACTTCCCAGTGCTAGAGAAACAACTACTCTGAGCAGTGGGAAACACATGCC
TCAGGAGAAAAGGCCGCTAAACTGTAACAGTAACACAGATTCACAAGGCTCCT
CTGACTTTGAAATTCCCTCCACTCCAGAAGCTGAGCTACCTCAACAAGAGCAT
CTGCAATATTTATACAAGAAGTTGGCAGGAGGAGAGGGTATAGTAATTGAAAA
AAGGAAAAGCGCACGTCATTCTAGAGCAACCATTAAAAAACCTACACAAACA
GGTAATAGTCAGACTCCTAATAGA*TGA*GTTCAAATGGAGTACTTAAAAATGTTC
ATATAACCTAAAAGGCAGCTCTGCGGCCGC

Translation 1

(SEQ ID NO: 2)
MSSFEGQMSSFEGQMAEYPTISIDRFDRENLRARAYFLSHCHKDHMKGLRASTLR
RRLECSLKVSLYCSPVTRELLLTNPRYRFWEKRIVSIEVETPTQISLIDEASGEKEEIV
VTLLPAGHCPGSVMFLFQGNNGTVLYTGDFRLAKGEAARMELLHSGGSVKDIQSV
YLDTTFCHPKYYQIPSRVHVNKLDMFRNMPDILHHLTTDRGTQIHACRHPKAEEYF
HWNKLPCGITSKNRIPLHIISIKPSTMWFGERTRKTNVIVRTGESSYRACFSFHSSYS
EIKDFLSYISPVNVYPNVIPLGTTLEKVKEILKPLCRSSQNIEPKYKPLGKLKRARIIH
LDSEEEEEDDDDLFDDPLPVPLRHKVPNQQTLHSEVLPMTALPDQPEKQTESTEC
FKAESMPTCLWANFVDCEESNSESEELEITAPAQGDTSPVPHHQQKAEGEVPQWE
VFFKRNDEITDDCLENLPSSTEAGGSQSPKLFSDSDGESTHISSQTSSQSTHISEQGSQ
GWDSQSDTVLLSSQERKSGDITSLNKGGSRPEIKENIPILQMEQNVFCPKDTYSDLK
GRDQDINTLPSARETTTLSSGKHMPQEKRPLNCNSNTDSQGSSDFEIPSTPEAELPQ
QEHLQYLYKKLAGGEGIVIEKRKSARHSRATIKKPTQTGNSQTPNR-

-continued

Sequence 2, Transcript of 20301 clone 1, longest cDNA sequence from haplotype 12

(SEQ ID NO: 3)

GGATCCGTGTTCGCCAACGCTATGAGTTCCTTCGAGGGCCAGATGGCGGAGT
ACCCAACTATCTCCATAGACCGTTTCGACCGGGAGAATCTGAGGGCTCGCGCT
TATTTCCTGTCCCACTGCCACAAGGATCACATGAAAGGATTAAGAGCCTCTAC
CTTGAAAAGAAGGTTGGAGTGCAGCTTGAAGGTCTCCTTATACTGTTCACCTGT
TACTAGAGAATTGTTATTAACCAACCCGAGGTACAGATTTTGGGAGAAACGAA
TTGTGTCAATTGAAGTTGAAACTCCTACCCAGATATCTTTAATTGATGAAGCAT
CAGGCGAGAAGGAAGAAATTGTTGTGACTCTCTTACCAGCTGGTCATTGCCCA
GGATCAGTTATGTTCTTATTTCAGGGCAACAATGGAACTGTCTTGTATACAGGA
GACTTCCGATTGGCAAGAGGAGAAGCTGCCAGAATGGAGCTTCTGCACTCGGG
GGGCAGTGTGAAAGACATCCAGAGTGTGTACTTAGACACCACTTTCTGCCATC
CAAAGTATTACCAAATTCCCAGTCGGGAGGAGTGTCTGAGAGGGATCTTGGAG
CTGGTCCGCAGCTGGATCACACGGAGCCCCTACCACGTGGTGTGGCTGAACTG
CAAAGCGGCCTATGGGTACGAGTACCTGTTCACCAACCTCAGCGAGGAGTTCG
GAGTCCAGGTTCACGTGAATAAACTGGACATGTTTCGAAACATGCCTGACATC
CTTCATCATCTCACAACAGACCGTGGCACTCAGATCCATGCCTGTCGGCATCCA
AAG(EXON10)AACTGGAGAGAGTTCGTACAGAGCCTGCTTTTCTTTTCACTCCT
CCTACAG*TGA*GATTAAAGATTTCTTGAGCTACATTAGTCCTGTGAATGTATATC
CAAATGTCATTCCACTGGGCACAACTCCGGAGAAAGTTAAAGAAATCTTAAAG
CCTTTATGCCGATCTTCGCAAAATATCGAGCCAAAGTATAAACCACTTGGAAA
ATTGAAGAGAGCTAGAATAATCCATCTAGACTCAGAGGAGGAGGAGGAGGAC
AATGACGATCTCTTTGATGATCCTCTGCCAGTACCTTTAAGGCACAAGGTTCCA
AATCAGCAGACTCTTCACTCTGAGGTACTTCCCATGACTGCTCTACCACAAGAC
CAGCCTGAAAAACAGACAGAAAGCACAGAATGCTTCAAAGCAGAGAGTATGC
CAACATGTCTCTGGGCAAACTTCGTAGATTGTGAAGAATCCNATAGTGAAAGT
GAAGAATTAGAAATCACGGCTCCAGCTCAAGGAGACACGAGTCCTGTCCCCCA
TCACCAGCAGAAGGCTGAAGGGGAAGTACCACAGTGGGAAGTGTTCTTTAAAA
GAAATGATGAAATCACAGATGACTGTTTGGAAAACCTTCCGTCCTCCACAGAG
GCAGGGGGCTCTCAGTCCCCAAAGCTTTTCAGTGACTCTGATGGGGAATCAAC
TCACATTTCTTCCCAGACTTCTTCTCAGTCAACACACATATCAGAACAAGGAAG
TCAAGGCTGGGACAGCCAATCAGACACTGTTTTGTTATCTTCCCAAGAGAGAA
AAAGTGGGGATATTACCTCCTTGAACAAAGGTGGCTCTAGACCAGAAATCAAA
GAGAATATTCCCATCCTTCAGATGGAACAAAATGTATTTTGCCCGAAGGATAC
TTACTCTGATTTGAAAGGCAGAGATCAAGATATAAACACACTTCCCAGTGCTA
GAGAAACAACTACTCTGAGCAGTGGGAAACACATGCCTCAGGAGAAAAGGCC
GCTAAACTGTAACAGTAACACAGATTCACAAGGCTCCTCTGACTTTGAAATTC
CCTCCACTCCAGAAGCTGAGCTACCTCAACAAGAGCATCTGCAATATTTATAC
AAGAAGTTGGCAGGAGGAGAGGGTATAGTAATTGAAAAAAGGAAAAGCGCAC
GTCATTCTAGAGCAACCACTAAAAAACCTACACAAACAGGTAATAGTCGGACT

-continued

```
CCTAATAGATGAGTTCAAATGGAGTACTTAAAAATGTTCATATAACCTAAAAG

GCAGCTCTGCGGCCGC
```

Translation 2

(SEQ ID NO: 4)

```
MSSFEGQMAEYPTISIDRFDRENLRARAYFLSHCHKDHMKGLRASTLKRRLECSLK

VSLYCSPVTRELLLTNPRYRFWEKRIVSIEVETPTQISLIDEASGEKEEIVVTLLPAGH

CPGSVMFLFQGNNGTVLYTGDFRLARGEAARMELLHSGGSVKDIQSVYLDTTFCH

PKYYQIPSREECLRGILELVRSWITRSPYHVVWLNCKAAYGYEYLFTNLSEEFGVQ

VHVNKLDMFRNMPDILHHLTTDRGTQIHACRHPKNWREFVQSLLFFSLLLQ-
```

Sequence 3 Transcript of 20106 clone 6, longest cDNA sequence from normal haplotype (SEQ ID NO: 5)

```
GGATCCGTGTTCGCCAACGCTATGAGTTCCTTCGAGGGCCAGATGGCGGAGT

ACCCAACTATCTCCATAGACCGTTTCGACCGGGAGAATTTGAGGGCTCGCGCT

TATTTCCTGTCCCACTGCCACAAGGATCACATGAAAGGATTAAGAGCCTCTAC

CTTGAAAAGAAGGTTGGAGTGCAGCTTGAAGGTCTCCTTATACTGTTCACCTGT

TACTAGAGAATTGTTATTAACCAACCCGAGGTACAGATTTTGGGAGAAACGAA

TTGTGTCAATTGAAGTTGAAACTCCTACCCAGATATCTTTAATTGATGAAGCAT

CAGGCGAGAAGGAAGAAATTGTTGTGACTCTCTTACCAGCTGGTCATTGCCCA

GGATCAGTTATGTTCTTATTTCAGGGCAACAATGGAACTGTCTTGTATACAGGA

GACTTCCGATTGGCAAAAGGAGAAGCTGCCAGAATGGAGCTTCTGCACTCGGG

GGGCAGTGTGAAAGACATCCAGGGTGTGTACTTAGACACCACTTTCTGCCATC

CAAAGTATTACCAAATTCCCAGTCGGGAGGAGTGTCTGAGAGGGATCTTGGAG

CTGGTCCGCAGCTGGATCACACGGAGCCCCTACCACGTGGTGTGGCTGAACTG

CAAAGCGGCCTATGGGTACGAGTACCTGTTCACCAACCTCAGCGAGGAGTTCG

GAGTCCAGGTTCACGTGAATAAACTGGACATGTTTCGAAACATGCCTGACATC

CTTCATCATCTCACAACAGACCGTGGCACTCAGATCCATGCCTGTCGGCATCCA

AAGGCAGAGGAATATTTTCATTGGAATAAATTACCCTGTGGAATAACATCCAA

AAATAGAATTCCACTCCACATAATCAGTATTAAGCCCTCCACTATGTGGTTTGG

AGAAAGAACTAGAAAAACCAATGTTATTGTGAGAACTGGAGAGAGTTCGTAC

AGAGCCTGCTTTTCTTTTCACTCCTCCTACAGTGAGATTAAAGATTTCTTGAGC

TACATTAGTCCTGTGAATGTATATCCAAATGTCATTCCACTGGGCACAACTCTG

GAGAAAGTTAAAGAAATCTTAAAGCCTTTATGCCGATCTTCGCAAAATATCGA

GCCAAAGTATAAACCACTTGGAAAATTGAAGAGAGCTAGAATAATCCATCTAG

ACTCAGAGGAGGAGGAGGAGGACAATGACGATCTCTTTGATGATCCTCTGCCA

GTACCTTTAAGGCACAAGGTTCCAAATCAGCAGACTCTTCACTCTGAGGTACTT

CCCATGACTGCTCTACCACAAGACCAGCCTGAAAAACAGACAGAAAGCACAG

AATGCTTCAAAGCAGAGAGTATGCCAACATGTCTCTGGGCAAACTTCGTAGAT

TGTGAAGAATCCAATAGTGAAAGTGAAGAATTAGAAATCACAGCTCCAGCTCA

AGGAGACACGAGTCCTGTCCCCCATCACCAGCAGAAGGCTGAAGGGGAAGTA

CCACAGTGGGAAGTGTTCTTTAAAAGAAATGATGAAATCACAGATGACTGTTT

GGAAAACCTTCCGTCCTCCACAGAGGCAGGGGCTCTCAGTCCCCAAAGCTTT

TCAGTGACTCTGATGGGGAATCAACTCACATTTCTTCCCAGACTTCTTCTCAGT
```

-continued

CAACACACATATCAGAACAAGGAAGTCAAGGCTGGGACAGCCAATCAGACAC

TGTTTTGTTATCTTCCCAAGAGAGAAAAAGTGGGGATATTACCTCCTTGAACAA

AGGTGGCTCTAGACCAGAAATCAAAGAGAATATTCCCATCCTTCAGATGGAAC

AAAATGTATTTTGCCCGAAGGATACTTACTCTGATTTGAAAGGCAGAGATCAA

GATATAAACACACTTCCCAGTGCTAGAGAAACAACTACTCTGAGCAGTGGGAA

ACACATGCCTCAGGAGAAAAGGCCGCTAAACTGTAACAGTAACACAGATTCAC

AAGGCTCCTCTGACTTTGAAATTCCCTCCACTCCAGAAGCTGAGCTACCTCAAC

AAGAGCATCTGCAATATTTATACAAGAAGTTGGCAGGAGGAGAGGGTATAGTA

ATTGAAAAAAGGAAAAGCGCACGTCATTCTAGAGCAACCACTAAAAAACCTA

CACAAACAGGTAATAGTCAGACTCCTAATAGA*TGA*GTTCAAATGGAGTACTTA

AAAATGTTCATATAACCTAAAAGGCAGCTCTGCGGCCGC

Translation 3
(SEQ ID NO: 6)
MSSFEGQMAEYPTISIDRFDRENLRARAYFLSHCHKDHMKGLRASTLKRRLECSLK

VSLYCSPVTRELLLTNPRYRFWEKRIVSIEVETPTQISLIDEASGEKEEIVVTLLPAGH

CPGSVMFLFQGNNGTVLYTGDFRLAKGEAARMELLHSGGSVKDIQGVYLDTTFCH

PKYYQIPSREECLRGILELVRSWITRSPYHVVWLNCKAAYGYEYLFTNLSEEFGVQ

VHVNKLDMFRNMPDILHHLTTDRGTQIHACRHPKAEEYFHWNKLPCGITSKNRIPL

HIISIKPSTMWFGERTRKTNVIVRTGESSYRACFSFHSSYSEIKDFLSYISPVNVYPNV

IPLGTTLEKVKEILKPLCRSSQNIEPKYKPLGKLKRARIIHLDSEEEEDNDDLFDDPL

PVPLRHKVPNQQTLHSEVLPMTALPQDQPEKQTESTECFKAESMPTCLWANFVDC

EESNSESEELEITAPAQGDTSPVPHHQQKAEGEVPQWEVFFKRNDEITDDCLENLPS

STEAGGSQSPKLFSDSDGESTHISSQTSSQSTHISEQGSQGWDSQSDTVLLSSQERKS

GDITSLNKGGSRPEIKENIPILQMEQNVFCPKDTYSDLKGRDQDINTLPSARETTTLS

SGKHMPQEKRPLNCNSNTDSQGSSDFEIPSTPEAELPQQEHLQYLYKKLAGGEGIVI

EKRKSARHSRATTKKPTQTGNSQTPNR-

Sequence 4, Genomic sequence of exons 7 and 8 (dotted
underlined) of 4810, a homozygous haplotype 16
affected animal
(SEQ ID NO: 7)
TCCCTCACCCATCTGTCTTATATATTATCCTATGGAAATCACTTTCTAACCATGT

CGATACAGTAAAAAATTCCAGGGAGCTCTCTTGTGGCCCAGTGGATTAAGGAT

CTGGCTGTTGTCACTGCAGCGGCGTGGGAGTGGCCAAAAAAGAAAACCCAAGT

GGACTGAAACCTCCTGTAAAATAACTGAGAGTTTCGACTTCACGCGTGTTGTAT

TTCACGTGATTAACAGCTCTTGTGTTCTGTTTATCTTCAGTGTGAAAGACATCC

AGAGTGTGTACTTAGACACCACTTTCTGCCATCCAAAGTATTACCAAATTCCCA

GTCGGGTACGTCTCTCTGGACGGGTGGCTGTATTTCTCAGGGGGCGGGCCGCA

GGCTAACAGGTCGGGTGGTAACGGGCCCCCTGGCCTTAATGTCTGGGGACGCT

GGGAACGGACAAGGCCTCAACTGCCTCTTCAAACCCCTGCCCAGGAGGAGTGT

CTGAGAGGGATCTTGGAGCTGGTCCGCAGCTGGATCACGCGGAGCCCCTACCA

CGTGGTGTGGCTGAACTGCAAAGCGGCCTATGGGTACGAGTACCTGTTCACCA

ACCTCAGCGAGGAGTTCGGAGTCCAG[A]TACCTGAGGGC

-continued

Sequence 5, genomic sequence of exons 7 and 8 (dotted underline) of 1304, a homozygous normal animal (SEQ ID NO: 8)

TCCCTCACCCATCTGTCTTATATATTATCCTATGGAAATCACTTCCTAACCATGTCG

ATACAGTAAAAAATTCCAGGGAGCTCTCTTGTGGCCCAGTGGATTAAGGATCTGG

CTGTTGTCACTGCAGCGGCATGGGAGTGGCCAAAAAAGAAAACCCAAGTGGACTG

AAACCTCCTGTAAAATAACTGAGAGTTTCGACTTCACGCGTGTTGTATTTCACGTG

ATTAACAGCTCTTGTGTTCTGTTTATCTTCAGTGTGAAAGACATCCAGAGTGTGTA

CTTAGACACCACTTTCTGCCATCCAAAGTATTACCAAATTCCCAGTCGGGTACGTC

TCTCTGGACGGGTGGCTGTATTTCTCAGGGGGCGGGCCGCAGGCTAACAGGTCGG

GTGGTAACGGGCCCCCTGGCCTTAATGTCTGGGGACGCTGGGAACGGACAAGGCC

TCAACTGCCTCTTCAAACCCCTGCCCAGGAGGAGTGTCTGAGAGGGATCTTGGAG

CTGGTCCGCAGCTGGATCACACGGAGCCCCTACCACGTGGTGTGGCTGAACTGCA

AAGCGGCCTATGGGTACGAGTACCTGTTCACCAACCTCAGCGAGGAGTTCGGAGT

CCAG[G]TACCTGAGGGCTC

Sequence 6, Genomic sequence of exons 10 and 11 (underlined) of 20301, a homozygous haplotype 12 animal (SEQ ID NO: 9)

CATGCTAAAAAGTCATCTGCATTTTTTTGAGACCNTGGTACAAATATATTTGTT

GAAAATGTTAAACCATTTTTCTTATTTTAAAATCTTTTTTAGGCAGAGGAATAT

TTTCATT{A}GAATAAATTACCCTGTGGAATAACATCCAAAAATAGAATTCCAC

TCCACATAATCAGTATTAAGCCCTCCACTATGTGGTTTGGAGAAAGAACTAGA

AAAACCAATGTTATTGTGAGGTAAGCAAGCAGCGTCTTTTGAGAGGAACCTTG

CTTTGAGGTAAATCGATAGTTTAAAGGCAGTCTAGCCTAACCTCAAGAGGGGG

GCATATCATGATTGTGGAAAATAACTTTTGAAAGTTAAACTCTGTTTAAATTAA

AGAGAAGCGGCTTCCAAAAGCTATCAATTGCTTACTACCATGAGCCAGTATTT

CCTGGGGTCTACTGAGTTTGACTGAGAAGATGGTTAGAGGCAGGCTGTCTTGC

TTGGCCGGAAGTTGGGAATTGACCTTGAAGGGGTTGGAAGCCCTTAGTGGAGC

AGAGGAGGCCCATACTGATCCTCATGTTTTAGCTCATGTCCTGAAACATTGGCC

GTTTGGAATGTTCACAGATATTTACATTTATGGAAAGAGTTCCCTCCTGGCCCA

GGAAAAAAATCCTTGATGGCAGGGTGATTTCATCCTGCAGTAGCCTAAAATGA

GAAGACTCGGAGTTTGGAACTTAGTTTTGATGAGTGACCCTTAATTTTGGGTTT

TCCTTTCCCTTTAGAACTGGAGAGAGTTCGTACAGAGCCTGCTTTTCTTTTCACT

CCTCCTACAGTGAGGTAAGAGG

Sequence 7, Genomic sequence of exons 10 and 11 (underlined) of 1304, a homozygous normal animal (SEQ ID NO: 10)

CATGCTAAAAAGTCATCTGCATTTTTTTGAGACCCTGGTACAAATATATTTGTTGA

AAATGTTAAACCATTTTTCTTATTTTAAAATCTTTTTTAGGCAGAGGAATATTTTCA

TT{G}GAATAAATTACCCTGTGGAATAACATCCAAAAATAGAATTCCACTCCACAT

AATCAGTATTAAGCCCTCCACTATGTGGTTTGGAGAAAGAACTAGAAAAACCAAT

GTTATTGTGAGGTAAGCAAGCAGCGTCTTTTGAGAGGAACCTTGCTTTGAGGTAAA

TCGATAGTTTAAAGGCAGTCTAGCCTAACCTCAAGAGGGGGGCATATCATGATTG

TGGAAAATAACTTTTGAAAGTTAAACTCTGTTTAAATTAAAGAGAAGCGGCTTCCA

```
AAAGCTATCAATTGCTTACTACCATGAGCCAGTATTTCCTGGGGTCTACTGAGTTT

GACTGAGAAGATGGTTAGAGGCAGGCTGTCTTGCTTGGCCGGAAGTTGGGAATTG

ACCTTGAAGGGGTTGGAAGCCCTTAGTGGAGCAGAGGAGGCCCATACTGATCCTC

ATGTTTTAGCTCATGTCCTGAAACATTGGCCGTTTGGAATGTTCACAGATATTTAC

ATTTATGGAAAGAGTTCCCTCCTGGCCCAGGAAAAAAATCCTTGATGGCAGGGTG

ATTTCATCCTGCAGTAGCCTAAAATGAGAAGACTCGGAGTTTGGAACTTAGTTTTG

ATGAGTGACCCTTAATTTTGGGTTTTCCTTTCCCTTTAGAACTGGAGAGAGTTCGT

ACAGAGCCTGCTTTTCTTTTCACTCCTCCTACAGTGAGGTAAGAGGATCCCATACT

CAGAACCTCGGCTGC
```

Porcine DCLRE1C (Artemis) gene sequence (SEQ ID NO: 45): Exon regions are underlined; the haplotype 12 and 16 causative mutations are boxed in light grey and dark grey, respectively.
>ENSSSCG00000011049|ENSSSCT00000012093

```
ATAACCGCGGAGGGCTGGCGCCCAGTCGGCTGTGTTCGCCAACGCTATGAGTT

CCTTCGAGGGCCAGATGGCGGAGTACCCAACTATCTCCATAGACCGTTTCGAC

CGGGAGAATCTGAGGGCTCGCGCTTATTTCCTGTCCCACTGCCACAAGGGTGA

GTGAGCGCGGCGCGCCGACCCCCTCCCGGGGACCAGGGCTGCGGCGGGTCTGG

CCCCGCGGGGAGGTAGCCCAGGGGCTGGAGAGGAGGAAGTTGGGGTGGGGGT

CCTGCAGGAGGAGTGCAGGCTTTGGGAGGTCTGGGGAGAGACTAGCGACTGC

ATCCTGTCGCAGGCGTGCTCTTCAGCCTGTTTGAGGCTTTATCGCCTCATAGGT

CCCGCGGGGCGGGACAGAGCAGCGACTGCCAGTTACTCACTGACCCAGGCCA

GTTTGATCAGGCACAGCTATTCGGTTTTTTTGGAAGCTCTCCCAGGGCCCAATA

GTCAAGGTTGTCGAGGATTACTTATTTCTTCCCCCAAATCCTCGCGATTTTGTT

ACAAAGACAGGTTTAAATGAAATTCTGCCATACCTCCAACCATTTATTAGCAA

GCACGCACGCATTCAAATTAAACGTCCTGCCTGTGAGCTTGACAACGTGCAAG

CTCCCCCTCTTTTTAGATGTTCTGTTCACATTCAGTATGAAAGGTTCCTTTTGTC

CTAGAGGTGGGATGAGGTTTACCTTACAGATGCCCAGGTCAGGCAACCAGAAT

GTTATTTCACAGCTGCACATGGTTAGGAATTAAGCCTGGAATGTCGCCCCCTAA

CGATATGGTCCCCAGGCCAGTTACTCCAGGCAAGTCTGGAGCATCTCTACATTT

TAGCCAGTCTCCAGAGCTAGAGTACCACCAATTTCACTACCATTTTCCATTCTT

TTTTTTTTTTTTTTCTTTTTGCCATTTCTTGGGCCGCTCCGGCGGCATATGGAG

GTTCCCAGGCTAGGGGTCCAATCGGAGCTGTAGCTGCCGGCCTACACCATAGC

CACAGCAACTCAGGATCCAAGCCGCGTCTGCAACCTACACCACAGCTCACGGC

AACGCCAGATCGTTAACCCACTGAGCAAGGCCAGGGATCGAACCCGCAACCTC

ATGGTTCCTAGTCGGATTCATTAACCACTGAGCCATGACGGGAAATCCCCATT

GTCCATTCTTAACATCTGGTATGCTGATGGATAGGTCAGTAACTTTTACCCATG

AAAACAGGTTTAATATTCAGTATGCTAATTAGCACATCCTTGGGCCTTGACCAG

AGATGAAGGTTAATTGAAGCATTCTAGAAGCTACCTCTTGGAGTGCTGATTTCC

AGCGTAGCTTAAGTAGGAGACCCCCGACCGCTCTTTTGAGGAGTGACTCAGAT

ATATTTGCACAAACATACCACACTGTGTGATTTTAAAGTAAATCAGTGATATGA

AAACAGACCCTTGGGCAGGCAGTGGGTGTGAAGACTAGCTGCTGTGTGTGTGT

GAAATCTTTGAAGTTACTGCTTTGGGGAAATGCGTCTGCTTTCTGGCTCTAAGC
```

-continued

```
TCTTTTAATTTATCACTCTTTAATGAGGAAATGCTGGACCTCCTCTCTAGCTGTG
CTAAAAACACGTGAGTCCCAGTGAAGGCCTTTCTGTTGCTTCGGGAGAATAAT
ATTTTTGGTTTTGTCTTGTTTTTCATTGAGAAGTCATTCCTGGAAGATGGTGTTT
GTACCTCAAAGGCCCTCTGGCGTCTCTGAACTCATCGAGGATGGTGGACGGGA
TTAAAGAATGGCTTCTTGGGAGTTCCCATTGTGGCGCAGTGGAAATGAACCCG
ACTAGGAACCATGAGGTGGCAGGTTCGATCCCTGGCTTCACTCAGTGGGTTAA
GGATCTGGTGTTGTCGTGAGCTGTGGTGTAGGTCACAGACATTGTTGTGCCTGT
GGCATAGGCCAGGAGCTACAGCTCTGATTAGACCCCATAGCTTGGGAACCTCT
GTATGCTGCTGGTGCGGCCCTAAAAAGACAAAAAGACCAAAAAGAAAAAAGA
AAAAAGGAAAAAAAACAAAGAATGGCTTCTTCGGGGCTCAGCCTTCATGCATC
AGAGTAGTGGCTTTGGAGAAAGAGTTTGCCTAAAGGAGTTCGTATTTATATTTT
TTATTGAATTTATTCTTTTATTATTTAGTAATTGTAGTTGTGAAATTGTCATTAG
TTTGTATATTAAGGAATACTCTCTCCTGCTGAGCAGTTTATAACTTTTCCTGTCC
TCTGTTCCCATGTGGGCCTGTCTTCCCAGTGAGGATGTACACTCAACAAGGTCA
GGAACTCAGCTTCTGTTCTCCAGGGTTGCCACATTGTCTCTTCGTGGTTTTTAAC
TTTTTGGGGAAGCTGACGTCCTTGGATGTGCTGTGGGCTGGCTTGTGTCCTCTC
CCTACCCCCATTCATCTTTTGAATCCCTAATCTCCGATGTGGCTGTATTTGGAG
AAAGGGCTTTTAGGAGGTGATGGAGGTTAAATGAGGTCATAAGGGTGGAGTCC
TAATTTTATAGGAGTGGTGGCCTTCTCTACACACACACACACACACACACACA
CACACACACTGAGGAATGCCGTGTAGGCACGCGGCATGAAAGTGGCTGCTGGT
AAGGAGAGGCCTCCCCAGAAACCAGCTTTGGTACCTTGATCTTGGACTTGAGC
TTCCAGAACCGTTAGAAATACATTTCTGGGTGTTTGCACTGTGGCACAGTGGGT
TAAAAACCTGACTGCAGTGGCTCAGATCTCCTGTAGCCGTGTGGGTTCCGTCCC
TGGCCCAGTGCAGTGGGTTAAGGATCCAGCCTTGCCACAGCTGTGGTGTAGGT
TGCAGCTGCAGCTTGGAGTCAATCCCTGCCCTGGGAACTTCCATATGCTGCAG
GGACAGCGGTAGGAAAAAACAAATAAACAAATAAATAAATAAATAAGGAGTT
CCCATTGTGGTACAACAGGGATGAATCCAACTAGGAACCATGAGGTTGCAGGT
TCGATCCCTGGCCTCGCTCAGTGGGTTAAGGATCCGACATTGCCATGAGCTGTG
GTGTGGGTCGAAGATGAGGCTCAGATCTGGTGTTGCTATGGCTGTGGTGTAGG
CTGGCAGCTGTATTTCAGATTCTACTCCTAGCCTGGGAATCTCCATGTACTGCA
CAGGGGCAGCCCTGAAAACCAAAAAAAAAAAAAAAAAAAAAAAAAAAAA
AAAAAAAATTTAATTACTTAATTTCTCATTAAAGCCATCCAGGCTGATATTTT
GTTATTGAAGCCTGAGCAGAATAATACAGTATATCTGATAAGATCTATAGTCTC
CTGTGAAAAAAATGCACATAAACATGTTAACATCACATTTTGATAAAAGTTGA
GGTAGGGAGTTCCCGTTGTGGCTCAGAGGGTTAAGAACCTGACTAGTATCCAT
GAAGATGTGGGTTTCATCGCTGGTCTTGCTCAATGGGTTAAGGATCCAGCATTG
CTGTGAGCTGTGAGCTGTGGTATAGGTTGCAAATGTGGCTCGAATCTGACATG
ACTGTGTTATAGGCCTGCAGCTGCAGCTCTGATTTGACCACTACCCCACGAATG
TCCATATGCTGCAGGTGTGGTCCTAAAAAAAAAAAAAGGTGAGGTGGGCCAT
GGACCTGCTTGATGCCTGTTCATGGTCCATCTGGGATCCAGTGCTGTGTTCAGG
```

-continued

```
GCAGGCTTTAAAGCATCTGTAAGGCCCAGAGGACAAGATGGGACCCATGGCCT

GAGATTGCAGCCCAGGGAGGGGTAGGACCCCTTCAGGAGGCAGCTTAATTTGA

TGTATTTTGGTCAAAGGAAAAGCCAAAGGCCCTGGAAAGGAGGCTTGGGGTGC

ATCCTGGTGGCAAATAGGGAACTCACCCAGGTTCCCTCCACTGGTGGGATGGG

GTGTCTTGATGGAACAGGATGCTGCCCAGAGGCTTAGTTTGGGAGCAAGGAGC

AGAGTCCAGGATCAGCCTCCTTATTGCTCTGACTCAAACTCTCTGGAAGACTTG

ATTAAGGAGAGTCCTGCCTGGGGACATACTCATTCTTTGGCCCTAAAGCCTGCC

TCAGGAGTGCCCTGAGGAGAGGCACCTTCTGAGGGCACATGGTCTGTCCGTGT

GTGGTCTGGTGACTGCCTTGTTTTTGAGAAATGAGGACCGCCATGTATACATCG

AGGGCATGCGTGTTGGTTGTAATTAGGATAATTCAATTTCTTTTTTTCTTTTTTA

TGAGAGTGGTAATGTTTATTTCAGGTTCTCTCTCTTTTTGTCTTTTTTAAAAA

AAATTTTTTTTCTTTTTTTGCCACACCCGCAGCATGTGGAAGTTCCAGGGCCA

GGGATTGAACCTGCGCCACACAGCAGTGATCAGAACCACAGTGGGGAAAATG

CAGAAGCCGAGTTCCCATTGTGACACATCGGAAATGAATCTGACTAGTAACCA

TGAGGTTCCGGGTTCGATCCCTGGCCTTGCTCCGTGGGTTAAGGATCCGGCATT

GCCATGGGCTGTGGTGTAGGTCACAGACGCGGCTCGGATCTTTCGTTGCCGTG

GCTGTGGTGTAGGCTGGCAGTTGCAGCTCTGATTAGATCCCTAGCCTGAGAAC

CTCCATATACTGTGGGTGTGGCTCTAAAAAGCAAAAAACCAAAAACAAAAACA

AAAAGAAGATGCAGGAGCCTTAACCCACTAGGCTATCAGAGAACTCCCTCGAT

TTTTTTCTGATGGGTGATTGTTTAACATCATCTCCCTCACAGCCCAGCTTGACTG

CCTTTGCCTTCTGCCTTCATCAAGGGCGGTCATGGGCAGTGTTTACATATATTC

ATCAAAAATGCACATGAAAGTCATTTTTGGTACATGATTTGACTTTTTTTTTTG

GTCTTTTTAGGGCTGTACCCATGGCATGCGAAGGTTCCCAGGCTAGGGCTA

ATTGGAGCTGCAGCTGCCAGCCTACACCACAGCTCACGGCAACGCCGGATCCT

TAACCCACTGAGTAAGGCCAGGGATCGAACCCACAACCCCTGGTTCCTAGTCG

GATTCATTTTCACCACGATGGGAACTCCCATTTTTGGTGTATGATTTGAAAAGA

CTTTCAAAATAACCTGCTTGTTTATGGGTTTGTTTTTGTTTTTTTAAGTAAAATG

AACTTTCCAACAGCATTCATGTATTAACCGCAAAAGAGCTGGAAAAGCATTAT

GTAGAAGAATAATTTCGTTTTAATTAGCTTTAAGCTTATTAAACTTATGATCAG

TGTTTAGAAATCTTATAATGAAGATGGTTATTCATGGTTAGACAGCAATGCATT

TTTTTTTTTTTTTTTGTCTTTTTGCCTTTTTCTAGGGCTGCTCCCGTGGCATGT

GGAGGCTCCCAGGCTAGGGGTCGAATCAGAGCTGTAGCTGTCGGCCTACACCA

TAGCCACAGCAATGCCAGATCCGAGCCATGTCTGCGACCTACACCACAGCTCA

TGGCAACGCCAGAACCTTAACCCACGGAGCAAGGCCAGGGATTGAACCCGCA

ACCTCATGGTTCCTAGTCGGATTCATTAACCACTGAGCCACGATGGGAACTCC

AACAATGCATTTTTTTTTAATTTAGTTTTTAAATTTTTTGGTTGCACCCAAGGC

CTTGGAAGTTCCCAGGCCAGAGACTGAATCCGAGCTGCAGGTACGGCAACACC

GGATCCTTTAACCCACTGTGTCAGGTCAGGGATGGAACCTGTGCCAATGCAGG

GGTCCAAGACACTGCAGTTGGATTCTGAACCCACTGTGCCACAGCGAGAGTCC

AAGCAATTCATTTTTTAAAAAATTCTTTTTTTCCTTTTTCTTTTGGACCCCCTTC

ACCTGATTCTCCCACCTCCTACCCCCCGACCTTTGTTAATCAGCAATATGTTCT
```

-continued

```
CAGTATCCGTGAGGTTGAATTTTTGCTTTTTCACATTTCATAGAAAAGTGAGAT
CATGCAGTATTTGTCTGTGTCTGACTATTTCACTTAGCTATGCCTTTGGGCTCCG
TTCATGTCACAAATGGCAAGAGTTCATTCTTTTTTACAGCTGACTAATATTCCA
TTGTGCATATGTATACCACAATGTCTTTATCCATTTATCTCTTGATAGACACTG
AGGTTGTTTCCATGTCTTGGCTCTTATAAATAATGCTGCAGCAAACACGAGGGC
ACAGATACCTTTTCCAGTGAGTGTTTTTGTTTTCTTCAGGTAAATAGCCAGAAG
TGAAATTGTTGGATCTTGTAGTTCTGTTTTTAATGTTTTGAGGAACCTCAGCCTC
CTGTACTGTCTTCCATAGTGGCTGCACCAATTTACATTCCCACCAACAGTGCAC
AAGCGTTCCCATTTCTCCACATTCTTTTCAACATTTGTTCTTTGCTTTCTTGTTG
ATCATAGCCGTAATGGGCATGATATCTCAATGTGGTTTTGACTTGCATGTCCCT
GATGATTAGTGATGTGGAGCATTTTTTCGTGTACCTTTTGGCCATACAATATGT
CTTGGGGAAAAAAGTCTATTCAGATCTGCCCATTAAAAAAAAAAAATCTCTTT
TTTTTTTTTTTTTTTTTTGCTGTTAAATTTGTATGAGTTCTTCCCCACCCCTTT
CATTTTATGCCCAGACTTGCAGCATGTGGAAGGTCTCATGCTTGGGTCAAATTG
GGACTGCAGCTATGGCCTATGCAACACCAACACCAGATCAGAGCCACAACTGA
GACCTATGCCAAAGCTTGCGGCAACTCTGGATCGGTAACCCACTGATGCAGGC
CAGGGATTGAATGTACATCTTCTCAAACATTATGTTAGGTTCTTTATATATTTTA
GATATTAGCCATGCATCAGATACATGATTTGCAAATATTTTCTCCTCTTAGTAG
GTTTTTTCATTTGTTAATGTTTCCTTTGCTATGAAGAGCTTTTTAGTTTGATGT
AGTCCCACTGTTTATTTTTGCTTTTGCTTTTGGTGCCATATTCAAAATAGCATCA
CCAAGACCTGCATCAGAGAGATTACTGCCTATGTTTTCTTATAGAAATTTTATG
GTTTCAGGTCTTACATTTAAGGCTTTAATCTGTTTTGAGTTATTTTTTGTATGCA
GTGTGGTGTGGTAAGACAGTGCTCAGGTTTCATTGTTTTGCATGTGGTTGTCCA
GTTTTCCCAACACAATTTATTGAAGAGACTTTCTTCATTGTATAGTCTTGACTTC
TTTACCATAAATTGATTGATGCTATATGTGTGGGTTTATTTCTGGGCCTTGTATT
TTTTTCTATTGATCTATCTATGTTTTTATGCCAGTGCCTTAATGTTTTTTTTGCTT
TTTCTTTAGGGCCACACCATGACACATGGAAGGAAGTTCCCAGGCTAAGGGTT
GAATTGGAGCTTCAGCTGCCGGCCTACACCACAGCCACAACACAGGATCTGAG
CTGCATCTGCGACTTGCACCACAGCTCACAGTAATGCCAGATCCCCAACCCAC
TGAGTGAGGCCACAGATTGAACCCGAGTCCTCATGGATGCTAGTCAGATTCAT
TATTGCTGCACCACAATGGGAACTCCCATAATGTTTTAATTACTTTAGCTTTGT
AATACATTTTGTAATCAGGGAGCATGATGTTTCCAATTCTTTTCTTTTTCAAGGT
TGCTTAAAAAGAAATCTTTTGTGGTTCTATACTAATTTTAGGATTATTTGTTCTA
TTTTTATGAAAAATGTCATTGGAATTTTGATATGGTTTGCATTGAACCTGTTGA
TTGCTTTGGGTAATATGGACATTTAATAATATTGATTCTTTCAACTCATGAGCTT
GGATTAGCTTTCCATAACTTTCCATTTATTCGTGTGATGGTAGTTTTTCTGTTAA
CGTCTTGTATTTTTCAATATGCAAGTCTTTCACGTCTTTGGTTAAACTTATTTAT
AGATATTCTTTTTGATGCAGTTGTGAATGGGATTGTTTCTAAATTTCTCTTTCTG
ATGGTTTGTTTTAAGAATGTAGAAATGGGAGTTCCCATCGTGGCACAGTGGTTA
ACGAATCCGACTAGGAACCATGAGGTTGTGGGTTCAATCCCTGGCCTTGCTCA
```

```
GTGGGTTAAGGATCTGGCGTTGTCGTGAGCTGTGGTGTAGGTTGCAGATGCGG

CTCGGATCCCATGTTGCTGTGGCTCTGGCGTAGGCCAGTGGCTACAGCTCCGAT

TGGACCCCTAGCCTGGGAATCTCCATATGCCGTGGAAGCAGCCCTAGAAGAGG

CAAAAAGACAAAAAAAAAAAAAAAAAAAAAAAAAAAAGAATGTAGAAATGCA

ATGGACTTTTTGTGTTTATGTATCCTGCAACTTTACTGAATTCTTGTATTAGTTC

TAACAGGTTTTGATGGAGTCTTTAGAGTTTTCTCTGTATGGTGTCATGTTGTGTT

TGTAAATAGTGTCAGTTTTATTTCCTCCTTTCTACTTTGGATGCCTATTATTTCT

TTTTCTTGCCTAATTGCTCTGGCTAGGACTTATAGTACTATGTTGAATAAAAGG

GCAAGAGTGGGCAGTCTTGTCTTGTTCCTGATATTAGAGGAAGTCTTCATCTTT

TGATCATTGATTATGATGTTTGCTGAGGGCTCACATATGCCCTTTATTATGTTG

AGGTATGTTCCCTCTATACCTGATTTGTTGAGAGTTTTGTTTTTTTTTTTTTAA

TCATAAATGGATGTTGAGTTTTGTTCAATGCTTTTTATGCATTTCTTGAGATGAT

TATATCATTTTTTATTCTTCATTTTGTTTATGTGATATATCACATTGGCTGATTTG

TGGATTTTGAACCATCTTTATGTCTCCAGAATAATAAATCCCACTTGATCATGA

TGTATGATCTTTTTAATGTATTGTTGAATTCTGTTTGCTGGTATTTAGTTGAAGA

GTTTTGCATCTATGTTCATCAGGGATATTGACCTGTAGTTTTATTTATTCTTTTT

TATGGTGTCCTTGTCTGGCTTTGGTACCAGGGTATTGCTAGCCTCATAAAATGA

GTTTTTTGAATGTTTGTAGAATTCACTAGCAAAGCCATCTGGTCCAAGACTGTT

TGTTGGGTTTTTAATTACTGATAGTAGAAAGGATATTCAATATCCTTACTAG

TTATCAGTCTGTTCAGGTATTCTGTTTCATCATGGTTCAATCATGGTAGGTTGTA

TGTTTCTAAGAACTTACCCATTTCTTCTAGGTTGTCCAGTTTGTCGATTTATAAA

TGTTCACAGAAGTTTCTTACCTTTCTTTTCTGTTGTAATGGTTGTAATAAATCTT

CTTCAATTTCTGATTTATTTATTTGAGTCCTATCTCTCTCTATTTTGTTTTT

TTGGTGAGTCTAGCAAAGGCTTGTCAATTTTGCTTACCTTTTCAAAGAATAAGT

TCTTAGTTTCATTGATTTTCTCTGTTATCTTTTTAGGTTCTAGTTCACTTATTTCT

TCCCTAATCTTAGTTATTTTCTTCCTTCTACTAATTTTGGGCTTTGTATGTTCTTC

TTTTTCTAGTTTCTTTCTTTCTTTCTTTTTCTTTTTAGAGCTGCACCTGCGAAAGT

TGCTGGGCTAGGGGTTGAATTGGAGCTGCAGCTGTTGGCCTGCGACACAGCCA

CAGCAACACCAGATTTGAGCTGCATCTGTGACCTACACCACTGGATCCCGCTG

AGCAAGGCCAGGGGTCGAACCCACCTCCTCACGGACACTATTGTCGGGTTCTT

AACCTGCTGTGCCACAACAGGAATTCCTTTATCTCAGTTACTGAAGTGTAAAGT

TAGGTTGATTATTTGAGATTTTTCTTATTTCTTGAGGTAAGCACTGAACCCTTGA

ATTTCCCCTTTAGAACTGATCTTGCTGCATCCTGAAAATTTTGGTATGTTTTTCT

TTTGTCTCAAGGTATTCTTAAATTTCTTTTTGATTTTTCTTTGACCCATTGGTTG

TTTAATAGCCTGTAACTTAATTTTCACATTTGTGAATTTTCTAGTTTTCTTCCTG

TAATTAATTTTTAGCTTCATACCATTGCAATTGGAAAAGATGCTTTATATGATT

TCAGTCTTCTTAAATGCGTTAAACCTTGCTTTGTGGCTTAATATGTGGTCTATCT

TGGAAATTGTTCTATGTGCACTTGAGAAGAATATGTATTCTGTTGCCATTGCAT

GGAATGTTCTGCATATATTTGTGAAGTTCATCTGGTCTAATATGTCATTTAAGT

CCAATATTTCCATACTGATATTCTATCTGAAATGTTCTATCCATGATGTAAGTA

GAATATTAAAGTCCCCTGCTTTTGCTATCTGTTTCTCCTTTTAAGTCTGTTAATA
```

```
TTTGCTTTATATATTTAGATGTTTCTGTGTTGGGTGTATAAATATTTACAAATGT
TGTATCTTCTTATTGGATAGATCCCTTCATCATTGTATAATATGGTAAGGTCTCT
CTCTCTCTCTCTTTTTTTTTTTTTCTTTTTAGGGCTGTACCTGCAGCATGTGGAG
GTTCCTAGGCTAGGGGTCAGTGTGGAATTGTAGCTGCCAGCCTATACCACAGC
CACAGCAATGCGGAATCCAAGCTGCATTTGTGACCTATACCATAGTTCACAGG
AGTGCTGGATCCTTAACCCTCTGAACGAGGCCAGGGATCGAACCTGTGTCCTC
ATGGATGCTATTCAGATTTGTTTCCGCTGAGCCATGATGGGAACCCCATGGTAA
TGTCTCTTATTACTGTCTTTGTTGTTGTTTTTACTTTTTTATGGGCTGCACACGTG
GCATATGAAAGTTCCTAGGCTAGCAATTGAAAGTGAGCTGAGGCTGAGGCCTA
TGCCACAGCCATGGCAACACTGGATCCAAGCTGCATCTGTGACCTACTCTGCA
GCTTGTGGCAATGCCGGATCCTTAACCTACTGAGTGAGGCCAGGGATCAAACC
TGCATCCTCACAGAGACTGTTGGGTCCTTAACCTGCTGAGCCACAGTGGGAAC
TCCCAGTCTTTGTTTTAAAGTCTATTTTGTCTAAGTATAGCTACTCTAGCTTTTT
TTTTTGGTTTCCATTTAGAATTAGGGTAATTAGAAGTTCCCATTGTGGCTCAGC
AGATTACAAACACAACTAGGATCCTTGAGGATGTGGGTTTGATCCTTGCCCTCC
CTCAGTGGACCTGGCATTTTCGTGAGCTATGGTGTAGGTCACAGATGTGACTTG
GATCCTGTGTTGCTGTGGCTGTGGCTGTCTGGTTTGCTTTAAATGTCACCTTTCT
CTTTAAGTTGCCTTTCTGTGTTTGTTAATTTGGAAAGCTGTGGAGCAAGCCTCT
GTGGGTGGTAATAACCCACCTTTCAACCCAGCAGTTATAGTAGGTTGAGAAGT
AATGAAACTTTTTTTTTCCCCTGGCCTAAGCTTGAATGGTTTCCTCAAGGATTC
CATGGAAGCAAACTTGAATATCTAGGTGGACTAACTTAAGTGATTGGAATTGA
ATGGGTCACTGAGAGCCTGGACCAAAGGGTAGTTGGATTGCAATGAAAGAAG
AGAGTAAGGGAAAATGATGGAAGCATTTCCCAAGGAGACCCGGTCACCTACTC
TTCTTTGGCTACTCTGAGTCATTTAGACTCTTCCCCCAGGGGTAGGACATCATT
CTCCTTTTAAATGGCTTCTGATGGCTTGGAGATGGTCCATTTTTTAGTGGTTCTT
ATCCTGTTTTCAGTGGATGCCTCACTTGCAGAAGCAAAAGCCAGTAGCTCATG
AATCAATTCTCTTCTAAAAGTGAAACTCTCATTTATTTTCTCTTAAAAGGAAGC
CTAAAATGATCAGATAACTCAGCTTCCTTGGGGCAAGGAATACTCTGAAAAAA
TAATATATTTCTGATTTTTTTTTTTGGCAGATCACATGAAAGGATTAAGAGC
CTCTACCTTGAAAAGAAGGTTGGAGTGCAGGTAATACATGTTGCTACTTATTTG
TGCGTGTGTTTTGTCTTTTTAGGGCCACACCTACGGCGTATGGAAGTTCCCAG
GCTAGGAGTCAAATCAGAATTGTAGCTGCTGGCCAATGCCACAGCCGTGCCTA
CCTGGGATCCGAGCCATGTCTGCGACCTACACCACAGCTCACCGCAATGCTGG
GTCTTTAACCCACTGAGCGAGGCCAGGGATCAAACCCACATCCTCGTGGATAC
TAGTCGGGTTCGTTACTGCTGAGCCACCAGGAGAACTCCTATGTGTGCGTTTTT
AAGTAAAATTTTACTTGAGCTGTAACTTCTACACAGAAATGTACAGACATCAT
AAGGGAACAGTCTGACAAACATTTGTAAGTGAACAGATCTGTGTAACTTCTGC
CCAGCTCAAGACGTAGGACAGAACCAAAATCCTGGAACAGACCCCGTCCCTCC
CCCAGTCAGTCTTCCCTGCCCACGGGCAACCTCTTTTCTGACGTCTGTTGTCAT
GTTTAACTTGGGCTGTTTTTGAACGCTATTTAAATTGTTTCATACTGAATAGACT
```

-continued

```
CTCCTACTTTTTTTCTTTTACTTAGCAGTATATGTGAATGATTCATCTGTGCTAT
TGGGCACAGCAATGGTCTGTCCATTCTGTCCATTTTCTTTCTTTCTTTCTTTTTCC
TTTTCTTTTCTTTTCAGGGCCACTTCCATGGCATATGGAAGTTCCCAGGCTAGG
GGTCGAATCGGGGCCGCAGCTGCCAGCCTATGCCACAGCCACAGCACTGTGGG
ATCTCAGCCATGTCCAAGACCTACACCACAGCTCACAGCAATGCCGGATCCTC
AACCCACTGAGGGAGGCCCGGGATTGAACCTCCATCCTCATGGATTCTAGTCA
GGTTCATAAGCTGGTGAGCCACAGTGGGAACTCCCACGTTTGTTTCTGAAAGG
GTGTGTATGTGTGTAAAGGGTTGTTTCCTTATAAAGAATTAAATAGCGTTGTTG
GTTCTCTTCTTAAAGCTGAGCCTTCGCATTCTTTTCCTTCAGCCATTGCTTAGAT
TCAAAATTATCAAGATATATCCAGTTGCCTCTTGAACCATGTGAGGGTTCGGGG
TGCTGACTTTCGTCGTGGTTGAAAATTGATGTGTAACATTACAGTCGGCCCTCC
CTATCCCCGGGTCTGCATCCATGGATTCAACCAACCGTGGACTGTGTCGTGCCA
TAGCACTCATTTAGTGAAAACAATTTCTCACATAAGTGGATTGTTGCTGTCGAA
TCCTGTGTTGTTCAGGGATCAGCTGGGTGTGGAAAGGAGTGTCTTGGCGTTTTG
ACTCTTTCACCTTTGACTTAGCAGCAGGCTTCTTTGCTAAGTGATATCAGCAGT
CTGTGTTTATGATAATGGTAACAAATACACACATGCACACACACACACACACA
CACACACACACACTAGATGTTGATGATATGGTAATGAGTAAAACAAAAATC
CCTCTCTTCTTGGAGCTGACAGTCTCTTTAGAGCCTCTTTTGGAAAGACACTAC
TATTGCTTCTATTTTACAGATGAGGAAACTCAGGAACCAGAGAGGTTAAATTA
GTTGCCCAAGGTCACACAGCTAGTGGCAGGACCAGGATTCCCACCAGGTCTGT
CTGATTTTAGAGCCTATGTATTAGTTGTCCATTGCTGCGTAACAAATTATCCCC
TGAAGTGACTTAAAAACAACACTCGTCATGTATTGTTATCTGTTGCTGTGCCTC
AGGGATTCTGACAGGGCACAGTGGGAGCGGCTGGTTTCTGCCTGACTGGGTAT
CATTTGGGGCGACCTTACCTAAAGGCTCGTTCATTCAATGTCTGATGCCTGGA
CTGGGGACACTTAAGTAGTTGGGACATTTTGGGTATCTCTGTCTCTAAACAAAT
CTTTGCAGCATGGTGGTTTCAGGATAGCTAGCGTCCAAAGTCCTGCAGTGCTAT
GTCCGTCCCAGTCTGTTGACCAAGGCAGTTACAAGGGTCTGTCCAGGTTCAAG
GGAGGTGAATGGAGACGCCTCCCGTCAAGGGAAAATGTCCATTCCCATGTGGT
TGGAGTGCACGTCAGCGTGGCCAGCTTTGGAAAGTATAATCTGCCGTAGATTG
TACCCCTAACCTTTCAGCTCTAGGGGTGAATTTTTCAAGCTTGTCATGAAATTG
ATTTCTGCCCAAAAGACACAGACAGAAGCGACTTGCACGAAGTAAATCTCAAG
CAGACTTTGGCTCCCCCTTCCTGTTTAGCAGAGGTAGTTTATCATTTGGTGGTG
TCTTTCCAGGCATAGCTGATCCTGTAACAACCATGTCTTTAAGATGAAAATAAA
CAATGAGGTCCTGCTGTACAGCACGGGGAACTATATTCAGTCTCCTGGGATAG
ACCACGATGGAAAAGAATATTTTTAAAAAGTGTGTGTGTATGTATGACCGAGT
CACTTTGCTGTCCAGCAGAATTGGCATAACAGTGTAAACCAACTATGCTTTAAT
ACTAATAATAACAAAAGATGAGAATGGTGAAGACCAAGCTTTGAGGAGGTCA
GAGAACATAATATTCATTCTCATCTGCTTCTTCCCCTTCACTTTATTTTATTTTTT
TAATTTATTTTTTAGGGCCACACCTGAGGCATTTAGAAATTCCCAGGCTAGGG
GTCGAATCAGAGCCTCAGCTGCCGGCCCACAGCACAGCCACAGCAACGCCAG
ATCTGAGCCGCATCTGTGACCTGCACCACAGGTCACGGCAATGCCGAATCCCT
```

-continued

```
AACCCACTGAGCGAGGCCAGGGTTTGAACCTGCATCCTCATGGATCCTAGTCG

GGCGCGTTACTGCTGAGCCACGATGGGAACTCCCCTTCCCTTTACAGTGATGG

GGCGGAGGTGGTCATTGGAGGTTAGGCCTATTGGGAACCATTCTAACACTTTT

GGTGCCAGCTCCGTTTCTGAATTATTCAGGGTATCTGATACATGTTGAAACAGG

AGATTTCCTAGTCACCCAGATGACTCATTTTGGATGGTACTAAAATGACTTTTT

TTTTTTTTTAATCTCTCTTTTCAGCTTGAAGGTCTCCTTATACTGTTCACCTGTTA

CTAGAGAATTGTTATTAACCAACCCGAGGTACAGATTTTGGGAGAAACGAATT

GTAAGTTTTATTTTTTTCGAATGCCACTAATTCTTTTTTTCAAGTGGGAACTACT

TTTCGAGGGAGATGGAACAAATGTATAAATATATTTATCTGCAGTATTTATGGT

GTCGCTATTCACTCTTTTGTCATTCCTTAATTGTGGAAGAGCTTGGCTTTTTATT

GTTGTCACTTTGTCTTTCTTGTCCTTGAACACGTTGACCTAGATTCTTAGTTTTG

TCTCGTCTCAAAGACCCTCTTGCCCAGCTGCATTTTAATAGTTTAAAGCATAAA

ATGTTCAGTGACATAATCGATAGATCCTTTTATTTAGACCATGGGTTAGGTGAG

GAAAAATGAAGAGGACTTAGGAGTTATAATAAGAAAGGAATAATAAGCTGAA

TAAAAACAGGATGGATAATTTGAATCTGACAGAATAAAGTGGATCTCTGCAGT

GGGAGGCGGATAGTAGAGGAGAGAAGACCATATGGCAGGTAGAAAATGTGAA

GATGGCAGAAAAATTTCTGTTGCAACAGTAGTTGCTATCCACATGAATGGATTT

CATTCAATTTGTGATCCAAAGACGAAGTCGTAGTTTAGGTTTAAAAAAAAAAA

ACAACCCAGCCTGGAGTTCCCGTCGTGGCTCAGTGGTTAACAAATCCGACTAG

GAACCGTGAGGTTGCGGGTTCGACCCCTGGCCTTGCTCAGTGGGTTAAGGATC

CGGCGTTGCCGTGAACTGTGGTGTAGGTTGCAGATGCGGCTTGGACCTGGCAT

GGATGTGGCTGTGGTGTAGGCTGGTGGCTACAGCTCCAATTTGACCCCTAGCCT

GGGAACCTCCATATGCCGCGGGAGTGGCCCTAGAAAAAGGCAAAAGACAAA

AGCAAACAAACAAAAAACCTAGCCTTAGTCTATAAGAGACGTAGATGACATTA

AAGGAAAAACACAGGTCGAAATTGGGGGAAAAAAAAAAGAGAAAAGATATA

CTGAACAATTAGAAGCTAAAAATGCCAAAGTGGCAACTTTTATATCATGTAAA

GAGCTGAAGGAAAAAAAGAAAATCTAAATTTTCAAGAGGGTAAAAGAAGATC

AAGAAGATGTGAACACACACACGTACTCACAACTGACAAAATAACCTCAA

ACTGGACTCTGTCGTAGTTGGTCATCTAGTGCTTGATGGAGAAAGAGAACCG

TCATTCGTAGGTAGAATTCTGCTTCATTATGTGGCTTAAACTGCCAGTAATTGG

GGCAGCTGGCAGAGAAGTCTGAACAAGCATCTCAAAGAGTCTTTTTGATGTCT

GACTGCCAATAACTTACAGCTCCCACCTCCAGCTTCCCTTTCTGCCCCACATCT

GGGCAAACTGATTAAAAAAAAAAAAAAAAAAAAAAAAAAAAAAAAAAAAA

AAAAGCCTGTCCTTTCCTGGGTGCCTACATGGAGTTCAAACATGAAAGCTCAG

GGCCACCTGTAACCACAGTGAAAACCAGGGCCCCTTGTTCCTATTTTCTCAAGC

TACCTGGGCCACTTCCTCCCAGCCTGGGTACCAGCCTCCGCTCCCAGAACGTC

CCAGGATATGGGTAGTGCAGTGTTTTCATACCCTCTTGGGTCATGTTTGGTGGA

ATTTTCAGTCTCAGCTTCTGATCTGTCCCTTAGGTGGGACCCGACAGAGGCCAT

CCCTATGGAGAGGGACCCAACAGCAAGGCTGCTAAGTAACCTTGGCCTTGGTG

TTAGGCCTGCAGTTGCTGTGGGTCATTCCGGCCAGCAGTCAGGAAGGGAAGCT
```

-continued

```
GAGGAAGAAGGGGAGAAGAGCAGGGATAGGCTGGAATCCACGGGGACAAGT

GGGGACCCATGCCTGCCTCTCACTCCTCCCAACCTTGGTAATGCTAACGCTGCT

GTTCCCTTGGCCACTGAGTCACACATACGAGCCCCAGGGCTCCGAGAAGCTGA

GCGGGAATATCCCGCAGAAGATGGAGCTGCGCTGTCCTGCCCGTGTCAGTGAA

CTGAGCCTGCAGATCAGCAACACAGGAGTTGTTGTCATTCCTGGTGCCTTGCA

GAGCATTGAAAAATGCTGCTGGCTGACGTCTGCCATCCGAGTCTTACCCAGGT

GTTTCTTGGGCTACTGCTGACCCAGACGTATACACAGCAGGAGCTTACAGGA

TAGTCCAGGCTCCGCTGAGTTGATGTAATTCAAGGCCACCTCGCAATCTAAGG

GGGAAGGGGGCAGCTTGATAGAAGCAGGTGGAGAGCTTACCAGACACTCTCA

GAAACTGAACACGAGGGACGTGGGAAGTAAGTAAATAGCCAGAAGGCTTAAA

TGACGTAATGAATGCATGTGAACTGATTGAAACACAGAGCTTTAAACCCAGCG

AAGGAAGGAAGATCTTTGGGTGCACGTGGAACATTGACCAAAATCAGCAAGT

GCTTTGTCACTGACGCCTTTCAAGAAATCCTAGTGATTTGTTCTTTGACCGTAA

TGCAGTGATATTGGAAATCAGAAATAAAAGGAGAGTTAAATTCATGAATGGGA

ACCTTTAGTTCCCATTCATGTGGGAACTAAAGGTTCACCACAAACAACTCTCAG

GTTAAAGAGGAAGTTGTAAAGAAAAATATACAATACTTAGGACTGAGGAACA

ATAAAAAGAGGACATTCAAAATGTGTGGAGCACAGCTCAATTAATACTTAAAA

GGATGGAGTTCCCATCGTGGCACAGTGGAAATGAATCCAACTAGGGACCATGA

GGTTGCGTGTTCGATCCCCGGCCTAGCTCTGTGGGTTGGTGATCCGGCATTGCT

GTGAGCTGTGGTGTAGGTTGCAGATGCAGCTCGGATCTGGCATTGCTGTGGCT

GTGGCGTAGGCCGGCAACAACAACTCTGATTAGAACCCTAGCCTGGGAACCTC

CATATGCTGCAGGTGCAGCCCTAAAAAGACAAAACCCCAAAAAAAAAAAAAA

AAATTAAAGGGAAATTGACAGCATTAAATGCATTTCTTAAAAAGCAAAGACGA

ATTAAATGGAAGAATTCTTTGACTTATTAACAAGGAAAAGAAGCAACAAAGCA

AATCTAAGGACATGTAAAAGAAGGAAATAATAAAGAGAAAATGACAGATTAG

TGATATAGAGACTAACTATCACAGAAAATTAACAAAAGTAAAAACTGGCCTTT

AGAGAAATAGAGATAATTTTCTGCCAAGATTGGTGAAAAAAGATGTATATAAA

AATACAGAATGATAGGTGTTCCCATTGTGGCACAGCGGAAACGAAGCCAACTA

GGAACCATGGGGTTGTGGGTTTGATCCCTGGCCTTGCTCAGTGGGTTAAGGATC

TGGCATTGCCATGAGCTGTGGTATAGGTCACAGATGCAGCTCGGATCCTGTGTT

GCTGTGGTGTAGGCTGCCAGCTGTAGCTCCGATTTGACCCCTAGCCTGGGAAC

CTCCATATACTGCAGGTATGGCCCTCAAAAGCAAACAAACAAACAAACCCAA

AACAGAATGATAAAAAGGAAAATAACTATTAATAAGAGCAATGCACAATGCC

TTATTTTCAAAATTAATGTGGTAGTGTATTTGATAATTTAGACACAGTGGATAA

ATACCTGGGAAAGTAGGAAAATACCAAATTAAGGCAAGAAAAGTAGGAAACT

TGAATAAAGAAATAGCCATCAGGCATTCCCATTATGACTCAGTGGGTTTAAGA

ACCCATATAGTCCCTGTGAGGCCTTTGTTAGTGNNGTAAGAATCTGGCATGGCT

GTACACTAGCATAGGTTGTAGATGCAGCTCGGATCCAGCATTGCTGTGGCTGT

GGCTGTGGCCTGCAGCTGCAGCTCTGATTTGACCCCTATCCTGGGAACTTCTAT

ATGCCACAGGTGGAGCTGCAAAAATGAAAAAAAATTTTTTTAATTTAAAAA

TTTTAAAACAGTTTTGAAAGATCTCTTCTTCAAAAAAGCCCCAGGTCCAGATGG
```

```
TTTTATGGGCACTTTGGCCACATGTTCAGAGAACAAGTAATTCTTGTTTTAGGA

GAGAATAAAAAGATAAGCCAGTCAACCTCACTGGCAAACCGGATAATGGTAG

CACATGGGAAGAAAGTCCATTTCATTCATGAGCATGTGTGAACATCCAAATT

AGGGTAATAGCTAACTGAACCTAACAGTGTTAAAAAAAAGTGCATCACAAATA

GAGTGTTTATTCTAGAAATGCATGAACATTTTTATACCTGAACCACAGTCACTG

TGAGTTTTATGGTATCAGTGGACTAAAGAGATGAACAATTATGTTCATTCATCA

GCTACTTACTGAATGCCTCTTTGTGCTGGTGACTGTTCCAGTAAATTGTCCAAG

GACCCTTGGACCGTTCTGCAGCAGCTTGAATCTGTAAATTTGGCCAGTGTGTCA

GGACTGATGGCAGACTGTTCTGCTGCAGAAAACCTAAACACATAGAACACCTG

ACTACCTGTCGTACAAAGACTAAGGTCAAAAGGAAAATGGGATGGGAGCAGG

AGGGATGGGGAGGTGAAGGGAGGGAGATTGAATTCATAGAACTGCTGTGTCA

AAGGATGTATAAGTATATATAATGTATTGCCACCTCCAGAAAGGTATTTTATTT

ATTTATTTATTTATTTATTTTGTTTGTTTGTTTGTTTGGAGCAGAGAAAGG

TTTATTGCAGGGCCCAGCAATGAAAACGGGTGGCTTATGCTCAAAAACTTTGA

ACACCCTGACGGTACCTGGGAAAAGTTTTTATAGGTAGAATTTGGAGTGAGGG

CTGCAGAGGGTGTGCCCAGAAAGGTATTTTTTTAGCTTTATTATTTTTTCAAGC

TGTTAAGCCATTACTGTCGTGAAGTCAGAAATGGTTCCACGGAGTCTATAACTT

CTCTTGGTCCCCTTTCTGTGTTTGAGATGGCAAAGGCACATAAAGTCATGGAAA

AACTGAAAATGTATACTTCTCTTCTTTTAATAGGTGTCAATTGAAGTTGAAACT

CCTACCCAGATATCTTTAATTGATGAAGCATCAGGCGAGGTAACTAAGTACTA

AATACTGTGTTTTAAAAAAATCATTACTTAGCATTAAATGATTGTGTACCTTT

CTCCTTGCTTGTGAATGCTCATTTAACCATAAATAAAATTTATAGTAAATGAGT

GGGTTTGTAGGGAAAAAAAAAACCATCTGTGATATATTTTCTATGTCCGAAGG

ATTAGTCTATGTCAGAGCTGCTTCTTTTTAGTATTACGTGCTAATTATAGGCGCT

CCGTAATCATGATATTACTAAAGAATTCTAATTCTAATTCTAATTCTAATTATA

ATTCTACTAAAGAATGTGATTGTCACATTTATTAAGTTTATTATAATGTTCAAG

ATGTAAAATGGTGCTCAGTGTTTTTGCAGCGTATTTAGGTATATTTTGATTTATT

TCCCCCCCCGAATCATTTTTTTATTCAAGAAGACATTATCCAGGTGGATCCATT

TTATTTTTTGTCCTTAAATTTAGAAGCAGGTCCTTTTGTGTGGCAGTTATCTTTT

TTAATAGTAAATAGGACTAAGGACCTACCTTTTATGTATTTATATATTTATAGC

TCAAATCATAGGTAGGGCTAGAAAGTGTTTTCCTCTTTTATGGCAAATCTAGTT

AAAATTTATTCTGTAGTCTGATTAGAACCTGCTTAATTGACACGTTTAATCTGG

AGGGTGTCCTTGGTGATGTGACTATAATGGGACAGGGGTCACTTTTTTTTTTT

TTTGTCTTTTTGCTATTTCTTGGGCTGCTCCTGCGGCATATGGAGGTTCCCAAGC

TAGGGATCTAATCGGAGCTGTAGCTGCTGGCTTACGCCAGAGCCACAGCAACC

CAGGATCCGAGCCACGTCTGCAACCTACACCACAGCTCATGGCAACGCCGGAT

CCTTAACCCACTGAGCAAGGCCAGGGATCGAACCCGCACCTTCATGGTTCCTA

GTCGGATTCGTTAACCACTGCGCCACAACGGGAACTCCAGGGGGGTCACTTTT

TACATTTCCTCCCTGGAGATTAGGCATTGAAGTCCTTTTTTTTTTTTTTTTTT

TTTTTTCTGTTTTTCTTTTGCTTTTTTTTCTTTTCTTTCTTGTCTTTTTTCTTTATCT
```

-continued

```
TTCCTTTCTTTTTTTTCAGTTTTTTATTTTGACTGCCTCACAGCACAGGGAGTTT

CTGGGCCAGGGATTAGATCTGAGCTGCAGTTTCAACCTTTGCACCATGGCAGG

GTCTCCTGAAGTCCTTCTAGAGCTACTGTCCCGAGGGAGGGGAGGCGGGATGC

CCTGAACCTTGCTAAGTGCCATCCTGAGCTCGGGTTGTGCACACGTTCGGGAG

ATGCTCTTGGTGACTGGCAGCCTGTGACATGTGCTGGTGAAAGGCTTTCTCAGA

ATTGGGCTCCAGACAGCAGGTGGCTCTTAAAGAGCAGGGTCCTGGTGCCCCAC

TCTCGTCCTTTCCTTTTCTTGTCCTGCACTGAGGCTTGCATGTGTGTGTCTCCAG

CTCCAACCTGGGGAGAGCCCATTTTATATTTATTTTTATTTTATTTTAATTTTT

TTTTATGGCTAAGCGTGCAACATATGGAGATTGCCAGGCTAGTAATCAAATCT

GAGCCATGACTGAGACCTATGCCAAAGTTGCCCCAATGCTGGATCCTTTAACC

CAATGTACCAGCCTGGGGGTCAAACCCAGGCCTCCTTAGCGACCTGAGCCACT

GCAGTTAGATTCTTAACCCGTTGCACCACAGCAGGAACTTTTTATTTTTATTTT

ATTTTTTTAATAAATTTTATTGGAGTATAGTTGACTTAGTTGTATTTCAGGTATT

CAGCAAAGTACATCGGTTATACAAATACATACCTTTTTGGATTCTTTTCCCATA

TAGGTTATAGCAGAGTTTTGAGCATAGTTCCCTCTGCCACACTGTGGGTCCTTG

TTACGCAACTCTTTTATACGTAGTAATGTGTATTTGTCAGTCCCAGCCCCCTAA

TTTATCCCTCCCACCCCACATGGTAACCCTAAATTTGGTTTCAAAAGGGAGAGT

CTGGAGTTCCCATCGTGGCTCAGTGGTTAACGAATCCGACTGGGAACCATGAG

GATGTGGGTTCGATCCCTGGCCTTGCTCAGTGGGTTAAGGATCTGGTGTTGTGG

TGAGCTGTGGTGTAGGTTGCAGACATGGCTCAGATCCCGCATTGCTGTGGCTGT

GGTGTAGGCCGGCAGCTCCAGCTCCGATTAGACCCCTAGCCTGGGAACCTCCA

TATGCTGCGGGAGCAGCCTTAGAAATGGAAAAAAAAAAAAAAAAAAAAAAGG

AGAGTCTGTCTAAAGGGGCCTTTGGAATAAACGATGTCAGACACACCTTATGA

CTAGAGAGCTGGAGTGTCCAGAGCTCTGCCCCACCATGTATCAAACCTTCAGA

GGCTATGCGTGGTGCCCATGAGGATGTGCCTAGTGGGGCAGTACAGCATGCTG

TGTGGTGACTTGGGACCAGGCTACATCAGAGTTTTAAAAAATGTTTTAAAATA

ACTTTATTGAGACATCATCCACGTACCATCCCACTCACCCCATTCAAGTTCACA

GTTCAGGAGTTTCCATTGTGGTGCAGCGGAAACATACCCAACTAGTATCCATT

AGGATGCTAGTTTGATCCCTGGCCTCACTCCGTGGGTCAGGGATCCGGCATTGC

TCTGAGCTGTGGTGTAGTTCCCAGATGCACCTGGGGCCTGGTGTGCCTGTGGCT

GTGGTGTAGGCCAGCAGGTGCAGCTCCGATTTGATCCCTAGCCTGGGAACTTC

CATGTGCCGTGGGTGTGGCCCTAAAAAGTGAAAATAAAAATAAAAGAAATAG

GCAGTTCAGTGGCTTTTTGTATATTCACAGAGTTGTATATCCACCATCACAAGC

AATTTCAGAATATTTTCATCACCCAGAAGACCACTTGGTACCCATTAGCAGTCA

CCCTCTATTTCTCCCTCCCTCTGGCTTCTAGTAACTACTAGTCTAGTTTAAGGCT

CTATGGTTTGCCCATTCTGGACATTTCATAAAAATGGACTCATATAACACGTGG

TCTTTTGTGAGTGCTTTCAGTTTGCATAACTTATCCATGCTGTGGTGGTTGTCAG

TACTTCATGTCTTTTTATGGCCGAATAACATCCCACTGTATGGCTAGACCACCT

GTTGCGTATTCAGTCATCAGTTGATGGACATTCGGGCTGTTTCTACTCTTTGGC

TGGCATGAAGGATGCTGCTCTGAATATTCATATATAGGTTTTTGTGTGTGGACC

TGTTTTCGTTTCTCAAGTGCAAGAGTGAAATTGCACTCTTGCACTTGAGTTTCT
```

-continued

```
CACAGCAAGAGTGAAATTGCTGTGTCATGTTGCAACTCTGCATGTAACCATTTG

TTTTGTGGGTGAGGATTCCACTTGTTTCCAGAATCTGGAGAGTGGGGAAATGA

GGAGAAAAGGCATACGTCCTTGGGACGTACTTGCATCTGTTCTGTTAAGGAGG

GCTTTGTTTAACTGGGTCCTAATGATAAATTTCTATTATTTTTTTTCTTTATTTT

CTTTTTAGAAGGAAGAAATTGTTGTGACTCTCTTACCAGCTGGTCATTGCCCAG

GATCAGTTATGTAAGGGGGTTCATCTCTTTCGCCCATTTATTCTGCGTAGAAAC

GTATTGTATTTGTAGAAATAAACATTGAGGGTCTAGAAAACAATATGTGTAGG

GAGATTTGATTCTCTTGATGGCAGTTCGTTTAATCTTTGTTTCCAAATTGAATTT

GGGGGACTGTGGTGCAGATCAAGTTTGAAACGTGGCTTTCTGACAATGCAAGA

CTTCAGTAGCCATTTCTCCACTGGCTTTGCATTTTCCTGTCGTGTGGATTTTTCT

CTCCACAAACAGGAATGATTTCATTGTACAGTTGAGGGAGCTCACGTATTTTGG

GGCCATCGCTTGCAAACTCAGTGGCATCTCCATCATGTTATTTTTTCCAACCTC

CCGGGAAGAGGTGGCAGCTGAGTGTCTGGTGTGGTTAAGCAGTACGGAAATTC

TGTTCATGCCATGTCAGGGTGGCTGTGTTTGGCAGGCAGCGTGGGCTGTGGCTT

TAATATATATTTGCTTTACTGGGATTTTGTATGAGACCTAAGTCACTGAGATAT

ATTTCGTTTTTCAGGTCTTATTTCAGGNGCACACATGGAACTGTCTTGTATACA

GGAGACTTCGATGGCAAAAAGGAGAAGCTGCCAGAATGGAGCTTCTGCACTCG

GGGGGCAGTACCGGGCTTTATATAATACTCGAATGTTAAGACTATGTTGTTGTA

AAGATTTTACTGCTCTTCCCCCCTACACATGTATGAGGCTTTGTTGCTTTTATTT

TTTATTTTTTTTGCTTTTTAGGGCCACACCCGCAGCATATTGAGGTTCTCAGGCT

AGGGGTCGAATCAGAGCTGCAGCTGCCAACGAACACCACAGCCACAGCAACG

CGGGATCCGAGCCCCACATGTGACCTACACCGCAGCTCACAGCAATGCCGGAT

CCTTAACCCATTGAGCGAGGCCAGGAATCGAACTCGTGTCCTCATGGTTCCTA

GTCAGATTTGTTTCCAGCTGTACCACAACGGAAACTCCTGCCTTTGTTTCTATT

AGAAGTCTAACTCAATTATAATATTTGCAACAGCAAAGCAAATTTTTCCTCTTG

AAATGAGGGGATGATGACATTCTGTGTGTGAATTGGGGTAGTAGTTACATGAA

CTGATCGAAATTCACTGAACCAGGAGTTCCCTGGTGACTCAGTGGGTTAGGGA

CCTGGCATTGTCGCTGCTGCAGTTTGGGTCGCTGCTGTGGTGGGGGTTCAGTCC

TTAGCCCAAGAATTTCCATATGCCCTGGGTGCAGCCAAAAAAGGTAAAAAAAA

AAAAAAAAATCCCTCACCCATCTGTCTTATATATTATCCTATGGAAATCACTTC

CTAACCATGTCGATACAGTAAAAAATTCCAGGGAGCTCTCTTGTGGCCCAGTG

GATTAAGGATCTGGCTGTTGTCACTGCAGCGGCATGGGAGTGGCCAAAAAAGA

AAACCCAAGTGGACTGAAACCTCCTGTAAAATAACTGAGAGTTTCGACTTCAC

GCGTGTTGTATTTCACGTGATTAACAGCTCTTGTGTTCTGTTTATCTTCAGTGTG

AAAGACATCCAGAGTGTGTACTTAGACACCACTTTCTGCCATCCAAAGTATTA

CCAAATTCCCAGTCGGGTACGTCTCTCTGGACGGGTGGCTGTATTTCTCAGGGG

GCGGGCCGCAGGCTAACAGGTCGGGTGGTAACGGGCCCCCTGGCCTTAATGTC

TGGGGACGCTGGGAACGGACAAGGCCTCAACTGCCTCTTCAAACCCCTGCCCA

GGAGGAGTGTCTGAGAGGGATCTTGGAGCTGGTCCGCAGCTGGATCACACGGA

GCCCCTACCACGTGGTGTGGCTGAACTGCAAAGCGGCCTATGGGTACGAGTAC
```

-continued

CTGTTCACCAACCTCAGCGAGGAGTTCGGAGTCCAGGTACCTGAGGGCTCTTT

CTCCCACCCCCACCCCCAAAGTCCCCTCTCACTGGAAACCCTATCAGATGGCCC

AGCCTTCCTCACCTTGGTTTACTCACTTCCGCTTGGGAGGACTTGACAGGTGGA

AAGAGCCCTTCGGTGAAAAGTCCCACAAAGGAAGTGTGTTTTGTTCAAAATAC

TGGGTCATGAAATAAACGTAGTGTTTGTCACGAGCATTGAAAATAAATGTGAA

CTAGGAAGTATCCGAGAGTATGGCTTGCAGTCAGAGTGGTTATTGTGTGAATA

TTTACATGGGGAGTCAGATATATCAACAGATCTTTCTCGACTTAACCAAAGGG

CTGTGTCCCAATAAAGCCATAAATCTGTCTGGCTCGAGTTCCCTGTAGAGGCTC

AGTGGTTAACGAACCACACTAGCATCCATGAGGGCGCAGGTTCGATCCCTGGC

CTCGCTCAGTGGGTTAAGGCTCCGCAGCATTGCCATGAACTGTGATGTAGGTG

GCAGACGCGGCTCGTATCTGGTGTTGCTGTGGCTGTGGTGTAGGCGAGGGGAT

GCAGCTCTGATTGGACCCCTAGCCTGGGAACCAACATATGCCACAGGTGTGGC

CCTAAAAAGACATTAAAAACAAACAAAAAATCTGTCAGGCTCCTCCCCTGGCA

GAGGAAGAGCCTCCTCCACTCTCCCTCTCCCTCGGGTTCTCACTTGCACACAAC

AAGGATCTGGAGATGCAGGCTGGCAGGTCCTGTAGCCGAGCCGGGATAGAGC

CTGCGGGCTTGTCGTACAAGGATGGAGTCCGGTGGTCTGGCAGGAGGTTGTTC

CTGCCGGGAGGTGCTGCAGCAGCGCCAGGGTAGAGTCAGGGGTCTGGCGGCA

CAGGGATGGAGACAGGCCCTCTCTCCAGGCAAGAGCGATCGGCTCAGGACGG

GAGCGGTTCTGAGTGGAAGGGAATTTCCCTTCAAAGGGACACCACCTTCTGAC

CTGGGCTCTTTTAACGACCCTTTCAGATCCATGGCCTCAGAGATCACAGTCTTG

ATCACAGTTGAAATCAGGTCACCATGAACCAGTTTTATGGACGCCTTCAGAGG

GTGGGCCACCCTGGGCTGGGAATGGTCCTGGCTGCCACTGGGTGTGGGTGTT

TCCTTAGGTCCCTACATCATGGACCTGTTTGGGGACCCACATTCTCTTGCCCCA

GGCCCACTAATTTCCTGTCCCAGCCCCGCCCCGCCCCGTGCTGTGTGTAAG

GGCTGAGTGTTGTTTTGCTCTCTGCATGGGGGTGGGTTTGGATCCTCTGGTCGG

TCCCACCTTAGTCACGTGGGGAAAGGTTATGGGGAGGCGCTCCAAGCGCACGC

CCCTGGTGCCTGCGTGTGTGTTCATTGTTTACGCAGGCCTCCTGTTTTTGGCAA

CAGCAAATGGCCTGTTTTGAATCACCCAGGTCCCCGTCCCTGTCCTCTCCTAAC

AGAGCCATTGCAAATAGCACGTATAAGTTAAACATGCATTTAAATAAGTTCCT

TTGTATCATTTTTAAAAATTAAATCCCACACGCAAAGGGACTTATTTAAAAAAC

ATTCTGAGATTGTTGTTGCTGTGTTTTTTGGTGTTAAAATGTCTTTTCAATTAAA

CCACAGCGATAATAGACTGTGTGTGTGCGCATGTATACACACGCACACGTACA

CACATCTTTATATATGCTCTGCTGGGTGCTGGGTTTTTTGTTTTTATTTCATGG

CTTCTTGACAAAATATAGAGGTACCAGCCACTTACCCGTCCCAAATTTGCTGTG

TAAATTTTCTCGATGTGCGAAATGGAAAAGACCCGGAAGCTCCCGCTCTGAGA

CCTGGGGGAGAAACCCCGGGCTGAGGAGGGGGTGGGGAGGGAGGCAGGATTT

CAGTGTGTGGCTCCCTCAAGTCTCTTAATCCCGCTGTAGGGATACAATGCTTGT

AGACAACAGTGAGGTTTTTTGGACAAAGAGACCTGAGAGGTGATTTATGACA

GCCTTTTCAAGCATCTTCATTTTCACGAGGATGAGCGTTTGTGTCTCTCTGGTG

CATCTCCGAGTTTACCTCTTTTTCTCTCCTTCCTAGGCCGGAAAAGTCAATTCAT

TGTTCCTGTTAGTCGTTAGTAAACAGGTAGTGAGAGGACTAGGCTACTGGATA

-continued

```
AGTAAGCAGTCATGCCTGGCTGCTGTGTGACAACAGTCCTGGTAGTAATTACC

CCAGCAGTTAACATCCTCCTGGAGTTCCCGTTGTGGCTCAGTGGTTAACGATTC

CGACTAGGAACCTTGAGGTTGCGGGTTTGATCCCTGGCCTCGTTCAGTGGGTTG

AGGATCCAGCGTTGCCGTGAGCTGTGGTGTAGGTCGAAGACGTGGCTCGGATC

CCGCGTTGCTGTGGCTCTGGCGTAGGCCGGCGGCTACAGCTCCGATTCGACCC

CTAGCCTGGGAACCTCCATATGCTGAGGGTGCCACCGTAGAAAAGACAAAAA

GATAAAACAAAACAAAAAACTTCCTAATCTGTTTTGTTGCTCAGACTTCAAAAT

GACAATACTGTTTCTTTTTTTTTTCTTTTTCTTTTTCTTTTTTTGGTGCCATTTCA

TTATCTCTGTGTTCATTTAGGTACTTGTTGTTTATTCTGAAATACCCAGAAAAG

ATTTAAGCAAAACTGACATGTTGGTTTTAAGTTTTAAGCAGTATTAGCTTTAGG

AGTTCCCTGGTGGCCCAGTAGGTTAAGGAACCAGCATTGTCACTGGAATGGCT

TTGGTTGCTGCTGTGGCACAGGTTCGATCCCTGGCTGGGAACTTCTGCATGCC

ACAGGTGTGGCCAAAAAAAACTCCAAACAAACAAAAACAAAAATTAAAAATG

AAATCATTAGCTTTAAGATTCTAATGGTGGCTGAGATCTTTTTTTTGGTCTTTT

TTCGTCTTTTTAGGGCTACCACACCTGCGGCATGCGGAGGTTCCCAGGCTAGGG

GTTTAATCAGAGCTGTAGCCGCAGGCCTACACCGCAGCCACAGCAATGCCAGA

TCCGAGCCGCATCTGCGACTGACACCACAGCTCACAGTAATACTGGATCCTTA

ACCCGCTGAGCGAGGCCAGGGATCAAACCCGCAACCTCATGGTTACTAGTCTG

ATTCGTTTCCGCTGCACCAAGACAGGAACTCCTGAGATTTTTTTGTTGTGTTTTT

CTGCATCTGCCCCCTCCCCCTCTGGCCAATCCACTGTGGCATAGGAGGATCCAG

ATCTCGGCTTCCTTGTTACGCTGGCTGCCCACCACCAGCTGCCCTTAAGTAGCA

TGTTGTATGTGTCTTCGAGAGCAACCTTCTTGATTATTTTTGTCTGCTGTATTTA

CTGCAATACTCCCAATATTTAGAATAAAGCTTTTTTTATTGATGATTTTTATTTT

TATTTTTCTAGCACAGCTGGTTTACAGTGTTCTGTCCATTTTCTACTGCACAGCA

AGGTGACCCAGTCGTACATACATATATACCTTCTTTTTTCTCACATCATCACGC

TCCATGATAAGTGACTAGATAGAGTTCCCAGTGCTACACAGCAGGATAGAATA

AAGCTTGATGTAGAGCAGGTGCACAGTAAATTTTGGTCGAGTGCCTCTTGCTA

AACTGAGGGACGGATTTACCTGATCCAGTGAAAGCCACCTACAGGAGGCGCTA

AATGCCGGGACCATGATCTCAGCGTCCTGGTGCAGTACTAATGTGCGTGGAAA

GAGAGGAAAACTAGGTCTCACGGCAGAAGAGAGAGTTCATTCTAACTGGATG

ATTTGCCCCGGCCTAGTTACCCTTGAAACACTTTGTTTACAGGAAATACAATTC

CAGTCATGTGCTTATTTGTGTTGTTTTCCTCAGGTTCACGTGAATAAACTGGAC

ATGTTTCGAAACATGCCTGACATCCTTCATCATCTCACAACAGACCGTGGCACT

CAGATCCATGCCTGTCGGCATCCAAAGGTACACAGTAAACTGCTCTGTTTGCG

AGATCCATGCAAGAATTTCAGGTCCAGGAGGAACCGGCGAAATTCCATTTTCT

AGGCCCTTCAGGTCGCAAATGTGAAAACTGAGGCTTAAGGTGTTAACCCAAGG

TCATTACTGTATTGCAGTACCCTGAACTTCATAATGAGTTAACAGACACAGAC

ACGCCATAGTTTTGTTTTGTTTTGTTTTGCTTTTTAGGGCTGCACTAGTGGCATG

TGGAAGTTCCCAGGCTCTTGAATCGGAGCTGCAGCTGCTGGGCCCACACCACA

GCCACAGCAACGCCAGATCTGAGCCTCATCTGAGACCTACACCGTAGGTCACA
```

-continued

```
GCAACGCCGGATCCTTTACCCACTGAGCGAGGCCAGGGATCAAACCCACATCC

TCAAGTGGCGGATACTAGTTGGTTTAGTTCCCGCTGAGCCACAATGGGAACTC

TGGTTTTCAACCTTTTAAAAATACTTGTCACTTTTTCTCCAACTTTATTTTGAAA

AATTTTAAAGCAGTATAGTAGTTAGACTAGTACCAAGACCTCTGTGTACTCTAT

TTTTTCTAACTGGCGTATAGTTGCTATGTACTGTTACGTAATTTACAGGTGTAC

AGTGTAGTGATTCACAATTTTTAAAGGTTGTAATCCATTTATAGTTACTATAAA

ATATTAGCTATATTCCCCCTATTGTATGATATACTCTTGTAGCTTCTTTATTTTT

TAGGTAGTAGTTTGTACCCCTCAACCCCCCACCCTGTCTTGCCCCTCCCCACTT

CCCTCTCCCCACTGGTAACCACTGATTTGTTCTCTATAGCTGTGAGTCTGCTTCT

TTTTTTTTGTTATATTCACTAATTTGCTATATTTTTTAGATTCCACATGTAAGTG

ATATCACACAGTATTTGTCTTTCTCTGACTTATTTCATTGAGTGTAATGTTCTCC

AAGTCCATCCGTGTTGCTGCAAATGGCATTATTTCATTCTTTTTATGGCTGACA

TTCCATTGTGTGTGTGTGTTCCACATCTTCTTTGTCCATTTATCTACTGATTG

ACACTTAGGTTGCTTCCATGTCTTGGCTCTTGTAAACAGTGCTGCTGTGGACAT

GGGGATGCAGTATCTCTTTTAATTAGTGTTTTTGGTTTTTGTGGGTATATACCCA

GGAGTGGAATTGCTGGCTCCTATGAACACCGTGTCCTCTTCTTCTGGATTCCGC

AGCTGCCCAGGTGTTAACAGTTTGCTTTCTGGCACCCTCTGTGTCTGTCTGTCT

GTCTCTCTGTGTAAGCAGCACCCCACCGTGCAGCCCACTTGAGAGTCAGATGC

AAACGTCATGACACGTCACCCTAAACAAAGTCGTATAACCACAGTACACTTCC

CACACTCAGGGAATTTAACATGAATGTGATACGACTGGGTATGATATGGTCCA

TATTCAGATTTCCTCAGTTGTCTCAATCCCTTATGGCTTGGTGGAGTGGGGAGC

AGGGCCATCCAGAATTTAATTTAAAAACATGTGTTGCATTCACTCAGGCTGCTT

TAGTCTTTTGATGTAGATCAAGTCTCCAGCTAAAGTCCAGGCCAGTTGTTTTCT

AGAATATTCCTCAATTCGAACTTACCTATTTCTTCATGTCTATATATGTATATAT

ATATTTTTTTTTCATGCTAAAAAGTCATCTGCATTTTTTTGAGACCCTGGTACA

AATATATTTGTTGAAAATGTTAAACCATTTTTCTTATTTTAAAATCTTTTTTAGG

CAGAGGAATATTTTCATTGGAATAAATTACCCTGTGGAATAACATCCAAAAAT

AGAATTCCACTCCACATAATCAGTATTAAGCCCTCCACTATGTGGTTTGGAGAA

AGAACTAGAAAAACCAATGTTATTGTGAGGTAAGCAAGCAGCGTCTTTTGAGA

GGAACCTTGCTTTGAGGTAAATCGATAGTTTAAAGGCAGTCTAGCCTAACCTC

AAGAGGGGGCATATCATGATTGTGGAAAATAACTTTTGAAAGTTAAACTCTG

TTTAAATTAAAGAGAAGCGGCTTCCAAAAGCTATCAATTGCTTACTACCATGA

GCCAGTATTTCCTGGGGTCTACTGAGTTTGACTGAGAAGATGGTTAGAGGCAG

GCTGTCTTGCTTGGCCGGAAGTTGGGAATTGACCTTGAAGGGGTTGGAAGCCC

TTAGTGGAGCAGAGGAGGCCCATACTGATCCTCATGTTTTAGCTCATGTCCTGA

AACATTGGCCGTTTGGAATGTTCACAGATATTTACATTTATGGAAAGAGTTCCC

TCCTGGCCCAGGAAAAAAATCCTTGATGGCAGGGTGATTTCATCCTGCAGTAG

CCTAAAATGAGAAGACTCGGAGTTTGGAACTTAGTTTTGATGAGTGACCCTTA

ATTTTGGGTTTTCCTTTCCCTTTAGAACTGGAGAGAGTTCGTACAGAGCCTGCT

TTTCTTTTCACTCCTCCTACAGTGAGGTAAGAGGATCCCATACTCAGAACCTCG

GCTGCTGAGGCATCTCTCTTCCTCCTGCTTAAGACTGGTGGGGACTCTTGCTCA
```

```
-continued
GGAAACACAGGCGAAGACATCTCGGTGGATGAGCTACGTTGCTTAAGTAGAAA

GGAAATGATCACCCCTTGTATCTAGCCTAAACTTTGAAGAAAATGTATGAATA

AGGTTTTATTCCCAACCTGCTTTCTAAATGTATTTTAAACCCCTCACTTCAGTTC

TGTTCACCCGTCGTAAAAAAATTGTCAGTATTACTATACAGCAGATGGAAATG

TGGTCAGTAGCTTGTGATTACCCATACTGGAAAAGAATCTGAAGCTCTATGCC

CGAAACTCACACAGTATTGTAAATCAACTATAGTTTAATTAAAAACCCCAAAC

AAAACCCCAAAAACTTCTTCAAGAAAGTAATAGTTAAGAATATAAATGAAAAG

ACTCCCAGAGTTGGTGCAATGGATTAAGGATCCAGCATTGTCTCTGCAGTGGC

TTGGGACGCTGCTGAGGTGCCAGTTCGATCCCCGGCCCAGGAATTTCCACATG

CCACAGGTCCAGCCAAAAATTAAAAAAGCATTTAAGACTTAGAGACTTGAAAT

AATTTGACACAAGCCCACCAAGATCTAAAAATGACAAAGCTGAAGCTCGTCTG

GGTTATAGAGATGTTTTGAGGAAGAGTGACAGAGTTCCTTTGTTTAACATGCTG

AGCTTTGCAGAAAATCAAGGTATTCGTGAAATTTTTGCATGTAGTTGTCCTTGT

TTGGATTAGAATAAACCATGAAGATGAATCGAGCAGTCTCAAAGATGTACTTC

CCCTTGGTATTGCTAACAATTATATGTGGGAAGAAAGAAATGCAATTCTAAGT

TCTTTCCCTGTGCATATTAAATACTTGGCTAAATTCTAACTTCCTTAAAGGGAA

TTTGTTAAATATAGGGTGAGTGACTTTAGATAAGGAAACTAGGAGTTCCCGTC

GTGGTTCAGTGGTTAACGAATCCGACTAGGAACCATGAGGTTGTGGGTTCAGT

CCCTGCCCTTGCTCAGTGGGTTATCGATCCGGCGTTGCCATGAGCTGTGGTGTA

GGTTGCAGTCACGGCTCGGATCTGGCATAGCTGTGGCTCTGGCTCTCAGCTTTG

GCTCCCCTAGACTGGGAACCTCCATATGCCTTGGATGTGGACCTAGAAAAGA

CAAAATAAAAATAAAAAATTAAAAAAATAAAAATAGATAAGGAAACTACTGT

CCTATAAAGAAATAGAGAATCTTTGAATCCCATTAACAAGTGAGACTCATTCC

TTACTGGGGAACAGAATCACCTGAAGAACATTTAAATATATTGATTCCAGGTC

CCGCTGTAGCTCAGTGTTAGAGGCTCTTTGGGGCTGGGGCATGTGTGTTGGGTA

TTTCTTTTTGAGAGCCCCGCTGGGTGCTCCCGTGCACCTGGCATTAGGAACCAC

AGCCTTGAGCGACCTCTGCTCTCTTTCCCCTGGTATCCCTTTATCTGTTGCTCTT

ACACCCAGTTTTTTCACCATAGAGATAACTGATGCATTTTATTTTCCTTCTTCCA

GATTAAAGATTTCTTGAGCTACATTAGTCCTGTGAATGTATATCCAAATGTCAT

TCCACTGGGCACAACTCTGGAGAAAGTTAAAGAAATGTGAGTCATTAGTACTT

GCGGAACTTCTGTGGTCCAATGGGATGGATCCAGAGGATAATTTCAGGCCTGA

AAATGGGGACAAGGCTGTAAAATGGACGTGGCTGTCAGTAGGGTTCTGGTTGG

GAGCATCTGGGCTTTTTCAAGTGAGTGCGTTTTATATAATCTTAAAAGCTTCTG

GGCATCTAGCATAATGGACTGGTTGGCAATGAAGACCTTGAAAAGGGCGGGAC

ACCTTCAAATCTTATTTCTGTGCCCTTTTGTATTTTATTTTCACTATATCTTAGCT

TTCAACCTCTAGAATGAAGAGATCAAATTTGTGAGATTCTTGCAAGAGATAAC

CCCATTAAATAGCGAACAGGAGGCAGTTTGCTGTACTGAATTCCCTGAATGCC

AGAAGGTGTTACCCTATTATTTAACAGTTCATCAGAATAGGGACATGCTTTTCT

GCAGTGCAAGAGCAAAGATAAAAGTTTTGCTTTCCGTCAGTCCTACAATTAGA

TGGGTTGTTTTAAATGCTTATATTTACTACTTTATTATATTGAAGTAATTTTAAA
```

-continued

```
TTATTAAACATTGCTGAAAAGTTTGTTTTTTTTTTTTTTTTTTCTTTTTTGGCC

TCTCTGTGGCAGATGAAGCTCCTGGGTCAGGGATCAGATCTAGCTGTTGTTGTG

ACTTAAGCCACAGTTGCGGCAATGCTGGATCCTTAACCCTCTGTGCCAGGGTG

GGGATTGAACCCACGTCCCAGTGCTCCCAAGACGCCACTGATCCCATTGCGCC

ACAGAGGGAACTCCAAACATTGCTGAAAAGTTTTTAAAAGCAGTGGTATGATT

TCCTCCATAGTCAAATTTTTATAATCTCTATAAATGATGCTTCTATTCCCAGCTT

TCCCAACAGGAAAAATAATATCTGTATTCATTTCAGCTTAAAGCCTTTATGCCG

ATCTTCGCAAAATATCGAGCCAAAGTATAAACCACTTGGAAAATTGAAGAGAG

CTAGAATAATCCATCTAGACTCAGGTAAGATGAATGACCCTGGGGTCAGAGGT

GTGGGTTTCTCTGCAGGAGCACTTTGCAGAGTTCTCTGGCCTGGTGAAAGCTGC

CCTGGGCAGAGTTGGACCCAGGATCCACTGTCGCTCAGACTTGTCATGTGGTCT

TGTAACGTGCTCTGCCCCCCTACCTTCAACCTATAAATGTAGGAGTCAGATTCC

CTTCACAGGTTTAGAAAAAGTGATAAAGAGAACTTAGTCTGTATTGAATGTTG

TCTTCAGCTTTCTGGGAATGTGCCCTGCAGCTTGTATTGGCCATAAGGAGAGGC

TCTGCTGTTACCCTTGAACATTTCCTTCAAGATACTAGTCAGTGCAGATAATGA

GAACTTTGTCTCCCATCATTTCCCATCACATTGATGTGTAGTGTTTATACGAAT

GGATTCTCTATACCTTCCTGCCTTCTTTCATTTTCTGATTGATTTTTAAAATGA

AGTATATTTGATTTACAATGTTGTGTTAATTTCTGCTGTACAGCAGAGTGGTGT

AGATATATATATATTCTTTTTAAAAGTATTCTTTTCTGTTATGGCTTGTCCTAGG

ATATTGAATATAGTTCCCTGTGCTGTGGAGTAAGATCTTGTAGTTGATCCATCC

TCTCTCTATATATATAATAGCTAACATCTGATAACCCCAGCCTCCCACTCCATC

CCTCTCTCAATGCCCTCCCCACTGGTAACCATAAATCTTCTCTATATCCGTGAA

TCTGTTCACCTATTTGGCTTGTTTGCATTTTTGGTTATTACATATAAAGCTGCTT

TCATCTGCTTACTTTGGGTTTATTTTCCTCTTCATTTAAAATTTCTTAATGTGGG

AGATGAGGTCATTGATTTGAGCCCTTTCGCCCTTAATACAAGCATCTAGTGCTA

TAAATTTCCCTCTTTGACTTGTGTTGTCATTTTCCTCCAGTTCAAAATAGTTTCT

AATTTTTCTTTTCCTCCCTCCCTCTCTCCCTTCTTTCTTTTCTTCATTTTTGGCTG

CCCTGAGGCATATGGAATTCCCAGGCCAGGGGTCAGATCCAAGCTGCAGTTGT

GACTTATGCTGCAGGTGCAGCAATGCCAGTGTGCTGGGCCAGGGATCGAACCT

GCGTCCCAGAGCTCCAGAGATGCCACTATTCCCTTTGCGCCACAGCAGGAACT

CCTCTAATTTTTCTTCCTTGAGGCGCGGGTTTATTTACAGGTACATTATTTCGTT

TCTGAATTCTGGAGGAATTTACAAAGATAATTGTGTCATATAATTTTATTGTGG

TCAGAAAAAATACAGTGCATGGATTTTACTGAGATTCATGGTCCAGAATAATG

GTCCATCTTGGTAAATGTTTCATGTGTACATGAAGAAAATATGTATACTGCTGT

TGGGTGGAGTGTTATATAAATGTCTAGTTAATAATGTTCAAGTCTTCTGCATCT

TTGCTGATTAACTTGTTCTACTTGCTCTATCAATTATTGAACGTTTTTGAAATGG

TGAATTTGTCAAAATTTGTTCTTCCACTTTTTGTGTCATCGATTTGAATAATCTT

TAAAACTCCTATGTCCTCTAGAGGAACTGACCCTTTCACCTTTGGGAAATAACT

CCCTTTATCCTTCTTTTTATTAGCTTTGAAATCTACCTCACTGGATAATAATACA

TCCATTCCATTTTCTTCTGATGTGTGTTGGCATAGTATATCTTTTTCCATCTCTTT

ATTTCTCACCTAATTGTCTTTATATTTAAAGTGGGTTTCCTGTAGGCAGTGTATT
```

-continued

```
GATGGATCTTGTTTCTTTTTACATCCATCTGATAAATTCTGCTTTTCAGTTGGAG

TGTTTTCAGGCTACTTAGGTTAATGTGATTACTGACCTTGTTAGGTTTACCATCT

TGCTATTTGTTCCATCTGTTCTTTCTTCTTTCTCTTCTACCTTCTTTTGGATTGAG

AACGGATAGAGATTCCATTTAATGTCTTATTTGTTTTATTAGCTGTAACTCTTTT

ATTCTTTTAGTGGTTTACAGTTTTCATCTGTAACCTATCAGAGTGAAAATTTCA

AGATATATATTCTACTTGAAGTATGGTATAGGAAGGTGACAACAGTATATTCC

ATTTCTCCCCTCCCAGTCTTTGTGCTATTATTGTCATACACTTTATTTCTCTGTTA

TAAACTCCACAATACATTACTGTTTTTTTTTTTTTTAACAAAGCTTTAAAAAT

TGATCGCTTATAGGATAATTTGGGAGTTCCTTTTGTGGCTCAGCAGTAACGAAT

CCATGAGGATTCAGGTTCGATTCCTCGCCTTGCCAGTGCGTTAGGAGTTGGCAT

TGCTGTGAGCTGCAGTGTATGTCGCAGTTGTGGCTCGGATCCTACACTGCTGTG

ACTGTGGTGTAGTCTGGCACCTGCAGCTCCAATTCGACCCCTAGCTTGGGAACT

TCCATATGCCCTGTGGGCCTGAAAAGCAAACAAACAAACAAAAAACCAACTAT

AATTTATATGCCATAAATTTCATCCTTTTAAGGTGAACAATTCCATGATTGTTA

CTGTAACGAAGTAGGTTACGTGCTAAGGCCTCTTCTCTTGGCTTGTGGATGGGT

GCCATGCTGATGTGTGCTCACATGGCCTTTCCTGGGTGCTTGTGCCTGGTTGGG

AGGGGTGAGTAAAGGAGGGGCTGGGGGATATTTGCTCTCTAATGTCAGTTCCT

TCTTTGGAGGCCCCATTTCCACTTTGGGGATTAGGACTTCGACAGGAATTTGTG

TGGGAAGGAACACACACTCAGTCTAAAACATACAATAAAATTTACGCTGTAAC

ATGGTAAGAAACTGACAACTGTTCTTCAGACAGAACACATTTTCATTCTCACCA

GCAATATATACGGATTCCAATCTCTCCACATCCTAGCTCACACTTTTTAGTGTC

TTTGATTTGTAGTTATTTAATGATGTCAAATAATATATCTCATTGTAGTTTCACT

TCCTTTCTCTATTGATGTTGATCTTTTTCCATGTTCTTATTGGGCATTTATTTATC

TTTTCTGGTGAAATGTCTATTCAGACCTTTTTGCCTGTTTTTAAATTGGCAAACT

CATTCCTGAGTTGTTAAGAGTTCTCTCTATAGGCTGGGTATGTCTAGTATTATTT

GCAAATATCTTTTTCCAGTCTATAGCTTGTCTTTTCACTCTCTTCATGGTGTCTT

TTGAAGTGTAAAATTTTAAATTCATCTAATTTCTTTTATAGCTTGTGCTTTTGGT

GTCATATCGAAGAAGCTATTGCTTAATCCAAGATCATAAAGATTTATTTTCATA

CTTTATCATTTCTGGGTCAGTTTTGACTTTTCCCCTTATTTATAGGCCATTTTCC

CACCTTTCTACACATTTGGTAATTTTTTATTGGATGCCACGCTTCTTGAACTTTA

TGTTGTTAGGCATAGCATACCTTTGGATTTCTGAAAACATTCCTAAACTTTATT

CTGGCACGTGGTTAAGTGACTTGGAAAGAGTTTGGTTGTGTCTGGCTTCTGTGC

AAGCCTCTTAGGCAAAAGCAGGGCAGCATTTAGTTTAGAATCCACTTTCCCCA

CTGCTGAGGCTAGGCGCTTCTTCACACTCGTAGGAATAGCCCGAGTTATGAGG

CGTTACTGGCTCTTGGGGGCAGGTACTGTTTCCGTCACCGTGTGCATCCTCAGC

ACGCTTTCCTTTTATTCCTCGGAGTGATTCTCTCCCTGGCCTCACAGCCAGGCG

CTGACTATTCGAGGGGCCCCTTGTGCAGCTCATCAGAGCTCCTCAGTACTGCTC

TCTCCTCTCTGGCCTCAGCTCTGTAAACTCCAGCCAACCTGGCTTCCTTGGACT

CCCAGTTATATCTCAACTCAGGGATGCCAGTGGGCTCTCCTTGCCAGGAAACT

GTCACAAACCCATACGCTGAGGCAATCTTAGGTATCACTTGTCTTTGTCTGATG
```

-continued

```
TTTAATTCCTTGAGAGACTTTGTTTCTCATATTTTATCTGGTTTTTAGTTGACAT
GGGAGGTTAAATTTAGTCCCTGTTAACTCTTTCTTGGCTGGAAGCATAAGTTCT
TTTTTTTTTTTTTAATACTTAAAATTTTGTACCTTTTATCTATCCAAATGATCCT
CGTTTTTAATGACGGTTTTATTTTTTTGGTTGGGCCACTAGTTTAAGAGTTCTTG
AGGTTATGTTCATTTCCACTTCTTCCTGCTTTTTCTTTATTAGCTTCAATTTTGAT
CCTTCTAGATTCCTTTGGTTCCTTATTCCTTATCATAGCAACTTTCATACCTTTT
ATTTGTACAGGTGTAGATCTTTCAACGACTCTTCAGTGTCCTTCTGTATTTTGTA
AGTCACAGATATTATCAGGTTTACTTTAGTTGCATGTATGGTACTGACTTTAAA
ATTCCTACCCTGTCCCATGCATGTACTTTAAGGTCTCCATGATGATCTCTGCCA
CTACGTTGACCAGTCTTTCACCTGTTCTAGTTCTTCTTTTTTAATGACCACATCG
GTGGCATATGGAAGTTTCCCGGCCAGAGACTGAATCTGAGCTACAAGCTATGC
TGTTGCTTGAGGCAGTGTTGCATCTTTTAACCCACTGTGCCGTGCTGGGGATCG
AACCTGAGTCTCCACAGTGACCTGACCACTGCATTTGGAACCTTTTCTAGTTCT
TAACATGCTCTGTTGATGCAAATTAGTGGTTACTATTACACATGCAGTGTTAAA
TCAGTTGCTCTGTGTTATTCTTTTCTCAGAATCTGAAGGGTACATGTAGAAGTC
GCTTGTCTCTTAGCATCTTTAAAAATATTTTAATTAGGAGTTCCCGTCGTGGCG
CAGTAGTTAACGAATCCGACTAGGAACCATGAGGTTGCAGGTTTGATCCCTGG
CCTTGCTCAGTGGGTTAAGGATCCAGGTTGCCGTGAGCTGTGGTGTAGGTTGCA
GACGCGGCTCAGATCCTGTGTTGCTGGGGCTCTGGCGTAGGCCGGTGGCTACA
GCTCCAATTAGACCCCTAGCCTGGGAACCTCCATATGCCATGGGAGCGGCCCT
AGAAAAGGCAAAAGACCAAAAATATATATATATATATTTTAATAAAACTGTG
CTCTTTATATAAGTTTAATCTTTATCTAATTTATATAATTTAATAGTTAACCATT
ATTATAATTATCTCAAGACCAATTTTATAAAATTACTGTTCCTTTACTGTAGAT
AATTTAGAAAATAGTTATGTAGAACCTTACAACTATATCTTTATTAGCATTTTC
ATGTATTTCCTTTCCATCCTGAATCATTTATATAAATACCTACACAAATCACGG
GGGTGATATTGAAAATATTCAACCTTGGTCTCATTGGTACCTACAATGAGACCA
GCAGTAGCCGTAGTGCAAGACCATAGTGCAAGACCAATTTCTTCATTTGTGCA
GCTCTTAGTTCCTGGACTGTGAAGAGGTGGGCAAGGGTCCTTAGGTGTAGGGT
CCAGGGCAGTGGGGACAGGAAGGACATCTGGAGCTGAAGGGAAGAGCCGTT
ACTAATTAGCCTGGAAGTGTTTACATAACAACTGTAAGACTGAATAGGTGTAT
ACAGACTGAAAGGCAGCTTGGATCACTTTGTGTGTATGTGTGTATATATACA
CATATACATATACTTAACCTCTTTACTGGAAAATTTTTATTCTTCAAAAGCACC
CGTTCAAGGGCTGCATATTTTAAATTGCATTATAACTATATAATTTTTGTCATGT
ACTTTGTCATATAGATTATGAACTTCAGTTTTATAAACATTGTGGTAAACATTG
TACAGAAGTCTGTGTCATAGCTCTCATTACTGGGTTCGATTATAGAAATTATGG
TGCTTGATATATACATATTGCCAAACTGTTTCCCAAAATGGTTATACCAGTTTA
TATAGACATCAGCAGTATATGATGGTTGAAAGTATCTATGAAGTATGACATTT
GTCCTTTTTAATTGAGTTTGGGTATGTTATCAGTTTGTGTAAATGTTAAGGATTT
CAACACTTCTGTAAGTACTGTGATTTTTCTGTGTCTATTTTCATAGAGAAATTTA
GTTTTTATATTCTAAAAAGAATACATGTCAGAATAAACTTCTAATAGTATAAAA
ACTTTGTTTTTCAGATACATAGAGGTGAGGTAATGTGAAAATGTTTTATTTTTA
```

```
CAGTTGAAACATACTGTAATGTTGGTATAGTCACTGATGCGAAACAGGAAGCT

GTCCACCTTAGCGATGATACAAAAACATTCCATTAAAAGATAATTTTGGCACA

TCAGTGGAGGAGCTATAACAAATGTATTAATCCATGGCTTAAAATGAAGCCAT

AACTTGGAAACTAGGATGATTCCAAATATAGTGGCTAGACATCTTAGTCACCTT

AAGTCCTTTAGAAAAGACGTAAGATGAAATAATTGCTTGTTGAAACAATTATA

AATTGTAAGAGAACACTAAGAACTGGCTCTCATCCTTAGCTCCCCCTGTCTGGT

TGCAGACCTTCTCTGGGCCTGTCTCCTTGGTAAAATGGGAGCTAGATGGTGGTT

TCTACGGACTCCTTTCTTTAAGAGTCCTGAAAAATGAAGTTTTTAGCTGTGTCT

TTGATTGCTGGGAAAAGTTAACTTATAATTTACTTGCTTTTAGCACTAGAACAG

TAAGTTGCCCTACACAGTAATCCTGTAAGCATTTAACTTCCTTCTCTGGGGGTA

AGTGGTATTAGAGGGCAGGAAAATGTTTGTTTTCCCCCAATGCCACGACATGT

CATTTTAGCTTATGTAAATTTCATGTATTGAATGATAAGAATTTCATTCTTGAA

GATTTCCTCATTTANAGGACACAGGTGGATATAAACATGCTCATGCAGCATGC

TTAACACAGTAATATGACACTAAAATGTGGCTTGTCTAACATTTTGGTTCAAGT

TGATATAATCTTTCTGTGTTTCCCCCAGTCTCATGGCCTTGTGCACTTAGCATAG

CCTGCGTAACAATTACCAGAGACTGGGCAACAACTTCTCTCAGTTCTGGATAC

CACTGGGATGTCCAGAATCAAAGTGCTGGCAGATGTGGTTCCCAGTAGGGCC

ATTTCAGCCACCTTCTCACCTTCAGTGCACTCGCATGGCCTTTCCTTTGTGCATG

GGCATGGAAAAGTGAGAAATCTGCTTCCTTTTCTCATAAGAACACTAACCCCG

TCGCATAGGTGCCCCCCCATGAGTTAATTATCTTCTAAAGGTCTTACCTCCAAA

TACCATCACGTTGCACTTAGGGCTTCAAATTATGAATTTTGGCAAGACGTGGAC

ATTCAGCCTATAACATGCACTAAGTGGGTATCAAAAAATGTTCATGAGGGCAA

ACTTTAAAAAACAATTCTTTTTATTGTATCAGCCAACTTGCTGAGCATCTACTA

TCTGCAAAGCATACACAGTCTGCAAACCTTGCTTCTAGTCTAGGTGGTTTGAAA

ACCTGGCTGACGAACAGAATCAGCTGTAGAACTTATAAAATAAGGCAAAATCA

AATTATTGGATCCTACTTTGAGAGACTGAGTAGGTCTGAAACAAAGCATAGAA

AGCTGTTTTAGTTTAAAAAAAAAAAACAAAACTTATCAGATGAGGACCCATGA

TTAAGAATTTGTAGCCTTATGGGGAACACAGATCTCTAGTCTCAATTCACAACC

TAGTGTTGTGACAAGTTGAAGGCTGGTAGTTAAATTGTTGAGAATATCTCAGA

GGGGCCTTTTAGTTTCTCTTGGAAGAAGAGTGAACTCCCAATTCCACAAATTAA

AAAATGCAGCTAAATGCTACAAATTGGATTTTTACTAAAAGCACCAATAGGTT

CCGTTTGCATTCTGTTACCTACACACCTGTTCTGTTTGTCCCACAGAGGAGGAG

GAGGAGGACGATGACGATCTCTTTGATGATCCTCTGCCAGTACCTTTAAGGCA

CAAGGTTCCAAATCAGCAGACTCTTCACTCTGAGGTACTTCCCATGACTGCTCT

ACCACAAGACCAGCCTGAAAAACAGACAGAAAGCACAGAATGCTTCAAAGCA

GAGAGTATGCCAACATGTCTCTGGGCAAACTTCGTAGATTGTGAAGAATCCAA

TAGTGAAAGTGAAGAATTAGAAATCACGGCTCCAGCTCAAGGAGACACGAGT

CCTGTCCCCCATCACCAGCAGAAGGCTGAAGGGGAAGTACCACAGTGGGAAG

TGTTCTTTAAAAGAAATGATGAAATCACAGATGACTGTTTGGAAAACCTTCCGT

CCTCCACAGAGGCAGGGGCTCTCAGTCCCCAAAGCTTTTCAGTGACTCTGAT
```

GGGGAATCAACTCACATTTCTTCCCAGACTTCTTCTCAGTCAACACACATATCA

GAACAAGGAAGTCAAGGCTGGGACAGCCAATCAGACACTGTTTTGTTATCTTC

CCAAGAGAGAAAAAGTGGGGATATTACCTCCTTGAACAAAGGTGGCTCTAGAC

CAGAAATCAAAGAGAATATTCCCATCCTTCAGATGGAACAAAATGTATTTTGC

CCGAAGGATACTTACTCTGATTTGAAAGGCAGAGATCAAGATATAAACACACT

TCCCAGTGCTAGAGAAACAACTACTCTGAGCAGTGGGAAACACATGCCTCAGG

AGAAAAGGCCGCTAAACTGTAACAGTAACACAGATTCACAAGGCTCCTCTGAC

TTTGAAATTCCCTCCACTCCAGAAGCTGAGCTACCTCAACAAGAGCATCTGCA

ATATTTATACAAGAAGTTGGCAGGAGGAGAGGGTATAGTAATTGAAAAAAGG

AAAAGCGCACGTCATTCTAGAGCAACCACTAAAAAACCTACACAAACAGGTA

ATAGTCAGACTCCTAATAGATGAGTTCAAATGGAGTACTTAAAAATGTTCATAT

AACCTAAAAGGCAGCTCTAAAAGGGGAAACAATAGGACCAAAAAATACAAAG

AAAACAAGAATGGGAGAACTCAGTACAAACATATCAGTAATTACATCAAATG

AAAATAGGGGAAAAACCATAAGCCAACTATATATTGTCTATAGGAAACTGGCT

TCAAGACTTGGGCAGGTTTACTGGTGAAAGGATGGAAACCTTCACCACATAAT

AAACATGAAAGATGGAGGGGCTATATTACTAGTGATAAAAGGTCCAGTTCACT

GAGACATAAACCCAAATGAGTATGTACTGGACAACAGCCACACATACAGAGC

AAAAACAACTGAAAGGAGAAAGATAAACTAAAGCACAATTACAGCTGCAACA

GAATTAGTCTACAGGAAATCAGCAAGGAGACGGAAGAACTGAACAGCACTAT

CAACCAACCAGATCTTCACAGAAGACACCATCTAGCACAGAATACACACTTTT

CAAGTTCACAGAATACAACATTCACCAAGATAGACCATATCCTGGTTCATAAA

AACTTGGATCTA

What is claimed is:

1. A transgenic porcine subject whose genome comprises a transgene comprising the nucleotide sequence of SEQ ID NO: 7 or 9, wherein one allele of a genomic Artemis gene is functionally disrupted by said transgene, wherein said disruption comprises a single nucleotide polymorphism selected from the group consisting of a G to A substitution as set forth at position 615 of SEQ ID NO:7 and a G to A substitution as set forth at position 116 of SEQ ID NO:9, wherein said transgenic porcine subject exhibits severe combined immunodeficiency disease (SCID) relative to a wild type porcine subject, said SCID characterized by decreased numbers of T and B lymphocytes, circulating antibody, and significantly abnormal thymus and lymph nodes.

2. A porcine semen comprising isolated sperm cells from the transgenic porcine subject of claim 1, wherein the genome of the isolated sperm cells comprises a transgene comprising the nucleotide sequence of SEQ ID NO: 7 or 9, wherein one allele of a genomic Artemis gene is functionally disrupted by said transgene, wherein said disruption comprises a single nucleotide polymorphism selected from the group consisting of a G to A substitution as set forth at position 615 of SEQ ID NO:7 and a G to A substitution as set forth at position 116 of SEQ ID NO:9, wherein said transgenic porcine subject exhibits severe combined immunodeficiency disease (SCID) relative to a wild type porcine subject, said SCID characterized by decreased numbers of T and B lymphocytes, circulating antibody, and significantly abnormal thymus and lymph nodes.

3. A transgenic porcine embryo obtained by fertilizing an oocyte with an isolated sperm cell from the transgenic porcine subject of claim 1, wherein the genome of the isolated sperm cell comprises a transgene comprising the nucleotide sequence of SEQ ID NO: 7 or 9, wherein one allele of a genomic Artemis gene is functionally disrupted by said transgene, wherein said disruption comprises a single nucleotide polymorphism selected from the group consisting of a G to A substitution as set forth at position 615 of SEQ ID NO:7 and a G to A substitution as set forth at position 116 of SEQ ID NO:9, wherein said transgenic porcine subject exhibits severe combined immunodeficiency disease (SCID) relative to a wild type porcine subject, said SCID characterized by decreased numbers of T and B lymphocytes, circulating antibody, and significantly abnormal thymus and lymph nodes.

* * * * *

SEQUENCE LISTING

<160> NUMBER OF SEQ ID NOS: 45

<210> SEQ ID NO 1
<211> LENGTH: 2097
<212> TYPE: DNA
<213> ORGANISM: Sus scrofa

<400> SEQUENCE: 1

```
ggatccgtgt tcgccaacgc tatgagttcc ttcgagggcc agatgagttc cttcgagggc      60
cagatggcgg agtacccaac tatctccata gaccgtttcg accggagaa tctgagggct     120 cgcgcttatt tcctgtccca ctgccacaag gatcacatga aggattaag agcctctacc     180 ttgagaagaa ggttggagtg cagcttgaag gtctccttat actgttcacc tgttactaga     240
gaattgttat taaccaaccc gaggtacaga ttttgggaga acgaattgt gtcaattgaa     300 gttgaaactc ctacccagat atctttaatt gatgaagcat caggcgagaa ggaagaaatt     360
gttgtgactc tcttaccagc tggtcattgc ccaggatcag ttatgttctt atttcagggc     420
aacaatggaa ctgtcttgta tacaggagac ttccgattgg caaaaggaga agctgccaga     480
atggagcttc tgcactcggg gggcagtgtg aaagacatcc agagtgtgta cttagacacc     540
actttctgcc atccaaagta ttaccaaatt cccagtcggg ttcacgtgaa taaactggac     600
atgtttcgaa acatgcctga catccttcat catctcacaa cagaccgtgg cactcagatc     660
```

```
catgcctgtc ggcatccaaa ggcagaggaa tattttcatt ggaataagtt accctgtgga      720
ataacatcca aaaatagaat tccactccac ataatcagca ttaagccctc cactatgtgg      780
tttggagaaa gaactagaaa aaccaatgtt attgtgagga ctggagagag ttcgtacaga      840
gcctgctttt cttttcactc ctcctacagt gagattaaag atttcttgag ctacattagc      900
cctgtgaatg tatatccaaa tgtcattcca ctgggcacaa ctctggagaa agttaaagaa      960
atcttaaagc ctttatgccg atcttcgcaa aatatcgagc caaagtataa accacttgga     1020
aaattgaaga gagctagaat aatccatcta gactcagagg aggaggagga ggacgatgac     1080
gatctctttg atgatcctct gccagtacct taaggcacaa aggttccaaa tcagcagact     1140
cttcactctg aggtacttcc catgactgct ctaccacaag accagcctga aaaacagaca     1200
gaaagcacag aatgcttcaa agcagagagt atgccaacat gtctctgggc aaacttcgta     1260
gattgtgaag aatccaatag tgaaagtgaa gaattagaaa tcacggctcc agctcaagga     1320
gacacgagtc ctgtccccca tcaccagcag aaggctgaag gggaagtacc acagtgggaa     1380
gtgttcttta aagaaatga tgaaatcaca gatgactgtt tggaaaacct tccgtcctcc     1440
acagaggcag ggggctctca gtccccaaag cttttcagtg actctgatgg ggaatcaact     1500
cacatttctt cccagacttc ttctcagtca acacacatat cagaacaagg aagtcaaggc     1560
tgggacagcc aatcagacac tgttttgtta tcttcccaag agagaaaaag tggggatatt     1620
acctccttga acaaaggtgg ctctagacca gaaatcaaag agaatattcc catccttcag     1680
atggaacaaa atgtattttg cccgaaggat acttactctg atttgaaagg cagagatcaa     1740
gatataaaca cacttcccag tgctagagaa acaactactc tgagcagtgg gaaacacatg     1800
cctcaggaga aaaggccgct aaactgtaac agtaacacag attcacaagg ctcctctgac     1860
tttgaaattc cctccactcc agaagctgag ctacctcaac aagagcatct gcaatattta     1920
tacaagaagt tggcaggagg agagggtata gtaattgaaa aaaggaaaag cgcacgtcat     1980
tctagagcaa ccattaaaaa acctacacaa acaggtaata gtcagactcc taatagatga     2040
gttcaaatgg agtacttaaa aatgttcata taacctaaaa ggcagctctg cggccgc        2097
```

<210> SEQ ID NO 2
<211> LENGTH: 672
<212> TYPE: PRT
<213> ORGANISM: Sus scrofa

<400> SEQUENCE: 2

```
Met Ser Ser Phe Glu Gly Gln Met Ser Ser Phe Glu Gly Gln Met Ala
1               5                   10                  15

Glu Tyr Pro Thr Ile Ser Ile Asp Arg Phe Asp Arg Glu Asn Leu Arg
                20                  25                  30

Ala Arg Ala Tyr Phe Leu Ser His Cys His Lys Asp His Met Lys Gly
            35                  40                  45

Leu Arg Ala Ser Thr Leu Arg Arg Arg Leu Glu Cys Ser Leu Lys Val
        50                  55                  60

Ser Leu Tyr Cys Ser Pro Val Thr Arg Glu Leu Leu Leu Thr Asn Pro
65                  70                  75                  80

Arg Tyr Arg Phe Trp Glu Lys Arg Ile Val Ser Ile Glu Val Glu Thr
                85                  90                  95

Pro Thr Gln Ile Ser Leu Ile Asp Glu Ala Ser Gly Glu Lys Glu Glu
                100                 105                 110

Ile Val Val Thr Leu Leu Pro Ala Gly His Cys Pro Gly Ser Val Met
            115                 120                 125
```

```
Phe Leu Phe Gln Gly Asn Asn Gly Thr Val Leu Tyr Thr Gly Asp Phe
    130                 135                 140

Arg Leu Ala Lys Gly Glu Ala Ala Arg Met Glu Leu Leu His Ser Gly
145                 150                 155                 160

Gly Ser Val Lys Asp Ile Gln Ser Val Tyr Leu Asp Thr Thr Phe Cys
                165                 170                 175

His Pro Lys Tyr Tyr Gln Ile Pro Ser Arg Val His Val Asn Lys Leu
                180                 185                 190

Asp Met Phe Arg Asn Met Pro Asp Ile Leu His His Leu Thr Thr Asp
            195                 200                 205

Arg Gly Thr Gln Ile His Ala Cys Arg His Pro Lys Ala Glu Glu Tyr
    210                 215                 220

Phe His Trp Asn Lys Leu Pro Cys Gly Ile Thr Ser Lys Asn Arg Ile
225                 230                 235                 240

Pro Leu His Ile Ile Ser Ile Lys Pro Ser Thr Met Trp Phe Gly Glu
                245                 250                 255

Arg Thr Arg Lys Thr Asn Val Ile Val Arg Thr Gly Glu Ser Ser Tyr
                260                 265                 270

Arg Ala Cys Phe Ser Phe His Ser Ser Tyr Ser Glu Ile Lys Asp Phe
            275                 280                 285

Leu Ser Tyr Ile Ser Pro Val Asn Val Tyr Pro Asn Val Ile Pro Leu
    290                 295                 300

Gly Thr Thr Leu Glu Lys Val Lys Glu Ile Leu Lys Pro Leu Cys Arg
305                 310                 315                 320

Ser Ser Gln Asn Ile Glu Pro Lys Tyr Lys Pro Leu Gly Lys Leu Lys
                325                 330                 335

Arg Ala Arg Ile Ile His Leu Asp Ser Glu Glu Glu Glu Asp Asp
            340                 345                 350

Asp Asp Leu Phe Asp Asp Pro Leu Pro Val Pro Leu Arg His Lys Val
    355                 360                 365

Pro Asn Gln Gln Thr Leu His Ser Glu Val Leu Pro Met Thr Ala Leu
370                 375                 380

Pro Gln Asp Gln Pro Glu Lys Gln Thr Glu Ser Thr Glu Cys Phe Lys
385                 390                 395                 400

Ala Glu Ser Met Pro Thr Cys Leu Trp Ala Asn Phe Val Asp Cys Glu
                405                 410                 415

Glu Ser Asn Ser Glu Ser Glu Glu Leu Glu Ile Thr Ala Pro Ala Gln
            420                 425                 430

Gly Asp Thr Ser Pro Val Pro His Gln Gln Lys Ala Glu Gly Glu
    435                 440                 445

Val Pro Gln Trp Glu Val Phe Phe Lys Arg Asn Asp Glu Ile Thr Asp
450                 455                 460

Asp Cys Leu Glu Asn Leu Pro Ser Ser Thr Glu Ala Gly Gly Ser Gln
465                 470                 475                 480

Ser Pro Lys Leu Phe Ser Asp Ser Asp Gly Glu Ser Thr His Ile Ser
                485                 490                 495

Ser Gln Thr Ser Ser Gln Ser Thr His Ile Ser Glu Gln Gly Ser Gln
            500                 505                 510

Gly Trp Asp Ser Gln Ser Asp Thr Val Leu Leu Ser Ser Gln Glu Arg
    515                 520                 525

Lys Ser Gly Asp Ile Thr Ser Leu Asn Lys Gly Gly Ser Arg Pro Glu
530                 535                 540
```

```
Ile Lys Glu Asn Ile Pro Ile Leu Gln Met Glu Gln Asn Val Phe Cys
545                 550                 555                 560

Pro Lys Asp Thr Tyr Ser Asp Leu Lys Gly Arg Asp Gln Asp Ile Asn
                565                 570                 575

Thr Leu Pro Ser Ala Arg Glu Thr Thr Thr Leu Ser Ser Gly Lys His
            580                 585                 590

Met Pro Gln Glu Lys Arg Pro Leu Asn Cys Asn Ser Asn Thr Asp Ser
        595                 600                 605

Gln Gly Ser Ser Asp Phe Glu Ile Pro Ser Thr Pro Glu Ala Glu Leu
    610                 615                 620

Pro Gln Gln Glu His Leu Gln Tyr Leu Tyr Lys Lys Leu Ala Gly Gly
625                 630                 635                 640

Glu Gly Ile Val Ile Glu Lys Arg Lys Ser Ala Arg His Ser Arg Ala
                645                 650                 655

Thr Ile Lys Lys Pro Thr Gln Thr Gly Asn Ser Gln Thr Pro Asn Arg
                660                 665                 670
```

<210> SEQ ID NO 3
<211> LENGTH: 2080
<212> TYPE: DNA
<213> ORGANISM: Sus scrofa
<220> FEATURE:
<221> NAME/KEY: misc_feature
<222> LOCATION: (1259)..(1259)
<223> OTHER INFORMATION: n is a, c, g, or t

<400> SEQUENCE: 3

```
ggatccgtgt tcgccaacgc tatgagttcc ttcgagggcc agatggcgga gtacccaact      60
atctccatag accgtttcga ccgggagaat ctgagggctc gcgcttattt cctgtcccac     120
tgccacaagg atcacatgaa aggattaaga gcctctacct tgaaaagaag gttggagtgc     180
agcttgaagg tctccttata ctgttcacct gttactagag aattgttatt aaccaacccg     240
aggtacagat tttgggagaa acgaattgtg tcaattgaag ttgaaactcc tacccagata     300
tctttaattg atgaagcatc aggcgagaag gaagaaattg ttgtgactct cttaccagct     360
ggtcattgcc caggatcagt tatgttctta tttcagggca acaatggaac tgtcttgtat     420
acaggagact tccgattggc aagaggagaa gctgccagaa tggagcttct gcactcgggg     480
ggcagtgtga agacatcca gagtgtgtac ttagacacca ctttctgcca tccaaagtat     540
taccaaattc ccagtcggga ggagtgtctg agagggatct tggagctggt ccgcagctgg     600
atcacacgga gccctacca cgtggtgtgg ctgaactgca aagcggccta tgggtacgag     660
tacctgttca ccaacctcag cgaggagttc ggagtccagg ttcacgtgaa taaactggac     720
atgtttcgaa acatgcctga catccttcat catctcacaa cagaccgtgg cactcagatc     780
catgcctgtc ggcatccaaa gaactggaga gagttcgtac agagcctgct tttcttttca     840
ctcctcctac agtgagatta agatttctt gagctacatt agtcctgtga atgtatatcc     900
aaatgtcatt ccactgggca caactccgga gaaagttaaa gaaatcttaa gcctttatg     960 ccgatcttcg caaatatcg agccaaagta taaccactt ggaaaattga agagagctag    1020
aataatccat ctagactcag aggaggagga ggaggacaat gacgatctct ttgatgatcc    1080
tctgccagta cctttaaggc acaaggttcc aaatcagcag actcttcact ctgaggtact    1140
tcccatgact gctctaccac aagaccagcc tgaaaaacag acagaaagca cagaatgctt    1200
caaagcagag agtatgccaa catgtctctg ggcaaacttc gtagattgtg aagaatccna    1260
tagtgaaagt gaagaattag aaatcacggc tccagctcaa ggagacacga gtcctgtccc    1320
```

-continued

```
ccatcaccag cagaaggctg aaggggaagt accacagtgg gaagtgttct ttaaaagaaa    1380
tgatgaaatc acagatgact gtttggaaaa ccttccgtcc tccacagagg caggggggctc   1440
tcagtcccca aagcttttca gtgactctga tggggaatca actcacattt cttcccagac    1500
ttcttctcag tcaacacaca tatcagaaca aggaagtcaa ggctgggaca gccaatcaga    1560
cactgttttg ttatcttccc aagagagaaa aagtggggat attacctcct tgaacaaagg    1620
tggctctaga ccagaaatca aagagaatat tcccatcctt cagatggaac aaaatgtatt    1680
ttgcccgaag gatacttact ctgatttgaa aggcagagat caagatataa acacacttcc    1740
cagtgctaga gaaacaacta ctctgagcag tgggaaacac atgcctcagg agaaaaggcc    1800
gctaaactgt aacagtaaca cagattcaca aggctcctct gactttgaaa ttccctccac    1860
tccagaagct gagctacctc aacaagagca tctgcaatat ttatacaaga agttggcagg    1920
aggagagggt atagtaattg aaaaaaggaa aagcgcacgt cattctagag caaccactaa    1980
aaaacctaca caaacaggta atagtcggac tcctaataga tgagttcaaa tggagtactt    2040
aaaaatgttc atataaccta aaaggcagct ctgcggccgc                          2080
```

<210> SEQ ID NO 4
<211> LENGTH: 277
<212> TYPE: PRT
<213> ORGANISM: Sus scrofa

<400> SEQUENCE: 4

```
Met Ser Ser Phe Glu Gly Gln Met Ala Glu Tyr Pro Thr Ile Ser Ile
1               5                   10                  15

Asp Arg Phe Asp Arg Glu Asn Leu Arg Ala Arg Ala Tyr Phe Leu Ser
            20                  25                  30

His Cys His Lys Asp His Met Lys Gly Leu Arg Ala Ser Thr Leu Lys
        35                  40                  45

Arg Arg Leu Glu Cys Ser Leu Lys Val Ser Leu Tyr Cys Ser Pro Val
    50                  55                  60

Thr Arg Glu Leu Leu Leu Thr Asn Pro Arg Tyr Arg Phe Trp Glu Lys
65                  70                  75                  80

Arg Ile Val Ser Ile Glu Val Glu Thr Pro Thr Gln Ile Ser Leu Ile
                85                  90                  95

Asp Glu Ala Ser Gly Lys Glu Glu Ile Val Val Thr Leu Leu Pro
            100                 105                 110

Ala Gly His Cys Pro Gly Ser Val Met Phe Leu Phe Gln Gly Asn Asn
        115                 120                 125

Gly Thr Val Leu Tyr Thr Gly Asp Phe Arg Leu Ala Arg Gly Glu Ala
    130                 135                 140

Ala Arg Met Glu Leu Leu His Ser Gly Gly Ser Val Lys Asp Ile Gln
145                 150                 155                 160

Ser Val Tyr Leu Asp Thr Thr Phe Cys His Pro Lys Tyr Tyr Gln Ile
                165                 170                 175

Pro Ser Arg Glu Glu Cys Leu Arg Gly Ile Leu Glu Leu Val Arg Ser
            180                 185                 190

Trp Ile Thr Arg Ser Pro Tyr His Val Val Trp Leu Asn Cys Lys Ala
        195                 200                 205

Ala Tyr Gly Tyr Glu Tyr Leu Phe Thr Asn Leu Ser Glu Glu Phe Gly
    210                 215                 220

Val Gln Val His Val Asn Lys Leu Asp Met Phe Arg Asn Met Pro Asp
225                 230                 235                 240
```

```
Ile Leu His His Leu Thr Thr Asp Arg Gly Thr Gln Ile His Ala Cys
            245                 250                 255

Arg His Pro Lys Asn Trp Arg Glu Phe Val Gln Ser Leu Leu Phe Phe
        260                 265                 270

Ser Leu Leu Leu Gln
        275
```

<210> SEQ ID NO 5
<211> LENGTH: 2217
<212> TYPE: DNA
<213> ORGANISM: Sus scrofa

<400> SEQUENCE: 5

```
ggatccgtgt tcgccaacgc tatgagttcc ttcgagggcc agatggcgga gtacccaact      60
atctccatag accgtttcga ccgggagaat ttgagggctc gcgcttattt cctgtcccac     120
tgccacaagg atcacatgaa aggattaaga gcctctacct gaaaagaag gttggagtgc      180
agcttgaagg tctccttata ctgttcacct gttactagaa aattgttatt aaccaacccg     240
aggtacagat tttgggagaa acgaattgtg tcaattgaag ttgaaactcc tacccagata     300
tctttaattg atgaagcatc aggcgagaag gaagaaattg ttgtgactct cttaccagct     360
ggtcattgcc caggatcagt tatgttctta tttcagggca caatggaac tgtcttgtat     420
acaggagact tccgattggc aaaaggagaa gctgccagaa tggagcttct gcactcgggg     480
ggcagtgtga agacatcca gggtgtgtac ttagacacca ctttctgcca tccaaagtat     540
taccaaattc ccagtcggga ggagtgtctg agagggatct tggagctggt ccgcagctgg     600
atcacacgga gccctacca cgtggtgtgg ctgaactgca agcggccta tgggtacgag       660
tacctgttca ccaacctcag cgaggagttc ggagtccagg ttcacgtgaa taaactggac     720
atgtttcgaa acatgcctga catccttcat catctcacaa cagaccgtgg cactcagatc     780
catgcctgtc ggcatccaaa ggcagaggaa tattttcatt ggaataaatt accctgtgga    840
ataacatcca aaaatagaat tccactccac ataatcagta ttaagccctc cactatgtgg    900
tttggagaaa gaactagaaa aaccaatgtt attgtgagaa ctggagagag ttcgtacaga    960
gcctgctttt cttttcactc ctcctacagt gagattaaag atttcttgag ctacattagt   1020
cctgtgaatg tatatccaaa tgtcattcca ctgggcacaa ctctggagaa agttaaagaa    1080
atcttaaagc ctttatgccg atcttcgcaa aatatcgagc caaagtataa accacttgga    1140
aaattgaaga gagctagaat aatccatcta gactcagagg aggaggagga ggacaatgac    1200
gatctctttg atgatcctct gccagtacct ttaaggcaca aggttccaaa tcagcagact    1260
cttcactctg aggtacttcc catgactgct ctaccacaag accagcctga aaaacagaca    1320
gaaagcacag aatgcttcaa agcagagagt atgccaacat gtctctgggc aaacttcgta    1380
gattgtgaag aatccaatag tgaaagtgaa gaattagaaa tcacagctcc agctcaagga    1440
gacacgagtc ctgtccccca tcaccagcag aaggctgaag gggaagtacc acagtgggaa    1500
gtgttcttta aagaaatga tgaaatcaca gatgactgtt tggaaaacct tccgtcctcc    1560
acagaggcag ggggctctca gtccccaaag cttttcagtg actctgatgg ggaatcaact    1620
cacatttctt cccagacttc ttctcagtca acacacatat cagaacaagg aagtcaaggc    1680
tgggacagcc aatcagacac tgttttgtta tcttcccaag agagaaaaag tggggatatt    1740
acctccttga caaaggtgg ctctagacca gaaatcaaag agaatattcc catccttcag    1800
atggaacaaa atgtatttg cccgaaggat acttactctg atttgaaagg cagagatcaa    1860
```

-continued

```
gatataaaca cacttcccag tgctagagaa acaactactc tgagcagtgg gaaacacatg    1920
cctcaggaga aaaggccgct aaactgtaac agtaacacag attcacaagg ctcctctgac    1980
tttgaaattc cctccactcc agaagctgag ctacctcaac aagagcatct gcaatattta    2040
tacaagaagt tggcaggagg agagggtata gtaattgaaa aaaggaaaag cgcacgtcat    2100
tctagagcaa ccactaaaaa acctacacaa acaggtaata gtcagactcc taatagatga    2160
gttcaaatgg agtacttaaa aatgttcata taacctaaaa ggcagctctg cggccgc       2217
```

<210> SEQ ID NO 6
<211> LENGTH: 712
<212> TYPE: PRT
<213> ORGANISM: Sus scrofa

<400> SEQUENCE: 6

```
Met Ser Ser Phe Glu Gly Gln Met Ala Glu Tyr Pro Thr Ile Ser Ile
1               5                   10                  15

Asp Arg Phe Asp Arg Glu Asn Leu Arg Ala Arg Ala Tyr Phe Leu Ser
            20                  25                  30

His Cys His Lys Asp His Met Lys Gly Leu Arg Ala Ser Thr Leu Lys
        35                  40                  45

Arg Arg Leu Glu Cys Ser Leu Lys Val Ser Leu Tyr Cys Ser Pro Val
    50                  55                  60

Thr Arg Glu Leu Leu Leu Thr Asn Pro Arg Tyr Arg Phe Trp Glu Lys
65                  70                  75                  80

Arg Ile Val Ser Ile Glu Val Glu Thr Pro Thr Gln Ile Ser Leu Ile
                85                  90                  95

Asp Glu Ala Ser Gly Glu Lys Glu Ile Val Val Thr Leu Leu Pro
            100                 105                 110

Ala Gly His Cys Pro Gly Ser Val Met Phe Leu Phe Gln Gly Asn Asn
        115                 120                 125

Gly Thr Val Leu Tyr Thr Gly Asp Phe Arg Leu Ala Lys Gly Glu Ala
    130                 135                 140

Ala Arg Met Glu Leu Leu His Ser Gly Gly Ser Val Lys Asp Ile Gln
145                 150                 155                 160

Gly Val Tyr Leu Asp Thr Thr Phe Cys His Pro Lys Tyr Tyr Gln Ile
                165                 170                 175

Pro Ser Arg Glu Glu Cys Leu Arg Gly Ile Leu Glu Leu Val Arg Ser
            180                 185                 190

Trp Ile Thr Arg Ser Pro Tyr His Val Val Trp Leu Asn Cys Lys Ala
        195                 200                 205

Ala Tyr Gly Tyr Glu Tyr Leu Phe Thr Asn Leu Ser Glu Glu Phe Gly
    210                 215                 220

Val Gln Val His Val Asn Lys Leu Asp Met Phe Arg Asn Met Pro Asp
225                 230                 235                 240

Ile Leu His His Leu Thr Thr Asp Arg Gly Thr Gln Ile His Ala Cys
                245                 250                 255

Arg His Pro Lys Ala Glu Glu Tyr Phe His Trp Asn Lys Leu Pro Cys
            260                 265                 270

Gly Ile Thr Ser Lys Asn Arg Ile Pro Leu His Ile Ser Ile Lys
        275                 280                 285

Pro Ser Thr Met Trp Phe Gly Glu Arg Thr Arg Lys Thr Asn Val Ile
    290                 295                 300

Val Arg Thr Gly Glu Ser Ser Tyr Arg Ala Cys Phe Ser Phe His Ser
```

```
            305                 310                 315                 320
Ser Tyr Ser Glu Ile Lys Asp Phe Leu Ser Tyr Ile Ser Pro Val Asn
                    325                 330                 335

Val Tyr Pro Asn Val Ile Pro Leu Gly Thr Thr Leu Glu Lys Val Lys
                    340                 345                 350

Glu Ile Leu Lys Pro Leu Cys Arg Ser Ser Gln Asn Ile Glu Pro Lys
                    355                 360                 365

Tyr Lys Pro Leu Gly Lys Leu Lys Arg Ala Arg Ile Ile His Leu Asp
                    370                 375                 380

Ser Glu Glu Glu Glu Asp Asn Asp Leu Phe Asp Asp Pro Leu
385                 390                 395                 400

Pro Val Pro Leu Arg His Lys Val Pro Asn Gln Gln Thr Leu His Ser
                    405                 410                 415

Glu Val Leu Pro Met Thr Ala Leu Pro Gln Asp Gln Pro Glu Lys Gln
                    420                 425                 430

Thr Glu Ser Thr Glu Cys Phe Lys Ala Glu Ser Met Pro Thr Cys Leu
                    435                 440                 445

Trp Ala Asn Phe Val Asp Cys Glu Glu Ser Asn Ser Glu Ser Glu Glu
                450                 455                 460

Leu Glu Ile Thr Ala Pro Ala Gln Gly Asp Thr Ser Pro Val Pro His
465                 470                 475                 480

His Gln Gln Lys Ala Glu Gly Glu Val Pro Gln Trp Glu Val Phe Phe
                    485                 490                 495

Lys Arg Asn Asp Glu Ile Thr Asp Asp Cys Leu Glu Asn Leu Pro Ser
                    500                 505                 510

Ser Thr Glu Ala Gly Gly Ser Gln Ser Pro Lys Leu Phe Ser Asp Ser
                515                 520                 525

Asp Gly Glu Ser Thr His Ile Ser Ser Gln Thr Ser Ser Gln Ser Thr
                    530                 535                 540

His Ile Ser Glu Gln Gly Ser Gln Gly Trp Asp Ser Gln Ser Asp Thr
545                 550                 555                 560

Val Leu Leu Ser Ser Gln Glu Arg Lys Ser Gly Asp Ile Thr Ser Leu
                    565                 570                 575

Asn Lys Gly Gly Ser Arg Pro Glu Ile Lys Glu Asn Ile Pro Ile Leu
                580                 585                 590

Gln Met Glu Gln Asn Val Phe Cys Pro Lys Asp Thr Tyr Ser Asp Leu
                    595                 600                 605

Lys Gly Arg Asp Gln Asp Ile Asn Thr Leu Pro Ser Ala Arg Glu Thr
                    610                 615                 620

Thr Thr Leu Ser Ser Gly Lys His Met Pro Gln Glu Lys Arg Pro Leu
625                 630                 635                 640

Asn Cys Asn Ser Asn Thr Asp Ser Gln Gly Ser Ser Asp Phe Glu Ile
                    645                 650                 655

Pro Ser Thr Pro Glu Ala Glu Leu Pro Gln Gln Glu His Leu Gln Tyr
                    660                 665                 670

Leu Tyr Lys Lys Leu Ala Gly Gly Glu Gly Ile Val Ile Glu Lys Arg
                    675                 680                 685

Lys Ser Ala Arg His Ser Arg Ala Thr Thr Lys Lys Pro Thr Gln Thr
                    690                 695                 700

Gly Asn Ser Gln Thr Pro Asn Arg
705                 710
```

<210> SEQ ID NO 7

```
<211> LENGTH: 626
<212> TYPE: DNA
<213> ORGANISM: Sus scrofa

<400> SEQUENCE: 7
tccctcaccc atctgtctta tatattatcc tatggaaatc actttctaac catgtcgata    60
cagtaaaaaa ttccagggag ctctcttgtg gcccagtgga ttaaggatct ggctgttgtc   120
actgcagcgg cgtgggagtg gccaaaaaag aaaacccaag tggactgaaa cctcctgtaa   180
aataactgag agtttcgact tcacgcgtgt tgtatttcac gtgattaaca gctcttgtgt   240
tctgtttatc ttcagtgtga aagacatcca gagtgtgtac ttagacacca ctttctgcca   300
tccaaagtat taccaaattc ccagtcgggt acgtctctct ggacgggtgg ctgtatttct   360 caggggggcgg gccgcaggct aacaggtcgg gtggtaacgg gccccctggc cttaatgtct   420
ggggacgctg ggaacggaca aggcctcaac tgcctcttca aaccctgcc caggaggagt   480 gtctgagagg gatcttggag ctggtccgca gctggatcac gcggagcccc taccacgtgg   540
tgtggctgaa ctgcaaagcg gcctatgggt acgagtacct gttcaccaac ctcagcgagg   600
agttcggagt ccagataccct gagggc                                        626

<210> SEQ ID NO 8
<211> LENGTH: 628
<212> TYPE: DNA
<213> ORGANISM: Sus scrofa

<400> SEQUENCE: 8
tccctcaccc atctgtctta tatattatcc tatggaaatc acttcctaac catgtcgata    60
cagtaaaaaa ttccagggag ctctcttgtg gcccagtgga ttaaggatct ggctgttgtc   120
actgcagcgg catgggagtg gccaaaaaag aaaacccaag tggactgaaa cctcctgtaa   180
aataactgag agtttcgact tcacgcgtgt tgtatttcac gtgattaaca gctcttgtgt   240
tctgtttatc ttcagtgtga aagacatcca gagtgtgtac ttagacacca ctttctgcca   300
tccaaagtat taccaaattc ccagtcgggt acgtctctct ggacgggtgg ctgtatttct   360 caggggggcgg gccgcaggct aacaggtcgg gtggtaacgg gccccctggc cttaatgtct   420
ggggacgctg ggaacggaca aggcctcaac tgcctcttca aaccctgcc caggaggagt   480 gtctgagagg gatcttggag ctggtccgca gctggatcac acggagcccc taccacgtgg   540
tgtggctgaa ctgcaaagcg gcctatgggt acgagtacct gttcaccaac ctcagcgagg   600
agttcggagt ccaggtacct gagggctc                                       628

<210> SEQ ID NO 9
<211> LENGTH: 824
<212> TYPE: DNA
<213> ORGANISM: Sus scrofa
<220> FEATURE:
<221> NAME/KEY: misc_feature
<222> LOCATION: (35)..(35)
<223> OTHER INFORMATION: n is a, c, g, or t

<400> SEQUENCE: 9
catgctaaaa agtcatctgc attttttttga gaccntggta caaatatatt tgttgaaaat    60
gttaaaccat ttttcttatt ttaaaatctt ttttaggcag aggaatatttt tcattagaat   120 aaattaccct gtggaataac atccaaaaat agaattccac tccacataat cagtattaag   180
ccctccacta tgtggtttgg agaaagaact agaaaaacca atgttattgt gaggtaagca   240
agcagcgtct tttgagagga accttgcttt gaggtaaatc gatagtttaa aggcagtcta   300
```

```
gcctaaccte aagagggggg catatcatga ttgtggaaaa taacttttga aagttaaact      360
ctgtttaaat taaagagaag cggcttccaa aagctatcaa ttgcttacta ccatgagcca      420
gtatttcctg gggtctactg agtttgactg agaagatggt tagaggcagg ctgtcttgct      480
tggccggaag ttgggaattg accttgaagg ggttggaagc ccttagtgga gcagaggagg      540
cccatactga tcctcatgtt ttagctcatg tcctgaaaca ttggccgttt ggaatgttca      600
cagatattta catttatgga aagagttccc tcctggccca ggaaaaaaat ccttgatggc      660
agggtgattt catcctgcag tagcctaaaa tgagaagact cggagtttgg aacttagttt      720
tgatgagtga cccttaattt tgggttttcc tttccctttta gaactggaga gagttcgtac      780
agagcctgct tttcttttca ctcctcctac agtgaggtaa gagg                      824
```

```
<210> SEQ ID NO 10
<211> LENGTH: 849
<212> TYPE: DNA
<213> ORGANISM: Sus scrofa

<400> SEQUENCE: 10
catgctaaaa agtcatctgc atttttttga gaccctggta caaatatatt tgttgaaaat       60
gttaaaccat ttttcttatt ttaaaatctt ttttaggcag aggaatattt tcattggaat      120
aaattaccct gtggaataac atccaaaaat agaattccac tccacataat cagtattaag      180
ccctccacta tgtggtttgg agaaagaact agaaaaacca atgttattgt gaggtaagca      240
agcagcgtct tttgagagga accttgcttt gaggtaaatc gatagtttaa aggcagtcta      300 gcctaaccte aagagggggg catatcatga ttgtggaaaa taacttttga aagttaaact      360
ctgtttaaat taaagagaag cggcttccaa aagctatcaa ttgcttacta ccatgagcca      420
gtatttcctg gggtctactg agtttgactg agaagatggt tagaggcagg ctgtcttgct      480
tggccggaag ttgggaattg accttgaagg ggttggaagc ccttagtgga gcagaggagg      540
cccatactga tcctcatgtt ttagctcatg tcctgaaaca ttggccgttt ggaatgttca      600
cagatattta catttatgga aagagttccc tcctggccca ggaaaaaaat ccttgatggc      660
agggtgattt catcctgcag tagcctaaaa tgagaagact cggagtttgg aacttagttt      720
tgatgagtga cccttaattt tgggttttcc tttccctttta gaactggaga gagttcgtac      780
agagcctgct tttcttttca ctcctcctac agtgaggtaa gaggatccca tactcagaac      840
ctcggctgc                                                             849
```

```
<210> SEQ ID NO 11
<211> LENGTH: 20
<212> TYPE: DNA
<213> ORGANISM: Sus scrofa

<400> SEQUENCE: 11
tcctctgacc aagcctctgt                                                  20
```

```
<210> SEQ ID NO 12
<211> LENGTH: 20
<212> TYPE: DNA
<213> ORGANISM: Sus scrofa

<400> SEQUENCE: 12
tcgtccatgt accagagcct                                                  20
```

```
<210> SEQ ID NO 13
```

```
<211> LENGTH: 20
<212> TYPE: DNA
<213> ORGANISM: Sus scrofa

<400> SEQUENCE: 13
tcctctgacc aagcctctgt                                               20

<210> SEQ ID NO 14
<211> LENGTH: 19
<212> TYPE: DNA
<213> ORGANISM: Sus scrofa

<400> SEQUENCE: 14
cgtccatgta ccagagccg                                                19

<210> SEQ ID NO 15
<211> LENGTH: 20
<212> TYPE: DNA
<213> ORGANISM: Sus scrofa

<400> SEQUENCE: 15
aaccagtccc tgaccaactg                                               20

<210> SEQ ID NO 16
<211> LENGTH: 26
<212> TYPE: DNA
<213> ORGANISM: Sus scrofa

<400> SEQUENCE: 16
tccatatttg ttaagggcag taatct                                        26

<210> SEQ ID NO 17
<211> LENGTH: 25
<212> TYPE: DNA
<213> ORGANISM: Sus scrofa

<400> SEQUENCE: 17
tgctcagagc tttacatgga tttag                                         25

<210> SEQ ID NO 18
<211> LENGTH: 20
<212> TYPE: DNA
<213> ORGANISM: Sus scrofa

<400> SEQUENCE: 18
ggcccatgtt gacataaagc                                               20

<210> SEQ ID NO 19
<211> LENGTH: 20
<212> TYPE: DNA
<213> ORGANISM: Sus scrofa

<400> SEQUENCE: 19
tcctctgcag ggtttcaaag                                               20

<210> SEQ ID NO 20
<211> LENGTH: 19
<212> TYPE: DNA
<213> ORGANISM: Sus scrofa

<400> SEQUENCE: 20
cagggtgtgg gactttgtt                                                19
```

```
<210> SEQ ID NO 21
<211> LENGTH: 18
<212> TYPE: DNA
<213> ORGANISM: Sus scrofa

<400> SEQUENCE: 21
tcagcttggg cagctagg                                                 18

<210> SEQ ID NO 22
<211> LENGTH: 20
<212> TYPE: DNA
<213> ORGANISM: Sus scrofa

<400> SEQUENCE: 22
ccacaggcac attgatcttg                                               20

<210> SEQ ID NO 23
<211> LENGTH: 22
<212> TYPE: DNA
<213> ORGANISM: Sus scrofa

<400> SEQUENCE: 23
agttgaaatc aaagtatccc aa                                            22

<210> SEQ ID NO 24
<211> LENGTH: 23
<212> TYPE: DNA
<213> ORGANISM: Sus scrofa

<400> SEQUENCE: 24
aactgtaaca agcgtccctt tct                                           23

<210> SEQ ID NO 25
<211> LENGTH: 22
<212> TYPE: DNA
<213> ORGANISM: Sus scrofa

<400> SEQUENCE: 25
agttgaaatc aaagtatccc aa                                            22

<210> SEQ ID NO 26
<211> LENGTH: 23
<212> TYPE: DNA
<213> ORGANISM: Sus scrofa

<400> SEQUENCE: 26
aactgtaaca agcgtccctt tcg                                           23

<210> SEQ ID NO 27
<211> LENGTH: 22
<212> TYPE: DNA
<213> ORGANISM: Sus scrofa

<400> SEQUENCE: 27
ggtattctcc tcctctacct ct                                            22

<210> SEQ ID NO 28
<211> LENGTH: 23
<212> TYPE: DNA
<213> ORGANISM: Sus scrofa

<400> SEQUENCE: 28
ctggattggc agaggctctt tat                                           23
```

-continued

```
<210> SEQ ID NO 29
<211> LENGTH: 22
<212> TYPE: DNA
<213> ORGANISM: Sus scrofa

<400> SEQUENCE: 29
ggtattctcc tcctctacct ct                                             22

<210> SEQ ID NO 30
<211> LENGTH: 23
<212> TYPE: DNA
<213> ORGANISM: Sus scrofa

<400> SEQUENCE: 30
ctggattggc agaggctctt tac                                            23

<210> SEQ ID NO 31
<211> LENGTH: 22
<212> TYPE: DNA
<213> ORGANISM: Sus scrofa

<400> SEQUENCE: 31
gaatgggagg tgagtaagta aa                                             22

<210> SEQ ID NO 32
<211> LENGTH: 18
<212> TYPE: DNA
<213> ORGANISM: Sus scrofa

<400> SEQUENCE: 32
ccagctgcaa gggagact                                                  18

<210> SEQ ID NO 33
<211> LENGTH: 22
<212> TYPE: DNA
<213> ORGANISM: Sus scrofa

<400> SEQUENCE: 33
gaatgggagg tgagtaagta aa                                             22

<210> SEQ ID NO 34
<211> LENGTH: 18
<212> TYPE: DNA
<213> ORGANISM: Sus scrofa

<400> SEQUENCE: 34
ccagctgcaa gggagacg                                                  18

<210> SEQ ID NO 35
<211> LENGTH: 22
<212> TYPE: DNA
<213> ORGANISM: Sus scrofa

<400> SEQUENCE: 35
gaatgggagg tgagtaagta aa                                             22

<210> SEQ ID NO 36
<211> LENGTH: 22
<212> TYPE: DNA
<213> ORGANISM: Sus scrofa

<400> SEQUENCE: 36
ggtcaaagtc gtgggtgtgt tt                                             22
```

<210> SEQ ID NO 37
<211> LENGTH: 22
<212> TYPE: DNA
<213> ORGANISM: Sus scrofa

<400> SEQUENCE: 37
agcattaaga ctgtgtgtgt gt                                              22

<210> SEQ ID NO 38
<211> LENGTH: 22
<212> TYPE: DNA
<213> ORGANISM: Sus scrofa

<400> SEQUENCE: 38
ggtcaaagtc gtgggtgtgt tc                                              22

<210> SEQ ID NO 39
<211> LENGTH: 21
<212> TYPE: DNA
<213> ORGANISM: Sus scrofa

<400> SEQUENCE: 39
ggatccgtgt tcgccaacgc t                                               21

<210> SEQ ID NO 40
<211> LENGTH: 28
<212> TYPE: DNA
<213> ORGANISM: Sus scrofa

<400> SEQUENCE: 40
gcggccgcag agctgccttt taggttat                                        28

<210> SEQ ID NO 41
<211> LENGTH: 20
<212> TYPE: DNA
<213> ORGANISM: Sus scrofa

<400> SEQUENCE: 41
ctcagtgggt tagggacctg                                                 20

<210> SEQ ID NO 42
<211> LENGTH: 20
<212> TYPE: DNA
<213> ORGANISM: Sus scrofa

<400> SEQUENCE: 42
gccatctgat agggtttcca                                                 20

<210> SEQ ID NO 43
<211> LENGTH: 20
<212> TYPE: DNA
<213> ORGANISM: Sus scrofa

<400> SEQUENCE: 43
gctaaagtcc aggccagttg                                                 20

<210> SEQ ID NO 44
<211> LENGTH: 20
<212> TYPE: DNA
<213> ORGANISM: Sus scrofa

<400> SEQUENCE: 44

```
caagagtccc caccagtctt                                                 20
```

<210> SEQ ID NO 45
<211> LENGTH: 44000
<212> TYPE: DNA
<213> ORGANISM: Sus scrofa
<220> FEATURE:
<221> NAME/KEY: misc_feature
<222> LOCATION: (18715)..(18716)
<223> OTHER INFORMATION: n is a, c, g, or t
<220> FEATURE:
<221> NAME/KEY: misc_feature
<222> LOCATION: (24141)..(24141)
<223> OTHER INFORMATION: n is a, c, g, or t
<220> FEATURE:
<221> NAME/KEY: misc_feature
<222> LOCATION: (41400)..(41400)
<223> OTHER INFORMATION: n is a, c, g, or t

<400> SEQUENCE: 45

```
ataaccgcgg agggctggcg cccagtcggc tgtgttcgcc aacgctatga gttccttcga    60
gggccagatg gcggagtacc caactatctc catagaccgt ttcgaccggg agaatctgag   120
ggctcgcgct tatttcctgt cccactgcca caagggtgag tgagcgcggc gcgccgaccc   180
cctcccgggg accagggctg cggcgggtct ggccccgcgg ggaggtagcc caggggctgg   240
agaggaggaa gttggggtgg gggtcctgca ggaggagtgc aggctttggg aggtctgggg   300
agagactagc gactgcatcc tgtcgcaggc gtgctcttca gcctgtttga ggctttatcg   360
cctcataggt cccgcggggc gggacagagc agcgactgcc agttactcac tgacccaggc   420
cagtttgatc aggcacagct attcggtttt tttggaagct ctcccagggc ccaatagtca   480
aggttgtcga ggattactta tttcttcccc caaatcctcg cgattttgtt acaaagacag   540
gtttaaatga aattctgcca tacctccaac catttattag caagcacgca cgcattcaaa   600
ttaaacgtcc tgcctgtgag cttgacaacg tgcaagctcc ccctcttttt agatgttctg   660
ttcacattca gtatgaaagg ttccttttgt cctagaggtg ggatgaggtt taccttacag   720
atgcccaggt caggcaacca gaatgttatt tcacagctgc acatggttag gaattaagcc   780
tggaatgtcg ccccctaacg atatggtccc caggccagtt actccaggca agtctggagc   840
atctctacat tttagccagt ctccagagct agagtaccac caatttcact accattttcc   900
attcttttt ttttttttt tcttttgcc atttcttggg ccgctccggc ggcatatgga   960
ggttcccagg ctaggggtcc aatcggagct gtagctgccg gcctacacca tagccacagc  1020
aactcaggat ccaagccgcg tctgcaacct acaccacagc tcacggcaac gccagatcgt  1080
taacccactg agcaaggcca gggatcgaac ccgcaacctc atggttccta gtcggattca  1140
ttaaccactg agccatgacg ggaaatcccc attgtccatt cttaacatct ggtatgctga  1200
tggataggtc agtaactttt acccatgaaa acaggtttaa tattcagtat gctaattagc  1260
acatccttgg gccttgacca gagatgaagg ttaattgaag cattctagaa gctacctctt  1320
ggagtgctga tttccagcgt agcttaagta ggagaccccc gaccgctctt ttgaggagtg  1380
actcagatat atttgcacaa acataccaca ctgtgtgatt ttaaagtaaa tcagtgatat  1440
gaaacagac cctgggcag gcagtgggtg tgaagactag ctgctgtgtg tgtgtgaaat  1500
cttgaagtt actgctttgg ggaaatgcgt ctgctttctg gctctaagct cttttaattt  1560
atcactcttt aatgaggaaa tgctggacct cctctctagc tgtgctaaaa acacgtgagt  1620
cccagtgaag gcctttctgt tgcttcggga gaataatatt tttggttttg tcttgttttt  1680
cattgagaag tcattcctgg aagatggtgt ttgtacctca aaggccctct ggcgtctctg  1740
```

```
aactcatcga ggatggtgga cgggattaaa gaatggcttc ttgggagttc ccattgtggc    1800
gcagtggaaa tgaacccgac taggaaccat gaggtggcag gttcgatccc tggcttcact    1860
cagtgggtta aggatctggt gttgtcgtga gctgtggtgt aggtcacaga cattgttgtg    1920
cctgtggcat aggccaggag ctacagctct gattagaccc catagcttgg gaacctctgt    1980
atgctgctgg tgcggcccta aaaagacaaa aagaccaaaa agaaaaaaga aaaaggaaa     2040 aaaaacaaag aatggcttct tcggggctca gccttcatgc atcagagtag tggctttgga    2100
gaaagagttt gcctaaagga gttcgtattt atatttttta ttgaatttat tcttttatta    2160
tttagtaatt gtagttgtga aattgtcatt agtttgtata ttaaggaata ctctctcctg    2220
ctgagcagtt tataactttt cctgtcctct gttcccatgt gggcctgtct tcccagtgag    2280
gatgtacact caacaaggtc aggaactcag cttctgttct ccagggttgc acattgtct     2340 cttcgtggtt tttaactttt tggggaagct gacgtccttg gatgtgctgt gggctggctt    2400
gtgtcctctc cctaccccca ttcatctttt gaatccctaa tctccgatgt ggctgtattt    2460
ggagaaaggg cttttaggag gtgatggagg ttaaatgagg tcataagggt ggagtcctaa    2520
ttttatagga gtggtggcct tctctacaca cacacacaca cacacacaca cacacacact    2580
gaggaatgcc gtgtaggcac gcggcatgaa agtggctgct ggtaaggaga ggcctcccca    2640
gaaaccagct ttggtacctt gatcttggac ttgagcttcc agaaccgtta gaaatacatt    2700
tctgggtgtt tgcactgtgg cacagtgggt taaaacctg actgcagtgg ctcagatctc     2760
ctgtagccgt gtgggttccg tccctggccc agtgcagtgg gttaaggatc cagccttgcc    2820
acagctgtgg tgtaggttgc agctgcagct tggagtcaat ccctgccctg gaacttcca    2880 tatgctgcag ggacagcggt aggaaaaaac aaataaacaa ataaataaat aaataaggag    2940
ttcccattgt ggtacaacag ggatgaatcc aactaggaac catgaggttg caggttcgat    3000
ccctggcctc gctcagtggg ttaaggatcc gacattgcca tgagctgtgg tgtgggtcga    3060
agatgaggct cagatctggt gttgctatgg ctgtggtgta ggctggcagc tgtatttcag    3120
attctactcc tagcctggga atctccatgt actgcacagg ggcagccctg aaaaccaaaa    3180
aaaaaaaaaa aaaaaaaaa aaaaaaaaaa aaaaatttta attacttaat ttctcattaa    3240
agccatccag gctgatattt tgttattgaa gcctgagcag aataatacag tatatctgat    3300
aagatctata gtctcctgtg aaaaaaatgc acataaacat gttaacatca cattttgata    3360
aaagttgagg tagggagttc ccgttgtggc tcagagggtt aagaacctga ctagtatcca    3420
tgaagatgtg ggtttcatcg ctggtcttgc tcaatgggtt aaggatccag cattgctgtg    3480
agctgtgagc tgtggtatag gttgcaaatg tggctcgaat ctgacatgac tgtgttatag    3540
gcctgcagct gcagctctga tttgaccact acccacgaa tgtccatatg ctgcaggtgt    3600
ggtcctaaaa aaaaaaaaaa ggtgaggtgg gccatggacc tgcttgatgc ctgttcatgg    3660
tccatctggg atccagtgct gtgttcaggg caggctttaa agcatctgta aggcccagag    3720
gacaagatgg gacccatggc ctgagattgc agcccaggga gggtaggac ccttcagga      3780 ggcagcttaa tttgatgtat tttggtcaaa ggaaaagcca aaggccctgg aaaggaggct    3840
tggggtgcat cctggtggca aatagggaac tcacccaggt tccctccact ggtgggatgg    3900
ggtgtcttga tggaacagga tgctgcccag aggcttagtt tgggagcaag gagcagagtc    3960
caggatcagc ctccttattg ctctgactca aactctctgg aagacttgat taaggagagt    4020
cctgcctggg gacatactca ttctttggcc ctaaagcctg cctcaggagt gccctgagga    4080
```

```
gaggcacctt ctgagggcac atggtctgtc cgtgtgtggt ctggtgactg ccttgttttt      4140
gagaaatgag gaccgccatg tatacatcga gggcatgcgt gttggttgta attaggataa      4200
ttcaatttct ttttttcttt tttatgagag tggtaatgtt tatttcaggt tctctctctc      4260
tttttgtctt tttaaaaaa aatttttttt tctttttttg ccacacccgc agcatgtgga      4320
agttccaggg ccagggattg aacctgcgcc acacagcagt gatcagaacc acagtgggga      4380
aaatgcagaa gccgagttcc cattgtgaca catcggaaat gaatctgact agtaaccatg      4440
aggttccggg ttcgatccct ggccttgctc cgtgggttaa ggatccggca ttgccatggg      4500
ctgtggtgta ggtcacagac gcggctcgga tctttcgttg ccgtggctgt ggtgtaggct      4560
ggcagttgca gctctgatta gatccctagc ctgagaacct ccatatactg tgggtgtggc      4620 tctaaaagc aaaaaccaa aaacaaaaac aaaagaaga tgcaggagcc ttaacccact       4680
aggctatcag agaactccct cgatttttt ctgatgggtg attgtttaac atcatctccc       4740
tcacagccca gcttgactgc ctttgccttc tgccttcatc aagggcggtc atgggcagtg      4800
tttacatata ttcatcaaaa atgcacatga aagtcatttt tggtacatga tttgactttt      4860
tttttttggt ctttttagg gctgtaccca tggcatgcga aggttcccag gctaggggct      4920
aattggagct gcagctgcca gcctacacca cagctcacgg caacgccgga tccttaaccc      4980
actgagtaag gccagggatc gaacccacaa cccctggttc ctagtcggat tcattttcac      5040
cacgatggga actcccattt tggtgtatg atttgaaaag actttcaaaa taacctgctt       5100
gtttatgggt ttgttttgt tttttaagt aaaatgaact ttccaacagc attcatgtat        5160
taaccgcaaa agagctggaa aagcattatg tagaagaata atttcgtttt aattagcttt      5220
aagcttatta aactatgat cagtgtttag aaatcttata atgaagatgg ttattcatgg       5280
ttagacagca atgcatttt ttttttttt ttttgtcttt ttgccttttt ctagggctgc         5340
tcccgtggca tgtggaggct cccaggctag gggtcgaatc agagctgtag ctgtcggcct       5400
acaccatagc cacagcaatg ccagatccga gccatgtctg cgacctacac cacagctcat       5460
ggcaacgcca gaaccttaac ccacggagca aggccaggga ttgaacccgc aacctcatgg       5520
ttcctagtcg gattcattaa ccactgagcc acgatgggaa ctccaacaat gcattttttt       5580
tttaatttag tttttaaatt ttttggttgc acccaaggcc ttggaagttc ccaggccaga      5640
gactgaatcc gagctgcagg tacggcaaca ccggatcctt aacccactg tgtcaggtca       5700 gggatggaac ctgtgccaat gcaggggtcc aagacactgc agttggattc tgaacccact      5760
gtgccacagc gagagtccaa gcaattcatt ttttaaaaaa ttcttttttt tccttttct      5820 tttggacccc cttcacctga ttctcccacc tcctaccccc cgacctttgt taatcagcaa      5880
tatgttctca gtatccgtga ggttgaattt ttgcttttc acatttcata gaaaagtgag      5940
atcatgcagt atttgtctgt gtctgactat ttcacttagc tatgcctttg ggctccgttc      6000
atgtcacaaa tggcaagagt tcattctttt ttacagctga ctaatattcc attgtgcata      6060
tgtataccac aatgtcttta tccatttatc tcttgataga cactgaggtt gtttccatgt      6120
cttggctctt ataaataatg ctgcagcaaa cacgagggca cagataccctt ttccagtgag     6180 tgttttttgtt ttcttcaggt aaatagccag aagtgaaatt gttggatctt gtagttctgt     6240
ttttaatgtt ttgaggaacc tcagcctcct gtactgtctt ccatagtggc tgcaccaatt      6300
tacattccca ccaacagtgc acaagcgttc ccatttctcc acattctttt caacatttgt      6360 tctttgctttt cttgttgatc atagccgtaa tgggcatgat atctcaatgt ggttttgact     6420
tgcatgtccc tgatgattag tgatgtggag catttttcg tgtacctttt ggccatacaa       6480
```

```
tatgtcttgg ggaaaaaagt ctattcagat ctgcccatta aaaaaaaaaa atctcttttt    6540
tttttttttt ttttttttgc tgttaaattt gtatgagttc ttccccaccc ctttcatttt    6600
atgcccagac ttgcagcatg tggaaggtct catgcttggg tcaaattggg actgcagcta    6660
tggcctatgc aacaccaaca ccagatcaga gccacaactg agacctatgc caaagcttgc    6720
ggcaactctg gatcggtaac ccactgatgc aggccaggga ttgaatgtac atcttctcaa    6780
acattatgtt aggttcttta tatattttag atattagcca tgcatcagat acatgatttg    6840
caaatatttt ctcctcttag taggttttttt cattttgtta atgtttcctt tgctatgaag    6900
agcttttttag tttgatgtag tcccactgtt tattttttgct tttgcttttg gtgccatatt    6960
caaaatagca tcaccaagac ctgcatcaga gagattactg cctatgtttt cttatagaaa    7020
ttttatggtt tcaggtctta catttaaggc tttaatctgt tttgagttat ttttttgtatg    7080
cagtgtggtg tggtaagaca gtgctcaggt ttcattgttt tgcatgtggt tgtccagttt    7140
tcccaacaca atttattgaa gagactttct tcattgtata gtcttgactt ctttaccata    7200
aattgattga tgctatatgt gtgggtttat ttctgggcct tgtatttttt tctattgatc    7260
tatctatgtt tttatgccag tgccttaatg tttttttttgc tttttcttta gggccacacc    7320
atgacacatg gaaggaagtt cccaggctaa gggttgaatt ggagcttcag ctgccggcct    7380
acaccacagc cacaacacag gatctgagct gcatctgcga cttgcaccac agctcacagt    7440
aatgccagat ccccaaccca ctgagtgagg ccacagattg aacccgagtc ctcatggatg    7500
ctagtcagat tcattattgc tgcaccacaa tgggaactcc cataatgttt taattacttt    7560
agctttgtaa tacattttgt aatcagggag catgatgttt ccaattcttt tcttttttcaa    7620
ggttgcttaa aaagaaatct tttgtggttc tatactaatt ttaggattat ttgttctatt    7680
tttatgaaaa atgtcattgg aattttgata tggtttgcat tgaacctgtt gattgctttg    7740
ggtaatatgg acatttaata atattgattc tttcaactca tgagcttgga ttagcttttcc    7800
ataactttcc atttattcgt gtgatggtag ttttttctgtt aacgtcttgt atttttttcaat    7860
atgcaagtct ttcacgtctt tggttaaact tatttataga tattcttttt gatgcagttg    7920
tgaatgggat tgtttctaaa tttctctttc tgatggtttg ttttaagaat gtagaaatgg    7980
gagttcccat cgtggcacag tggttaacga atccgactag gaaccatgag gttgtgggtt    8040
caatccctgg ccttgctcag tgggttaagg atctggcgtt gtcgtgagct gtggtgtagg    8100
ttgcagatgc ggctcggatc ccatgttgct gtggctctgg cgtaggccag tggctacagc    8160
tccgattgga cccctagcct gggaatctcc atatgccgtg gaagcagccc tagaagaggc    8220
aaaaagacaa aaaaaaaaaa aaaaaaaaa aaaagaatg tagaaatgca atggactttt    8280
tgtgtttatg tatcctgcaa ctttactgaa ttccttgtatt agttctaaca ggttttgatg    8340
gagtctttag agttttctct gtatggtgtc atgttgtgtt tgtaaatagt gtcagtttta    8400
tttcctcctt tctactttgg atgcctatta tttcttttttc ttgcctaatt gctctggcta    8460
ggacttatag tactatgttg aataaaaggg caagagtggg cagtcttgtc ttgttcctga    8520
tattagagga agtcttcatc ttttttgatcat tgattatgat gtttgctgag ggctcacata    8580
tgcccttttat tatgttgagg tatgttccct ctatacctga tttgttgaga gttttgtttt    8640
tttttttttt taatcataaa tggatgttga gttttgttca atgcttttta tgcatttctt    8700
gagatgatta tatcattttt tattcttcat tttgttatg tgatatatca cattggctga    8760
tttgtggatt ttgaaccatc tttatgtctc cagaataata aatcccactt gatcatgatg    8820
```

```
tatgatctttt  ttaatgtatt  gttgaattct  gtttgctggt  atttagttga  agagttttgc   8880
atctatgttc   atcagggata  ttgacctgta  gttttattta  ttcttttttta tggtgtcctt   8940
gtctggcttt   ggtaccaggg  tattgctagc  ctcataaaat  gagttttttg  aatgtttgta   9000
gaattcacta   gcaaagccat  ctggtccaag  actgtttgtt  ggggttttt   aattactgat   9060
agtagaaagg   atattcaata  tccttactag  ttatcagtct  gttcaggtat  tctgtttcat   9120
catggttcaa   tcatggtagg  ttgtatgttt  ctaagaactt  acccatttct  tctaggttgt   9180
ccagtttgtc   gatttataaa  tgttcacaga  agtttcttac  ctttcttttc  tgttgtaatg   9240
gttgtaataa   atcttcttca  atttctgatt  ttatttattt  gagtcctatc  tctctctcta   9300
tttttgtttt   tttggtgagt  ctagcaaagg  cttgtcaatt  ttgcttacct  tttcaaagaa   9360
taagttctta   gtttcattga  ttttctctgt  tatcttttta  ggttctagtt  cacttatttc   9420
ttccctaatc   ttagttattt  tcttccttct  actaattttg  ggctttgtat  gttcttcttt   9480
ttctagtttc   tttcttttctt tctttttcttt tttagagctg cacctgcgaa  agttgctggg   9540
ctaggggttg   aattggagct  gcagctgttg  gcctgcgaca  cagccacagc  aacaccagat   9600
ttgagctgca   tctgtgacct  acaccactgg  atcccgctga  gcaaggccag  gggtcgaacc   9660
cacctcctca   cggacactat  tgtcgggttc  ttaacctgct  gtgccacaac  aggaattcct   9720
ttatctcagt   tactgaagtg  taaagttagg  ttgattattt  gagattttttc ttatttcttg   9780
aggtaagcac   tgaaccccttg aatttcccct  ttagaactga  tcttgctgca  tcctgaaaat   9840
tttggtatgt   ttttcttttg  tctcaaggta  ttcttaaatt  tcttttttgat ttttttctttg  9900
acccattggt   tgtttaatag  cctgtaactt  aattttcaca  tttgtgaatt  ttctagtttt   9960
cttcctgtaa   ttaattttta  gcttcatacc  attgcaattg  gaaaagatgc  tttatatgat  10020
ttcagtcttc   ttaaatgcgt  taaaccttgc  tttgtggctt  aatatgtggt  ctatcttgga  10080
aattgttcta   tgtgcacttg  agaagaatat  gtattctgtt  gccattgcat  ggaatgttct  10140
gcatatattt   gtgaagttca  tctggtctaa  tatgtcattt  aagtccaata  tttccatact  10200
gatattctat   ctgaaatgtt  ctatccatga  tgtaagtaga  atattaaagt  cccctgcttt  10260
tgctatctgt   ttctccttttt aagtctgtta  atatttgctt  tatatattta  gatgtttctg  10320
tgttgggtgt   ataaatattt  acaaatgttg  tatcttctta  ttggatagat  cccttcatca  10380
ttgtataata   tggtaaggtc  tctctctctc  tctctttttt  tttttttttct ttttagggct  10440
gtacctgcag   catgtggagg  ttcctaggct  aggggtcagt  gtggaattgt  agctgccagc  10500
ctataccaca   gccacagcaa  tgcggaatcc  aagctgcatt  tgtgacctat  accatagttc  10560
acaggagtgc   tggatcctta  accctctgaa  cgaggccagg  gatcgaacct  gtgtcctcat  10620
ggatgctatt   cagatttgtt  tccgctgagc  catgatggga  accccatggt  aatgtctctt  10680
attactgtct   ttgttgttgt  ttttactttt  ttatgggctg  cacacgtggc  atatgaaagt  10740
tcctaggcta   gcaattgaaa  gtgagctgag  gctgaggcct  atgccacagc  catggcaaca  10800
ctggatccaa   gctgcatctg  tgacctactc  tgcagcttgt  ggcaatgccg  gatccttaac  10860
ctactgagtg   aggccaggga  tcaaacctgc  atcctcacag  agactgttgg  gtccttaacc  10920
tgctgagcca   cagtgggaac  tcccagtctt  tgttttaaag  tctatttttgt ctaagtatag  10980
ctactctagc   tttttttttt  ggtttccatt  tagaattagg  gtaattagaa  gttcccattg  11040
tggctcagca   gattacaaac  acaactagga  tccttgagga  tgtgggtttg  atccttgccc  11100
tccctcagtg   gacctggcat  tttcgtgagc  tatggtgtag  gtcacagatg  tgacttggat  11160
cctgtgttgc   tgtggctgtg  gctgtctggt  ttgctttaaa  tgtcaccttt  ctctttaagt  11220
```

```
tgcctttctg tgtttgttaa tttggaaagc tgtggagcaa gcctctgtgg gtggtaataa    11280
cccacctttc aacccagcag ttatagtagg ttgagaagta atgaaacttt ttttttcccc    11340
tggcctaagc ttgaatggtt tcctcaagga ttccatggaa gcaaacttga atatctaggt    11400
ggactaactt aagtgattgg aattgaatgg gtcactgaga gcctggacca aagggtagtt    11460
ggattgcaat gaaagaagag agtaagggaa aatgatggaa gcatttccca aggagacccg    11520
gtcacctact cttctttggc tactctgagt catttagact cttcccccag gggtaggaca    11580
tcattctcct tttaaatggc ttctgatggc ttggagatgg tccatttttt agtggttctt    11640
atcctgtttt cagtggatgc ctcacttgca gaagcaaaag ccagtagctc atgaatcaat    11700
tctcttctaa aagtgaaact ctcatttatt ttctcttaaa aggaagccta aatgatcag     11760 ataactcagc ttccttgggg caaggaatac tctgaaaaaa taatatattt ctgattttt     11820 ttttttttggc agatcacatg aaaggattaa gagcctctac cttgaaaaga aggttggagt    11880
gcaggtaata catgttgcta cttatttgtg cgtgtgtttt tgtcttttta gggccacacc    11940
tacggcgtat ggaagttccc aggctaggag tcaaatcaga attgtagctg ctggccaatg    12000
ccacagccgt gcctacctgg gatccgagcc atgtctgcga cctacaccac agctcaccgc    12060
aatgctgggt ctttaaccca ctgagcgagg ccagggatca aacccacatc ctcgtggata    12120
ctagtcgggt tcgttactgc tgagccacca ggagaactcc tatgtgtgcg tttttaagta    12180
aaattttact tgagctgtaa cttctacaca gaaatgtaca gacatcataa gggaacagtc    12240
tgacaaacat ttgtaagtga acagatctgt gtaacttctg cccagctcaa gacgtaggac    12300
agaaccaaaa tcctggaaca gaccccgtcc ctcccccagt cagtcttccc tgcccacggg    12360
caacctcttt tctgacgtct gttgtcatgt ttaacttggg ctgttttga acgctattta     12420 aattgtttca tactgaatag actctcctac ttttttttctt ttacttagca gtatatgtga    12480
atgattcatc tgtgctattg ggcacagcaa tggtctgtcc attctgtcca tttttctttct   12540 ttctttcttt ttccttttct tttcttttca gggccacttc catggcatat ggaagttccc    12600
aggctagggg tcgaatcggg gccgcagctg ccagcctatg ccacagccac agcactgtgg    12660
gatctcagcc atgtccaaga cctacaccac agctcacagc aatgccggat cctcaaccca    12720
ctgagggagg cccggattg aacctccatc ctcatggatt ctagtcaggt tcataagctg      12780
gtgagccaca gtgggaactc ccacgtttgt ttctgaaagg gtgtgtatgt gtgtaaaggg     12840
ttgtttcctt ataaagaatt aaatagcgtt gttggttctc ttcttaaagc tgagccttcg    12900
cattcttttc cttcagccat tgcttagatt caaaattatc aagatatatc cagttgcctc    12960
ttgaaccatg tgagggttcg gggtgctgac tttcgtcgtg gttgaaaatt gatgtgtaac    13020
attacagtcg gccctcccta tccccgggtc tgcatccatg gattcaacca accgtggact    13080
gtgtcgtgcc atagcactca tttagtgaaa acaatttctc acataagtgg attgttgctg    13140
tcgaatcctg tgttgttcag ggatcagctg ggtgtggaaa ggagtgtctt ggcgttttga    13200
ctctttcacc tttgacttag cagcaggctt ctttgctaag tgatatcagc agtctgtgtt    13260
tatgataatg gtaacaaata cacacatgca cacacacaca cacacacaca cacacacaca    13320
ctagatgttg atgatatggt aatgagtaaa acaaaaatcc ctctcttctt ggagctgaca    13380
gtctctttag agcctctttt ggaaagacac tactattgct tctatttttac agatgaggaa    13440 actcaggaac cagagaggtt aaattagttg cccaaggtca cacagctagt ggcaggacca    13500
ggattcccac caggtctgtc tgattttaga gcctatgtat tagttgtcca ttgctgcgta    13560
```

```
acaaattatc ccctgaagtg acttaaaaac aacactcgtc atgtattgtt atctgttgct  13620
gtgcctcagg gattctgaca gggcacagtg ggagcggctg gtttctgcct gactgggtat  13680
catttggggg cgaccttacc taaaggctcg ttcattcaat gtctgatgcc tggactgggg  13740
acacttaagt agttgggaca ttttgggtat ctctgtctct aaacaaatct ttgcagcatg  13800
gtggtttcag gatagctagc gtccaaagtc ctgcagtgct atgtccgtcc cagtctgttg  13860
accaaggcag ttacaagggt ctgtccaggt tcagggagg tgaatggaga cgcctcccgt  13920
caagggaaaa tgtccattcc catgtggttg gagtgcacgt cagcgtggcc agctttggaa  13980
agtataatct gccgtagatt gtacccctaa cctttcagct ctaggggtga attttttcaag  14040 cttgtcatga aattgatttc tgcccaaaag acacagacag aagcgacttg cacgaagtaa  14100
atctcaagca gactttggct cccccttcct gtttagcaga ggtagtttat catttggtgg  14160 tgtcttttcca ggcatagctg atcctgtaac aaccatgtct ttaagatgaa aataaacaat  14220
gaggtcctgc tgtacagcac ggggaactat attcagtctc ctgggataga ccacgatgga  14280
aaagaatatt tttaaaaagt gtgtgtgtat gtatgaccga gtcactttgc tgtccagcag  14340
aattggcata acagtgtaaa ccaactatgc tttaatacta ataataacaa aagatgagaa  14400
tggtgaagac caagctttga ggaggtcaga gaacataata ttcattctca tctgcttctt  14460
ccccttcact ttatttttatt tttttaattt atttttttag ggccacacct gaggcattta  14520
gaaattccca ggctaggggt cgaatcagag cctcagctgc cggcccacag cacagccaca  14580
gcaacgccag atctgagccg catctgtgac ctgcaccaca ggtcacggca atgccgaatc  14640
cctaacccac tgagcgaggc cagggtttga acctgcatcc tcatggatcc tagtcgggcg  14700
cgttactgct gagccacgat gggaactccc cttcccttta cagtgatggg gcggaggtgg  14760
tcattggagg ttaggcctat tgggaaccat tctaacactt ttggtgccag ctccgtttct  14820
gaattattca gggtatctga tacatgttga aacaggagat ttcctagtca cccagatgac  14880
tcattttgga tggtactaaa atgacttttt tttttttta atctctcttt tcagcttgaa  14940
ggtctcctta tactgttcac ctgttactag agaattgtta ttaaccaacc cgaggtacag  15000
attttgggag aaacgaattg taagttttat ttttttcgaa tgccactaat tcttttttttc  15060 aagtgggaac tacttttcga gggagatgga acaaatgtat aaatatattt atctgcagta  15120
tttatggtgt cgctattcac tcttttgtca ttccttaatt gtggaagagc ttggcttttt  15180
attgttgtca cttttgtcttt cttgtccttg aacacgttga cctagattct tagttttgtc  15240
tcgtctcaaa gaccctcttg cccagctgca ttttaatagt ttaaagcata aaatgttcag  15300
tgacataatc gatagatcct tttatttaga ccatgggtta ggtgaggaaa aatgaagagg  15360
acttaggagt tataataaga aaggaataat aagctgaata aaaacaggat ggataatttg  15420
aatctgacag aataaagtgg atctctgcag tgggaggcgg atagtagagg agagaagacc  15480
atatggcagg tagaaaatgt gaagatggca gaaaaatttc tgttgcaaca gtagttgcta  15540
tccacatgaa tggatttcat tcaatttgtg atccaaagac gaagtcgtag tttaggttta  15600
aaaaaaaaaa acaacccagc ctggagttcc cgtcgtggct cagtggttaa caaatccgac  15660
taggaaccgt gaggttgcgg gttcgacccc tggccttgct cagtgggtta aggatccggc  15720
gttgccgtga actgtggtgt aggttgcaga tcgcgcttgg acctggcatg gatgtggctg  15780
tggtgtaggc tggtggctac agctccaatt tgacccctag cctgggaacc tccatatgcc  15840
gcgggagtgg ccctagaaaa aggcaaaaag acaaagcaa acaaacaaaa aacctagcct  15900
tagtctataa gagacgtaga tgacattaaa ggaaaaacac aggtcgaaat tgggggaaaa  15960
```

```
aaaaaagaga aaagatatac tgaacaatta gaagctaaaa atgccaaagt ggcaactttt    16020
atatcatgta aagagctgaa ggaaaaaaag aaaatctaaa ttttcaagag ggtaaaagaa    16080
gatcaagaag atgtgaacac acacacacgt actcacaact gacaaaataa cctcaaactg    16140
gactctgtcg tagttggtca tctagtgctt gatgggagaa agagaaccgt cattcgtagg    16200
tagaattctg cttcattatg tggcttaaac tgccagtaat tggggcagct ggcagagaag    16260
tctgaacaag catctcaaag agtctttttg atgtctgact gccataact  tacagctccc    16320 acctccagct tcccttcctg ccccacatct gggcaaactg attaaaaaaa aaaaaaaaa    16380 aaaaaaaaa  aaaaaaaaa  aaaaagcctg tcctttcctg ggtgcctaca tggagttcaa    16440
acatgaaagc tcagggccac ctgtaaccac agtgaaaacc agggcccctt gttcctattt    16500
tctcaagcta cctgggccac ttcctcccag cctgggtacc agcctccgct ccccagaacg    16560
tcccaggata tgggtagtgc agtgttttca taccctcttg ggtcatgttt ggtggaattt    16620
tcagtctcag cttctgatct gtcccttagg tgggacccga cagaggccat ccctatggag    16680
agggacccaa cagcaaggct gctaagtaac cttggccttg tgttaggcc  tgcagttgct    16740 gtgggtcatt ccggccagca gtcaggaagg gaagctgagg aagaagggga gaagagcagg    16800
gataggctgg aatccacggg gacaagtggg gacccatgcc tgcctctcac tcctcccaac    16860
cttggtaatg ctaacgctgc tgttcccttg gccactgagt cacacatacg agccccaggg    16920
ctccgagaag ctgagcggga atatcccgca gaagatggag ctgcgctgtc ctgcccgtgt    16980
cagtgaactg agcctgcaga tcagcaacac aggagttgtt gtcattcctg gtgccttgca    17040
gagcattgaa aaatgctgct ggctgacgtc tgccatccga gtcttaccca ggtgtttctt    17100
ggggctactg ctgacccaga cgtatacaca gcaggagctt acaggatagt ccaggctccg    17160
ctgagttgat gtaattcaag gccacctcgc aatctaaggg ggaaggggc  agcttgatag    17220 aagcaggtgg agagcttacc agacactctc agaaactgaa cacgagggac gtgggaagta    17280
agtaaatagc cagaaggctt aaatgacgta atgaatgcat gtgaactgat tgaaacacag    17340
agctttaaac ccagcgaagg aaggaagatc tttgggtgca cgtggaacat tgaccaaaat    17400
cagcaagtgc tttgtcactg acgcctttca agaaatccta gtgatttgtt ctttgaccgt    17460
aatgcagtga tattggaaat cagaaataaa aggagagtta aattcatgaa tgggaacctt    17520
tagttcccat tcatgtggga actaaaggtt caccacaaac aactctcagg ttaaagagga    17580
agttgtaaag aaaaatatac aatacttagg actgaggaac aataaaaaga ggacattcaa    17640
aatgtgtgga gcacagctca attaatactt aaaaggatgg agttcccatc gtggcacagt    17700
ggaaatgaat ccaactaggg accatgaggt tgcgtgttcg atccccggcc tagctctgtg    17760
ggttggtgat ccggcattgc tgtgagctgt ggtgtaggtt gcagatgcag ctcggatctg    17820
gcattgctgt ggctgtggcg taggccggca acaacaactc tgattagaac cctagcctgg    17880
gaacctccat atgctgcagg tgcagcccta aaaagacaaa accccaaaaa aaaaaaaaa    17940 aattaaaggg aaattgacag cattaaatgc atttcttaaa aagcaaagac gaattaaatg    18000
gaagaattct ttgacttatt aacaaggaaa agaagcaaca aagcaaatct aaggacatgt    18060
aaaagaagga aataataaag agaaaatgac agattagtga tatagagact aactatcaca    18120
gaaaattaac aaaagtaaaa actggccttt agagaaatag agataatttt ctgccaagat    18180
tggtgaaaaa agatgtatat aaaaatacag aatgataggt gttcccattg tggcacagcg    18240
gaaacgaagc caactaggaa ccatgggggtt gtgggtttga tccctggcct tgctcagtgg    18300
```

```
gttaaggatc tggcattgcc atgagctgtg gtataggtca cagatgcagc tcggatcctg    18360
tgttgctgtg gtgtaggctg ccagctgtag ctccgatttg accoctagcc tgggaacctc    18420 catatactgc aggtatggcc ctcaaaagca aacaaacaa acaaacccaa acagaatga     18480 taaaaaggaa aataactatt aataagagca atgcacaatg ccttattttc aaaattaatg    18540
tggtagtgta tttgataatt tagacacagt ggataaatac ctgggaaagt aggaaaatac    18600
caaattaagg caagaaaagt aggaaacttg aataaagaaa tagccatcag gcattcccat    18660
tatgactcag tgggtttaag aacccatata gtccctgtga ggcctttgtt agtgnngtaa    18720
gaatctggca tggctgtaca ctagcatagg ttgtagatgc agctcggatc cagcattgct    18780
gtggctgtgg ctgtggcctg cagctgcagc tctgatttga ccoctatcct gggaacttct    18840 atatgccaca ggtggagctg caaaaatgaa aaaaaatt ttttaattt aaaaattta      18900 aaacagtttt gaaagatctc ttcttcaaaa agccccagg tccagatggt tttatgggca    18960
ctttggccac atgttcagag aacaagtaat tcttgttta ggagagaata aaaagataag    19020
ccagtcaacc tcactggcaa accggataat ggtagcacat ggggaagaaa gtccatttca    19080
ttcatgagca tgtgtgaaca tccaaattag ggtaatagct aactgaacct aacagtgtta    19140
aaaaaaagtg catcacaaat agagtgttta ttctagaaat gcatgaacat ttttataccct   19200 gaaccacagt cactgtgagt tttatggtat cagtggacta agagatgaa caattatgtt     19260 cattcatcag ctacttactg aatgcctctt tgtgctggtg actgttccag taaattgtcc    19320 aaggacccctt ggaccgttct gcagcagctt gaatctgtaa atttggccag tgtgtcagga   19380
ctgatggcag actgttctgc tgcagaaaac ctaaacacat agaacacctg actacctgtc    19440
gtacaaagac taaggtcaaa aggaaatgg gatgggagca ggagggatgg ggaggtgaag    19500 ggagggagt tgaattcata gaactgctgt gtcaaaggat gtataagtat atataatgta    19560
ttgccacctc cagaaaggta ttttatttat ttatttattt atttattttg tttgtttgtt    19620
tgtttgtttg gagcagagaa aggtttattg cagggcccag caatgaaaac gggtggctta    19680
tgctcaaaaa ctttgaacac ccctgacggta cctgggaaaa gttttatag gtagaatttg    19740 gagtgagggc tgcagagggt gtgcccagaa aggtattttt ttagctttat tattttttca    19800
agctgttaag ccattactgt cgtgaagtca gaaatggttc cacggagtct ataacttctc    19860
ttggtcccct ttctgtgttt gagatggcaa aggcacataa agtcatgaa aaactgaaaa     19920 tgtatacttc tcttcttta ataggtgtca attgaagttg aaactcctac ccagatatct     19980
ttaattgatg aagcatcagg cgaggtaact aagtactaaa tactgtgttt ttaaaaaat     20040 cattacttag cattaaatga ttgtgtacct ttctccttgc ttgtgaatgc tcatttaacc    20100
ataaataaaa tttatagtaa atgagtgggt ttgtagggaa aaaaaaaacc atctgtgata    20160
tattttctat gtccgaagga ttagtctatg tcagagctgc ttctttttag tattacgtgc    20220
taattatagg cgctccgtaa tcatgatatt actaaagaat tctaattcta attctaattc   20280
taattataat tctactaaag aatgtgattg tcacatttat taagtttatt ataatgttca    20340
agatgtaaaa tggtgctcag tgttttttgca gcgtatttag gtatattttg atttatttcc   20400
ccccccgaat cattttttta ttcaagaaga cattatccag gtggatccat tttattttt    20460 gtccttaaat ttagaagcag gtccttttgt gtggcagtta tcttttttaa tagtaaatag    20520
gactaaggac ctacctttta tgtatttata tatttatagc tcaaatcata ggtagggcta    20580
gaaagtgttt tcctctttta tggcaaatct agttaaaatt tattctgtag tctgattaga    20640
acctgcttaa ttgacacgtt taatctggag ggtgtccttg gtgatgtgac tataatggga    20700
```

```
caggggtcac ttttttttttt tttttgtctt tttgctattt cttgggctgc tcctgcggca   20760 tatgaggtt cccaagctag ggatctaatc ggagctgtag ctgctggctt acgccagagc    20820
cacagcaacc caggatccga gccacgtctg caacctacac cacagctcat ggcaacgccg   20880
gatccttaac ccactgagca aggccaggga tcgaacccgc accttcatgg ttcctagtcg   20940
gattcgttaa ccactgcgcc acaacgggaa ctccagggg gtcactttttt acatttcctc   21000 cctggagatt aggcattgaa gtcctttttt tttttttttt tttttttttt tctgtttttc   21060
ttttgctttt ttttctttttc tttcttgtct tttttcttta tctttccttt cttttttttc   21120 agtttttat tttgactgcc tcacagcaca gggagtttct gggccaggga ttagatctga    21180
gctgcagttt caacctttgc accatggcag ggtcctga agtccttcta gagctactgt     21240
cccgagggag gggaggcggg atgccctgaa ccttgctaag tgccatcctg agctcgggtt   21300
gtgcacacgt tcgggagatg ctcttggtga ctggcagcct gtgacatgtg ctggtgaaag   21360
gctttctcag aattgggctc cagacagcag gtggctctta aagagcaggg tcctggtgcc   21420
ccactctcgt cctttccttt tcttgtcctg cactgaggct tgcatgtgtg tgtctccagc   21480
tccaacctgg gggagagccc attttatatt tatttttatt ttattttaat tttttttttat 21540 ggctaagcgt gcaacatatg gagattgcca ggctagtaat caaatctgag ccatgactga   21600
gacctatgcc aaagttgccc caatgctgga tcctttaacc caatgtacca gcctgggggt   21660
caaacccagg cctccttagc gacctgagcc actgcagtta gattcttaac ccgttgcacc   21720
acagcaggaa ctttttattt ttattttatt tttttaataa attttattgg agtatagttg   21780
acttagttgt atttcaggta ttcagcaaag tacatcggtt atacaaatac ataccttttt   21840
ggattctttt cccatatagg ttatagcaga gttttgagca tagttccctc tgccacactg   21900
tgggtccttg ttacgcaact cttttatacg tagtaatgtg tatttgtcag tcccagcccc   21960
ctaatttatc cctcccaccc cacatggtaa ccctaaattt ggtttcaaaa gggagagtct   22020
ggagttccca tcgtggctca gtggttaacg aatccgactg gaaccatga ggatgtgggt    22080 tcgatccctg gccttgctca gtgggttaag gatctggtgt tgtggtgagc tgtggtgtag    22140
gttgcagaca tggctcagat cccgcattgc tgtggctgtg gtgtaggccg gcagctccag   22200
ctccgattag acccctagcc tgggaacctc catatgctgc gggagcagcc ttagaaatgg   22260 aaaaaaaaa aaaaaaaaaa aaggagagtc tgtctaaagg ggcctttgga ataaacgatg    22320
tcagacacac cttatgacta gagagctgga gtgtccagag ctctgcccca ccatgtatca   22380
aaccttcaga ggctatgcgt ggtgcccatg aggatgtgcc tagtggggca gtacagcatg   22440
ctgtgtggtg acttgggacc aggctacatc agagttttaa aaaatgtttt aaaataactt   22500
tattgagaca tcatccacgt accatcccac tcaccccatt caagttcaca gttcaggagt   22560
ttccattgtg gtgcagcgga aacatacccca actagtatcc attaggatgc tagtttgatc  22620
cctggcctca ctccgtgggt cagggatccg gcattgctct gagctgtggt gtagttccca   22680
gatgcacctg gggcctggtg tgcctgtggc tgtggtgtag gccagcaggt gcagctccga   22740
tttgatccct agcctgggaa cttccatgtg ccgtgggtgt ggccctaaaa agtgaaaata   22800 aaataaaag aaataggcag ttcagtggct ttttgtatat tcacagagtt gtatatccac    22860
catcacaagc aatttcagaa tattttcatc acccagaaga ccacttggta cccattagca   22920
gtcaccctct atttctccct ccctctggct tctagtaact actagtctag tttaaggctc   22980
tatggtttgc ccattctgga catttcataa aaatggactc atataacacg tggtctttg    23040
```

```
tgagtgcttt cagtttgcat aacttatcca tgctgtggtg gttgtcagta cttcatgtct   23100
ttttatggcc gaataacatc ccactgtatg gctagaccac ctgttgcgta ttcagtcatc   23160
agttgatgga cattcgggct gtttctactc tttggctggc atgaaggatg ctgctctgaa   23220
tattcatata taggtttttg tgtgtggacc tgttttcgtt tctcaagtgc aagagtgaaa   23280
ttgcactctt gcacttgagt ttctcacagc aagagtgaaa ttgctgtgtc atgttgcaac   23340
tctgcatgta accatttgtt ttgtgggtga ggattccact tgtttccaga atctggagag   23400
tggggaaatg aggagaaaag gcatacgtcc ttgggacgta cttgcatctg ttctgttaag   23460
gagggctttg tttaactggg tcctaatgat aaatttctat tattttttt tctttatttt    23520 cttttagaa ggaagaaatt gttgtgactc tcttaccagc tggtcattgc ccaggatcag    23580
ttatgtaagg gggttcatct ctttcgccca tttattctgc gtagaaacgt attgtatttg   23640
tagaaataaa cattgagggt ctagaaaaca atatgtgtag ggagatttga ttctcttgat   23700
ggcagttcgt ttaatctttg tttccaaatt gaatttgggg gactgtggtg cagatcaagt   23760
ttgaaacgtg gctttctgac aatgcaagac ttcagtagcc atttctccac tggctttgca   23820
ttttcctgtc gtgtggattt ttctctccac aaacaggaat gatttcattg tacagttgag   23880
ggagctcacg tattttgggg ccatcgcttg caaactcagt ggcatctcca tcatgttatt   23940
ttttccaacc tcccgggaag aggtggcagc tgagtgtctg gtgtggttaa gcagtacgga   24000
aattctgttc atgccatgtc agggtggctg tgtttggcag gcagcgtggg ctgtggcttt   24060
aatatatatt tgctttactg ggattttgta tgagacctaa gtcactgaga tatatttcgt   24120
ttttcaggtc ttatttcagg ngcacacatg gaactgtctt gtatacagga gacttcgatg   24180
gcaaaaagga gaagctgcca gaatggagct tctgcactcg gggggcagta ccgggcttta   24240
tataatactc gaatgttaag actatgttgt tgtaaagatt ttactgctct tccccctac    24300 acatgtatga ggctttgttg cttttatttt ttatttttt tgcttttag ggccacaccc     24360 gcagcatatt gaggttctca ggctaggggt cgaatcagag ctgcagctgc caacgaacac   24420
cacagccaca gcaacgcggg atccgagccc cacatgtgac ctacaccgca gctcacagca   24480
atgccggatc cttaacccat tgagcgaggc caggaatcga actcgtgtcc tcatggttcc   24540
tagtcagatt tgtttccagc tgtaccacaa cggaaactcc tgcctttgtt tctattagaa   24600
gtctaactca attataatat ttgcaacagc aaagcaaatt tttcctcttg aaatgagggg   24660
atgatgacat tctgtgtgtg aattggggta gtagttacat gaactgatcg aaattcactg   24720
aaccaggagt tccctggtga ctcagtgggt tagggacctg gcattgtcgc tgctgcagtt   24780
tgggtcgctg ctgtggtggg ggttcagtcc ttagcccaag aatttccata tgccctgggt   24840
gcagccaaaa aaggtaaaaa aaaaaaaaaa aatccctcac ccatctgtct tatatattat   24900
cctatggaaa tcacttccta accatgtcga tacagtaaaa aattccaggg agctctcttg   24960
tggcccagtg gattaaggat ctggctgttg tcactgcagc ggcatgggag tggccaaaaa   25020
agaaaaccca agtggactga aacctcctgt aaaataactg agagtttcga cttcacgcgt   25080
gttgtatttc acgtgattaa cagctcttgt gttctgttta tcttcagtgt gaaagacatc   25140
cagagtgtgt acttagacac cactttctgc catccaaagt attaccaaat tcccagtcgg   25200
gtacgtctct ctggacgggt ggctgtattt ctcagggggc gggccgcagg ctaacaggtc   25260
gggtggtaac gggccccctg gccttaatgt ctgggacgc tgggaacgga caaggcctca    25320
actgcctctt caaccccctg cccaggagga gtgtctgaga gggatcttgg agctggtccg   25380
cagctggatc acacggagcc cctaccacgt ggtgtggctg aactgcaaag cggcctatgg   25440
```

```
gtacgagtac ctgttcacca acctcagcga ggagttcgga gtccaggtac ctgagggctc   25500
tttctcccac ccccaccccc aaagtcccct ctcactggaa accctatcag atggcccagc   25560
cttcctcacc ttggtttact cacttccgct tgggaggact tgacaggtgg aaagagccct   25620
tcggtgaaaa gtcccacaaa ggaagtgtgt tttgttcaaa atactgggtc atgaaataaa   25680
cgtagtgttt gtcacgagca ttgaaaataa atgtgaacta ggaagtatcc gagagtatgg   25740
cttgcagtca gagtggttat tgtgtgaata tttacatggg gagtcagata tatcaacaga   25800
tctttctcga cttaaccaaa gggctgtgtc ccaataaagc cataaatctg tctggctcga   25860
gttccctgta gaggctcagt ggttaacgaa ccacactagc atccatgagg gcgcaggttc   25920
gatccctggc ctcgctcagt gggttaaggc tccgcagcat tgccatgaac tgtgatgtag   25980
gtggcagacg cggctcgtat ctggtgttgc tgtggctgtg gtgtaggcga ggggatgcag   26040
ctctgattgg accectagcc tgggaaccaa catatgccac aggtgtggcc ctaaaaagac   26100
attaaaaaca aacaaaaaat ctgtcaggct cctccctgg cagaggaaga gcctcctcca   26160
ctctccctct ccctcgggtt ctcacttgca cacaacaagg atctggagat gcaggctggc   26220
aggtcctgta gccgagccgg gatagagcct gcgggcttgt cgtacaagga tggagtccgg   26280
tggtctggca ggaggttgtt cctgccggga ggtgctgcag cagcgccagg gtagagtcag   26340
gggtctggcg gcacagggat ggagacaggc cctctctcca ggcaagagcg atcggctcag   26400
gacgggagcg gttctgagtg aagggaatt tcccttcaaa gggacaccac cttctgacct   26460
gggctctttt aacgaccctt tcagatccat ggcctcagag atcacagtct tgatcacagt   26520
tgaaatcagg tcaccatgaa ccagttttat ggacgccttc agagggtggg ccaccctggg   26580
ctggggaatg gtcctggctg ccactgggtg tgggtgtttc cttaggtccc tacatcatgg   26640
acctgtttgg ggacccacat tctcttgccc caggcccact aatttcctgt cccagccccc   26700
gcccccgccc ccgtgctgtg tgtaagggct gagtgttgtt ttgctctctg catgggggtg   26760
ggtttggatc ctctggtcgg tcccacctta gtcacgtggg gaaaggttat ggggaggcgc   26820
tccaagcgca cgcccctggt gcctgcgtgt gtgttcattg tttacgcagg cctcctgttt   26880
ttggcaacag caaatggcct gttttgaatc acccaggtcc ccgtccctgt cctctcctaa   26940
cagagccatt gcaaatagca cgtataagtt aaacatgcat ttaaataagt tcctttgtat   27000 cattttaaa aattaaatcc cacacgcaaa gggacttatt taaaaacat tctgagattg   27060 ttgttgctgt gttttttggt gttaaaatgt cttttcaatt aaaccacagc gataatagac   27120
tgtgtgtgtg cgcatgtata cacacgcaca cgtacacaca tctttatata tgctctgctg   27180
ggtgctgggt tttttgttt ttatttcatg gcttcttgac aaaatataga ggtaccagcc   27240
acttacccgt cccaaatttg ctgtgtaaat tttctcgatg tgcgaaatgg aaaagacccg   27300
gaagctcccg ctctgagacc tgggggagaa accccgggct gaggaggggg tggggaggga   27360
ggcaggattt cagtgtgtgg ctccctcaag tctcttaatc ccgctgtagg gatacaatgc   27420
ttgtagacaa cagtgaggtt ttttttggaca aagagacctg agaggtgatt tatgacagcc   27480
ttttcaagca tcttcatttt cacgaggatg agcgtttgtg tctctctggt gcatctccga   27540
gtttacctct ttttctctcc ttcctaggcc ggaaaagtca attcattgtt cctgttagtc   27600
gttagtaaac aggtagtgag aggactaggc tactggataa gtaagcagtc atgcctggct   27660
gctgtgtgac aacagtcctg gtagtaatta ccccagcagt taacatcctc ctggagttcc   27720
cgttgtggct cagtggttaa cgattccgac taggaacctt gaggttgcgg gtttgatccc   27780
```

```
tggcctcgtt cagtgggttg aggatccagc gttgccgtga gctgtggtgt aggtcgaaga   27840
cgtggctcgg atcccgcgtt gctgtggctc tggcgtaggc cggcggctac agctccgatt   27900 cgaccoctag cctgggaacc tccatatgct gagggtgcca ccgtagaaaa gacaaaaaga   27960
taaaacaaaa caaaaaactt cctaatctgt tttgttgctc agacttcaaa atgacaatac   28020
tgtttctttt ttttttcttt ttcttttttct tttttttggt gccatttcat tatctctgtg   28080
ttcatttagg tacttgttgt ttattctgaa atacccagaa aagatttaag caaaactgac   28140
atgttggttt taagttttaa gcagtattag ctttaggagt tccctggtgg cccagtaggt   28200
taaggaacca gcattgtcac tggaatggct ttggttgctg ctgtggcaca ggttcgatcc   28260
ctggctgggg aacttctgca tgccacaggt gtggccaaaa aaaactccaa acaaacaaaa   28320
acaaaaatta aaaatgaaat cattagcttt aagattctaa tggtggctga gatctttttt   28380 tttggtctttt tttcgtcttt ttagggctac cacacctgcg gcatgcggag gttcccaggc   28440
taggggttta atcagagctg tagccgcagg cctacaccgc agccacagca atgccagatc   28500
cgagccgcat ctgcgactga caccacagct cacagtaata ctggatcctt aacccgctga   28560
gcgaggccag ggatcaaacc cgcaacctca tggttactag tctgattcgt ttccgctgca   28620
ccaagacagg aactcctgag atttttttgt tgtgttttc tgcatctgcc ccctcccect   28680 ctggccaatc cactgtggca taggaggatc cagatctcgg cttccttgtt acgctggctg   28740
cccaccacca gctgcccttta agtagcatgt tgtatgtgtc ttcgagagca accttcttga   28800 ttattttgt ctgctgtatt tactgcaata ctcccaatat ttagaataaa gctttttta   28860 ttgatgattt ttatttttat ttttctagca cagctggttt acagtgttct gtccattttc   28920
tactgcacag caaggtgacc cagtcgtaca tacatatata ccttcttttt tctcacatca   28980
tcacgctcca tgataagtga ctagatagag ttcccagtgc tacacagcag gatagaataa   29040
agcttgatgt agagcaggtg cacagtaaat tttggtcgag tgcctcttgc taaactgagg   29100
gacggattta cctgatccag tgaaagccac ctacaggagg cgctaaatgc cgggaccatg   29160
atctcagcgt cctggtgcag tactaatgtg cgtggaaaga gaggaaaact aggtctcacg   29220
gcagaagaga gagttcattc taactggatg atttgccccg gcctagttac ccttgaaaca   29280 cttttgtttac aggaaataca attccagtca tgtgcttatt tgtgttgttt tcctcaggtt   29340
cacgtgaata aactggacat gttttcgaaac atgcctgaca tccttcatca tctcacaaca   29400
gaccgtggca ctcagatcca tgcctgtcgg catccaaagg tacacagtaa actgctctgt   29460
ttgcgagatc catgcaagaa tttcaggtcc aggaggaacc ggcgaaattc cattttctag   29520
gcccttcagg tcgcaaatgt gaaaactgag gcttaaggtg ttaacccaag gtcattactg   29580
tattgcagta ccctgaactt cataatgagt taacagacac agacacgcca tagttttgtt   29640
ttgttttgtt ttgcttttta gggctgcact agtggcatgt ggaagttccc aggctcttga   29700
atcggagctg cagctgctgg gcccacacca cagccacagc aacgccagat ctgagcctca   29760
tctgagacct acaccgtagg tcacagcaac gccggatcct ttacccactg agcgaggcca   29820
gggatcaaac ccacatcctc aagtggcgga tactagttgg tttagttccc gctgagccac   29880
aatgggaact ctggttttca accttttaaa aatacttgtc actttttctc caactttatt   29940
ttgaaaaatt ttaaagcagt atagtagtta gactagtacc aagacctctg tgtactctat   30000 ttttctaac tggcgtatag ttgctatgta ctgttacgta atttacaggt gtacagtgta   30060
gtgattcaca attttttaaag gttgtaatcc atttatagtt actataaaat attagctata   30120
ttccccctat tgtatgatat actcttgtag cttctttatt ttttaggtag tagtttgtac   30180
```

```
ccctcaaccc cccaccctgt cttgcccctc cccacttccc tctccccact ggtaaccact   30240
gatttgttct ctatagctgt gagtctgctt cttttttttt gttatattca ctaatttgct   30300
atatttttta gattccacat gtaagtgata tcacacagta tttgtctttc tctgacttat   30360
ttcattgagt gtaatgttct ccaagtccat ccgtgttgct gcaaatggca ttatttcatt   30420
cttttatgg ctgacattcc attgtgtgtg tgtgtgttcc acatcttctt tgtccattta    30480
tctactgatt gacacttagg ttgcttccat gtcttggctc ttgtaaacag tgctgctgtg   30540
gacatgggga tgcagtatct cttttaatta gtgttttgg ttttgtggg tatataccca     30600
ggagtggaat tgctggctcc tatgaacacc gtgtcctctt cttctggatt ccgcagctgc   30660
ccaggtgtta acagtttgct ttctggcacc ctctgtgtct gtctgtctgt ctctctgtgt   30720
aagcagcacc ccaccgtgca gcccacttga gagtcagatg caaacgtcat gacacgtcac   30780
cctaaacaaa gtcgtataac cacagtacac ttcccacact cagggaattt aacatgaatg   30840
tgatacgact gggtatgata tggtccatat tcagatttcc tcagttgtct caatccctta   30900
tggcttggtg gagtggggag cagggccatc cagaatttaa tttaaaaaca tgtgttgcat   30960
tcactcaggc tgctttagtc ttttgatgta gatcaagtct ccagctaaag tccaggccag   31020
ttgttttcta gaatattcct caattcgaac ttacctattt cttcatgtct atatatgtat   31080
atatatattt tttttttcat gctaaaaagt catctgcatt tttttgagac cctggtacaa   31140
atatatttgt tgaaaatgtt aaaccatttt tcttatttta aaatcttttt taggcagagg   31200
aatattttca ttggaataaa ttaccctgtg gaataacatc caaaaataga attccactcc   31260
acataatcag tattaagccc tccactatgt ggtttggaga aagaactaga aaaaccaatg   31320
ttattgtgag gtaagcaagc agcgtctttt gagaggaacc ttgctttgag gtaaatcgat   31380
agtttaaagg cagtctagcc taacctcaag aggggggcat atcatgattg tggaaaataa   31440
cttttgaaag ttaaactctg tttaaattaa agagaagcgg cttccaaaag ctatcaattg   31500
cttactacca tgagccagta tttcctgggg tctactgagt ttgactgaga agatggttag   31560
aggcaggctg tcttgcttgg ccggaagttg ggaattgacc ttgaagggg tggaagccct    31620
tagtggagca gaggaggccc atactgatcc tcatgtttta gctcatgtcc tgaaacattg   31680
gccgtttgga atgttcacag atatttacat ttatggaaag agttccctcc tggcccagga   31740
aaaaaatcct tgatggcagg gtgatttcat cctgcagtag cctaaaatga gaagactcgg   31800
agtttggaac ttagttttga tgagtgaccc ttaattttgg gttttccttt cccttagaa    31860
ctggagagag ttcgtacaga gcctgctttt cttttcactc ctcctacagt gaggtaagag   31920
gatcccatac tcagaacctc ggctgctgag gcatctctct tcctcctgct taagactggt   31980
ggggactctt gctcaggaaa cacaggcgaa gacatctcgg tggatgagct acgttgctta   32040
agtagaaagg aaatgatcac cccttgtatc tagcctaaac tttgaagaaa atgtatgaat   32100
aaggttttat tcccaacctg ctttctaaat gtattttaaa cccctcactt cagttctgtt   32160
cacccgtcgt aaaaaaattg tcagtattac tatacagcag atggaaatgt ggtcagtagc   32220
ttgtgattac ccatactgga aagaatctg aagctctatg cccgaaactc acacagtatt     32280
gtaaatcaac tatagtttaa ttaaaaaccc caaacaaaac cccaaaaact tcttcaagaa   32340
agtaatagtt aagaatataa atgaaaagac tcccagagtt ggtgcaatgg attaaggatc   32400
cagcattgtc tctgcagtgg cttgggacgc tgctgaggtg ccagttcgat ccccggccca   32460
ggaatttcca catgccacag gtccagccaa aaattaaaaa agcatttaag acttagagac   32520
```

```
ttgaaataat ttgacacaag cccaccaaga tctaaaaatg acaaagctga agctcgtctg    32580
ggttatagag atgttttgag gaagagtgac agagttcctt tgtttaacat gctgagcttt    32640
gcagaaaatc aaggtattcg tgaaattttt gcatgtagtt gtccttgttt ggattagaat    32700
aaaccatgaa gatgaatcga gcagtctcaa agatgtactt cccctttggta ttgctaacaa    32760 ttatatgtgg gaagaaagaa atgcaattct aagttctttc cctgtgcata ttaaatactt    32820
ggctaaattc taacttcctt aaagggaatt tgttaaatat agggtgagtg actttagata    32880
aggaaactag gagttcccgt cgtggttcag tggttaacga atccgactag gaaccatgag    32940
gttgtgggtt cagtccctgc ccttgctcag tgggttatcg atccggcgtt gccatgagct    33000
gtggtgtagg ttgcagtcac ggctcggatc tggcatagct gtggctctgg ctctcagctt    33060
tggctcccct agactgggaa cctccatatg ccttggatgt ggacctagaa aaagacaaaa    33120
taaaaataaa aaattaaaaa aataaaaata gataaggaaa ctactgtcct ataaagaaat    33180
agagaatctt tgaatcccat taacaagtga gactcattcc ttactgggga acagaatcac    33240
ctgaagaaca tttaaatata ttgattccag gtcccgctgt agctcagtgt tagaggctct    33300
ttggggctgg ggcatgtgtg ttgggtattt cttttttgaga gccccgctgg gtgctcccgt    33360
gcacctggca ttaggaacca cagccttgag cgacctctgc tctctttccc ctggtatccc    33420
tttatctgtt gctcttacac ccagtttttt caccatagag ataactgatg catttattt     33480 tccttcttcc agattaaaga tttcttgagc tacattagtc ctgtgaatgt atatccaaat    33540
gtcattccac tgggcacaac tctggagaaa gttaaagaaa tgtgagtcat tagtacttgc    33600
ggaacttctg tggtccaatg ggatggatcc agaggataat ttcaggcctg aaaatgggga    33660
caaggctgta aaatggacgt ggctgtcagt agggttctgg ttgggagcat ctgggctttt    33720
tcaagtgagt gcgttttata taatcttaaa agcttctggg catctagcat aatggactgg    33780
ttggcaatga agaccttgaa aagggcggga caccttcaaa tcttatttct gtgcccttt     33840 gtatttatt ttcactatat cttagctttc aacctctaga atgaagagat caaatttgtg     33900
agattcttgc aagagataac cccattaaat agcgaacagg aggcagtttg ctgtactgaa    33960
ttccctgaat gccagaaggt gttaccctat tatttaacag ttcatcagaa tagggacatg    34020
cttttctgca gtgcaagagc aaagataaaa gttttgcttt ccgtcagtcc tacaattaga    34080
tgggttgttt taaatgctta tatttactac tttattatat tgaagtaatt ttaaattatt    34140
aaacattgct gaaaagtttg ttttttttt tttttttttt cttttttggc ctctctgtgg     34200
cagatgaagc tcctgggtca gggatcagat ctagctgttg ttgtgactta agccacagtt    34260
gcggcaatgc tggatcctta accctctgtg ccagggtggg gattgaaccc acgtcccagt    34320
gctcccaaga cgccactgat cccattgcgc cacagaggga actccaaaca ttgctgaaaa    34380 gttttttaaaa gcagtggtat gatttcctcc atagtcaaat ttttataatc tctataaatg    34440
atgcttctat tccagctttt cccaacagga aaaataatat ctgtattcat ttcagcttaa    34500
agcctttatg ccgatcttcg caaaatatcg agccaaagta taaccactt ggaaaattga     34560 agagagctag aataatccat ctagactcag gtaagatgaa tgaccctggg gtcagaggtg    34620
tgggtttctc tgcaggagca cttttgcgag ttctctggcc tggtgaaagc tgccctgggc    34680
agagttggac ccaggatcca ctgtcgctca gacttgtcat gtggtcttgt aacgtgctct    34740
gcccccctac cttcaaccta taaatgtagg agtcagattc ccttcacagg tttagaaaaa    34800
gtgataaaga gaacttagtc tgtattgaat gttgtcttca gctttctggg aatgtgccct    34860
gcagcttgta ttggccataa ggagaggctc tgctgttacc cttgaacatt tccttcaaga    34920
```

```
tactagtcag tgcagataat gagaactttg tctcccatca tttcccatca cattgatgtg    34980
tagtgtttat acgaatggat tctctatacc ttcctgcctt ctttcatttt ctgattgatt    35040
ttttaaaatg aagtatattt gatttacaat gttgtgttaa tttctgctgt acagcagagt    35100
ggtgtagata tatatatatt ctttttaaaa gtattctttt ctgttatggc ttgtcctagg    35160
atattgaata tagttccctg tgctgtggag taagatcttg tagttgatcc atcctctctc    35220
tatatatata atagctaaca tctgataacc ccagcctccc actccatccc tctctcaatg    35280
ccctccccac tggtaaccat aaatcttctc tatatccgtg aatctgttca cctatttggc    35340
ttgtttgcat ttttggttat tacatataaa gctgctttca tctgcttact ttgggtttat    35400
tttcctcttc atttaaaatt tcttaatgtg ggagatgagg tcattgattt gagccctttc    35460
gcccttaata caagcatcta gtgctataaa tttccctctt tgacttgtgt tgtcattttc    35520
ctccagttca aaatagtttc taattttttct tttcctccct ccctctctcc cttctttctt    35580
ttcttcattt ttggctgccc tgaggcatat ggaattccca ggccagggg cagatccaag     35640 ctgcagttgt gacttatgct gcaggtgcag caatgccagt gtgctgggcc agggatcgaa    35700
cctgcgtccc agagctccag agatgccact attcccttg cgccacagca ggaactcctc      35760 taattttct tccttgaggc gcgggtttat ttacaggtac attatttcgt ttctgaattc      35820
tggaggaatt tacaaagata attgtgtcat ataattttat tgtggtcaga aaaatacag     35880 tgcatggatt ttactgagat tcatggtcca gaataatggt ccatcttggt aaatgtttca    35940
tgtgtacatg aagaaaatat gtatactgct gttgggtgga gtgttatata aatgtctagt    36000
taataatgtt caagtcttct gcatctttgc tgattaactt gttctacttg ctctatcaat    36060
tattgaacgt ttttgaaatg gtgaatttgt caaaatttgt tcttccactt tttgtgtcat    36120
cgatttgaat aatctttaaa actcctatgt cctctagagg aactgaccct ttcacctttg    36180
ggaaataact cccttatcc ttcttttat tagctttgaa atctacctca ctggataata     36240
atacatccat tccattttct tctgatgtgt gttggcatag tatatctttt tccatctctt    36300
tatttctcac ctaattgtct ttatatttaa agtgggtttc ctgtaggcag tgtattgatg    36360
gatcttgttt cttttacat ccatctgata aattctgctt ttcagttgga gtgttttcag     36420
gctacttagg ttaatgtgat tactgacctt gttaggttta ccatcttgct atttgttcca    36480
tctgttcttt cttctttctc ttctacctc ttttggattg agaacggata gagattccat     36540
ttaatgtctt atttgttta ttagctgtaa ctctttatt cttttagtgg tttacagttt       36600
tcatctgtaa cctatcagag tgaaaatttc aagatatata ttctacttga agtatggtat    36660
aggaaggtga caacagtata ttccatttct cccctcccag tctttgtgct attattgtca    36720
tacactttat ttctctgtta taaactccac aatacattac tgtttttttt ttttttttaa    36780
caaagcttta aaattgatc gcttatagga taatttggga gttccttttg tggctcagca     36840
gtaacgaatc catgaggatt caggttcgat tcctcgcctt gccagtgcgt taggagttgg    36900
cattgctgtg agctgcagtg tatgtcgcag ttgtggctcg gatcctacac tgctgtgact    36960
gtggtgtagt ctggcacctg cagctccaat tcgaccccta gcttgggaac ttccatatgc    37020
cctgtgggcc tgaaaagcaa acaaacaaac aaaaaaccaa ctataattta tatgccataa   37080
atttcatcct tttaaggtga acaattccat gattgttact gtaacgaagt aggttacgtg    37140
ctaaggcctc ttctcttggc ttgtggatgg gtgccatgct gatgtgtgct cacatggcct    37200
ttcctgggtg cttgtgcctg gttgggaggg gtgagtaaag gaggggctgg gggatatttg    37260
```

```
ctctctaatg tcagttcctt ctttggaggc cccatttcca ctttggggat taggacttcg    37320
acaggaattt gtgtgggaag gaacacacac tcagtctaaa acatacaata aaatttacgc    37380
tgtaacatgg taagaaactg acaactgttc ttcagacaga acacattttc attctcacca    37440
gcaatatata cggattccaa tctctccaca tcctagctca cactttttag tgtctttgat    37500
ttgtagttat ttaatgatgt caaataatat atctcattgt agtttcactt cctttctcta    37560
ttgatgttga tcttttttcca tgttcttatt gggcatttat ttatcttttc tggtgaaatg    37620
tctattcaga cctttttgcc tgttttttaaa ttggcaaact cattcctgag ttgttaagag    37680
ttctctctat aggctgggta tgtctagtat tatttgcaaa tatcttttttc cagtctatag    37740 cttgtctttt cactctcttc atggtgtctt ttgaagtgta aaattttaaa ttcatctaat    37800
ttcttttata gcttgtgctt ttggtgtcat atcgaagaag ctattgctta atccaagatc    37860
ataaagattt attttcatac tttatcattt ctgggtcagt tttgactttt cccttatttt    37920
ataggccatt ttcccacctt tctacacatt tggtaatttt ttattggatg ccacgcttct    37980
tgaactttat gttgttaggc atagcatacc tttggatttc tgaaaacatt cctaaacttt    38040
attctggcac gtggttaagt gacttggaaa gagtttggtt gtgtctggct tctgtgcaag    38100
cctcttaggc aaaagcaggg cagcatttag tttagaatcc actttcccca ctgctgaggc    38160
taggcgcttc ttcacactcg taggaatagc ccgagttatg aggcgttact ggctcttggg    38220
ggcaggtact gtttccgtca ccgtgtgcat cctcagcacg cttttccttttt attcctcgga    38280 gtgattctct ccctggcctc acagccaggc gctgactatt cgaggggccc cttgtgcagc    38340
tcatcagagc tcctcagtac tgctctctcc tctctggcct cagctctgta aactccagcc    38400
aacctggctt ccttggactc ccagttatat ctcaactcag ggatgccagt gggctctcct    38460
tgccaggaaa ctgtcacaaa cccatacgct gaggcaatct taggtatcac ttgtctttgt    38520
ctgatgttta attccttgag agactttgtt tctcatattt tatctggttt ttagttgaca    38580
tgggaggtta aatttagtcc ctgttaactc tttcttggct ggaagcataa gttctttttt    38640
ttttttttta atacttaaaa ttttgtacct tttatctatc caaatgatcc tcgttttaa    38700 tgacggtttt attttttttgg ttgggccact agtttaagag ttcttgaggt tatgttcatt    38760
tccacttctt cctgcttttt ctttattagc ttcaattttg atccttctag attcctttgg    38820
ttccttattc cttatcatag caactttcat accttttatt tgtacaggtg tagatctttc    38880
aacgactctt cagtgtcctt ctgtattttg taagtcacag atattatcag gtttacttta    38940
gttgcatgta tggtactgac tttaaaattc ctaccctgtc ccatgcatgt actttaaggt    39000
ctccatgatg atctctgcca ctacgttgac cagtctttca cctgttctag ttcttctttt    39060
ttaatgacca catcggtggc atatggaagt ttcccggcca gagactgaat ctgagctaca    39120
agctatgctg ttgcttgagg cagtgttgca tcttttaacc cactgtgccg tgctggggat    39180
cgaacctgag tctccacagt gacctgacca ctgcatttgg aacctttttct agttcttaac    39240 atgctctgtt gatgcaaatt agtggttact attacacatg cagtgttaaa tcagttgctc    39300
tgtgttattc ttttctcaga atctgaaggg tacatgtaga agtcgcttgt ctcttagcat    39360
cttaaaaaat attttaatta ggagttcccg tcgtggcgca gtagtaacg aatccgacta    39420 ggaaccatga ggttgcaggt ttgatccctg gccttgctca gtgggttaag gatccaggtt    39480
gccgtgagct gtggtgtagg ttgcagacgc ggctcagatc ctgtgttgct ggggctctgg    39540
cgtaggccgg tggctacagc tccaattaga ccccctagcct gggaacctcc atatgccatg    39600
ggagcggccc tagaaaaggc aaaaagacca aaaatatata tatatatatt ttaataaaac    39660
```

```
tgtgctcttt atataagttt aatctttatc taatttatat aatttaatag ttaaccatta   39720
ttataattat ctcaagacca atttataaa attactgttc ctttactgta gataatttag    39780
aaaatagtta tgtagaacct tacaactata tctttattag cattttcatg tatttccttt   39840
ccatcctgaa tcatttatat aaatacctac acaaatcacg ggggtgatat tgaaaatatt   39900
caaccttggt ctcattggta cctacaatga gaccagcagt agccgtagtg caagaccata   39960
gtgcaagacc aatttcttca tttgtgcagc tcttagttcc tggactgtga agaggtgggc   40020
aagggtcctt aggtgtaggg tccagggcag tgggggacag gaaggacatc tggagctgaa   40080
gggaagagcc gttactaatt agcctggaag tgtttacata caactgtaa gactgaatag    40140 gtgtatacag actgaaaggc agcttggatc actttgtgtg tatgtgtgtg tatatataca   40200
catatacata tacttaacct ctttactgga aaattttat tcttcaaaag cacccgttca    40260
agggctgcat attttaaatt gcattataac tatataattt ttgtcatgta ctttgtcata   40320
tagattatga acttcagttt tataaacatt gtggtaaaca ttgtacagaa gtctgtgtca   40380
tagctctcat tactgggttc gattatagaa attatggtgc ttgatatata catattgcca   40440
aactgtttcc caaaatggtt ataccagttt atatagacat cagcagtata tgatggttga   40500
aagtatctat gaagtatgac atttgtcctt tttaattgag tttgggtatg ttatcagttt   40560
gtgtaaatgt taaggatttc aacacttctg taagtactgt gattttctg tgtctatttt    40620 catagagaaa tttagttttt atattctaaa aagaatacat gtcagaataa acttctaata   40680
gtataaaaac tttgttttc agatacatag aggtgaggta atgtgaaaat gttttatttt    40740
tacagttgaa acatactgta atgttggtat agtcactgat gcgaaacagg aagctgtcca   40800
ccttagcgat gatacaaaaa cattccatta aaagataatt ttggcacatc agtggaggag   40860
ctataacaaa tgtattaatc catggcttaa aatgaagcca taacttggaa actaggatga   40920
ttccaaatat agtggctaga catcttagtc accttaagtc ctttagaaaa gacgtaagat   40980
gaaataattg cttgttgaaa caattataaa ttgtaagaga acactaagaa ctggctctca   41040
tccttagctc cccctgtctg gttgcagacc ttctctgggc ctgtctcctt ggtaaaatgg   41100
gagctagatg gtggtttcta cggactcctt tcttaagag tcctgaaaaa tgaagttttt    41160
agctgtgtct ttgattgctg ggaaaagtta acttataatt tacttgcttt tagcactaga   41220
acagtaagtt gccctacaca gtaatcctgt aagcatttaa cttccttctc tgggggtaag   41280
tggtattaga gggcaggaaa atgtttgttt tcccccaatg ccacgacatg tcattttagc   41340
ttatgtaaat ttcatgtatt gaatgataag aatttcattc ttgaagattt cctcatttan   41400
aggacacagg tggatataaa catgctcatg cagcatgctt aacacagtaa tatgacacta   41460
aaatgtggct tgtctaacat tttggttcaa gttgatataa tctttctgtg tttccccag    41520 tctcatggcc ttgtgcactt agcatagcct gcgtaacaat taccagagac tgggcaacaa   41580
cttctctcag ttctggatac cactgggatg tccagaatca aagtgctggc agatgtggtt   41640
cccagtaggg gccatttcag ccaccttctc accttcagtg cactcgcatg gccttccttt   41700
tgtgcatggg catggaaaag tgagaaatct gcttcctttt ctcataagaa cactaaccc    41760 gtcgcatagg tgccccccca tgagttaatt atcttctaaa ggtcttacct ccaaatacca   41820
tcacgttgca cttagggctt caaattatga attttggcaa gacgtggaca ttcagcctat   41880
aacatgcact aagtgggtat caaaaaatgt tcatgagggc aaacttttaaa aaacaattct  41940 ttttattgta tcagccaact tgctgagcat ctactatctg caaagcatac acagtctgca   42000
```

```
aaccttgctt ctagtctagg tggtttgaaa acctggctga cgaacagaat cagctgtaga    42060
acttataaaa taaggcaaaa tcaaattatt ggatcctact ttgagagact gagtaggtct    42120
gaaacaaagc atagaaagct gttttagttt aaaaaaaaaa aacaaaactt atcagatgag    42180
gacccatgat taagaatttg tagccttatg gggaacacag atctctagtc tcaattcaca    42240
acctagtgtt gtgacaagtt gaaggctggt agttaaattg ttgagaatat ctcagagggg    42300 cctttttagtt tctcttggaa gaagagtgaa ctcccaattc cacaaattaa aaaatgcagc    42360
taaatgctac aaattggatt tttactaaaa gcaccaatag gttccgtttg cattctgtta    42420
cctacacacc tgttctgttt gtcccacaga ggaggaggag gaggacgatg acgatctctt    42480
tgatgatcct ctgccagtac ctttaaggca caaggttcca aatcagcaga ctcttcactc    42540
tgaggtactt cccatgactg ctctaccaca agaccagcct gaaaaacaga cagaaagcac    42600
agaatgcttc aaagcagaga gtatgccaac atgtctctgg gcaaacttcg tagattgtga    42660
agaatccaat agtgaaagtg aagaattaga aatcacggct ccagctcaag gagacacgag    42720
tcctgtcccc catcaccagc agaaggctga agggaagta ccacagtggg aagtgttctt    42780
taaaagaaat gatgaaatca cagatgactg tttggaaaac cttccgtcct ccacagaggc    42840 aggggctct cagtccccaa agcttttcag tgactctgat ggggaatcaa ctcacatttc    42900
ttcccagact tcttctcagt caacacacat atcagaacaa ggaagtcaag gctgggacag    42960
ccaatcagac actgttttgt tatcttccca agagagaaaa agtggggata ttacctcctt    43020
gaacaaaggt ggctctagac cagaaatcaa agagaatatt cccatccttc agatggaaca    43080
aaatgtattt tgcccgaagg atacttactc tgatttgaaa ggcagagatc aagatataaa    43140
cacacttccc agtgctagag aaacaactac tctgagcagt gggaaacaca tgcctcagga    43200
gaaaaggccg ctaaactgta acagtaacac agattcacaa ggctcctctg actttgaaat    43260
tccctccact ccagaagctg agctacctca acaagagcat ctgcaatatt tatacaagaa    43320
gttggcagga ggagaggta tagtaattga aaaaaggaaa agcgcacgtc attctagagc    43380
aaccactaaa aaacctacac aaacaggtaa tagtcagact cctaatagat gagttcaaat    43440
ggagtactta aaaatgttca tataacctaa aaggcagctc taaaagggga aacaatagga    43500
ccaaaaaata caaagaaaac aagaatggga gaactcagta caaacatatc agtaattaca    43560
tcaaatgaaa atagggaaa aaccataagc caactatata ttgtctatag gaaactggct    43620
tcaagacttg ggcaggttta ctggtgaaag gatggaaacc ttcaccacat aataaacatg    43680
aaagatggag gggctatatt actagtgata aaaggtccag ttcactgaga cataaaccca    43740
aatgagtatg tactggacaa cagccacaca tacagagcaa aaacaactga aaggagaaag    43800
ataaactaaa gcacaattac agctgcaaca gaattagtct acaggaaatc agcaaggaga    43860
cggaagaact gaacagcact atcaaccaac cagatcttca cagaagacac catctagcac    43920
agaatacaca cttttcaagt tcacagaata caacattcac caagatagac catatcctgg    43980
ttcataaaaa cttggatcta                                               44000
```